United States Patent
Desmazeau et al.

(10) Patent No.: US 6,958,383 B2
(45) Date of Patent: Oct. 25, 2005

(54) STREPTOGRAMIN DERIVATIVES, PREPARATION METHOD AND COMPOSITIONS CONTAINING SAME

(75) Inventors: Pascal Desmazeau, Tigery (FR); Gilles Doerflinger, Les Ulis (FR); Yves Ribeill, Raleigh, NC (US); Eric Bacque, Morsang sur Orge (FR); Jean-Claude Barriere, Bures sur Yvette (FR); Gilles Dutruc-Rosset, Paris (FR); Gérard Puchault, Marcilly (FR)

(73) Assignee: Aventis Pharma S. A., Antony Cedex (FR)

( * ) Notice: Subject to any disclaimer, the term of this patent is extended or adjusted under 35 U.S.C. 154(b) by 330 days.

(21) Appl. No.: 10/161,804

(22) Filed: Jun. 5, 2002

(65) Prior Publication Data

US 2002/0151676 A1 Oct. 17, 2002

Related U.S. Application Data

(62) Division of application No. 09/643,197, filed on Aug. 22, 2000, now abandoned, which is a continuation of application No. PCT/FR99/00409, filed on Feb. 24, 1999.

(51) Int. Cl.$^7$ .............................................. C07K 7/50
(52) U.S. Cl. ...................................... 530/317; 514/11
(58) Field of Search ............................ 530/317; 514/11

(56) References Cited

U.S. PATENT DOCUMENTS

| | | | |
|---|---|---|---|
| 6,541,451 B1 | 4/2003 | Bacque et al. | ................. 514/11 |
| 6,569,854 B1 | 5/2003 | Achard et al. | ........... 514/233.2 |
| 2002/0132765 A1 | 9/2002 | Bacque et al. | ................. 514/9 |

OTHER PUBLICATIONS

Gavini (Archiv der Pharmazie 333 (10) 341–6, 2000).
Fudou (Journal of Antibiotics 54 (2) 149–52, 2001).
Juvvadi (Journal of Peptide Research 53 (3) 244–51, 1999).
Avrahami (Biochemistry 40 (42) 12591–603, 2001).
Ludbrook (Clinical and Experimental Pharmacology and Physiology 28 (5,6) 488–92, 2001).
Bryant (Pediatric Allergy and Immunology 9 (3) 108–15, 1998).
Bezeau (Journal of Clinical and Experimental Neuropsychology 23 (3) 399–406, 2001).
Bolton (Journal of Clinical Pharmacology 38 (5) 408–12, 1998).
Willenheimer (Progress in Cardiovascular Diseases 44 (3) 155–67, 2001).
Chung (Plastic and Reconstructive Surgery 109 (1) 1–6, 2002).
Alkinson (Chronobiology International 18 (6) 1041–53, 2001.

*Primary Examiner*—David Lukton
(74) *Attorney, Agent, or Firm*—Balaram Gupta

(57) ABSTRACT

Group B streptogramin derivatives of general formula (I):

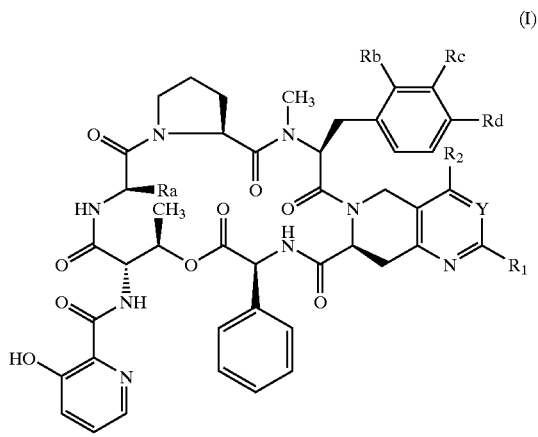

wherein Ra, Rb, Rc, Rd, $R_1$, $R_2$ and Y are as defined in the description, including preparation methods and compositions containing same. Such derivatives are particularly useful as antimicrobial agents, optionally combined with at least one group A streptogramin derivative.

1 Claim, No Drawings

STREPTOGRAMIN DERIVATIVES, PREPARATION METHOD AND COMPOSITIONS CONTAINING SAME

This is a divisional application, filed under 35 U.S.C. §111(a) in accordance with 37 C.F.R. §1.53(b), of U.S. patent application Ser. No. 09/643,197, filed Aug. 22, 2000, now abandoned which is a continuation application, filed under 35 U.S.C. §111(a), of International Application No. PCT/FR99/00409, filed Feb. 24, 1999, all of which are incorporated herein by reference Application No. PCT/FR99/00409 claims priority to French application 98/02316, filed Feb. 26, 1998.

The present invention relates to group B streptogramin derivatives of general formula:

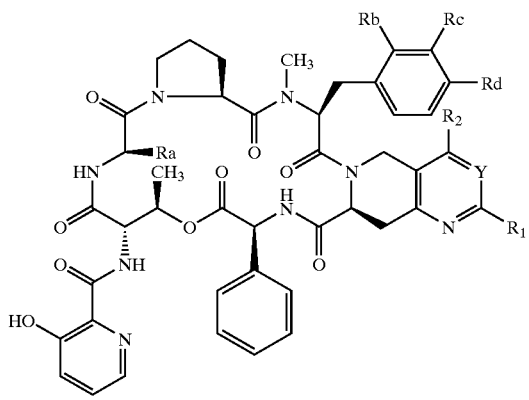

(I)

in which

Y is a nitrogen atom or a radical =CR$_3$—,

R$_1$ is a hydrogen atom, a radical alkyl (1 to 8 carbons), alkenyl (2 to 8 carbons), cycloalkyl (3 to 8 carbons), heterocyclyl which is saturated or unsaturated (3 to 8 members), phenyl, phenyl which is substituted [with one or more halogen atoms or hydroxyl, alkyl, alkyloxy, alkylthio, alkylsulphinyl, alkylsulphonyl, amino, alkylamino or dialkylamino radicals] or a radical NR'R", R' and R", which are identical or different, being capable of being hydrogen atoms or alkyl radicals (1 to 3 carbons), or being capable of forming together with the nitrogen atom to which they are attached a 3- to 8-membered heterocycle optionally containing another heteroatom chosen from oxygen, sulphur or nitrogen which is optionally substituted [with a radical alkyl, alkenyl (2 to 8 carbons), cycloalkyl (3 to 6 carbons), heterocyclyl which is saturated or unsaturated (4 to 6 members), benzyl, phenyl or phenyl which is substituted as defined above for the definition of R$_1$] or alternatively when Y is a radical =CR$_3$—, R$_1$ may also be halomethyl, hydroxymethyl, alkyloxymethyl, alkylthiomethyl in which the alkyl portion is optionally substituted with NR'R", alkylsulphinylmethyl, alkylsulphonylmethyl, acyloxymethyl, benzoyloxymethyl, cyclopropylaminomethyl or —(CH$_2$)$_n$NR'R" (n being an integer from 1 to 4 and R' and R" being defined as above), or alternatively if R$_3$ is a hydrogen atom, R$_1$ may also be formyl, carboxyl, alkyloxycarbonyl, or —CONR'R" for which R' and R" are defined as above, or alternatively when Y is a nitrogen atom, R$_1$ may also be a radical —XR° for which X is an oxygen or sulphur atom, a sulphinyl or sulphonyl radical, or an NH radical and R° is a radical alkyl (1 to 8 carbons), cycloalkyl (3 to 6 carbons), heterocyclyl which is saturated or unsaturated (3 to 8 members), heterocyclylmethyl (3 to 8 members) in which the heterocyclyl portion is attached to the methyl radical by a carbon atom, phenyl, phenyl which is substituted [with one or more halogen atoms or hydroxyl, alkyl, alkyloxy, alkylthio, alkylsulphinyl, alkylsulphonyl, amino, alkylamino or dialkylamino radicals] or a radical —(CH$_2$)$_n$NR'R" for which R' and R" are defined as above and n is an integer from 2 to 4, or alternatively if X represents NH, R° may also represent the hydrogen atom, R$_2$ is a hydrogen atom or an alkyl radical (1 to 3 carbons), R$_3$ is a hydrogen atom or an alkyl, carboxyl, alkyloxycarbonyl or carbamoyl radical having the structure —CO—NR'R" in which R' and R" are defined as above, Ra is a methyl or ethyl radical, and Rb, Rc and Rd have the definitions below:

1) Rb and Rc are hydrogen atoms and Rd is a hydrogen atom or a methylamino or dimethylamino radical,
2) Rb is a hydrogen atom, Rc is a hydrogen, chlorine or bromine atom, or represents an alkenyl radical (3 to 5C), and Rd is a radical —NMe—R''' for which R''' represents a radical alkyl, hydroxyalkyl (2 to 4C), or alkenyl (2 to 8C) which is optionally substituted with phenyl, cycloalkyl(3 to 6C)methyl, benzyl, benzyl which is substituted [with one or more halogen atoms or hydroxyl, alkyl, alkyloxy, alkylthio, alkylsulphinyl, alkylsulphonyl, amino, alkylamino or dialkylamino radicals], heterocyclylmethyl or heterocyclylethyl in which the heterocyclyl portion is saturated or unsaturated and contains 5 to 6 members and 1 or 2 heteroatoms chosen from sulphur, oxygen or nitrogen which is optionally substituted [with a radical alkyl, alkenyl (2 to 8 carbons), cycloalkyl (3 to 6 carbons), heterocyclyl which is saturated or unsaturated (4 to 6 members), phenyl, phenyl which is substituted as defined above for the definition of R$_1$ or benzyl], or alternatively R''' represents a radical cyanomethyl, or —CH$_2$CORe for which either Re is —OR'e, R'e being hydrogen, alkyl (1 to 6 carbons), alkenyl (2 to 6 carbons), benzyl or heterocyclylmethyl in which the heterocyclyl portion contains 5 to 6 members and 1 or 2 heteroatoms chosen from sulphur, oxygen or nitrogen, or Re is an alkylamino, alkylmethylamino, heterocyclylamino or heterocyclylmethylamino radical in which the heterocyclyl portion is saturated and contains 5 to 6 members and 1 or 2 heteroatoms chosen from sulphur, oxygen or nitrogen which is optionally substituted with an alkyl, benzyl or alkyloxycarbonyl radical,
3) Rb is a hydrogen atom, Rd is a radical —NHCH$_3$ or —N(CH$_3$)$_2$ and Rc is a chlorine or bromine atom, or represents an alkenyl radical (3 to 5C), [if Rd is —N(CH$_3$)$_2$],
4) Rb and Rd are hydrogen atoms and Rc is a halogen atom, or an alkylamino or dialkylamino, alkyloxy, trifluoromethoxy, thioalkyl, alkyl (1 to 6C) or trihalomethyl radical,
5) Rb and Rc are hydrogen atoms and Rd is a halogen atom, or an ethylamino, diethylamino or methylethylamino, alkyloxy or trifluoromethoxy, alkylthio, alkylsulphinyl, alkylsulphonyl, alkyl (1 to 6C), phenyl or trihalomethyl radical,
6) Rb is a hydrogen atom and Rc is a halogen atom or an alkylamino or dialkylamino, alkyloxy or trifluoromethoxy, thioalkyl or alkyl (1 to 3C) radical, and Rd is a halogen atom or an amino, alkylamino or dialkylamino, alkyloxy or trifluoromethoxy, thioalkyl, alkyl (1 to 6C) or trihalomethyl radical, 7) Rc is a hydrogen atom and Rb and Rd represent a methyl radical, as well as their salts, which exhibit a particularly advantageous antibacterial activity, alone or combined with a group A streptogramin derivative.

In the general formula (I) above, the halogen atoms may be chosen from fluorine, chlorine, bromine or iodine; the alkyl or acyl radicals are straight or branched and, unless otherwise stated, contain 1 to 4 carbon atoms. The same is true for the alkyl radicals which will be mentioned below. The alkenyl radicals may also be in the form of a straight or branched chain.

Moreover, by way of example, when R' and R" together form a heterocycle with the nitrogen atom to which they are attached, the latter contains 1 or 2 heteroatoms and may for example be chosen from pyrrolidinyl, piperidino, morpholino, thiomorpholino, piperazinyl, methyl piperazinyl, imidazolidinyl, methylimidazolidinyl. By way of example, when $R_1$ or $R°$ represents heterocyclyl, when —NR'R" and/or R'" are substituted with heterocyclyl or when R'" represents heterocyclylmethyl, the heterocyclyl radical contains 1 or 2 heteroatoms and may for example be chosen from pyridyl, pyrazinyl, pyrimidinyl, thienyl, furyl, imidazolyl, which are optionally substituted, or from the heterocycles mentioned above at a preference for —NR'R".

Among the known streptogramins, pristinamycin (RP 7293), an antibacterial of natural origin produced by *Streptomyces pristinaespiralis* was first isolated in 1955. The pristinamycin marketed under the name Pyostacine® consists mainly of pristinamycin $I_A$ combined with pristinamycin $II_A$.

Another antibacterial of the class of streptogramins: virginiamycin, has been prepared from *Streptomyces virginiae*, ATCC 13161 [Antibiotics and Chemotherapy, 5, 632 (1955)]. Virginiamycin (Staphylomycin®) consists mainly of the factor S combined with factor $M_1$.

Semisynthetic derivatives of streptogramins represented by the structure:

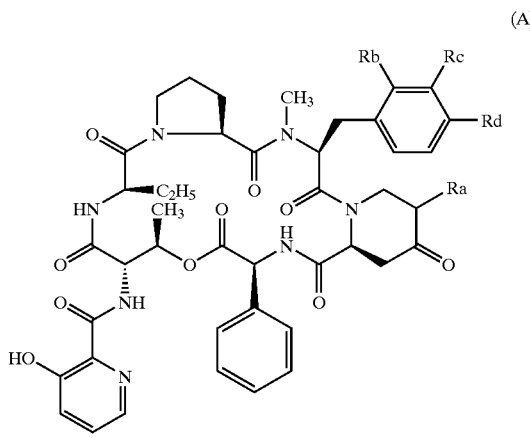

(A)

in which,

Ra is a radical having the structure —CH$_2$R'a for which

R'a is a radical of the heterocyclylthio type which may be substituted or alternatively represents a radical having the structure =CHR'a for which R'a is an alkylamino, alkyloxy or alkylthio radical which are substituted, or a radical of the heterocyclylamino, heterocyclyloxy or heterocyclylthio type which may be substituted, Rb and Rc are hydrogen atoms and Rd is a hydrogen atom or a dimethylamino radical, or alternatively Ra is a hydrogen atom and Rb is hydrogen or methyl, Rc and Rd are hydrogen or various substituents have been described in patents or patent applications EP 133097, EP 248703, EP 770132 and EP 772630. Combined with a semisynthetic component of the group A streptogramins, they manifest a synergistic action and can be used as antibacterial agents either by the injection route alone, or solely by the oral route.

The streptogramin derivatives of general formula (I) are particularly advantageous because of their potent activity both by the oral and parenteral routes, which offers them an undeniable advantage in the case especially of treatments of serious infections, in a hospital setting by the injection route, followed by an ambulatory treatment by the oral route which is easier to administer to patients. Thus, the practitioner is no longer obliged to change the patient's medicament between the end of the hospital treatment and the overall end of the treatment.

According to the invention, the streptogramin derivatives for which Y is a radical =CR$_3$— and R$_3$ is other than an alkyl radical may be prepared by the action of an enamino ester of general formula:

(II)

in which $R_1$ is defined as above and R represents the residue of an easily hydrolysable ester or an alkyl radical, on the corresponding 5δ-methylenepristinamycin derivative of general formula:

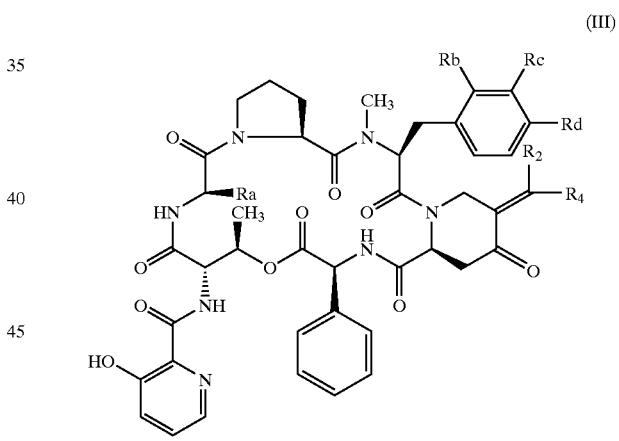

(III)

in which Ra, Rb, Rc and Rd are defined as above, $R_2$ is defined as above and $R_4$ is a hydrogen atom, or $R_2$ represents a hydrogen atom and $R_4$ is a hydrogen atom or a dialkylamino radical, followed where appropriate by the conversion of the ester obtained to an acid, and then optionally by its decarboxylation, or by the conversion of the acid to a carbamoyl radical according to the derivative of general formula (I) desired, and/or followed where appropriate by the conversion of the derivative of general formula (I) for which $R_1$ is hydroxymethyl to a derivative for which $R_1$ is a radical formyl, and then where appropriate carboxyl, and then where appropriate alkyloxycarbonyl or —CONR'R" and/or optionally followed by the mono-N-demethylation of the derivative of general formula (I) for which Rd is a dimethylamino radical to a derivative for which Rd is methylamino, and then optionally followed by the conversion to a salt when they exist.

Residue of an easily hydrolysable ester is understood to mean, for example and with no limitation being implied, the residue of the benzyl, methyl, trimethylsilylethyl, ethyl, allyl or t-butyl ester.

The reaction is generally carried out in an organic solvent such as an alcohol for example (methanol, ethanol in particular), at a temperature of between 40° C. and the reflux temperature of the reaction mixture.

The conversion to an acid, an amide, or the decarboxylation in order to obtain a derivative in which $R_3$ is carboxyl, carbamoyl having the structure —CO—NR'R" or a hydrogen atom, is carried out according to known methods which do not adversely affect the rest of the molecule and more particularly according to the methods mentioned below in the examples.

In particular, when it is desired to obtain a pristinamycin derivative of general formula (I) for which $R_3$ is a carboxyl radical, the benzyl ester is advantageously prepared. The hydrolysis of the esters is carried out according to known methods which do not adversely affect the rest of the molecule, for example the methods mentioned by T. W. Greene Protective Groups in Organic Synthesis, A. Wiley—Interscience Publication (1981), or by Mc Omie, Protective Groups in Organic Chemistry, Plenum Press (1973). By way of example, the residue of the benzyl ester may be hydrolysed by treatment with 1,4-cyclohexadiene in the presence of palladium hydroxide on carbon, in an alcoholic medium (methanol, ethanol for example), at a temperature of between 0 and 60° C.

When it is desired to prepare a derivative of general formula (I) for which $R_3$ is —CO—NR'R", the product of general formula (I) obtained for which $R_3$ is carboxyl is treated according to the usual methods for converting acids to amides, which do not adversely affect the rest of the molecule. In particular, the corresponding amine is reacted with the acid in the presence of a condensing agent (carbodiimide for example) at a temperature of between 0 and 60° C., in an organic solvent such as a chlorinated solvent (chloroform, dichloromethane for example), an amide (dimethylformamide, N-methylpyrrolidone for example).

When it is desired to obtain a streptogramin derivative of general formula (I) for which $R_3$ is a hydrogen atom, the product for which $R_3$ is carboxyl is decarboxylated according to the customary methods which do not adversely affect the rest of the molecule. In particular, the procedure may be carried out according to the method described by Barton, Tetrahedron, 44(17), 5479–86 (1988), by formation of the N-hydroxypyridine-2-thione ester, and then photolysis in the presence of tert-butylthiol for example.

The mono-N-demethylation of the streptogramin derivative of general formula (I) for which Rd is dimethylamino may be carried out according to the method described in patent application EP 821697 by treatment with a periodate in an acetic medium followed by a treatment in an aqueous acid medium or a treatment with an agent capable of consuming formaldehyde in situ.

The conversion of the radical $R_1$=hydroxymethyl to a formyl radical may be carried out by the action of selenium oxide by analogy with J. Korean Chem. Soc., 38(7), 537–8 (1994).

The conversion of the radical $R_1$=formyl to a carboxyl radical is carried out according to the customary methods which do not adversely affect the rest of the molecule. In particular, tin oxide may be used as described in Heterocycles 32(10), 1933–40 (1991).

The conversion of the radical $R_1$=carboxyl to an alkyloxycarbonyl radical is carried out according to the customary methods which do not adversely affect the rest of the molecule. In particular as described in The Chemistry of Acid Derivatives, Part I, page 411, Ed. S. Patai, John Wiley & Sons (1979).

The conversion of the radical $R_1$=carboxyl to a carbamoyl radical having the structure —CO—NR'R" is carried out according to the customary methods which do not adversely affect the rest of the molecule. In particular, the corresponding amine is reacted with the acid in the presence of a condensing agent according to conventional methods of peptide chemistry: M. Bodanszky, Principles of Peptides Synthesis, Springer Verlag, Berlin-Heidelberg-New-York-Tokyo (1984).

According to the invention, the streptogramin derivatives of general formula (I) for which Y is a radical =$CR_3$— and $R_3$ is a hydrogen atom or an alkyl radical may be prepared by the action of a pyridinium salt of general formula:

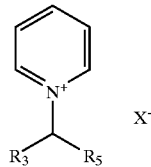

(IV)

in which $R_3$ is defined as above, $R_5$ is the residue of a ketone $R_1$—CO— for which $R_1$ is defined as above with the exception of representing a radical —NR'R", or optionally represents a protected hydroxyl radical or a nitrophenyl radical or alternatively $R_5$ represents the cyano radical so as to obtain a streptogramin derivative for which $R_1$ is an amino radical, and $X^-$ is an anion, on the corresponding 5δ-methylene-pristinamycin of general formula (III) in which $R_4$ is a hydrogen atom and Ra, Rb, Rc, Rd and $R_2$ are defined as above optionally followed by the liberation of the hydroxyl radical or where appropriate the reduction of the nitrophenyl radical so as to obtain a derivative for which $R_1$ is an aminophenyl radical, or optionally followed by the action of an amine of general formula HNR'R" on the streptogramin derivative of general formula (I) for which $R_1$ is halomethyl, so as to obtain the corresponding derivative for which $R_1$ is a radical —$CH_2NR'R$", or followed where appropriate by the conversion of the derivative of general formula (I) for which $R_1$ is hydroxymethyl to a derivative for which $R_1$ is a radical formyl, and then where appropriate carboxyl, and then where appropriate alkyloxycarbonyl or —CONR'R" and/or optionally the mono-N-demethylation of the derivative of general formula (I) for which Rd is a dimethylamino radical to a derivative for which Rd is methylamino, and then optionally followed by the conversion to a salt, when they exist.

With no limitation being implied, the anion $X^-$ advantageously represents a halide anion (bromide, chloride or iodide for example).

The reaction is generally carried out in the presence of an ammonium salt (ammonium acetate for example), in a solvent such as an alcohol (methanol, ethanol for example), a nitrile (acetonitrile for example), an ester (ethyl acetate for example) or a ketone (acetone for example), at a temperature of between 40° C. and the reflux temperature of the reaction mixture.

When the radical $R_1$ contains a hydroxyl substituent, it is preferable to protect this radical beforehand according to the methods which do not adversely affect the rest of the molecule. The protection and deprotection of the hydroxyl radical is carried out according to the customary methods.

For example, the protection is carried out using an acetyl radical or using any other hydroxyl-protecting group whose introduction and removal are mentioned for example by T. W. Greene Protective Groups in Organic Synthesis, A. Wiley—Interscience Publication (1981), or by Mc Omie, Protective Groups in Organic Chemistry, Plenum Press (1973).

When it is desired to obtain a product for which $R_1$ is aminophenyl, it is preferable to prepare the corresponding nitrophenyl derivative and then to carry out the reduction of the nitro radical of the derivative obtained. In particular, it is possible to carry out the procedure by reduction in an acid medium (hydrochloric acid) in the presence of iron.

When it is desired to obtain the streptogramin derivative of general formula (I) for which $R_1$ is a radical —$CH_2NR'R''$, an amine HNR'R'' is reacted with the corresponding streptogramin derivative of general formula (I) for which $R_1$ is halomethyl, by carrying out the procedure in the presence of a tertiary amine (triethylamine, diisopropylethylamine for example) or an excess of the amine, in an organic solvent such as an ether (tetrahydrofuran, dioxane for example), an alcohol (methanol for example), a chlorinated solvent (chloroform, dichloromethane for example), a nitrile (acetonitrile for example) or dimethyl sulphoxide at a temperature of between 40° C. and the reflux temperature of the reaction mixture.

The mono-N-demethylation of the streptogramin derivative of general formula (I) for which Rd is dimethylamino may be carried out according to the method described in patent application EP 821697. The conversion of the radical $R_1$=hydroxymethyl to a formyl radical may be carried out by the action of selenium oxide by analogy with J. Korean Chem. Soc., 38 (7), 537–8 (1994).

The conversion of the radical $R_1$ formyl to a carboxyl radical is carried out according to the customary methods which do not adversely affect the rest of the molecule. In particular, tin oxide may be used as described in Heterocycles 32(10), 1933–40 (1991).

The conversion of the radical $R_1$=carboxyl to an alkyloxycarbonyl radical is carried out according to the customary methods which do not adversely affect the rest of the molecule. In particular as described in The Chemistry of Acid Derivatives, Part I, page 411, Ed. S. Patai, John Wiley & Sons (1979).

The conversion of the radical $R_1$=carboxyl to a carbamoyl radical having the structure —CO—NR'R'' is carried out according to the customary methods which do not adversely affect the rest of the molecule. In particular, the corresponding amine is reacted with the acid in the presence of a condensing agent according to conventional methods of peptide chemistry: M. Bodanszky, Principles of Peptides Synthesis, Springer Verlag, Berlin-Heidelberg-New-York-Tokyo (1984).

According to the invention, the streptogramin derivatives of general formula (I) for which Y is a nitrogen atom may be prepared by the action of a salt of an amidine or of a derivative of isourea or of isothiourea of general formula:

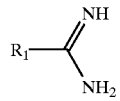

(V)

in which $R_1$ is defined as for the general formula (I), with the exception of representing a radical XR° for which X is sulphonyl or sulphinyl, or a radical NR'R'' other than amino, on a streptogramin derivative of general formula (III) for which $R_4$ is dialkylamino, and then in order to obtain a streptogramin derivative of general formula (I) for which $R_1$ is a radical XR° for which X is sulphonyl or sulphinyl, oxidation of the corresponding derivative for which X is a sulphur atom, and then in order to obtain the streptogramin derivative of general formula (I) for which $R_1$ is a radical NR'R'', substitution of the sulphonyl derivative obtained by the action of the corresponding amine HNR'R'' and/or optionally in order to obtain a derivative for which Rd is methylamino, demethylation of the derivative of general formula (I) for which Rd is a dimethylamino radical, and then optionally conversion to a salt, when they exist.

The reaction of the derivative of general formula (V) is generally carried out in an organic solvent such as an amide (dimethylformamide, dimethylacetamide for example) or a nitrile (acetonitrile for example), in the presence of a base such as in particular a tertiary amine (diisopropylethylamine, triethylamine for example) or an alkali metal bicarbonate (sodium or potassium bicarbonate for example), at a temperature of between 50 and 100° C. The reaction is advantageously carried out using the hydrochloride, the sulphate or the hydrogen sulphate of the derivative of general formula (V).

The oxidation to a sulphinyl or sulphonyl derivative is carried out respectively by treatment with 1 or 2 equivalents of Oxone° in an acid medium (for example 0.1 to 2N, preferably 0.5 to 1N sulphuric acid), at a temperature of between −60 and 60° C., in a solvent such as an alcohol (methanol, ethanol, i-propanol for example). Depending on the product prepared, it may be optionally necessary for the oxidation operation to be followed by a treatment which reduces N-oxides by any known and specific method which does not adversely affect the rest of the molecule. In particular, it is possible to carry out the procedure by heating in the presence of iron in acetic acid, or by treatment with sodium bisulphite.

The subsequent operation of substituting with an amine may be carried out by the action of the corresponding amine of formula HNR'R'', either in excess or in the presence of a base such as for example an alkali metal bicarbonate (sodium or potassium bicarbonate for example), by carrying out the procedure at a temperature of between 20 and 100° C., in an organic solvent such as an amide (dimethylformamide, dimethylacetamide for example) or a nitrile (acetonitrile for example).

The mono-N-demethylation of the streptogramin derivative of general formula (I) for which Rd is dimethylamino may be carried out according to the method described in patent application EP 821697.

The conversion of the radical $R_1$=hydroxymethyl to a formyl radical may be carried out by the action of selenium oxide by analogy with J. Korean Chem. Soc., 38(7), 537–8 (1994).

The conversion of the radical $R_1$=formyl to a carboxyl radical is carried out according to the customary methods which do not adversely affect the rest of the molecule. In particular, tin oxide may be used as described in Heterocycles 32(10), 1933–40 (1991).

The conversion of the radical $R_1$=carboxyl to an alkyloxycarbonyl radical is carried out according to the customary methods which do not adversely affect the rest of the molecule. In particular as described in The Chemistry of Acid Derivatives, Part I, page 411, Ed. S. Patai, John Wiley & Sons (1979).

The conversion of the radical $R_1$=carboxyl to a carbamoyl radical having the structure —CO—NR'R'' is carried out according to the customary methods which do not adversely affect the rest of the molecule. In particular, the corresponding amine is reacted with the acid in the presence of a condensing agent according to conventional methods of peptide chemistry: M. Bodanszky, Principles of Peptides Synthesis, Springer Verlag, Berlin-Heidelberg-New-York-Tokyo (1984).

According to the invention, the streptogramin derivatives of general formula (I) for which Y is a radical =$CR_3$—, $R_1$ is a hydrogen atom, an alkyl, alkenyl, cycloalkyl, aromatic heterocyclyl, phenyl, substituted phenyl, halomethyl, hydroxymethyl, alkyloxymethyl, alkylthiomethyl, alkylsulphinylmethyl, alkylsulphonylmethyl or —$(CH_2)_n$NR'R" radical, or alternatively when $R_3$ is a hydrogen atom, for which $R_1$ is formyl, carboxyl, alkoxycarbonyl or —CONR'R" as defined above and $R_2$ is a hydrogen atom, may also be prepared by the action of the formyl enamine of general formula:

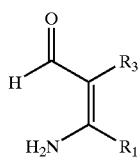

(VI)

in which $R_1$ is a hydrogen atom, an alkyl, alkenyl, cycloalkyl, aromatic heterocyclyl, phenyl, substituted phenyl, hydroxymethyl, alkyloxymethyl, alkylthiomethyl or —$(CH_2)_n$NR'R" radical and $R_3$ is defined as above with the exception of representing carboxyl, on a streptogramin derivative of general formula:

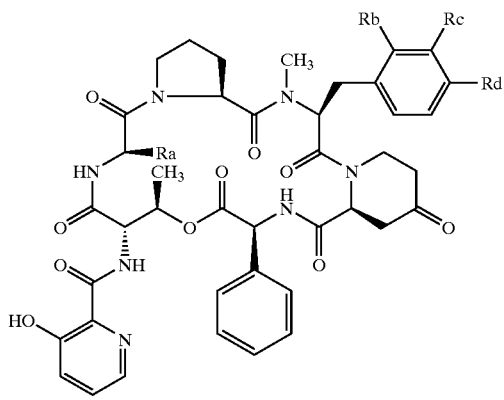

(VII)

in which Ra, Rb, Rc and Rd are defined as above, followed where appropriate by the conversion of the derivative for which $R_3$ is amide or ester to a derivative for which $R_3$ is carboxyl and/or followed where appropriate by the oxidation of the derivative for which $R_1$ is alkylthiomethyl to a derivative for which $R_1$ is alkylsulphinylmethyl or alkylsulphonylmethyl, or followed where appropriate by the conversion of the derivative for which $R_1$ is a hydroxymethyl radical to a derivative for which $R_1$ is halomethyl, and then where appropriate the conversion of the derivative for which $R_1$ is halomethyl to a derivative for which $R_1$ is —$CH_2$NR'R", or followed where appropriate by the conversion of the derivative of general formula (I) for which $R_1$ is hydroxymethyl to a derivative for which $R_1$ is a radical formyl, and then where appropriate carboxyl, alkyloxycarbonyl and/or —CONR'R", and/or optionally the mono-N-demethylation of the derivative of general formula (I) for which Rd is a dimethylamino radical to a derivative for which Rd is methylamino, and then optionally followed by conversion to a salt, when they exist.

The reaction is carried out in an organic solvent such as an alcohol (methanol, ethanol for example) at a temperature of between 20° C. and the reflux temperature of the reaction mixture, in the presence of an ammonia donor such as for example ammonium acetate.

The oxidation of the alkylthiomethyl radical to an alkylsulphinylmethyl or alkylsulphonylmethyl radical is carried out under the conditions described above, by treatment with Oxone®.

The production of a streptogramin derivative of general formula (I) for which $R_1$ is halomethyl from a derivative for which $R_1$ is hydroxymethyl is carried out according to the customary methods. In particular by the action of a halogenating agent such as for example thionyl chloride.

The reaction of an amine HNR'R" on the streptogramin derivative of general formula (I) for which $R_1$ is halomethyl is carried out as described above.

The conversion of the radical $R_1$=hydroxymethyl to a formyl radical may be carried out by the action of selenium oxide by analogy with J. Korean Chem. Soc., 38(7), 537–8 (1994).

The conversion of the radical $R_1$=formyl to a carboxyl radical is carried out according to the customary methods which do not adversely affect the rest of the molecule. In particular, tin oxide may be used as described in Heterocycles 32(10), 1933–40 (1991).

The conversion of the radical $R_1$=carboxyl to an alkyloxycarbonyl radical is carried out according to the customary methods which do not adversely affect the rest of the molecule. In particular as described in The Chemistry of Acid Derivatives, Part I, page 411, Ed. S. Patai, John Wiley & Sons (1979).

The conversion of the radical $R_1$=carboxyl to a carbamoyl radical having the structure —CO—NR'R" is carried out according to the customary methods which do not adversely affect the rest of the molecule. In particular, the corresponding amine is reacted with the acid in the presence of a condensing agent according to conventional methods of peptide chemistry: M. Bodanszky, Principles of Peptides Synthesis, Springer Verlag, Berlin-Heidelberg-New-York-Tokyo (1984). The direct conversion of the radical $R_1$=formyl to a carbamoyl radical may be carried out as described in the examples.

The mono-N-demethylation of the streptogramin derivative of general formula (I) for which Rd is dimethylamino may be carried out according to the method described in patent application EP 821697.

The enamino esters of general formula (II) are either commercially available or may be prepared according to or by analogy with the methods described in Tetrahedron Letters 38(3), 443–6(1997) and FR 2216270.

The 5δ-methylenepristinamycin derivatives of general formula (III) for which Ra is a methyl radical, or for which Ra is an ethyl radical but Rb, Rc and Rd do not simultaneously have the definitions: "Rb and Rc represent hydrogen and Rd represents hydrogen or dimethylamino", may be prepared from pristinamycin I$_C$, virginiamycin S4, vernamycin Bδ, pristinamycin I$_B$, or from their derivatives or analogues of general formula (VII) in which Ra is defined as above and the substituents Rb, Rc and Rd are either defined as in the general formula (I) in 1), with the exception of simultaneously representing Rb=Rc=hydrogen and Rd=hydrogen or dimethylamino, when Ra is ethyl, or are defined as for the general formula (I) in 2) to 7), by carrying out the procedure by analogy with the methods described in European applications EP 133097 or EP 133098 or by analogy with the methods described below in the examples.

The pyridinium salts of general formula (IV) are prepared according to or by analogy with the method described by F. Kröhnke, Synthesis, (1976) 1–24, or according to or by analogy with the methods described below in the examples.

The amidines of formula (V) are commercially available or are prepared according to or by analogy with the method described by S. Patai, The Chemistry of amidines and Imidates, Interscience Publication, J. Wiley & Sons, Chap. 7, p. 283 (1975).

The formyl enamines of general formula (VI) may be prepared by analogy in J. Chem. Soc., Perkin trans I, 9, 2103 (1984).

The products of general formula (VII) for which Ra, Rb, Rc and Rd are defined as for the general formula (I) in 1) are natural group B streptogramins.

The preparation and separation of the components of the natural group B streptogramins is carried out by fermentation and isolation of the constituents from fermentation broth according to or by analogy with the method described by J. Preud'homme et al., Bull. Soc. Chim. Fr., vol. 2, 585 (1968) or according to Antibiotics and Chemotherapy, 5, 632 (1955).

Components of the group B streptogramins are also described in Streptogramine als Modelsysteme für den Kationentransport durch Membranen, Dissertation zur Erlangung des Doktorgrades der Mathematisch-Naturwissenschaftlichen Facultät der Georg-August Universität zu Göttingen, Göttingen 1979, in Antibiotics III, 521 (1975) and in Antibiotics of the virginiamycin family, Inhibitors which contain synergistic components, C. Cocito, Microbiological Reviews, 145–98 (1979).

Alternatively, the preparation of the natural components of group B may be carried out by specific fermentation, as described in patent application FR 2,689,518.

The streptogramin derivatives of general formula (VII) for which Ra, Rb, Rc and Rd are defined as for the general formula (I) in 3) are prepared as described in European application EP 772630.

The streptogramin derivatives of general formula (VII) for which Ra, Rb, Rc and Rd are defined as for the general formula (I) in 4) to 7) are prepared as described in European application EP 770132.

The streptogramin derivatives of general formula (VII) for which Ra, Rb and Rc are defined as for the general formula (I) in 5) and Rd is alkylsulphinyl or alkylsulphonyl may be prepared by oxidation of the corresponding product for which Rd is alkylthio.

The streptogramin derivatives of general formula (VII) for which Ra, Rb, Rc and Rd are defined as for the general formula (I) in 2) may be prepared from pristinamycin $I_B$ (Ra=ethyl) or from vernamycin Bδ (Ra=methyl) or from a streptogramin derivative of general formula (I) for which Ra, Rb and Rc are defined as in 3) and Rd is —NHCH$_3$, by the action of a halogenated derivative of general formula:

R'''—X           (VIII)

in which R''' is defined as for the general formula (I) in 2) and X is an iodine, bromine or chlorine atom, followed where appropriate by the chlorination or the bromination of the product obtained, when it is desired to obtain a derivative for which Rc is a chlorine or bromine atom, after starting with pristinamycin $I_B$ or with vernamycin Bδ.

The reaction is generally carried out in an organic solvent such as an amide (dimethylformamide for example), a chlorinated solvent (chloroform, dichloromethane for example), an alcohol (methanol, ethanol for example)/chlorinated solvent mixture, a nitrile (acetonitrile for example), in dimethyl sulphoxide or N-methylpyrrolidone, at a temperature of between 20 and 100° C., optionally in the presence of sodium iodide or an alkali metal bicarbonate (sodium or potassium). Preferably, the procedure is carried out under nitrogen. It is understood that when the radical R''' contains an amino radical, it is preferable to protect this radical prior to the reaction. The protection and deprotection are carried out according to the methods indicated in the references cited above.

Where appropriate, the halogenation is advantageously carried out with an N-halosuccinimide, in an organic solvent such as a chlorinated solvent (dichloromethane, chloroform for example) or a nitrile (acetonitrile for example), at a temperature of between 20 and 80° C.

According to another alternative, the streptogramin derivatives of general formula (VII) for which Ra and Rb are defined as for the general formula (I), Rc is a hydrogen atom and Rd is a cyanomethyl methyl amino or alkyloxycarbonylmethyl methyl amino radical may also be prepared from pristinamycin $I_A$ (Ra=ethyl) or from pristinamycin $I_C$ (Ra=methyl) by the action of a halogenated derivative of general formula (VIII) in which R''' represents cyanomethyl or alkyloxycarbonylmethyl.

The reaction is generally carried out in an organic solvent such as an amide (dimethylformamide for example) at a temperature of between 70 and 100° C. Preferably, the procedure is carried out under nitrogen.

The streptogramin derivatives of general formula (III) for which Ra is a methyl radical and Rb, Rc and Rd are defined as in the general formula (I) or for which Ra is an ethyl radical and Rb, Rc and Rd are defined as in the general formula (I) in 2) to 7) as well as the streptogramin derivatives of general formula (VII) for which Ra, Rb, Rc and Rd are defined as for the general formula (I) in 2), except for R''' representing ethyl if Rb and Rc are hydrogen, are new products.

All these new intermediate products can be represented by the general formula:

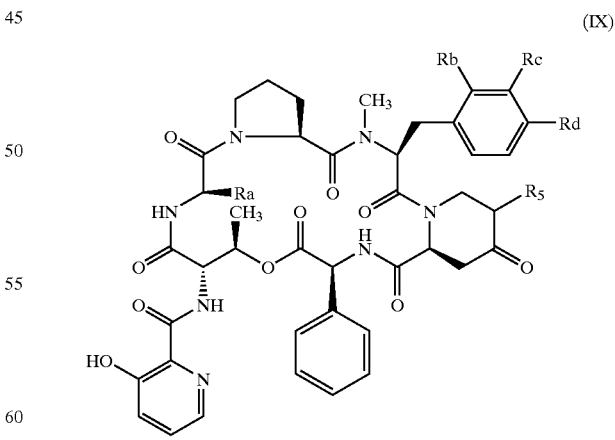

(IX)

in which Ra is a methyl radical and Rb, Rc and Rd are defined as in the general formula (I) or Ra is an ethyl radical and Rb, Rc and Rd are defined as in the general formula (I) in 2) to 7) and $R_5$ represents a disubstituted methylenyl radical having the structure

for which $R_2$ and $R_4$ are defined as above, or alternatively in which Ra, Rb, Rc and Rd are defined as for the general formula (I) in 2), except for R''' representing ethyl if Rb and Rc are hydrogen, and $R_5$ is a hydrogen atom.

It is understood that the products of general formula (IX) are also within the scope of the present invention.

The streptogramin derivatives of general formula (I) or (IX) may be purified where appropriate by physical methods such as crystallization or chromatography.

Some of the streptogramin derivatives of general formula (I) may be converted to the state of addition salts with acids, by known methods. It is understood that these salts, when they exist, are also included within the scope of the present invention.

As examples of addition salts with pharmaceutically acceptable acids, there may be mentioned the salts formed with inorganic acids (hydrochlorides, hydrobromides, sulphates, nitrates, phosphates) or with organic acids (succinates, fumarates, tartrates, acetates, propionates, maleates, citrates, methanesulphonates, ethanesulphonates, phenyl sulphonates, p-toluenesulphonates, isethionates, naphthylsulphonates or camphorsulphonates, or with substitution derivatives of these compounds).

The derivatives carrying a carboxyl substituent may be converted to metal salts or to addition salts with nitrogenous bases according to methods known per se. These salts may be obtained by the action of a metal base (for example an alkali metal or alkaline-earth metal base), of ammonia or of an amine, on a product according to the invention, in an appropriate solvent such as an alcohol, an ether or water, or by an exchange reaction with a salt of an organic acid. The salt formed precipitates after optional concentration of the solution, it is separated by filtration, decantation or freeze-drying. As examples of pharmaceutically acceptable salts, there may be mentioned the salts with the alkali metals (sodium, potassium, lithium) or with the alkaline-earth metals (magnesium, calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine).

The streptogramin derivatives according to the present invention have antibacterial properties and properties synergizing the antibacterial activity of the group A streptogramin derivatives. They are particularly advantageous because of their activity alone or combined with components of the group A streptogramins and especially because of their activity both by the oral and parenteral route which opens the way for an ambulatory relay treatment without modifying the nature of the medicament.

When they are combined with a component or a group A streptogramin derivative, they may in particular be chosen, depending on whether it is desired to obtain an orally or parenterally administrable form, from the natural components: pristinamycin $II_A$, pristinamycin $II_B$, pristinamycin $II_C$, pristinamycin $II_D$, pristinamycin $II_E$, pristinamycin $II_F$, pristinamycin $II_G$ or from the semisynthetic derivatives as described in patents or patent applications U.S. Pat. No. 4,590,004 and EP 191662 or alternatively from the semisynthetic derivatives of general formula:

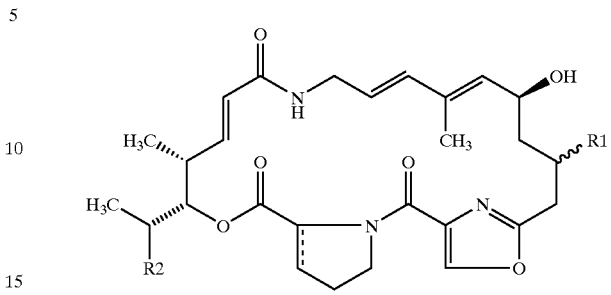

(α)

in which $R_1$ is a radical —NR'R" for which R' is a hydrogen atom or a methyl radical, R" is a hydrogen atom, an alkyl, cycloalkyl, allyl, propargyl, benzyl or —OR''' radical, R''' being a hydrogen atom, an alkyl, cycloalkyl, allyl, propargyl or benzyl radical, or —$NR_3R_4$, it being possible for $R_3$ and $R_4$ to represent a methyl radical, or to form together with the nitrogen atom to which they are attached a saturated or unsaturated 4- or 5-membered heterocycle which may in addition contain another heteroatom chosen from nitrogen, oxygen or sulphur, $R_2$ is a hydrogen atom or a methyl or ethyl radical, and the bond ==== represents a single bond or a double bond, as well as their salts.

It is understood that the combinations of the derivatives according to the invention and of the group A streptogramins are also included within the scope of the present invention.

In vitro, combined with pristinamycin $II_B$, the products of general formula (I), according to the invention, have proved active at concentrations of between 0.25 and 16 mg/l on Staphylococcus aureus 209P. In vivo, on experimental infections of mice with Staphylococcus aureus IP 8203, the streptogramin derivatives of general formula (I) have proved active at doses of between 15 and 150 mg/kg orally, combined with pristinamycin $II_B$ and between 5 and 150 mg/kg subcutaneously, combined with dalfopristin ($CD_{50}$), [30/70 combinations].

Finally, the products according to the invention are particularly advantageous because of the low toxicity observed in the Staphylococcus aureus IP 8203 Septicaemia model in mice. All the products, in a 30/70 combination with a group A component proved atoxic with the exception of a few of them for which a low mortality was observed at the maximum administered dose of 300 mg/kg orally or subcutaneously, in 2 administrations at an interval of 5 hours.

Some of the intermediate products defined by the general formula (IX) also exhibit antibacterial properties, especially the subgroup of streptogramin derivatives of general formula (VII). In vivo, on experimental infections of mice with Staphylococcus aureus IP 8203, they proved active orally combined with pristinamycin $II_B$ (30/70 combinations) at doses of between 25 and 150 mg/kg.

Of particular interest are the products of general formula (I) for which Y is a nitrogen atom or a radical =C $R_3$—, $R_1$ is a hydrogen atom, a radical alkyl (1 to 8 carbons), cycloalkyl (3 to 8 carbons), heterocyclyl which is saturated or unsaturated (3 to 8 members), phenyl, phenyl which is substituted [with one or more amino, alkylamino or dialkylamino radicals] or a radical NR'R", R' and R", which are identical or different, being capable of being hydrogen atoms or alkyl radicals (1 to 3 carbons), or being capable of forming together with the nitrogen atom to which they are attached a 3- to 8-membered heterocycle optionally containing another heteroatom chosen from oxygen, sulphur or nitrogen which is optionally substituted with an alkyl radical, or alternatively when Y is a radical =CR$_3$—, R$_1$ may also be halomethyl, hydroxymethyl, alkylthiomethyl in which the alkyl portion is optionally substituted with NR'R", alkylsulphinylmethyl, alkylsulphonylmethyl, alkyloxymethyl, cyclopropylaminomethyl or —(CH$_2$)$_n$NR'R" (n being an integer from 1 to 4 and R' and R" being defined as above), or alternatively if R$_3$ is a hydrogen atom, R$_1$ may also be formyl or —CONR'R" for which R' and R" are defined as above, or alternatively when Y is a nitrogen atom, R$_1$ may also be a radical —XR° for which X is an oxygen or sulphur atom, a sulphinyl or sulphonyl radical, or an NH radical and R° is a radical alkyl (1 to 8 carbons), heterocyclylmethyl (3 to 8 members) in which the heterocyclyl portion is attached to the methyl radical by a carbon atom, or a radical —(CH$_2$)$_n$NR'R" for which R' and R" are defined as above and n is an integer from 2 to 4, R$_2$ is hydrogen atom or an alkyl radical (1 to 3 carbons),
R$_3$ is a hydrogen atom or a carboxyl or alkyloxycarbonyl radical,
Ra is a methyl or ethyl radical, and
Rb, Rc and Rd have the definitions below:
  Rb and Rc are hydrogen atoms and Rd is a hydrogen atom or a methylamino or dimethylamino radical,
  Rb is a hydrogen atom, Rd is a radical —NHCH$_3$ or —N(CH$_3$)$_2$ and Rc is a chlorine or bromine atom.

And among these products, more particularly preferred are the products of general formula (I) for which
Y is a nitrogen atom or a radical =CR$_3$—,
R$_1$ is a hydrogen atom, a radical alkyl (1 to 3 carbons), cycloalkyl (3 to 8 carbons), heterocyclyl which is saturated or unsaturated (3 to 8 members), phenyl, phenyl which is substituted with an amino radical, or alternatively when Y is a radical =CR$_3$—, R$_1$ may also be acyloxymethyl, or alternatively when Y is a nitrogen atom, R$_1$ may also be a radical —XR° for which X is an oxygen or sulphur atom or a radical NH and R° is an alkyl radical (1 to 4 carbons) or a radical —(CH$_2$)$_n$NR'R" for which R' and R" which are identical or different may be hydrogen atoms or alkyl radicals (1 to 3 carbons), or form together with the nitrogen atom to which they are attached a 3- to 8-membered heterocycle optionally containing another heteroatom chosen from oxygen, sulphur or nitrogen optionally substituted with an alkyl radical, and n is an integer from 2 to 4, R$_2$ is a hydrogen atom or an alkyl radical (1 to 3 carbons),
R$_3$ is a hydrogen atom or an alkyloxycarbonyl radical,
Ra is a methyl or ethyl radical, and
Rb, Rc and Rd have the definitions below:
  Rb and Rc are hydrogen atoms and Rd is a hydrogen atom or a methylamino or dimethylamino radical,
  Rb is a hydrogen atom, Rd is a radical —NHCH$_3$ or —N(CH$_3$)$_2$ and Rc is a chlorine atom.

And most particularly the following products:
2"-methylpyrido[2,3-5γ,5δ]pristinamycin I$_E$;
2"-cyclopropylpyrido[2,3-5γ,5δ]pristinamycin I$_E$;
pyrido[2,3-5γ,5δ]pristinamycin I$_E$;
2"-ethylpyrido[2,3-5γ,5δ](4ζ-methylamino)(4ζ-dedimethylamino)pristinamycin I$_E$;
4ε-chloro-2"-ethylpyrido[2,3-5γ,5δ](4ζ-methylamino)(4ζ-dedimethylamino)pristinamycin I$_E$.

The streptogramin derivatives of general formula (α) are prepared from components of natural pristinamycin of general formula:

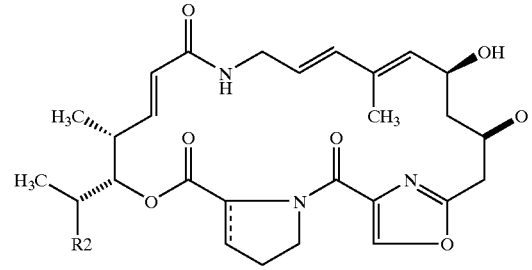

(β)

in which R$_2$ is defined as for the general formula (α), by the action of an amine of general formula:

H$_2$N—R"  (γ)

in which R" is defined as for the general formula (α), followed by the action of an agent for reducing the intermediate enamine (or oxime) obtained, and then, when it is desired to obtain a streptogramin derivative of general formula (α) for which R' is a methyl radical, followed by a second reductive amination, by the action of formaldehyde or of a derivative generating formaldehyde in situ and the reduction of the intermediate enamine.

The action of the amine is carried out in an organic solvent such as an alcohol (methanol, ethanol for example), a chlorinated solvent (dichloromethane, dichloroethane, chloroform for example), a nitrile (acetonitrile for example), pyridine, at a temperature of between 0 and 30° C., and optionally in the presence of a dehydrating agent such as for example magnesium sulphate, sodium sulphate or molecular sieves. Preferably, the procedure is carried out under an inert atmosphere (argon for example). It is also possible to cause the amine salt to react.

Preferably, to prepare the derivatives for which the bond === represents a double bond, the reaction is carried out in an organic solvent such as a nitrile (acetonitrile for example) in the presence of an acid such as an organic acid (acetic acid for example); in this case, the addition of a dehydrating agent is not necessary.

When a streptogramin derivative of general formula (α) for which R" is a radical —OR'" is prepared, it is possible to isolate the intermediate oxime of general formula:

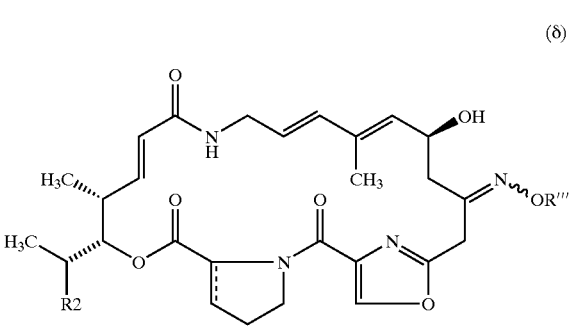

(δ)

in which R$_2$ and R'" are defined as for the general formula (α), and then to reduce this product to a derivative of general formula (α) for which R' is a hydrogen atom, and optionally use it in the subsequent reductive amination operation.

The reduction is carried out by the action of a reducing agent, for example an alkali metal borohydride (sodium cyanoborohydride or triacetoxyborohydride for example) in the presence of an organic acid (acetic acid for example) in an organic solvent as mentioned above for the amination reaction. Where appropriate, the subsequent reductive amination operation, intended to obtain the disubstituted amine, is carried out under similar conditions.

The following examples, given with no limitation being implied, illustrate the present invention.

In the text which follows, examples A to AF illustrate the preparation of the intermediate products, especially of products of general formula (IX). Examples 1 to 33 illustrate the streptogramin derivatives of general formula (I) according to the invention.

In the examples which follow, the NMR spectra were studied in deuterochloroform, the nomenclature used is that of J. O. Antounio et al., Eur. Biochem., 58, 259 (1975) and in particular:

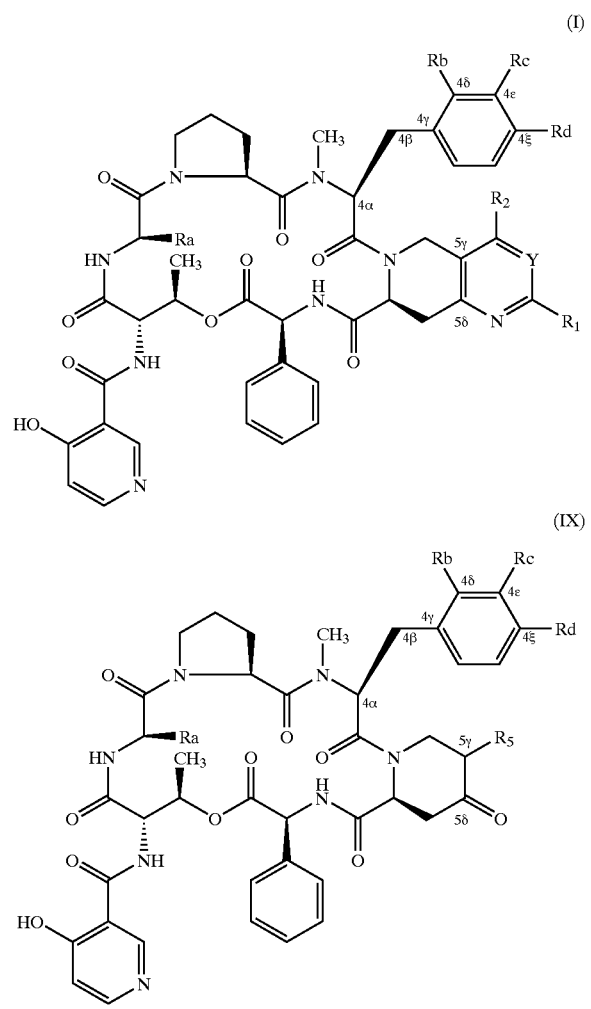

The column chromatographies are performed, unless otherwise stated, at atmospheric pressure using a 0.063–0.02 mm silica. In a few specified cases, the purifications are done by flash chromatography using a 0.04–0.063 mm silica, or by high-performance liquid chromatography (HPLC) on $C_8$ or $C_{18}$ graft silica.

PREPARATION OF THE DERIVATIVES OF GENERAL FORMULA (I)

EXAMPLE 1

2 g of 5δ-methylenepristinamycin $I_A$ and 0.26 g (2.3 mmol) of methyl 3-aminocrotonate are introduced into a three-necked flask containing 20 cm³ of methanol. The mixture is refluxed for 6 hours and then an additional 0.1 g of methyl 3-aminocrotonate is added and the reflux is maintained for 1 hour. The reaction mixture is concentrated to dryness at 40° C. under reduced pressure (2.7 kPa) to give 2.4 g of a yellow solid which is purified by chromatography on 30 g of silica [eluent:dichloromethane-methanol 95/5 by volume] to give a solid which is concreted from 60 cm³ of an ether-petroleum ether mixture, filtered and then dried at 40° C. under reduced pressure (90 Pa). 0.96 g of 3"-methoxycarbonyl-2"-methylpyrido[2,3-5γ,5δ] pristinamycin $I_E$ is thus obtained in the form of a yellow solid melting at 195° C.

$^1$H NMR spectrum (400 MHz, CDCl₃, δ in ppm): 0.92 (t, J=7.5 Hz, 3H: CH₃ at position 2γ); from 1.20 to 1.40 (mt, 2H: 1H of CH₂ at position 3β and 1H of CH₂ at position 3γ); 1.30 (d, J=7 Hz, 3H: CH₃ at position 1γ); 1.50 (dd, J=16.5 and 5 Hz, 1H: 1H of CH₂ at position 5β); from 1.50 to 1.85 (mt: the 3H corresponding to the other H of CH₂ at position 3γ and to CH₂ at position 2β); 2.05 (mt, 1H: the other H of CH₂ at position 3β); 2.77 (s, 3H: ArCH₃); 2.85 (s, 6H: ArN(CH₃)₂); 2.94 (mt, 1H: 1H of CH₂ at position 4β); 3.11 (d, J=16.5 Hz, 1H: the other H of CH₂ at position 5β); from 3.20 to 3.35 (mt, 2H: the other H of CH₂ at position 4β and 1H of CH₂ at position 3δ); 3.25 (s, 3H: NCH₃); 3.50 (mt, 1H: the other H of CH₂ at position 3δ); 3.90 (mt, 1H: 1H of CH₂ at position 5ε); 3.95 (s, 3H: COOCH₃); 4.61 (dd, J=7 and 4.5 Hz, 1H: CH at position 3α); 4.80 (mt, 1H: CH at position 2α); 4.89 (broad d, J=10 Hz, 1H: CH at position 1α); 5.14 (dd, J=11 and 5 Hz, 1H: CH at position 4α); 5.40 (broad d, J=5 Hz, 1H: CH at position 5α); 5.46 (d, J=17 Hz, 1H: the other H of CH₂ at position 5ε); 5.60 (d, J=8.5 Hz, 1H: CH at position 6α); 5.88 (broad q, J=7 Hz, 1H: CH at position 1β); 6.33 (d, J=8 Hz, 2H: aromatic H at position 4ε); 6.55 (d, J=9.5 Hz, 1H: CONH at position 2); 6.86 (d, J=8 Hz, 2H: aromatic H at position 4δ); from 7.20 to 7.40 (mt: the 5 aromatic H at position 6α); 7.45 (mt, 2H: 1' H₄ and 1' H₅); 7.89 (s, 1H: aromatic H at position γ with respect to N); 7.95 (broad s, 1H: 1' H₆); 8.40 (d, J=10 Hz, 1H: CONH at position 1); 8.66 (d, J=8.5 Hz, 1H: CONH at position 6); 11.64 (s, 1H: OH).

EXAMPLE 2

20.8 g of 5δ-methylenepristinamycin $I_A$, 3.94 g of ethyl 3,3-diaminoacrylate hydrochloride and 3.3 cm³ of triethylamine are introduced into a three-necked flask containing 200 cm³ of ethanol. The mixture is refluxed for 3 hours. After cooling, the precipitate formed is filtered, taken up in 100 cm³ of water and the pH adjusted to 8 with a solution of sodium bicarbonate and then the product is extracted with twice 100 cm³ of ethyl acetate. The organic phases are combined, dried over magnesium sulphate, filtered and concentrated to dryness at 40° C. under reduced pressure (2.7 kPa) to give 22 g of a yellow solid which is purified by chromatography on 500 g of silica [eluent:dichloromethane/methanol 97.5/2.5 by volume] to give a solid which is dissolved in 20 cm³ of dichloromethane and then precipitated by addition of 60 cm³ of diisopropyl ether. After filtration and drying at 40° C. under reduced pressure (90 Pa), 1.35 g of 3"-ethoxycarbonyl-2"-aminopyrido [2,3-5γ, 5δ]pristinamycin I$_E$ are obtained in the form of a yellow solid melting at 190° C.

$^1$H NMR spectrum (400 MHz, CDCl$_3$, δ in ppm): 0.86 (t, J=7.5 Hz, 3H: CH$_3$ at position 2γ); from 1.15 to 1.30 (mt, 3H: 1H of CH$_2$ at position 3β—1H of CH$_2$ at position 3γ and 1H of CH$_2$ at position 5β); 1.26 (d, J=7 Hz, 3H: CH$_3$ at position 1γ); 1.35 (t, J=7 Hz, 3H: CH$_3$ of ethyl); 1.53 (mt, 1H: the other H of CH$_2$ at position 3γ); 1.61 and 1.70 (2 mts, 1H each: CH$_2$ at position 2β); 2.00 (mt, 1H: the other H of CH$_2$ at position 3β); from 2.75 to 2.95 (mt, 1H: the other H of CH$_2$ at position 5β); 2.84 (s, 6H: ArN(CH$_3$)$_2$); 2.90 (dd, J=13 and 5 Hz, 1H: 1H of CH$_2$ at position 4β); from 3.10 to 3.25 (mt, 2H: the other H of CH$_2$ at position 4β and 1H of CH$_2$ at position 3δ); 3.20 (s, 3H: NCH$_3$); 3.45 (mt, 1H: the other H of CH$_2$ at position 3δ); 3.74 (d, J=17 Hz, 1H: 1H of CH$_2$ at position 5ε); 4.30 (mt, 2H: COOCH$_2$ of ethyl); 4.55 (dd, J=8 and 5 Hz, 1H: CH at position 3α); 4.77 (mt, 1H: CH at position 2α); 4.86 (dd, J=10 and 1.5 Hz, 1H: CH at position 1α); 5.12 (dd, J=11 and 5 Hz, 1H: CH at position 4α); 5.28 (2 d, respectively J=6 Hz and J=17 Hz, 1H each: CH at position 5α and the other H of CH$_2$ at position 5ε); 5.58 (d, J=8.5 Hz, 1H: CH at position 6α); 5.83 (dq, J=7 and 1.5 Hz, 1H: CH at position 1β); from 6.00 to 6.50 (broad unresolved complex, 2H: ArNH$_2$); 6.36 (d, J=8 Hz, 2H: aromatic H at position 4ε); 6.61 (d, J=9.5 Hz, 1H: CONH at position 2); 6.84 (d, J=8 Hz, 2H aromatic H at position 4δ); from 7.15 to 7.35 (mt: the 5 aromatic H at position 6α); 7.40 (mt, 2H: 1' H$_4$ and 1' H$_5$); 7.78 (s, 1H: aromatic H at position γ with respect to N); 7.89 (broad d, J=4 Hz, 1H: 1' H$_6$); 8.40 (d, J=10 Hz, 1H: CONH at position 1); 8.60 (d, J=8.5 Hz, 1H: CONH at position 6); 11.61 (unresolved complex, 1H: OH).

Ethyl 3,3-diaminoacrylate hydrochloride may be prepared according to H. Meyer et al., Liebigs Ann. Chem., 1895–1908 (1977).

EXAMPLE 3

By carrying out the procedure as in Example 1 but starting with 50 cm$^3$ of methanol, 3 g of 5δ-methylenepristinamycin I$_A$ and 0.65 g of benzyl 3-aminocrotonate and heating under reflux for 36 hours, a precipitate is obtained, after cooling the reaction mixture to room temperature and adding 50 cm$^3$ of distilled water, which is filtered on sintered glass and then washed successively with 50 cm$^3$ of distilled water and 25 cm$^3$ of diisopropyl ether. The solid obtained is dissolved hot in 25 cm$^3$ of methanol and after cooling, the crystals formed are filtered, washed with 10 cm$^3$ of methanol, dried at 40° C. (90 Pa) to give 1.2 g of 3"-benzyloxycarbonyl-2"-methylpyrido[2,3-5γ,5δ]pristinamycin I$_E$ in the form of a pale-yellow solid melting at 250° C.

$^1$H NMR spectrum (400 MHz, CDCl$_3$, δ in ppm): 0.93 (t, J=7.5 Hz, 3H: CH$_3$ at position 2γ); from 1.10 to 1.40 (mt, 2H: 1H of CH$_2$ at position 3β and 1H of CH$_2$ at position 3γ); 1.30 (d, J=7 Hz, 3H: CH$_3$ at position 1γ); 1.50 (dd, J=17 and 5 Hz, 1H: 1H of CH$_2$ at position 5β); 1.58 (mt, 1H: the other H of CH$_2$ at position 3γ); 1.67 and 1.75 (2 mts, 1H each: CH$_2$ at position 2β); 2.06 (mt, 1H: the other H of CH$_2$ at position 3β); 2.78 (s, 3H: ArCH$_3$); 2.85 (s, 6H: ArN(CH$_3$)$_2$); 2.95 (mt, 1H: 1H of CH$_2$ at position 4β); 3.10 (d, J=17 Hz, 1H: the other H of CH$_2$ at position 5β); from 3.15 to 3.30 (mt, 2H: the other H of CH$_2$ at position 4β and 1H of CH$_2$ at position 3δ); 3.26 (s, 3H: NCH$_3$); 3.50 (mt, 1H: the other H of CH$_2$ at position 3δ); 3.90 (d, J=17 Hz, 1H: 1H of CH$_2$ at position 5ε); 4.62 (dd, J=8 and 6.5 Hz, 1H: CH at position 3α); 4.81 (mt, 1H: CH at position 2α); 4.90 (broad d, J=10 Hz, 1H: CH at position 1α); 5.15 (dd, J=11 and 5 Hz, 1H: CH at position 4α); 5.37 (s, 2H: COOCH$_2$Ar); 5.40 (d, J=5 Hz, 1H: CH at position 5α); 5.45 (d, J=17 Hz, 1H: the other H of CH$_2$ at position 5ε); 5.61 (d, J=8.5 Hz, 1H: CH at position 6α); 5.88 (broad q, J=7 Hz, 1H: CH at position 1β); 6.33 (d, J=8 Hz, 2H: aromatic H at position 4ε); 6.58 (d, J=9.5 Hz, 1H: CONH at position 2); 6.87 (d, J=8 Hz, 2H: aromatic H at position 4δ); from 7.20 to 7.50 (mt: the 12H corresponding to the 5 aromatic H at position 6α- to 1' H$_4$- to 1' H$_5$ and to the aromatic H of benzyloxycarbonyl); 7.92 (s, 1H: aromatic H at position γ with respect to N); 7.95 (mt, 1H: 1' H$_6$); 8.41 (d, J=10 Hz, 1H: CONH at position 1); 8.68 (d, J=8.5 Hz, 1H: CONH at position 6); 11.66 (s, 1H: OH).

1.95 g of 3"-benzyloxycarbonyl-2"-methyl-pyrido[2,3-5γ,5δ]pristinamycin I$_E$ and then 1.6 g of 20% palladium hydroxide on carbon and 2 cm$^3$ of 1,4-cyclo-hexadiene are introduced under a nitrogen stream into a three-necked flask containing 50 cm$^3$ of methanol. The mixture is heated at 60° C. for 30 minutes and then cooled to room temperature. The catalyst is filtered on Whatman filter paper and the filtrate concentrated at 45° C. under reduced pressure (2.7 kPa) so as to obtain a final volume of 5 cm$^3$. 100 cm$^3$ of diisopropylether are then added and the precipitate formed is filtered, washed with 25 cm$^3$ of diisopropylether and then dried at 40° C. under reduced pressure (90 Pa) to give 0.95 g of 3"-carboxy-2"-methylpyrido[2,3-5γ,5δ]pristinamycin I$_E$ in the form of a cream-coloured solid melting at 234° C.

$^1$H NMR spectrum (400 MHz, CDCl$_3$, δ in ppm): 0.92 (t, J=7.5 Hz, 3H: CH$_3$ at position 2γ); from 1.15 to 1.35 (mt, 2H: 1H of CH$_2$ at position 3β and 1H of CH$_2$ at position 3γ); 1.32 (d, J=7 Hz, 3H: CH$_3$ at position 1γ); 1.39 (mt, 1H: 1H of CH$_2$ at position 5β); 1.60 (mt, 1H: the other H of CH$_2$ at position 3γ); 1.71 and 1.80 (2 mts, 1H each: CH$_2$ at position 2β); 2.05 (mt, 1H: 1H of CH$_2$ at position 3β); 2.67 (s, 3H: ArCH$_3$); 2.78 (s, 6H: ArN(CH$_3$)$_2$); 2.92 (mt, 1H: 1H of CH$_2$ at position 4β); 3.05 (very broad d, J=16 Hz, 1H: the other H of CH$_2$ at position 5β); from 3.15 to 3.35 (mt, 1H: the other H of CH$_2$ at position 4β); 3.25 (s, 3H: NCH$_3$); 3.48 (mt, 1H: 1H of CH$_2$ at position 3δ); 3.57 (mt, 1H: the other H of CH$_2$ at position 3δ); 4.01 (d, J=17 Hz, 1H: 1H of CH$_2$ at position 5ε); 4.60 (mt, 1H: CH at position 3α); 4.88 (mt, 1H: CH at position 2α); 4.94 (broad d, J=10 Hz, 1H: CH at position 1α); 5.12 (mt, 1H: CH at position 4α); 5.40 (unresolved complex, 1H: CH at position 5α); 5.43 (d, Hz J=17 Hz, 1H: the other H of CH$_2$ at position 5ε); 5.69 (d, J=8.5 Hz, 1H: CH at position 6α); 5.88 (broad q, J=7 Hz, 1H: CH at position 1β); 6.29 (d, J=8 Hz, 2H: aromatic H at position 4ε); 6.85 (d, J=8 Hz, 2H: aromatic H at position 4δ); 7.13 (broad d, 1H: CONH at position 2); from 7.20 to 7.45 (mt: the 7H corresponding to the 5 aromatic H at position 6α- to 1' H$_4$ and to 1' H$_5$); 7.79 (broad s, 1H: aromatic H at position γ with respect to N); 7.92 (broad s, 1H: 1' H$_6$); 8.34 (d, J=10 Hz, 1H: CONH at position 1); 8.65 (d, J=8.5 Hz, 1H: CONH at position 6); 11.61 (s, 1H: OH).

Benzyl 3-aminocrotonate may be prepared as described by J. Daxoll, J. Chem. Soc., 3802–3808 (1953).

EXAMPLE 4

By carrying out the procedure as in Example 1 but starting with 150 cm$^3$ of methanol, 20 g of 5δ-methylenepristinamycin I$_B$ and 0.26 g of methyl 3-aminocrotonate and after refluxing for 6 hours, 20 g of a yellow product are obtained, which product is purified by two successive chromatographies on 1 kg and 200 g of silica respectively [eluent: dichloromethane/methanol 98/2 by volume] to give after drying at 40° C., under reduced pressure (90 Pa), 13.4 g of 3"-methoxycarbonyl-2"- methylpyrido [2,3-5γ,5δ](4ζ-methylamino)(4ζ-dedimethylamino)pristinamycin I$_E$ in the form of a yellow solid melting at 208° C.

$^1$H NMR spectrum (400 MHz, CDCl$_3$, δ in ppm): 0.92 (t, J=7.5 Hz, 3H: CH$_3$ at position 2γ); from 1.15 to 1.35 (mt, 2H: 1H of CH$_2$ at position 3β and 1H of CH$_2$ at position 3γ); 1.29 (d, J=7 Hz, 3H: CH$_3$ at position 1γ); from 1.55 to 1.80 (mt: the 3H corresponding to the other H of CH$_2$ at position 3γ and to CH$_2$ at position 2β); 1.57 (dd, J=16 and 5.5 Hz, 1H: 1H of CH$_2$ at position 5β); 2.03 (mt, 1H: the other H of CH$_2$ at position 3β); 2.67 (s, 3H: ArCH$_3$); 2.76 (s, 6H: ArNCH$_3$); 2.91 (dd, J=13 and 5 Hz, 1H: 1H of CH$_2$ at position 4β); from 3.10 to 3.30 (mt, 2H: the other H of CH$_2$ at position 4β and 1H of CH$_2$ at position 3δ); 3.13 (d, J=16 Hz, 1H: the other H of CH$_2$ at position 5β); 3.22 (s, 3H: NCH$_3$); 3.49 (mt, 1H: the other H of CH$_2$ at position 3δ); 3.88 (d, J=17 Hz, 1H: 1H of CH$_2$ at position 5ε); 3.92 (s, 3H: COOCH$_3$); 4.60 (dd, J=8 and 5.5 Hz, 1H: CH at position 3α); 4.78 (mt, 1H: CH at position 2α); 4.87 (broad d, J=10 Hz, 1H: CH at position 1α); 5.12 (dd, J=11 at position 5 Hz, 1H: CH at position 4α); 5.38 (d, J=5.5 Hz, 1H: CH at position 5α); 5.44 (d, J=17 Hz, 1H: the other H of CH$_2$ at position 5ε); 5.61 (d, J=8.5 Hz, 1H: CH at 6α); 5.87 (broad q, J=7 Hz, 1H: CH at position 1β); 6.18 (d, J=8 Hz, 2H: aromatic H at position 4ε); 6.52 (broad d, 1H: CONH at position 2); 6.79 (d, J=8 Hz, 2H: aromatic H at position 4δ); from 7.15 to 7.35 (mt: the 5 aromatic H at position 6α); 7.42 (mt, 2H: 1' H$_4$ and 1' H$_5$); 7.88 (s, 1H: aromatic H at position γ with respect to N); 7.92 (mt, 1H: 1' H$_6$); 8.39 (d, J=10 Hz, 1H: CONH at position 1); 8.64 (d, J=8.5 Hz, 1H: CONH at position 6); 11.62 (s, 1H: OH).

EXAMPLE 5

3.4 g of 5δ-methylenepristinamycin I$_A$, 1 g of 3,3-dimethyl-2-oxo-1-butylpyridinium bromide and then 3 g of ammonium acetate are introduced into a three-necked flask containing 100 cm$^3$ of methanol. The mixture is refluxed for 3 hours and then concentrated to dryness at 40° C. under reduced pressure (2.7 kPa). 100 cm$^3$ of distilled water are then added and then the mixture is extracted with twice 100 cm$^3$ of ethyl acetate. The organic phases are decanted off, combined, dried over sodium sulphate, filtered and then concentrated to dryness at 40° C. under reduced pressure (2.7 kPa) to give 3.6 g of an orange-coloured solid which is purified by two successive chromatographies on 40 g of silica (eluent: dichloromethane/methanol 95/5 by volume) to give a product which is taken up in 60 cm$^3$ of an ether-petroleum ether mixture. After filtration and drying at 40° C. under reduced pressure (90 Pa), 0.64 g of 2"-tert-butylpyrido [2,3-5γ,5δ]pristinamycin I$_E$ is obtained in the form Hz of a cream-coloured solid melting at 196° C.

$^1$H NMR spectrum (400 MHz, CDCl$_3$, δ in ppm): 0.91 (t, J=7.5 Hz, 3H: CH$_3$ at position 2γ); from 1.15 to 1.40 (mt, 2H: 1H of CH$_2$ at position 3β and 1H of CH$_2$ at position 3γ); 1.31 (d, J=7 Hz, 3H: CH$_3$ at position 1γ); 1.32 (s, 9H: ArC(CH$_3$)$_3$); 1.60 (mt, 1H: the other H of CH$_2$ at position 3γ); 1.66 and 1.75 (2 mts: the 2H corresponding to CH$_2$ at position 2β); 1.98 (dd, J=16 and 5.5 Hz, 1H: 1H of CH$_2$ at position 5β); 2.02 (mt, 1H: the other H of CH$_2$ at position 3β); 2.86 (s, 6H: ArN(CH$_3$)$_2$); 3.01 (dd, J=14 and 6.5 Hz, 1H: 1H of CH$_2$ at position 4β); from 3.10 to 3.40 (mt, 3H: the other H of CH$_2$ at position 4β—the other H of CH$_2$ at position 5β and 1H of CH$_2$ at position 3δ); 3.18 (s, 3H: NCH$_3$); 3.51 (mt, 1H: the other H of CH$_2$ at position 3δ); 3.94 (d, J=17 Hz, 1H: 1H of CH$_2$ at position 5ε); 4.58 (t, J=7.5 Hz, 1H: CH at position 3α); 4.81 (mt, 1H: CH at position 2α); 4.90 (broad d, J=10 Hz, 1H: CH at position 1α); from 5.35 to 5.50 (mt, 3H: CH at position 4α—the other H of CH$_2$ at position 5εand CH at position 5α); 5.65 (d, J=8.5 Hz, 1H: CH at position 6α); 5.88 (broad q, J=7 Hz, 1H: CH at position 1β); 6.43 (d, J=8 Hz, 2H: aromatic H at 4ε); 6.75 (d, J=10 Hz, 1H: CONH at position 2); 6.87 (d, J=8 Hz, 2H: aromatic H at position 4δ); 7.12 (d, J=8 Hz, 1H: aromatic H at position β with respect to N); from 7.25 to 7.45 (mt: the 8H corresponding to the 5 aromatic H at position 6α—to the aromatic H at position γ with respect to N—to 1' H$_4$ and to 1' H$_5$); 7.87 (mt, 1H: 1' H$_6$); 8.49 (d, J=10 Hz, 1H: CONH at position 1); 8.73 (d, J=8.5 Hz, 1H: CONH at position 6); 11.70 (s, 1H: OH).

3,3-dimethyl-2-oxo-1-butylpyridinium bromide may be prepared as described by F. Kroencke, Chem. Ber., 69, 921–923 (1936).

EXAMPLE 6

404 g of 5δ-methylenepristinamycin I$_A$, 78.8 g of 1-acetonylpyridinium chloride and then 354 g of ammonium acetate are introduced into a three-necked flask containing 2 liters of acetone. The mixture is refluxed for 1 hour and then concentrated to dryness at 40° C. under reduced pressure (2.7 kPa). 10 liters of distilled water are then added and then the mixture is extracted with 500 cm$^3$ of dichloromethane and then with 3 liters of ethyl acetate. The organic phases are decanted off, combined, dried over sodium sulphate, filtered and then concentrated to dryness at 40° C. under reduced pressure (2.7 kPa) to give 205 g of an orange-coloured solid which is purified by chromatography on 1 kg of silica (eluent: dichloromethane/methanol 98/2 by volume) to give 64.7 g of a product which is taken up in 60 cm$^3$ of diisopropyl ether and then recrystallized twice from 100 cm$^3$ of methanol. After filtration and drying at 40° C. under reduced pressure (90 Pa), 23.3 g of a product which is 2"-methylpyrido[2,3-5γ, 5δ]pristinamycin I$_E$ are obtained in the form of a yellow solid melting at 253° C.

$^1$H NMR spectrum (400 MHz, CDCl$_3$, δ in ppm): 0.94 (t, J=7.5 Hz, 3H: CH$_3$ at position 2γ); from 1.20 to 1.35 (mt, 2H: 1H of CH$_2$ at position 3β and 1H of CH$_2$ at position 3γ); 1.31 (d, J=7 Hz, 3H: CH$_3$ at position 1γ); 1.59 (mt, 1H: the other H of CH$_2$ at position 3γ); from 1.60 to 1.85 (mt: the 2H corresponding to CH$_2$ at position 2β); 1.69 (dd, J=16 and 6 Hz, 1H: 1H of CH$_2$ at position 5β); 2.06 (mt, 1H: the other H of CH$_2$ at position 3β); 2.48 (s, 3H: ArCH$_3$); 2.86 (s, 6H: ArN(CH$_3$) $_2$); 2.98 (dd, J=13.5 and 5.5 Hz, 1H: 1H of CH$_2$ at position 4β); 3.15 (d, J=16 Hz, 1H: the other H of CH$_2$ at position 5β); from 3.15 to 3.30 (mt, 2H: the other H of CH$_2$ at position 4β and 1H of CH$_2$ at position 3δ); 3.24 (s, 3H: NCH$_3$); 3.50 (mt, 1H: the other H of CH$_2$ at position 3δ); 3.92 (d, J=17 Hz, 1H: 1H of CH$_2$ at position 5ε); 4.61 (dd, J=8 and 5.5 Hz, 1H: CH at position 3α); 4.81 (mt, 1H: CH at position 2α); 4.90 (broad d, J=10 Hz, 1H: CH at position 1α); 5.23 (dd, J=10 and 5.5 Hz, 1H: CH at position 4α); 5.42 (d and broad d respectively, J=17 Hz and J=5.5 Hz, 1H each: the other H of CH$_2$ at position 5e and CH at position 5α); 5.63 (d, J=8.5 Hz, 1H: CH at position 6α); 5.90 (broad q, J=7 Hz, 1H: CH at position 1β); 6.36 (d, J=8 Hz, 2H: aromatic H at position 4ε); 6.61 (d, J=9.5 Hz, 1H: CONH at position 2); 6.87 (d, J=8 Hz, 2H: aromatic H at 4δ); 6.96 (d, J=8 Hz, 1H: aromatic H at position β with respect to N); from 7.20 to 7.40 (mt: the 5 aromatic H at position 6α); 7.34 (d, J=8 Hz, 1H: aromatic H at position γ with respect to N); 7.41 (limiting AB, 2H: 1' H$_4$ and 1' H$_5$); 7.92 (mt, 1H: 1' H$_6$); 8.44 (d, J=10 Hz, 1H: CONH at position 1); 8.65 (d, J=8.5 Hz, 1H: CONH at position 6); 11.66 (s, 1H: OH).

1-acetonylpyridinium chloride may be prepared according to H. Dreser, Arch. Pharm., 232, 183 (1894).

EXAMPLE 7

By carrying out the procedure as in Example 6 but starting with 50 g of 5δ-methylenepristinamycin $I_A$ in 1 liter of acetone, 13.7 g of 1-(2-oxobutyl)-pyridinium bromide, 44 g of ammonium acetate and heating for 1 hour under reflux and then adding 2.6 g of 1-(2-oxobutyl)pyridinium bromide and refluxing for an additional one hour, 19.5 g of a product are obtained after purification by chromatography on 200 g of silica (eluent: dichloromethane/methanol 97/3 by volume), which product can be purified by crystallization in the following manner. 8 g of this solid are dissolved hot in a mixture of 30 cm³ of methanol and 1 cm³ of distilled water. After cooling, the crystals obtained are collected to give 3.9 g of a solid which is recrystallized under similar conditions. After filtration and drying at 40° C. under reduced pressure (90 Pa), 1.7 g of 2"-ethylpyrido[2,3-5γ, 5δ]-pristinamycin $I_E$ are obtained in the form of a white solid melting at 263° C.

$^1$H NMR spectrum (400 MHz, CDCl₃, δ in ppm): 0.89 (t, J=7.5 Hz, 3H: CH₃ at position 2γ); from 1.15 to 1.35 (mt, 2H: 1H of CH₂ at position 3β and 1H of CH₂ at position 3γ); 1.22 (t, J=7.5 Hz, 3H: CH₃ of ethyl); 1.28 (d, J=7 Hz, 3H: CH3 at position 1γ); 1.53 (mt, 1H: the other H of CH₂ at position 3γ); from 1.60 to 1.80 (mt: the 2H corresponding to CH₂ at position 2β); 1.76 (dd, J=16 and 5.5 Hz, 1H: 1H of CH₂ at position 5β); 2.00 (mt, 1H: the other H of CH₂ at position 3β); 2.72 (q, J=7.5 Hz, 2H: ArCH₂ of ethyl); 2.82 (s, 6H: ArN(CH₃)₂); 2.94 (dd, J=13.5 and 5.5 Hz, 1H: 1H of CH₂ at position 4 β); from 3.10 to 3.25 (mt, 3H: the other H of CH₂ at position 4β—the other H of CH₂ at position 5β and 1H of CH₂ at position 3β); 3.18 (s, 3H: NCH₃); 3.46 (mt, 1H: the other H of CH₂ at position 3β); 3.90 (d, J=17 Hz, 1H: 1H of CH₂ at position 5ε); 4.57 (dd, J=8 and 5.5 Hz, 1H: CH at position 3α); 4.75 (mt, 1H: CH at position 2α); 4.84 (broad d, J=10 Hz, 1H: CH at position 1α); 5.21 (dd, J=9 and 5.5 Hz, 1H: CH at position 4α); 5.38 (d, J=17 Hz, 1H: the other H of CH₂ at position 5ε); 5.39 (broad d, J=5.5 Hz, 1H: CH at position 5α); 5.60 (d, J=8.5 Hz, 1H: CH at position 6α); 5.85 (broad q, J=7 Hz, 1H: CH at position 1β); 6.32 (d, J=8 Hz, 2H: aromatic H at position 4ε); 6.53 (d, J=9.5 Hz, 1H: CONH at position 2); 6.82 (d, J=8 Hz, 2H: aromatic H at position 4δ); 6.93 (d, J=8 Hz, 1H: aromatic H at position β with respect to N); from 7.25 to 7.40 (mt: the 5 aromatic H at position 6α); 7.29 (d, J=8 Hz, 1H: the aromatic H at position γ with respect to N); 7.33 (mt, 2H: 1' H₄ and 1' H₅); 7.85 (mt, 1H: 1' H₆); 8.39 (d, J=10 Hz, 1H: CONH at position 1); 8.63 (d, J=8.5 Hz, 1H: CONH at position 6); 11.62 (s, 1H: OH).

1-(2-Oxobutyl)pyridinium bromide may be prepared by analogy with 1-(2-oxobutyl)pyridinium iodide as described by R. P. Soni, J. P. Saxena, J. Indian Chem. Soc. 58, 885–887 (1981).

15 g of 1-bromo-2-butanone and 40 cm³ of pyridine are introduced into a three-necked flask containing 150 cm³ of ethanol and the mixture is heated for 2 hours under reflux. After concentrating to dryness at 40° C. under reduced pressure (2.7 kPa), the residue is taken up in 100 cm³ of diethyl ether. After filtration, washing with twice 70 cm³ of diethyl ether, the precipitate is dried to give 22 g of a yellow solid melting at 181° C.

$^1$H NMR spectrum (250 MHz, (CD₃)₂SO d6, δ in ppm): 1.06 (t, J=7 Hz, 3H: CH₃ of ethyl); 2.70 (q, J=7 Hz, 2H: COCH₂ of ethyl); 5.83 (s, 2H: NCH₂CO); 8.25 (dd, J=8 and 5 Hz, 2H: aromatic H at position β of pyridine); 8.69 (t, J=8 Hz, 2H: aromatic H at position γ of pyridine); 8.91 (d, J=5 Hz, 2H: aromatic H at position α of pyridine).

EXAMPLE 8

By carrying out the procedure as in Example 5 but starting with 9.8 g of 5δ-methylenepristinamycin $I_A$ in 500 cm³ of methanol, 2.7 g of 1-cyclopropylcarbonyl-methylpyridinium bromide, 8.6 g of ammonium acetate and heating for 40 minutes under reflux, 1.1 g of product are obtained after purification by chromatography on 150 g of silica (eluent: dichloromethane/methanol 97/3 by volume), which product may be recrystallized from 11 cm³ of boiling methanol. After cooling, the crystals obtained are filtered and then rinsed with 5 cm³ of methanol to give 0.47 g of 2"-cyclopropylpyrido[2,3-5γ, 5δ]pristinamycin $I_E$ in the form of white crystals melting at 198° C.

$^1$H NMR spectrum (400 MHz, CDCl₃, δ in ppm): from 0.80 to 1.00 (mt, 4H: the 2 CH₂ of cyclopropyl); 0.91 (t, J=7.5 Hz, 3H: CH₃ at position 2γ); from 1.15 to 1.35 (mt, 2H: 1H of CH₂ at position 3β and 1H of CH₂ at position 3γ); 1.30 (d, J=7 Hz, 3H: CH₃ at position 1γ); from 1.55 to 1.80 (mt: the 2H corresponding to CH₂ at position 2β); 1.57 (mt, 1H: the other H of CH₂ at position 3γ); 1.68 (dd, J=16 and 6.5 Hz, 1H: 1H of CH₂ at position 5β); 1.96 (mt, 1H: ArCH₂ of cyclopropyl); 2.04 (mt, 1H: the other H of CH₂ at position 3β); 2.86 (s, 6H: ArN(CH₃)₂); 2.96 (dd, J=13 and 6 Hz, 1H: 1H of CH₂ at position 4β); 3.10 (d, J=16 Hz, 1H: the other H of CH₂ at position 5β); from 3.10 to 3.30 (mt, 2H: the other H of CH₂ at position 4β and 1H of CH₂ at position 3δ); 3.22 (s, 3H: NCH₃); 3.49 (mt, 1H: the other H of CH₂ at position 3β); 3.90 (d, J=17 Hz, 1H: 1H of CH₂ at position 5ε); 4.60 (dd, J=8 and 6 Hz, 1H: CH at position 3α); 4.79 (mt, 1H: CH at position 2α); 4.88 (broad d, J=10 Hz, 1H: CH at position 1α); 5.23 (dd, J=10 and 6 Hz, 1H: CH at position 4α); 5.36 (broad d, J=6.5 Hz, 1H: CH at position 5α); 5.38 (d, J=17 Hz, 1H: the other H of CH₂ at position 5ε); 5.62 (d, J=8.5 Hz, 1H: CH at position 6α); 5.88 (broad q, J=7 Hz, 1H: CH at position 1β); 6.34 (d, J=8 Hz, 2H: aromatic H at position 4ε); 6.58 (d, J=9.5 Hz, 1H: CONH at position 2); from 6.75 to 6.90 (mt, 3H: aromatic H at position 4δ and aromatic H at position β with respect to N); 7.08 (d, J=8 Hz, 1H: aromatic H at position γ with respect to N); from 7.20 to 7.35 (mt: the 5 aromatic H at position 6α); 7.40 (limiting AB, 2H: 1' H₄ and 1' H₅); 7.91 (mt, 1H: 1' H₆); 8.43 (d, J=10 Hz, 1H: CONH at position 1); 8.63 (d, J=8.5 Hz, 1H: CONH at position 6); 11.62 (s, 1H: OH).

1-Cyclopropylcarbonylmethylpyridinium bromide may be prepared in the following manner:

2.4 g of 1-bromomethylcyclopropylketone and 5.8 cm³ of pyridine are introduced into a three-necked flask containing 40 cm³ of ethanol and then the mixture is heated for 2 hours under reflux. After concentrating to dryness at 40° C. under reduced pressure (2.7 kPa), the residue is taken up in twice 30 cm³ of diethyl ether. After filtration, washing with diethyl ether, the precipitate is dried under reduced pressure (90 Pa) to give 3.4 g of 1-cyclopropylcarbonylmethylpyridinium bromide in the form of a cream-coloured solid melting at 160° C.

$^1$H NMR spectrum (300 MHz, (CD₃)₂SO d6, δ in ppm): 1.08 and 1.16 (2 mts, 2H each: the 2 CH₂ of cyclopropane); 2.34 (mt, 1H: COCH of cyclopropane); 6.06 (s, 2H: NCH₂CO); 8.24 (dd, J=8 and 5 Hz, 2H: aromatic H at position β of pyridine); 8.70 (t, J=8 Hz, 2H: aromatic H at position γ of pyridine); 8.96 (d, J=5 Hz, 2H: aromatic H at position α of pyridine).

Bromomethylcyclopropylketone may be prepared according to V. K. Jinaraj et al., Ind. J. Chem., Sect. B, 22, 841–45 (1983).

EXAMPLE 9

By carrying out the procedure as in Example 5 but starting with 10 g of 5δ-methylenepristinamycin $I_A$ in 300 cm³ of methanol, 2.2 g of 1-cyanomethylpyridinium bromide, 8.5 g of ammonium acetate and heating for 3 hours under reflux, a product is obtained after purification by chromatography on 70 g of silica (eluent: dichloromethane/methanol 90/10 by volume), which product is repurified 3 times by the same method, changing the nature of the eluent (dichloromethane/methanol 95/5, and then dichloromethane/methanol 97/3 and then dichloromethane/methanol 95/5) to give 0.16 g of 2"-aminopyrido[2,3-5γ, 5δ]pristinamycin $I_E$ in the form of a white solid melting at 222° C.

$^1$H NMR spectrum (400 MHz, CDCl$_3$, δ in ppm): 0.90 (t, J=7.5 Hz, 3H: CH$_3$ at position 2γ); from 1.15 to 1.35 (mt, 2H: 1H of CH$_2$ at position 3β and 1H of CH$_2$ at position 3γ); 1.28 (d, J=7 Hz, 3H: CH$_3$ at position 1γ); from 1.45 to 1.80 (mt, the 4H corresponding to the other H of CH$_2$ at position 3γ—to 1H of CH$_2$ at position 5β and to CH$_2$ at position 2β); 2.01 (mt, 1H: the other H of CH$_2$ at position 3β); from 2.80 to 3.00 (mt, 2H: the other H of CH$_2$ at position 5β and 1H of CH$_2$ at position 4β); 2.89 (s, 6H: ArN(CH$_3$)$_2$); from 3.10 to 3.25 (mt, 2H: the other H of CH$_2$ at position 4β and 1H of CH$_2$ at position 3δ); 3.20 (s, 3H: NCH$_3$); 3.45 (mt, 1H: the other H of CH$_2$ at position 3δ); 3.80 (d, J=17 Hz, 1H: 1H of CH$_2$ at position 5ε); 4.27 (unresolved complex, 2H: ArNH$_2$); 4.57 (dd, J=8.5 and 5.5 Hz, 1H: CH at position 3α); 4.76 (mt, 1H: CH at position 2α); 4.86 (dd, J=10 and 1.5 Hz, 1H: CH at position 1α); 5.18 (dd, J=10 and 6 Hz, 1H: CH at position 4α); 5.27 (d, J=17 Hz, 1H: the other H of CH$_2$ at position 5ε); 5.32 (broad d, J=5.5 Hz, 1H: CH at position 5α); 5.60 (d, J=8.5 Hz, 1H: CH at position 6α); 5.86 (broad q, J=7 Hz, 1H: CH at position 1β); 6.30 (d, J=8 Hz, 1H: aromatic H at position β with respect to N); 6.37 (d, J=8 Hz, 2H: aromatic H at position 4ε); 6.54 (d, J=9.5 Hz, 1H: CONH at position 2); 6.83 (d, J=8 Hz, 2H: aromatic H at position 4ε); 7.09 (d, J=8 Hz, 1H: aromatic H at position γ with respect to N); from 7.15 to 7.40 (mt: the 7H corresponding to the 5 aromatic H at position 6α- to 1' H$_4$ and to 1' H$_5$); 7.84 (dd, J=4 and 1.5 Hz, 1H: 1' H$_6$); 8.38 (d, J=10 Hz, 1H: CONH at position 1); 8.55 (d, J=8.5 Hz, 1H: CONH at position 6); 11.61 (s, 1H: OH)

EXAMPLE 10

By carrying out the procedure as in Example 5 but starting with 30 g of 5δ-methylenepristinamycin I$_A$ in 300 cm$^3$ of methanol, 7.1 g of 1-(3-chloro-2-oxopropyl)pyridinium chloride (at 50%), 26 g of ammonium acetate and heating for 10 minutes under reflux, 1.4 g of a product are obtained after 2 successive chromatographies on 400 g of silica (eluent: dichloromethane/methanol 98/2 by volume), which product is purified by HPLC on 10 μm C$_8$ silica (eluent: water:acetonitrile:70/30 by volume containing 0.1% trifluoroacetic acid). The fractions are combined, the acetonitrile removed at 40° C. under reduced pressure (2.7 kPa) and the aqueous phase adjusted to pH 7 with 3 cm$^3$ of water saturated with sodium bicarbonate. The aqueous phase is washed with twice 60 cm$^3$ of dichloromethane. The organic phases are pooled, dried over sodium sulphate, filtered and then concentrated to dryness under reduced pressure (2.7 kPa) to give 0.4 g of a yellow solid which is concreted from 60 cm$^3$ of a diethyl ether/petroleum ether mixture, filtered and then dried under reduced pressure (90 Pa). 0.3 g of 2"-chloromethylpyrido[2,3-5γ, 5δ]pristinamycin I$_E$ is thus obtained in the form of a cream-coloured solid melting at 194° C.

$^1$H NMR spectrum (400 MHz, CDCl$_3$, δ in ppm): 0.92 (t, J=7.5 Hz, 3H: CH$_3$ at position 2γ); from 1.15 to 1.35 (mt, 2H: 1H of CH$_2$ at position 3β and 1H of CH$_2$ at position 3γ); 1.30 (d, J=7 Hz, 3H: CH$_3$ at position 1γ); 1.57 (mt, 1H: the other H of CH$_2$ at position 3γ); from 1.60 to 1.80 (mt: the 2H corresponding to CH$_2$ at position 2β); 1.63 (dd, J=16 and 6 Hz, 1H: 1H of CH$_2$ at position 5β); 2.03 (mt, 1H: the other H of CH$_2$ at position 3β); 2.85 (s, 6H: ArN(CH$_3$)$_2$); 2.95 (dd, J=13 and 5.5 Hz, 1H: 1H of CH$_2$ at position 4β); 3.12 (d, J=16 Hz, 1H: the other H of CH$_2$ at position 5β); from 3.15 to 3.30 (mt, 2H: the other H of CH$_2$ at position 4β and 1H of CH$_2$ at position 3δ); 3.23 (s, 3H: NCH$_3$); 3.49 (mt, 1H: the other H of CH$_2$ at position 3δ); 3.93 (d, J=17 Hz, 1H: 1H of CH$_2$ at position 5ε); 4.58 (limiting AB, J=14 Hz, 2H: ArCH$_2$Cl); from 4.55 to 4.75 (mt, 1H: CH at position 3α); 4.79 (mt, 1H: CH at position 2α); 4.88 (broad d, J=10 Hz, 1H: CH at position 1α); 5.18 (dd, J=10.5 and 5.5 Hz, 1H: CH at position 4α); 5.40 (broad d, J=6 Hz, 1H: CH at position 5α); 5.46 (d, J=17 Hz, 1H: the other H of CH$_2$ at position 5ε); 5.60 (d, J=8.5 Hz, 1H: CH at position 6α); 5.87 (broad q, J=7 Hz: 1H: CH at position 1β); 6.36 (d, J=8 Hz, 2H: aromatic H at position 4ε); 6.55 (d, J=9.5 Hz, 1H: CONH at position 2); 6.86 (d, J=8 Hz, 2H aromatic H at position 4δ); 7.22 (d, J=8 Hz, 1H: aromatic H at position β with respect to N); from 7.25 to 7.40 (mt: the 5 aromatic H at position 6α); 7.38 (d, J=8 Hz, 1H: aromatic H at position γ with respect to N); 7.42 (mt, 2H: 1' H$_4$ and 1' H$_5$); 7.89 (mt, 1H: 1' H$_6$); 8.40 (d, J=10 Hz, 1H: CONH at position 1); 8.68 (d, J=8.5 Hz, 1H: CONH at position 6); 11.64 (s, 1H: OH).

1-(3-Chloro-2-oxopropyl)pyridinium chloride may be prepared in the following manner:

66.9 g of 1,3-dichloroacetone chloride are introduced into a three-necked flask containing 800 cm$^3$ of diethyl ether. 28 cm$^3$ of pyridine are added dropwise and the mixture is kept stirring overnight. The precipitate obtained is filtered, washed with twice 100 cm$^3$ of diethyl ether and then dried at 40° C. under 90 Pa to give 29.2 g of 1-(3-chloro-2-oxopropyl)-pyridinium chloride in the form of a cream-coloured solid melting at 92° C. and which is used as it is.

EXAMPLE 11

By carrying out the procedure as in Example 6 but starting with 36.5 g of 5δ-methylenepristinamycin I$_A$ in 350 cm$^3$ of methanol, 9.6 g of 1-(3-acetoxy-2-oxopropyl)pyridinium chloride, 32.2 g of ammonium acetate and heating for 40 minutes under reflux, a solid is obtained which is chromatographed on 350 g of silica (eluent: dichloromethane/methanol gradient 100/0 then 99/1 then 98/2 then 96/4 by volume) to give 1.3 g of a yellow solid. The latter is purified by HPLC on 10 μm C$_8$ silica (eluent: water/acetonitrile 70/30 by volume, containing 0.1% trifluoroacetic acid). The fractions are combined, the acetonitrile removed at 40° C. under reduced pressure (2.7 kPa) and the pH of the aqueous phase adjusted to 7 by addition of water saturated with sodium bicarbonate. The aqueous phase is extracted with 3 times 200 cm$^3$ of dichloromethane. The organic phases are pooled, dried over magnesium sulphate, filtered and concentrated at 40° C. under reduced pressure (2.7 kPa to give 0.5 g of 2"-hydroxymethylpyrido[2,3-5γ, 5δ]pristinamycin I$_E$ in the form of a white solid melting at 190° C.

$^1$H NMR spectrum (400 MHz, CDCl$_3$, δ in ppm): 0.92 (t, J=7.5 Hz, 3H: CH$_3$ at position 2γ); from 1.20 to 1.35 (mt, 2H: 1H of CH$_2$ at position 3β and 1H of CH$_2$ at position 3γ); 1.31 (d, J=7 Hz, 3H: CH$_3$ at position 1γ); 1.50 (dd, J=16 and 6 Hz, 1H: 1H of CH$_2$ at position 5β); from 1.50 to 1.70 (mt: the 2H corresponding to 1H of CH$_2$ at position 2β and the other H of CH$_2$ at position 3γ); 1.75 (mt, 1H: the other H of CH$_2$ at position 2β); 2.05 (mt, 1H: the other H of CH$_2$ at position 3β); 2.82 (s, 6H: ArN(CH$_3$)$_2$); 2.93 (dd, J=12 and 5 Hz, 1H: 1H of CH$_2$ at position 4β); 3.11 (d, J=16 Hz, 1H: the other H of CH₂ at position 5β); from 3.15 to 3.30 (mt, 2H: the other H of CH₂ at position 4β and 1H of CH₂ at position 3δ); 3.25 (s, 3H: NCH₃); 3.48 (mt, 1H: the other H of CH₂ at position 3δ); 3.91 (d, J=17 Hz, 1H: 1H of CH₂ at position 5ε); 3.94 (unresolved complex, 1H: OH); 4.61 (dd, J=8 and 5.5 Hz, 1H: CH at position 3α); 4.67 Hz(broad s, 2H: ArCH₂O); 4.80 (mt, 1H: CH at position 2α); 4.89 (broad d, J=10 Hz, 1H: CH at position 1α); 5.14 (dd, J=12 and 5 Hz, 1H: CH at position 4α); 5.37 (broad d, J=6 Hz, 1H: CH at position 5α); 5.44 (d, J=17 Hz, 1H: the other H of CH₂ at position 5ε); 5.60 (d, J=8.5 Hz, 1H:

EXAMPLE 12

By carrying out the procedure as in Example 5 but starting with 6 g of 5δ-methylenepristinamycin $I_A$ in 100 cm³ of methanol, 1.9 g of 1-phenacylpyridinium bromide, 5.3 g of ammonium acetate and heating for 30 minutes under reflux, a solid is obtained after purification by chromatography on 90 g of silica [eluent: dichloromethane/methanol 95/5 by volume] which is taken up in 60 cm³ of an ether-petroleum ether mixture. After filtration and drying at 40° C. under reduced pressure (90 Pa), 0.8 g of 2"-phenylpyrido-[2,3-5γ, 5δ]pristinamycin $I_E$ is obtained in the form of a yellow solid melting at 212° C.

¹H NMR spectrum (400 MHz, CDCl₃, δ in ppm): 0.93 (t, J=7.5 Hz, 3H: CH₃ at position 2γ); from 1.20 to 1.40 (mt, 2H: 1H of CH₂ at position 3β and 1H of CH₂ at position 3γ); 1.32 (d, J=7 Hz, 3H: CH₃ at position 1γ); from 1.50 to 1.85 (mt: the 4H corresponding to 1H of CH₂ at position 5β)—to the other H of CH₂ at position 3γ and to CH₂ at position 2β); 2.06 (mt, 1H: the other 1H of CH₂ at position 3β); 2.70 (s, 6H: ArN(CH₃)₂); 2.98 (dd, J=13 and 5.5 Hz, 1H: 1H of CH₂ at position 4β); from 3.15 to 3.35 (mt, 3H: the other H of CH₂ at position 5β—the other H of CH₂ at position 4β and 1H of CH₂ at position 3δ); 3.26 (s, 3H: NCH₃); 3.50 (mt, 1H: the other H of CH₂ at position 3δ); 4.00 (d, J=17 Hz, 1H: 1H of CH₂ at position 5ε); 4.64 (dd, J=8 and 5.5 Hz, 1H: CH at position 3α); 4.82 (mt, 1H: CH at position 2α); 4.89 (broad d, J=10 Hz, 1H: CH at position 1α); 5.23 (dd, J=11 and 5.5 Hz, 1H: CH at position 4α); 5.46 (broad d, J=5.5 Hz, 1H: CH at position 5α); 5.50 (d, J=17 Hz, 1H: the other H of CH₂ at position 5ε); 5.66 (d, J=8.5 Hz, 1H: CH at position 6α); 5.90 (broad q, J=7 Hz, 1H: CH at position 1β); 6.34 (d, J=8 Hz, 2H: aromatic H at position 4ε); 6.60 (d, J=10 Hz, 1H: CONH at position 2); 6.88 (d, J=8 Hz, 2H aromatic H at position 4δ); from 7.25 to 7.50 (mt: the 11H corresponding to the 5 aromatic H at position 6α—to the aromatic H at position γ with respect to N—to the aromatic H at the para position of the phenyl—to the aromatic H at the meta position of the phenyl—to 1' H₄ and to 1' H₅); 7.56 (d, J=8 Hz, 1H: aromatic H at position β with respect to N); 8.00 (mt, 3H: 1' H₆ and aromatic H at the ortho position of the phenyl); 8.45 (d, J=10 Hz, 1H: CONH at position 1); 8.58 (d, J=8.5 Hz, 1H: CONH at position 6); 11.66 (s, 1H: OH).

1-Phenacylpyridinium bromide may be prepared according to F. Kroencke and H. Timmler, Chem. Ber., 69, 614 (1936).

EXAMPLE 13

By carrying out the procedure as in Example 5 but starting with 29.6 g of 5δ-methylenepristinamycin $I_A$ in 200 cm³ of methanol, 10.9 g of 1-(4-nitrophenacyl)-pyridinium bromide and 26 g of ammonium acetate and heating for 40 minutes under reflux, a solid is obtained after purification by chromatography on 500 g of silica [eluent:dichloromethane/methanol 95/5 by volume] which is taken up in 60 cm³ of an ether-petroleum ether mixture. After filtration and drying at 40° C. under reduced pressure (90 Pa), 16 g of 2"-(4-nitrophenyl)pyrido[2,3-5γ, 5δ]pristinamycin $I_E$ are obtained in the form of an orange-coloured solid melting at 345° C.

¹H NMR spectrum (400 MHz, CDCl₃, δ in ppm): 0.94 (t, J=7.5 Hz, 3H: CH₃ at position 2γ); from 1.20 to 1.40 (mt, 2H: 1H of CH₂ at position 3β and 1H of CH₂ at position 3γ); 1.31 (d, J=7 Hz, 3H: CH₃ at position 1γ); from 1.55 to 1.85 (mt: the 4H corresponding to the other H of CH₂ at position 3γ—to 1H of CH₂ at position 5β and to CH₂ at position 2β); 2.08 (mt, 1H: the other H of CH₂ at position 3β); 2.68 (s, 6H: ArN(CH₃)₂); 2.96 (dd, J=13 and 5 Hz, 1H: 1H of CH₂ at position 4β); from 3.15 to 3.35 (mt, 3H: the other H of CH₂ at position 5β—the other H of CH₂ at position 4 β and 1H of CH₂ at position 3δ); 3.26 (s, 3H: NCH₃); 3.61 (mt, 1H: the other H of CH₂ at position 3δ); 3.99 (d, J=17 Hz, 1H: 1H of CH₂ at position 5ε); 4.64 (dd, J=7 and 6 Hz, 1H: CH at position 3α); 4.81 (mt, 1H: CH at position 2α); 4.90 (broad d, J=10 Hz, 1H: CH at position 1α); 5.17 (dd, J=11.5 and 5 Hz, 1H: CH at position 4α); 5.44 (broad d, J=5 Hz, 1H: CH at position 5α); 5.53 (d, J=17 Hz, 1H: the other H of CH₂ at position 5ε); 5.63 (d, J=8.5 Hz, 1H: CH at position 6α); 5.88 (broad q, J=7 Hz, 1H: CH at position 1β); 6.32 (d, J=8 Hz, 2H: aromatic H at position 4ε); 6.58 (d, J=9.5 Hz, 1H: CONH at position 2); 6.88 (d, J=8 Hz, 2H: aromatic H at position 4δ); from 7.20 to 7.40 (mt: the 5 aromatic H at position 6α); from 7.45 to 7.55 (mt, 2H: 1' H₄ and 1' H₅); 7.49 (d, J=8 Hz, 1H: aromatic H at position γ with respect to N); 7.64 (d, J=8 Hz, 1H: aromatic H at position β with respect to N); 7.90 (broad d, J=4 Hz, 1H: 1' H₆); 8.20 and 8.31 (2 d, J=8.5 Hz, 2H each: respectively the aromatic H at the meta position with respect to the NO₂ and the aromatic H at the ortho position with respect to the NO₂); 8.42 (d, J=10 Hz, 1H: CONH at position 1); 8.70 (d, J=8.5 Hz, 1H: CONH at position 6); 11.66 (s, 1H: OH).

9.1 g of 2"-(4-nitrophenyl)pyrido[2,3-5γ, 5δ]-pristinamycin $I_E$ and then 50 g of iron powder and 1 cm³ of concentrated hydrochloric acid are introduced into a three-necked flask containing 90 cm³ of ethanol and 20 cm³ of distilled water and then the mixture is refluxed for 30 minutes. The insoluble matter is removed by filtration, washed with 60 cm³ of ethanol and then the filtrate is concentrated to dryness at 40° C. under reduced pressure (2.7 kPa). The residue obtained is taken up in 300 cm³ of water, the pH adjusted to 8 by addition of sodium bicarbonate and the aqueous phase extracted with twice 100 cm³ of dichloromethane. After drying over sodium sulphate, filtration and concentration to dryness under reduced pressure, 11.5 g of a chestnut-coloured solid are obtained, which solid is purified by chromatography on 120 g of silica [eluent: dichloromethane/methanol 95/5 by volume]. The solid obtained is concreted from 60 cm³ of an ether-petroleum ether mixture, filtered and dried at 40° C. under reduced pressure (90 Pa) to give 1.5 g of 2"-(4-aminophenyl)pyrido [2,3-5γ, 5δ]pristinamycin $I_E$ in the form of a yellow solid melting at 226° C.

¹H NMR spectrum (400 MHz, CDCl₃, δ in ppm): 0.93 (t, J=7.5 Hz, 3H: CH₃ at position 2γ); from 1.15 to 1.40 (mt, 2H: 1H of CH₂ at position 3β and 1H of CH₂ at position 3γ); 1.30 (d, J=7 Hz, 3H: CH₃ at position 1γ); from 1.50 to 1.85 (mt: the 4H corresponding to the other H of CH₂ at position 3γ—to 1H of CH₂ at position 5β and to CH₂ at position 2β); 2.04 (mt, 1H: the other H of CH₂ at position 3β); 2.73 (s, 6H: ArN(CH₃)₂); 2.96 (dd, J=13 and 4.5 Hz, 1H: 1H of CH₂ at position 4β); from 3.15 to 3.35 (mt, 3H: the other H of CH₂ at position 5β—the other H of CH₂ at position 4 β and 1H of CH₂ at position 3δ); 3.24 (s, 3H: NCH₃); 3.50 (mt, 1H:

the other H of $CH_2$ at position 3δ); 3.80 (unresolved complex, 2H: $NH_2$); 3.97 (d, J=17 Hz, 1H: 1H of $CH_2$ at position 5ε); 4.63 (mt, 1H: CH at position 3α); 4.81 (mt, 1H: CH at position 2α); 4.90 (broad d, J=10 Hz, 1H: CH at position 1α); 5.21 (dd, J=10 and 4.5 Hz, 1H: CH at position 4α); 5.42 (mt, 1H: CH at position 5α); 5.45 (d, J=17 Hz, 1H: the other H of $CH_2$ at position 5ε); 5.64 (d, J=8.5 Hz, 1H: CH at position 6α); 5.89 (mt, 1H: CH at position 1β); 6.33 (d, J=8 Hz, 2H: aromatic H at position 4ε); 6.58 (d, J=9.5 Hz, 1H: CONH at position 2); 6.74 (d, J=8 Hz, 2H: aromatic H at the ortho position with respect to the $NH_2$); 6.88 (d, J=8 Hz, 2H: aromatic H at position 4δ); from 7.20 to 7.50 (mt: the 9H corresponding to the 5 aromatic H at position 6α—to 1' $H_4$—to 1' $H_5$—to the aromatic H at position γ with respect to N and to the aromatic H at position β with respect to N); 7.82 (d, J=8 Hz, 2H: aromatic H at the meta position with respect to $NH_2$); 7.98 (unresolved complex, 1H: 1' $H_6$); 8.44 (d, J=10 Hz, 1H: CONH at position 1); 8.64 (d, J=8.5 Hz, 1H: CONH at position 6); 11.66 (s, 1H: OH).

EXAMPLE 14

By carrying out the procedure as in Example 5 but starting with 10 g of 5δ-methylenepristinamycin $I_A$ in 100 cm³ of methanol, 4 g of 1-(4-diethylamino-phenacyl)pyridinium bromide and 9 g of ammonium acetate and heating for 40 minutes under reflux, a solid is obtained after purification by chromatography on 150 g of silica [eluent: dichloromethane/methanol 95/5 by volume] which is taken up in 60 cm³ of an ether-petroleum ether mixture. After filtration and drying at 40° C. under reduced pressure (90 Pa), 2.4 g of 2"-(4-diethylaminophenyl)pyrido[2,3-5γ, 5δ]pristinamycin $I_E$ are obtained in the form of a yellow solid melting at 210° C.

¹H NMR spectrum (400 MHz, $CDCl_3$, δ in ppm): 0.93 (t, J=7.5 Hz, 3H: $CH_3$ at position 2γ); from 1.15 to 1.40 (mt, 2H: 1H of $CH_2$ at position 3β and 1H of $CH_2$ at position 3γ); 1.22 (t, J=7 Hz, 6H: the 2 $CH_3$ of diethylamino); 1.31 (d, J=7 Hz, 3H: $CH_3$ at position 1γ); 1.58 (mt: 1H: the other H of $CH_2$ at position 3γ); from 1.60 to 1.85 (mt: the 3H corresponding to 1H of $CH_2$ at position 5β and to $CH_2$ at position 2β); 2.05 (mt, 1H: the other H of $CH_2$ at position 3β); 2.75 (s, 6H: $ArN(CH_3)_2$); 2.98 (dd, J=13 and 5.5 Hz, 1H: 1H of $CH_2$ at position 4β); from 3.15 to 3.35 (mt, 3H: the other H of $CH_2$ at position 5β—the other H of $CH_2$ at position 4β and 1H of $CH_2$ at position 3δ); 3.24 (s, 3H: $NCH_3$); 3.42 (mt, 4H: the 2 $NCH_2$ of diethylamino); 3.50 (mt, 1H: the other H of $CH_2$ at position 3δ); 3.97 (d, J=17 Hz, 1H: 1H of $CH_2$ at position 5ε); 4.62 (dd, J=8 and 5.5 Hz, 1H: CH at position 3α); 4.81 (mt, 1H: CH at position 2α); 4.90 (broad d, J=10 Hz, 1H: CH at position 1α); 5.24 (dd, J=10 and 5.5 Hz, 1H: CH at position 4α); 5.43 (2 d, respectively J=6 Hz and J=17 Hz, 2H: CH at position 5α and the other H of $CH_2$ at position 5ε); 5.66 (d, J=8.5 Hz, 1H: CH at position 6α); 5.89 (broad q, J=7 Hz, 1H: CH at position 1β); 6.34 (d, J=8 Hz, 2H: aromatic H at position 4ε); 6.60 (d, J=9.5 Hz, 1H: CONH at position 2); 6.72 (d, J=8 Hz, 2H: aromatic H at the ortho position with respect to diethylamino); 6.87 (d, J=8 Hz, 2H: aromatic H at position 4δ); from 7.20 to 7.40 (mt: the 6H corresponding to the 5 aromatic H at position 6α and to the aromatic H at position γ with respect to N); from 7.40 to 7.50 (mt, 3H: 1' $H_4$–1' $H_5$ and aromatic H at position β with respect to N); 7.85 (d, J=8 Hz, 2H: aromatic H at the meta position with respect to diethylamino); 7.98 (mt, 1H: 1' $H_6$); 8.44 (d, J=10 Hz, 1H: CONH at position 1); 8.63 (d, J=8.5 Hz, 1H: CONH at position 6); 11.67 (s, 1H: OH).

1-(4-Diethylaminophenacyl)pyridinium bromide may be prepared in the following manner:

10 g of 4-diethylaminophenacyl bromide are introduced into a three-necked flask containing 200 cm³ of tetrahydrofuran and then 15 cm³ of pyridine are added dropwise. The stirring is continued for 90 hours and then the precipitate formed is filtered and then washed with 60 cm³ of diethyl ether. After drying at 40° C. under reduced pressure (90 Pa), 14.1 g of 4-diethylaminophenylpyridinium bromide are obtained in the form of a white solid melting at >260° C.

¹H NMR spectrum (300 MHz, $(CD_3)_2SO$ d6, δ in ppm): 1.18 (t, J=7 Hz, 6H: the 2 $CH_3$ of diethylamino); 3.50 (q, J=7 Hz, 4H: the 2 $NCH_2$ of diethylamino); 6.39 (s, 2H: $NCH_2COAr$); 6.84 (d, J=8 Hz, 2H: aromatic H at the ortho position with respect to diethylamino); 7.88 (d, J=8 Hz, 2H: aromatic H at the meta position with respect to diethylamino); 8.28 (dd, J=8 and 5 Hz, 2H: aromatic H at position β of pyridine); 8.74 (t, J=8 Hz, 2H: aromatic H at position γ of pyridine); 9.02 (d, J=5 Hz, 2H: aromatic H at position a of pyridine).

EXAMPLE 15

By carrying out the procedure as in Example 5 but starting with 5 g of 5δ-methylenepristinamycin $I_A$ in 75 cm³ of methanol, 2.05 g of 1-[2-oxo-2-(2-pyridyl)ethyl]pyridinium bromide hydrobromide and 4.3 g of ammonium acetate and heating for 3 hours under reflux, a solid is obtained which is purified by preparative HPLC on 400 g of 10 μm Kromasil® $C_8$ silica [eluent: water/acetonitrile 70/30 by volume containing 0.1% trifluoroacetic acid]. After concentrating the fractions in order to remove the acetonitrile, the aqueous phase is neutralized to pH 7–8 with a 10% solution of sodium bicarbonate. The precipitate obtained during the neutralization is filtered, taken up in 25 cm³ of dry dichloromethane and then the organic phase dried over sodium sulphate, filtered and concentrated to dryness under reduced pressure to give a solid which is taken up in 10 cm³ of diisopropyl ether. After filtration and drying at 40° C. under reduced pressure (90 Pa), 0.94 g of 2"-(2-pyridyl)pyrido[2, 3-5γ,5δ]pristinamycin $I_E$ is obtained in the form of a beige solid 1.38 g melting at 190° C.

¹H NMR spectrum (400 MHz, $CDCl_3$, δ in ppm): 0.93 (t, J=7.5 Hz, 3H: $CH_3$ at position 2γ); from 1.20 to 1.40 (mt, 2H: 1H of $CH_2$ at position 3β and 1H of $CH_2$ at position 3γ); 1.32 (d, J=7 Hz, 3H: $CH_3$ at position 1γ); 1.58 (mt: 1H: the other H of $CH_2$ at position 3γ); from 1.60 to 1.85 (mt: the 2H corresponding to $CH_2$ at position 2β); 1.66 (dd, J=16 and 5 Hz, 1H: 1H of $CH_2$ at position 5β); 2.07 (mt, 1H: the other H of $CH_2$ at position 3β); 2.65 (s, 6H: $ArN(CH_3)_2$); 2.96 (dd, J=13 and 5.5 Hz, 1H: 1H of $CH_2$ at position 4β); from 3.15 to 3.35 (mt, 3H: the other H of $CH_2$ at position 4β—the other H of $CH_2$ at position 5β and 1H of $CH_2$ at position 3δ); 3.26 (s, 3H: $NCH_3$); 3.51 (mt, 1H: the other H of $CH_2$ at position 3δ); 4.00 (d, J=17 Hz, 1H: 1H of $CH_2$ at position 5ε); 4.64 (dd, J=8 and 6.5 Hz, 1H: CH at position 3α); 4.82 (mt, 1H: CH at position 2α); 4.91 (broad d, J=10 Hz, 1H: CH at position 1α); 5.19 (dd, J=12 and 5.5 Hz, 1H: CH at position 4α); 5.44 (broad d, J=5 Hz, 1H: CH at position 5α); 5.52 (d, J=17 Hz, 1H: the other H of $CH_2$ at position 5ε); 5.66 (d, J=8.5 Hz, 1H: CH at position 6α); 5.90 (broad q, J=7 Hz, 1H: CH at position 1β); 6.31 (d, J=8 Hz, 2H: aromatic H at position 4ε); 6.58 (d, J=9.5 Hz, 1H: CONH at position 2); 6.88 (d, J=8 Hz, 2H: aromatic H at position 4δ); from 7.25 to 7.40 (mt: the 6H corresponding to the 5 aromatic H at position 6α and to $H_5$ of pyridine); from 7.40 to 7.55 (mt, 3H: aromatic H at position γ with respect to N—1' $H_5$ and 1' $H_4$); 7.78 (split t, J=8 and 1.5 Hz, 1H: $H_4$ of pyridine); 8.02 (broad d, J=4 Hz, 1H: 1' $H_6$); 8.23 (d, J=8 Hz, 1H: aromatic H at position β with respect to N); 8.42 (mt, 2H: $H_3$ of pyridine and CONH at position 1); 8.66 (d, J=8.5 Hz, 1H: CONH at position 6); 8.68 (broad mt, 1H: $H_6$ of pyridine); 11.67 (s, 1H: OH).

1-[2-Oxo-2-(2-pyridyl)ethyl]pyridinium bromide hydrobromide may be prepared by analogy with F. Krönhke et al., Synthesis, 1–24 (1976):

5 g of 2-bromoacetylpyridine hydrobromide and 7 cm³ of pyridine are introduced into a three-necked flask containing 50 cm³ of tetrahydrofuran. The stirring is maintained for 2 days at room temperature and then the precipitate formed is filtered, washed with 30 cm³ of tetrahydrofuran and then dried at 40° C. under reduced pressure (90 Pa) to give 6.9 g of 1-[2-oxo-2-(2-pyridyl)ethyl]pyridinium hydrobromide in the form of a beige solid which is used as it is.

2-Bromoacetylpyridine hydrobromide may be prepared as described by J. L. Garcia Ruano et al., Tetrahedron, 43, 4407–4416 (1987).

EXAMPLE 16

5 g of 5δ-methylenepristinamycin $I_A$, 2.1 g of 1-[2-oxo-2-(3-pyridyl)ethyl]pyridinium hydrobromide and 4.4 g of ammonium acetate are introduced into a three-necked flask containing 75 cm³ of methanol. After refluxing for 1 hour, the reaction mixture is concentrated by half and then poured over 200 cm³ of distilled water. The orange precipitate which appeared is filtered to give 3.5 g of a solid which is purified by chromatography on 50 g of silica [eluent: dichloromethane/methanol 97/3]. After concentrating the fractions, 1 g of a yellow solid is obtained which is crystallized from 30 cm³ of methanol. 0.4 g of 2"-(3-pyridyl)pyrido[2,3-5γ,5δ]pristinamycin $I_E$ is obtained after filtration and drying at 40° C. under reduced pressure (90 Pa) in the form of a white solid melting at 265° C.

¹H NMR spectrum (400 MHz, CDCl₃, δ in ppm): 0.92 (t, J=7.5 Hz, 3H: CH₃ at position 2γ); from 1.20 to 1.40 (mt, 2H: 1H of CH₂ at position 3β and 1H of CH₂ at position 3γ); 1.31 (d, J=7 Hz, 3H: CH₃ at position 1γ); 1.58 (mt, 1H: the other H of CH₂ at position 3γ); from 1.50 to 1.85 (mt: the 3H corresponding to CH₂ at position 2β and to 1H of CH₂ at position 5β); 2.05 (mt, 1H: the other H of CH₂ at position 3β); 2.68 (s, 6H: ArN(CH₃)₂); 2.95 (dd, J=13 and 5.5 Hz, 1H: 1H of CH₂ at position 4β); from 3.20 to 3.35 (mt, 3H: the other H of CH₂ at position 4β—the other H of CH₂ at position 5β and 1H of CH₂ at position 3δ); 3.26 (s, 3H: NCH₃); 3.49 (mt, 1H: the other H of CH₂ at position 3δ); 3.98 (d, J=17 Hz, 1H: 1H of CH₂ at position 5ε); 4.61 (dd, J=8 and 6 Hz, 1H: CH at position 3α); 4.80 (mt, 1H: CH at position 2α); 4.89 (broad d, J=10 Hz, 1H: CH at position 1α); 5.17 (dd, J=12 and 5.5 Hz, 1H: CH at position 4α); 5.43 (broad d, J=5.5 Hz, 1H: CH at position 5α); 5.49 (d, J=17 Hz, 1H: the other H of CH₂ at position 5ε); 5.63 (d, J=8.5 Hz, 1H: CH at position 6α); 5.88 (broad q, J=7 Hz, 1H: CH at position 1β); 6.30 (d, J=8 Hz, 2H: aromatic H at position 4ε); 6.55 (d, J=9.5 Hz, 1H: CONH at position 2); 6.86 (d, J=8 Hz, 2H: aromatic H at position 4δ); from 7.25 to 7.40 (mt: the 6H corresponding to the 5 aromatic H at position 6α—to H₅ of pyridine); from 7.40 to 7.55 (mt, 3H: aromatic H at position γ with respect to N—1' H₅ and 1' H₄); 7.58 (d, J=8 Hz, 1H: aromatic H at position β with respect to N); 8.00 (dd, J=4 and 1.5 Hz, 1H: 1' H₆); 8.31 (dt, J=8 and 1.5 Hz, 1H: H₄ of pyridine); 8.40 (d, J=10 Hz, 1H: CONH at position 1); 8.63 (dd, J=5 and 1.5 Hz, 1H: H₆ of pyridine); 8.67 (d, J=8.5 Hz, 1H: CONH at position 6); 9.20 (d, J=1.5 Hz, 1H: H₂ of pyridine); 11.64 (s, 1H: OH).

1-[2 Oxo-2-(3-pyridyl)ethyl]pyridinium hydrobromide may be prepared according to F. Krönhke, Synthesis, 1–24 (1976).

EXAMPLE 17

2 g of 2"-ethylpyrido[2,3-5γ,5δ]-pristinamycin $I_E$, 0.17 cm₃ of ethylene glycol, 2.2 cm₃ of acetic acid and 0.44 g of tetra-n-butylammonium periodate are introduced into a three-necked flask containing 30 cm³ of dichloromethane. The mixture is stirred for 18 hours at room temperature and then washed with 3 times 20 cm³ of water. The organic phase is decanted off, dried over magnesium sulphate, filtered and concentrated at 45° C. under reduced pressure (2.7 kPa). The residue obtained is taken up in 50 cm³ of water and 10 cm³ of 0.5 N sulphuric acid and stirred for 5 minutes. The insoluble matter is removed by filtration and the aqueous phase extracted with 3 times 30 cm³ of ethyl acetate. The aqueous phase is adjusted to about pH 8 with a saturated solution of sodium bicarbonate and then extracted with 3 times 30 cm³ of dichloromethane. The chloromethylene phases are pooled, dried over sodium sulphate, filtered and concentrated to dryness under reduced pressure to give 1.7 g of a beige foam which is purified by chromatography on 50 g of silica [eluent: dichloromethane/methanol 97/3 by volume]. 0.4 g of 2"-ethylpyrido[2,3-5γ,5δ](4ζ-methylamino)(4ζdedimethylamino)pristinamycin $I_E$ is thus obtained after drying at 40° C. under 90 Pa in the form of a cream-coloured solid melting at 194° C.

¹H NMR spectrum (400 MHz, CDCl₃, δ in ppm): 0.93 (t, J=7.5 Hz, 3H: CH₃ at position 2γ); from 1.20 to 1.40 (mt, 2H: 1H of CH₂ at position 3β and 1H of CH₂ at position 3γ); 1.27 (t, J=7.5 Hz, 3H: CH₃ of ethyl); 1.32 (d, J=7 Hz, 3H: CH₃ at position 1γ); 1.59 (mt, 1H: the other H of CH₂ at position 3γ); from 1.60 to 1.85 (mt: the 2H corresponding to CH₂ at position 2β); 1.81 (dd, J=16 and 5.5 Hz, 1H: 1H of CH₂ at position 5β); 2.06 (mt, 1H: the other H of CH₂ at position 3β); 2.72 (s, 3H: ArNCH₃); 2.77 (q, J=7.5 Hz, 2H: ArCH₂ of ethyl); 2.97 (dd, J=13.5 and 5.5 Hz, 1H: 1H of CH₂ at position 4β); from 3.15 to 3.30 (mt, 3H: the other H of CH₂ at position 4β—the other H of CH₂ at position 5β and 1H of CH₂ at position 3δ); 3.22 (s, 3H: NCH₃); 3.51 (mt, 1H: the other H of CH₂ at position 3δ); 3.67 (unresolved complex, 1H: ArNH); 3.93 (d, J=17 Hz, 1H: 1H of CH₂ at position 5ε); 4.61 (dd, J=8 and 6 Hz, 1H: CH at position 3α); 4.81 (mt, 1H: CH at position 2α); 4.90 (broad d, J=10 Hz, 1H: CH at position 1α); 5.26 (dd, J=10 and 5.5 Hz, 1H: CH at position 4α); 5.42 (broad d and d respectively, J=5.5 Hz and J=17 Hz, 1H each: CH at position 5α and the other H of CH₂ at position 5α); 5.65 (d, J=8.5 Hz, 1H CH at position 6α); 5.90 (broad q, J=7 Hz, 1H: CH at position 1β); 6.24 (d, J=8 Hz, 2H: aromatic H at position 4ε); 6.60 (d, J=9.5 Hz, 1H: CONH at position 2); 6.82 (d, J=8 Hz, 2H: aromatic H at position 4δ); 6.99 (d, J=8 Hz, 1H: aromatic H at position β with respect to N); from 7.25 to 7.40 (mt: the 5 aromatic H at position 6α); 7.33 (d, J=8 Hz, 1H: aromatic H at position γ with respect to N); 7.40 (limiting AB, 2H: 1' H₄ and 1' H₅); 7.92 (mt, 1H: 1' H₆); 8.47 (d, J=10 Hz, 1H: CONH at position 1); 8.69 (d, J=8.5 Hz, 1H: CONH at position 6); 11.67 (s, 1H: OH).

EXAMPLE 18

By carrying out the procedure as in Example 5 but starting with 10 g of 5δ-methylenepristinamycin $I_B$ in 150 cm³ of methanol, 4.1 g of 1-[2-oxo-2-(2-pyridyl)ethyl]pyridinium hydrobromide and 8.7 g of ammonium acetate and heating for 3 hours under reflux, 7.5 g of a solid are obtained, which solid is purified by preparative HPLC on 400 g of 10 μm Kromasil® C₈ silica [eluent: water-acetonitrile 70/30 by volume containing 0.1% trifluoroacetic acid]. After concentrating the fractions in order to remove the acetonitrile, the aqueous phase is neutralized to pH 7–8 with a 10% solution of sodium bicarbonate. The precipitate obtained during the neutralization is filtered, taken up in 50 cm³ of dry dichloromethane and then the organic phase dried over magnesium sulphate, filtered and concentrated to dryness under reduced pressure to give a solid which is taken up in 50 cm³ of diisopropyl ether. After filtration and drying at 40° C. under reduced pressure (90 Pa), 1.12 g of 2"-(2-pyridyl)pyrido[2,3-5γ,5δ](4ζ-methylamino)(4ζ-dedimethylamino) pristinamycin I$_E$ are obtained in the form of a pink solid melting at 200° C.

¹H NMR spectrum (400 MHz, CDCl₃, δ in ppm): 0.93 (t, J=7.5 Hz, 3H: CH₃ at position 2γ); from 1.20 to 1.40 (mt, 2H: 1H of CH₂ at position 3β and 1H of CH₂ at position 3γ); 1.32 (d, J=7 Hz, 3H: CH₃ at position 1γ); 1.58 (mt: 1H: the other H of CH₂ at position 3γ); from 1.60 to 1.85 (mt, 2H: CH₂ at position 2β); 1.70 (dd, J=16 and 5.5 Hz, 1H: 1H of CH₂ at position 5β); 2.06 (mt, 1H: the other H of CH₂ at position 3β); 2.53 (s, 3H: ArNCH₃); 2.94 (dd, J=13 and 5.5 Hz, 1H: 1H of CH₂ at position 4β); from 3.15 to 3.30 (mt, 2H: the other H of CH₂ at position 4β and 1H of CH₂ at position 3δ); 3.25 (s, 3H: NCH₃); 3.29 (d, J=16 Hz, 1H: the other H of CH₂ at position 5β); 3.50 (mt, 1H: the other H of CH₂ at position 3δ); 3.99 (d, J=17 Hz, 1H: 1H of CH₂ at position 5ε); 4.62 (dd, J=8 and 6 Hz, 1H: CH at position 3α); 4.81 (mt, 1H CH at position 2α); 4.90 (broad d, J=10 Hz, 1H: CH at position 1α); 5.16 (dd, J=10.5 and 5.5 Hz, 1H: CH at position 4α); 5.43 (broad d, J=5.5 Hz, 1H: CH at position 5α); 5.52 (d, J=17 Hz, 1H the other H of CH₂ at position 5ε); 5.67 (d, J=8.5 Hz, 1H: CH at position 6α); 5.90 (broad q, J=7 Hz, 1H: CH at position 1β); 6.15 (d, J=8 Hz, 2H: aromatic H at position 4ε); 6.58 (d, J=9.5 Hz, 1H: CONH at position 2); 6.81 (d, J=8 Hz, 2H: aromatic H at position 4δ); from 7.25 to 7.40 (mt: the 6H corresponding to the 5 aromatic H at position 6α and to H₅ of pyridine); from 7.40 to 7.55 (mt, 3H: aromatic H at position γ with respect to N—1' H₅ and 1' H₄); 7.78 (split t, J=8 and 1.5 Hz, 1H: H₄ of pyridine); 8.01 (broad d, J=4 Hz, 1H: 1' H₆); 8.20 (d, J=8 Hz, 1H: aromatic H at position β with respect to N); 8.38 (d, J=8 Hz, 1H: H₃ with respect to pyridine); 8.46 (d, J=10 Hz, 1H: CONH at position 1); 8.66 (d, J=8.5 Hz, 1H: CONH at position 6); 8.70 (broad d, J=4 Hz, 1H: H₆ of pyridine); 11.68 (s, 1H: OH).

1-[2-Oxo-2-(2-pyridyl)ethyl]pyridinium hydrobromide may be prepared according to F. Krönhke et al., Synthesis, 1–24 (1976).

EXAMPLE 19

15 g of 2"-methylpyrido[2,3-5γ,5δ]-pristinamycin I$_E$, 1.25 cm₃ of ethylene glycol, 16.4 cm³ of acetic acid and 3.33 g of tetra-n-butylammonium periodate are introduced into a three-necked flask containing 60 cm³ of methylene chloride. The mixture is stirred for 10 hours at room temperature and then the reaction mixture is washed with twice 50 cm³ of distilled water. The organic phase is decanted off and then concentrated to dryness at 40° C. under reduced pressure (2.7 kPa). The residue is taken up in 100 cm³ of water and 200 cm³ of 0.5 N sulphuric acid and then washed with 5 times 100 cm³ of ethyl acetate. The aqueous phase is decanted off, adjusted to pH 7–8 with 200 Cm³ of a saturated sodium bicarbonate solution and then extracted with twice 150 cm³ of ethyl acetate. The organic phase is dried over magnesium sulphate and then concentrated to dryness (40 20 C.-2.7 kPa) to give 32 g of a solid which is chromatographed on 1 kg of silica [eluent: dichloromethane/methanol gradient 99/1 to 97.5/2.5]. After concentration to dryness of the fractions and then crystallization from ethyl acetate, 4.7 g of 2"-methylpyrido[2,3-5γ,5δ](4ζ-methylamino)(4ζ-dedimethylamino)pristinamycin I$_E$ are obtained after drying at 40° C. under reduced pressure (90 Pa) in the form of white crystals melting at 244° C.

¹H NMR spectrum (400 MHz, CDCl₃, δ in ppm): 0.92 (t, J=7.5 Hz, 3H: CH₃ at position 2γ); from 1.20 to 1.40 (mt, 2H: 1H of CH₂ at position 3β and 1H of CH₂ at position 3γ); 1.31 (d, J=7 Hz, 3H: CH₃ at position 1γ); 1.57 (mt: 1H: the other H of CH₂ at position 3γ); from 1.60 to 1.85 (mt, 2H: CH₂ at position 2β); 1.73 (dd, J=16 and 6.5 Hz, 1H: 1H of CH₂ at position 5β); 2.05 (mt, 1H: the other H of CH₂ at position 3β); 2.49 (s, 3H: ArCH₃); 2.69 (s, 3H: ArNCH₃); 2.95 (dd, J=13.5 and 5.5 Hz, 1H: 1H of CH₂ at position 4β); from 3.15 to 3.30 (mt, 2H: the other H of CH₂ at position 4β and 1H of CH₂ at position 3δ); 3.16 (d, J=16 Hz, 1H: the other H of CH₂ at position 5β); 3.22 (s, 3H: NCH₃); 3.49 (mt, 1H: the other H of CH₂ at position 3β); 3.68 (unresolved complex, 1H: ArNH); 3.91 (d, J=17 Hz, 1H: 1H of CH₂ at position 5ε); 4.60 (dd, J=8 and 5.5 Hz, 1H: CH at position 3α); 4.79 (mt, 1H: CH at position 2α); 4.88 (dd, J=10 and 1.5 Hz, 1H: CH at position 1α); 5.21 (dd, J=10 and 5.5 Hz, 1H: CH at position 4α); 5.40 (d, J=17 Hz, 1H: the other H of CH₂ at position 5ε); 5.41 (broad d, J=5.5 Hz, 1H: CH at position 5α); 5.63 (d, J=8.5 Hz, 1H: CH at position 6α); 5.88 (dq, J=7 and 1.5 Hz, 1H: CH at position 1β); 6.23 (d, J=8 Hz, 2H: aromatic H at position 4ε); 6.58 (d, J=9.5 Hz, 1H: CONH at position 2); 6.81 (d, J=8 Hz, 2H: aromatic H at position 4δ); 6.96 (d, J=8 Hz, 1H: aromatic H at position β with respect to N); from 7.20 to 7.40 (mt: the 5 aromatic H at position 6α); 7.33 (d, J=8 Hz, 1H: aromatic H at position γ with respect to N); 7.40 (limiting AB, 2H: 1' H₄ and 1' H₅); 7.91 (mt, 1H: 1' H₆); 8.44 (d, J=10 Hz, 1H: CONH at position 1); 8.65 (d, J=8.5 Hz, 1H: CONH at position 6); 11.65 (s, 1H: OH).

EXAMPLE 20

1.7 g of 2"-chloromethylpyrido[2,3-5γ,5δ]-pristinamycin I$_E$ and 0.6 cm³ of morpholine are added successively to a three-necked flask containing 30 cm³ of tetrahydrofuran and then the mixture is refluxed. After 18 hours, an additional 0.3 cm³ of morpholine is added and 0.3 cm³ of triethylamine and then the reflux is maintained for 6 hours. The reaction mixture is then concentrated to dryness under reduced pressure at 40° C. at 2.7 kPa. The residue obtained is taken up in twice 50 cm³ of water and then the aqueous phase is extracted with twice 50 cm³ of dichloromethane. The organic phases are combined, dried over sodium sulphate, filtered and then concentrated to dryness to give 1.3 g of product which is purified by chromatography on 80 g of silica [eluent: dichloromethane/methanol gradient from 98/2 to 97.3 by volume] to give 0.3 g of a solid which is concreted in a mixture with 0.26 g of the same product obtained from another test, from 60 cm³ of an ether-petroleum ether mixture (20/80 by volume). After filtration and drying at 40° C. under reduced pressure (90 Pa), 0.3 g of 2"-(N-morpholinomethyl)pyrido-[2,3-5γ, 5δ]pristinamycin I$_E$ is obtained in the form of a yellow solid melting at 189° C.

¹H NMR spectrum (400 MHz, CDCl₃, δ in ppm): 0.92 (t, J=7.5 Hz, 3H: CH₃ at position 2γ); from 1.15 to 1.40 (mt, 2H: 1H of CH₂ at position 3β and 1H of CH₂ at position 3γ); 1.29 (d, J=7 Hz, 3H: CH₃ at position 1γ); from 1.50 to 1.70 (mt, the 2H corresponding to the other H of CH₂ at position 3γ and to 1H of CH₂ at position 2β); 1.75 (mt, 1H the other H of CH₂ at position 2β); 1.87 (dd, J=16 and 6 Hz, 1H: 1H of CH₂ at position 5β); 2.03 (mt, 1H the other H of CH₂ at position 3β); 2.50 (mt, 4H the 2 NCH₂ of morpholine); 2.87 (s, 6H ArN(CH₃)₂); 2.98 (dd, J=13.5 and 6 Hz, 1H: 1H of CH₂ at position 4β); from 3.10 to 3.35 (mt, 3H: the other H of CH₂ at position 5β—the other H of CH₂ at position 4β and 1H of CH₂ at position 3δ); 3.22 (s, 3H: NCH₃); 3.50 (mt, 1H: the other H of CH₂ at position 3δ); 3.59 (s, 2H:

ArCH$_2$N); 3.74 (mt, 4H: the 2 OCH$_2$ of morpholine); 3.94 (d, J=17 Hz, 1H: 1H of CH$_2$ at position 5ε); 4.60 (dd, J=8 and 5 Hz, 1H: CH at position 3α); 4.79 (mt, 1H: CH at position 2α); 4.88 (broad d, J=10 Hz, 1H: CH at position 1α); 5.29 (dd, J=9 and 6 Hz, 1H: CH at position 4α); 5.43 (mt, 1H: CH at position 5α); 5.45 (d, J=17 Hz, 1H: the other H of CH$_2$ at position 5ε) 5.63 (d, J=8.5 Hz, 1H: CH at position 6α); 5.90 (broad q, J=7 Hz, 1H: CH at position 1β); 6.36 (d, J=8 Hz, 2H: aromatic H at position 4ε); 6.58 (d, J=9.5 Hz, 1H: CONH at position 2); 6.85 (d, J=8 Hz, 2H: aromatic H at position 4δ); from 7.20 to 7.45 (mt: the 9H corresponding to the 5 aromatic H at position 6α—to the aromatic H at position β with respect to N—to the aromatic H at position γ with respect to N—to 1' H$_5$ and 1' H$_4$); 7.84 (broad d, J=4 Hz, 1H: 1' H$_6$); 8.43 (d, J=10 Hz, 1H: CONH at position 1); 8.70 (d, J=8.5 Hz, 1H: CONH at position 6); 11.66 (s, 1H: OH).

2"-Chloromethylpyrido[2,3-5γ,5δ]pristinamycin I$_E$ may be obtained as described in Example 10.

EXAMPLE 21

By carrying out the procedure as in Example 20 but starting with 50 cm$^3$ of tetrahydrofuran, 3.2 g of 2"-chloromethylpyrido[2,3-5γ,5δ]-pristinamycin I$_E$ and 1.1 cm$^3$ of N-methylpiperazine, 2.3 g of a solid are obtained after refluxing for 2 hours, which solid is purified by two successive chromatographies on 100 g of silica [eluent: dichloromethane/methanol 95/5 by volume] to give 0.4 g of 2"-(4-methyl-1-piperazinylmethyl)pyrido[2,3-5γ5δ]-pristinamycin I$_E$ in the form of a yellow solid melting at 221° C.

$^1$H NMR spectrum (400 MHz, CDCl$_3$, δ in ppm): 0.93 (t, J=7.5 Hz, 3H: CH$_3$ at position 2γ); from 1.20 to 1.40 (mt, 2H: 1H of CH$_2$ at position 3α and 1H of CH$_2$ at position 3γ); 1.31 (d, J=7 Hz, 3H: CH$_3$ at position 1γ); from 1.50 to 1.85 (mt: the 4H corresponding to the other H of CH$_2$ at position 3γ—to CH$_2$ at position 2βand to 1H of CH$_2$ at position 5β); 2.03 (mt, 1H: the other H of CH$_2$ at position 3β); 2.32 (s, 3H: NCH$_3$ of piperazine); from 2.40 to 2.70 (mt, 8H: the 4 NCH$_2$ of piperazine); 2.90 (s, 6H: ArN(CH$_3$)$_2$); 2.99 (dd, J=13.5 and 6 Hz, 1H: 1H of CH$_2$ at position 4β); from 3.15 to 3.35 (mt, 3H the other H of CH$_2$ at position 5β—the other H of CH$_2$ at position 4β and 1H of CH$_2$ at position 3δ); 3.22 (s, 3H: NCH$_3$); 3.50 (mt, 1H: the other H of CH$_2$ at position 3δ); 3.62 (s, 2H: ArCH$_2$N); 3.95 (d, J=17 Hz, 1H: 1H of CH$_2$ at position 5ε); 4.60 (dd, J=7.5 and 5.5 Hz, 1H CH at position 3α); 4.80 (mt, 1H: CH at position 2α); 4.89 (broad d, J=10 Hz, 1H: CH at position 1α); 5.28 (dd, J=9 and 6 Hz, 1H CH at position 4α); 5.51 (mt, 1H: CH at position 5α); 5.55 (d, J=17 Hz, 1H: the other H of CH$_2$ at position 5ε); 5.65 (d, J=8.5 Hz, 1H: CH at position 6α); 5.89 (broad q, J=7 Hz, 1H: CH at position 1β); 6.37 (d, J=8 Hz, 2H: aromatic H at position 4ε); 6.59 (d, J=9.5 Hz, 1H: CONH at position 2); 6.86 (d, J=8 Hz, 2H: aromatic H at position 4δ); from 7.20 to 7.45 (mt: the 9H corresponding to the 5 aromatic H at position 6α—to the aromatic H at position β with respect to N—to the aromatic H at position γ with respect to N—to 1' H$_5$ and 1' H$_4$); 7.87 (broad d, J=4 Hz, 1H: 1' H$_6$); 8.43 (d, J=10 Hz, 1H: CONH at position 1); 8.70 (d, J=8.5 Hz, 1H: CONH at position 6); 11.64 (unresolved complex, 1H: OH).

EXAMPLE 22

4.6 g of 5δ-dimethylaminomethylenepristinamycin I$_A$, 1.1 g of O-methylisourea hydrogen sulphate and 1.75 g of sodium bicarbonate are introduced into a three-necked flask containing 30 cm$^3$ of dimethylformamide. The mixture is heated at 65° C. for 18 hours. After cooling, 100 cm$^3$ of distilled water are added and the product is extracted with 3 times 100 cm$^3$ of ethyl acetate. The organic phases are combined, washed with 200 cm$^3$ of brine, dried over magnesium sulphate, filtered and concentrated to dryness at 40° C. under reduced pressure (2.7 kPa) to give 5.05 g of a yellow oil which is purified by chromatography on 90 g of silica [eluent: dichloromethane/methanol 97/3 by volume] to give 1.2 g of a solid. The solid obtained is purified by HPLC on 450 g of 10 μm C8 silica (eluent: phosphate buffer pH 2.9/acetonitrile: 60/40 by volume). The fractions are combined, the acetonitrile removed at 40° C. under reduced pressure (2.7 kPa) and the aqueous phase adjusted to pH 7 with water saturated with sodium bicarbonate and then extracted with dichloromethane. The organic phase is decanted off, dried over magnesium sulphate, filtered and concentrated at 40° C. under reduced pressure (2.7 kPa) to give a solid which is triturated in 10 cm$^3$ of diisopropyl ether. After filtration and drying at 40° C. (90 Pa), 0.40 g of 2"-methoxypyrimido[4,5–5γ,5δ]pristinamycin I$_E$ is obtained in the form of a white solid melting at 195–198° C.

$^1$H NMR spectrum (400 MHz, CDCl$_3$, δ in ppm): 0.91 (t, J=7.5 Hz, 3H: CH$_3$ at position 2γ); from 1.20 to 1.35 (mt, 3H: 1H of CH$_2$ at position 3β—1H of CH$_2$ at position 3γ and 1H of CH$_2$ at position 5β); 1.31 (d, J=7 Hz, 3H: CH$_3$ at position 1γ); 1.58 (mt, 1H: the other H of CH$_2$ at position 3γ); from 1.60 to 1.85 (mt, the 2H corresponding to CH$_2$ at position 2β); 2.05 (mt, 1H: the other H of CH$_2$ at position 3β); 2.85 (s, 6H: ArN(CH$_3$)$_2$); 2.91 (dd, J=12 and 4.5 Hz, 1H: 1H of CH$_2$ at position 4β); 2.93 (d, J=16.5 Hz, 1H: the other H of CH$_2$ at position 5β); from 3.15 to 3.30 (mt, 1H: 1H of CH$_2$ at position 3δ); 3.21 (t, J=12 Hz, 1H: the other H of CH$_2$ at position 4β); 3.25 (s, 3H: NCH$_3$); 3.50 (mt, 1H: the other H of CH$_2$ at position 3δ); 3.76 (d, J=17 Hz, 1H: 1H of CH$_2$ at position 5ε); 3.95 (s, 3H: ArOCH$_3$); 4.61 (dd, J=8 and 5.5 Hz, 1H: CH at position 3α); 4.80 (mt, 1H: CH at position 2α); 4.88 (dd, J=10 and 1.5 Hz, 1H: CH at position 1α); 5.07 (dd, J=12 and 4.5 Hz, 1H: CH at position 4α); 5.33 (broad d, J=5.5 Hz, 1H: CH at position 5α); 5.41 (d, J=17 Hz, 1H: the other H of CH$_2$ at position 5ε); 5.64 (d, J=8.5 Hz, 1H: CH at position 6α); 5.88 (split q, J=7 and 1.5 Hz, 1H: CH at position 1β); 6.33 (d, J=8 Hz, 2H: aromatic H at position 4ε); 6.51 (d, J=10 Hz, 1H: CONH at position 2); 6.85 (d, J=8 Hz, 2H: aromatic H at position 4δ); from 7.20 to 7.40 (mt: the 5 aromatic H at position 6α); 7.44 (dd, J=8.5 and 1.5 Hz, 1H: 1' H$_4$); 7.49 (dd, J=8.5 and 4 Hz, 1H: 1' H$_5$); 7.94 (dd, J=4 and 1.5 Hz, 1H: 1' H$_6$); 8.16 (s, 1H: CH=N); 8.37 (d, J=10 Hz, 1H: CONH at position 1); 8.69 (d, J=8.5 Hz, 1H: CONH at position 6); 11.63 (s, 1H: OH).

EXAMPLE 23

By carrying out the procedure as in Example 22 but starting with 12 cm$^3$ of dimethylformamide, 2.76 g of 5δ-dimethylaminomethylenepristinamycin I$_A$, 0.54 g of S-methylisothiouronium sulphate and 0.35 g of sodium bicarbonate and after 4 hours at 65° C., 2.5 g of a yellow solid are obtained after cooling, addition of 100 cm$^3$ of ethyl acetate to the reaction mixture, washing of the organic phase with 3 times 80 cm$^3$ of water, decantation of the organic phase which is dried over magnesium sulphate, filtered and concentrated to dryness at 40° C. under reduced pressure (2.7 kPa). The solid is chromatographed on 200 g of silica [eluent: dichloromethane/methanol 95/5 by volume] to give 1.9 g of a solid which is purified by HPLC on 450 g of 10 μm C$_8$ silica [eluent: water-acetonitrile 35–65 by volume containing 0.1% trifluoroacetic acid]. The fractions are combined, the acetonitrile removed at 40° C. under reduced pressure (2.7 kPa) and the aqueous phase adjusted to pH 7–8 with water saturated with sodium bicarbonate. The white precipitate formed is filtered, washed with twice 5 cm³ of diisopropyl ether and dried at 40° C. under 90 Pa to give 0.7 g of 2"-methylthiopyrimido[4,5-5γ,5δ]-pristinamycin $I_E$ in the form of a cream-coloured solid melting at 197° C.

1H NMR spectrum (400 MHz, CDCl₃, δ in ppm): 0.91 (t, J=7.5 Hz, 3H: CH₃ at position 2γ); from 1.15 to 1.40 (mt, 3H: 1H of CH₂ at position 3β—1H of CH₂ at position 3γ and 1H of CH₂ at position 5β); 1.31 (d, J=7 Hz, 3H: CH₃ at position 3γ); 1.59 (mt, 1H: the other H of CH₂ at position 3γ); 1.67 and 1.76 (2 mts, 1H each: CH₂ at position 2β); 2.06 (mt, 1H: the other H of CH₂ at position 3β); 2.52 (s, 3H: ArSCH₃); from 2.80 to 3.00 (mt, 2H: 1H of CH₂ at position 4β and the other H of CH₂ at position 5β); 2.88 (s, 6H: ArN(CH₃)₂); from 3.15 to 3.35 (mt, 2H: 1H of CH₂ at position 3δ and the other H of CH₂ at position 4β); 3.26 (s, 3H: NCH₃); 3.50 (mt, 1H: the other H of CH₂ at position 3δ); 3.77 (d, J=17 Hz, 1H: 1H of CH₂ at position 5ε); 4.61 (dd, J=8 and 5.5 Hz, 1H: CH at position 3α); 4.80 (mt, 1H: CH at position 2α); 4.89 (broad d, J=10 Hz, 1H: CH at position 1α); 5.06 (dd, J=12 and 4.5 Hz, 1H: CH at position 4α); 5.32 (broad d, J=5.5 Hz, 1H: CH at position 5α); 5.41 (d, J=17 Hz, 1H: the other H of CH₂ at position 5ε); 5.65 (d, J=8.5 Hz, 1H: CH at position 6α); 5.88 (broad q, J=7 Hz, 1H: CH at position 1β); 6.35 (d, J=8 Hz, 2H: aromatic H at position 4ε); 6.52 (d, J=10 Hz, 1H: CONH at position 2); 6.86 (d, J=8 Hz, 2H: aromatic H at position 4δ); from 7.20 to 7.40 (mt: the 5 aromatic H at position 6α); 7.47 (broad d, J=8,5 Hz, 1H: 1' H₄); 7.52 (dd, J=8.5 and 4 Hz, 1H 1' H₅); 7.96 (broad d, J=4 Hz, 1H: 1' H₆); 8.18 (s, 1H: CH═N); 8.38 (d, J=10 Hz, 1H: CONH at position 1); 8.70 (d, J=8.5 Hz, 1H: CONH at position 6); 11.64 (s, 1H: OH).

EXAMPLE 24

16.2 g of 2"-methylthiopyrimido[4,5-5γ,5δ]-pristinamycin $I_E$ at 95% purity are introduced into a three-necked flask containing 130 cm³ of methanol and then 551 cm³ of 0.5 N sulphuric acid are added at 4° C. followed by 19.94 g of Oxone® over 6 minutes. The mixture is stirred for 2 hours at 4° C. and then for 18 hours at room temperature. The reaction mixture is cooled to 4° C., diluted with 150 cm³ of dichloromethane and then the pH adjusted to 3 with a dilute sodium hydroxide solution. The aqueous phase is decanted off and then washed with twice 100 cm³ of dichloromethane. The organic phases are combined, washed with 50 cm³ of a saturated sodium chloride solution, dried and concentrated under reduced pressure (2.7 kPa) so as to obtain a final volume of 200 cm³. To the chloromethylene solution obtained, placed in a three-necked flask, there are added 100 cm³ of distilled water and, with vigorous stirring, 3 cm³ of a 50% (w/v) solution of sodium bisulphite and then a saturated sodium bicarbonate solution up to pH 6. After decantation, the aqueous phase is washed with twice 100 cm³ of dichloromethane. The organic phases are combined, dried over sodium sulphate, filtered and concentrated to dryness at 40° C. under reduced pressure (2.7 kPa) to give 15.3 g of a solid which is purified by flash chromatography [eluent: dichloromethane/methanol 95/5 by volume]. 10.2 g of product are thus obtained in the form of a yellow solid, which solid may be used as it is.

An analytical sample may be obtained by purification by flash chromatography [eluent: dichloromethane/methanol 98/2 by volume] of 0.6 g of product. After concentration of the fractions at 40° C. under reduced pressure (2.7 kPa), trituration in 5 cm³ of diethyl ether, filtration and drying at 50°C. (90 Pa), 0.35 g of 2"-methylsulphonylpyrimido-[4,5-5γ,5δ]pristinamycin $I_E$ is obtained in the form of a pale-yellow solid melting at 214° C.

¹H NMR spectrum (400 MHz, CDCl₃, δ in ppm): 0.92 (t, J=7.5 Hz, 3H: CH₃ at position 2γ); from 1.25 to 1.40 (mt, 2H: 1H of CH₂ at position 3β-1H of CH₂ at position 3γ); 1.32 (d, J=7 Hz, 3H: CH₃ at position 1γ); 1.44 (dd, J=17 and 5.5 Hz, 1H: 1H of CH₂ at position 5β); from 1.55 to 1.85 (mt: the 3H corresponding to CH₂ at position 2β and the other H of CH₂ at position 3γ); 2.08 (mt, 1H: the other H of CH₂ at position 3β); 2.86 (s, 6H: ArN(CH₃)₂); 2.95 (dd, J=12 and 4.5 Hz, 1H: 1H of CH₂ at position 4β); 3.11 (d, J=17 Hz, 1H: the other H of CH₂ at position 5β); 3.20 (t, J=12 Hz, 1H: the other H of CH₂ at position 4β); from 3.20 to 3.35 (mt, 1H: 1H of CH₂ at position 3δ); 3.27 (s, 6H: NCH₃ and ArSO₂CH₃); 3.51 (mt, 1H: the other H of CH₂ at position 3δ); 3.87 (d, J=17 Hz, 1H: 1H of CH₂ at position 5ε); 4.61 (dd, J=7.5 and 6 Hz, 1H: CH at position 3α); 4.81(mt, 1H: CH at position 2α); 4.91 (broad d, J=10 Hz, 1H: CH at position 1α); 5.11 (dd, J=12 and 4.5 Hz, 1H: CH at position 4α); 5.42 (broad d, J=5.5 Hz, 1H: CH at position 5α); 5.54 (d, J=17 Hz, 1H: the other H of CH₂ at position 5ε); 5.63 (d, J=8.5 Hz, 1H: CH at position 6α); 5.88 (broad q, J=7 Hz, 1H CH at position 1β); 6.34 (d, J=8 Hz, 2H: aromatic H at position 4ε); 6.56 (d, J=10 Hz, 1H: CONH at position 2); 6.87 (d, J=8 Hz, 2H: aromatic H at position 4δ); from 7.20 to 7.40 (mt: the 5 aromatic H at position 6α); 7.49 (broad d, J=8,5 Hz, 1H: 1' H₄); 7.54 (dd, J=8.5 and 4 Hz, 1H: 1' H₅); 7.98 (broad d, J=4 Hz, 1H: 1' H₆); 8.41 (d, J=10 Hz, 1H: CONH at position 1); 8.53 (s, 1H: CH═N); 8.84 (d, J=8.5 Hz, 1H: CONH at position 6); 11.65 (s, 1H: OH).

EXAMPLE 25

1.9 cm³ of pyrrolidine are introduced into a three-necked flask containing 25 cm³ of dioxane and 2 g of 2"-(4-methylbenzylsulphonyl)pyrimido[4,5-5γ,5δ]-pristinamycin $I_E$ and then the mixture is heated at 90° C. for 3 hours. After concentrating the reaction mixture to dryness at 40° C. under reduced pressure (2.7 kPa), the residue obtained is chromatographed on 150 g of silica [eluent: dichloromethane/methanol 96/4 by volume] to give 0.46 g of a cream-coloured solid which is recrystallized from 10 cm³ of methanol. The crystals are filtered, rinsed with a minimum of methanol and then dried at 40° C. under reduced pressure (90 Pa) to give 0.32 g of 2"-(1-pyrrolidinyl)pyrimido[4,5-5γ, 5δ]-pristinamycin $I_E$ in the form of white crystals melting at 255° C.

¹H NMR spectrum (400 MHz, CDCl₃, δ in ppm): 0.92 (t, J=7.5 Hz, 3H: CH₃ at position 2γ); from 1.20 to 1.40 (mt, 3H: 1H of CH₂ at position 3β—1H of CH₂ at position 3γ and 1H of CH₂ at position 5β); 1.29 (d, J=7 Hz, 3H: CH₃ at position 1γ); 1.56 (mt, 1H: the other H of CH₂ at position 3γ); from 1.60 to 1.85 (mt: the 2H corresponding to CH₂ at position 2β); 1.93 (mt, 4H: the 2 CH₂ of pyrrolidine); 2.03 (mt, 1H: the other H of CH₂ at position 3β); 2.86 (s, 6H: ArN(CH₃)₂); 2.88 (d, J=17.5 Hz, 1H: the other H of CH₂ at position 5β); 2.94 (dd, J=12 and 4.5 Hz, 1H: 1H of CH₂ at position 4β); from 3.15 to 3.30 (mt, 2H: the other H of CH₂ at position 4β and 1H of CH₂ at position 3δ); 3.23 (s, 3H: NCH₃); from 3.45 to 3.60 (mt, 1H: the other H of CH₂ at position 3δ); 3.53 (mt, 4H: the 2 NCH₂ of pyrrolidine); 3.74 (d, J=17 Hz, 1H: 1H of CH₂ at position 5ε); 4.61 (dd, J=8 and 7 Hz, 1H: CH at position 3α); 4.78 (mt, 1H: CH at position 2α); 4.86 (broad d, J=10 Hz, 1H: CH at position 1α); 5.11 (dd, J=12 and 4.5 Hz, 1H: CH at position 4α); 5.29 (d, J=17 Hz, 1H: the other H of CH₂ at position 5ε); 5.31 (mt, 1H: CH at position 5α); 5.62 (d, J=8.5 Hz, 1H: CH at position 6α); 5.87 (broad q, J=7 Hz, 1H: CH at position 1β);

6.38 (d, J=8 Hz, 2H: aromatic H at position 4ε); 6.55 (d, J=9.5 Hz, 1H: CONH at position 2); 6.86 (d, J=8 Hz, 2H: aromatic H at position 4δ); from 7.20 to 7.40 (mt: the 5 aromatic H at position 6α); 7.43 (limiting AB, 2H: 1' H$_4$ and 1' H$_5$); 7.91 (mt, 1H: 1' H$_6$); 7.99 (s, 1H: CH=N); 8.39 (d, J=10 Hz, 1H: CONH at position 1); 8.62 (d, J=8.5 Hz, 1H: CONH at position 6); 11.64 (s, 1H: OH).

2"-(4-Methylbenzylsulphonyl)pyrimido-[4,5-5γ, 5δ]pristinamycin I$_E$ may be prepared in the following manner:

1 liter of 1 N sulphuric acid is added to a three-necked flask containing 800 cm³ of methanol and 24.6 g of 2"-(4-methylbenzylthio)pyrimido[4,5-5γ, 5δ]-pristinamycin I$_E$. The mixture is cooled to 0° C. and then 28.4 g of Oxone® are added. The stirring is maintained for 18 hours at room temperature and then the mixture is neutralized by slow addition of sodium bicarbonate so as to obtain a pH of 8 and then extracted with 3 times 1 liter of dichloromethane. The organic phases are combined, dried over magnesium sulphate, filtered and concentrated to dryness at 45° C. under reduced pressure (2.7 kPa) to give 30 g of a solid which is chromatographed on 1.2 kg of silica [eluent: dichloromethane/methanol/acetic acid, 89/10/1 by volume]. After concentration to dryness at 45° C. under reduced pressure (2.7 kPa) of the fractions, the product is triturated in 100 cm³ of diethyl ether, filtered and dried at 40° C. under reduced pressure (90 Pa). 21.7 g of 2"-(4-methylbenzylsulphonyl)-pyrimido[4,5-5γ,5δ](4ζ-dimethylamino N oxide)-(4ζ-dedimethylamino) pristinamycin I$_E$ are thus obtained in the form of a pale-yellow solid melting at 247° C.

¹H NMR spectrum (400 MHz, CDCl$_3$, δ in ppm): 0.91 (t, J=7.5 Hz, 3H: CH$_3$ at position 2γ); 0.99 (dd, J=17 and 5.5 Hz, 1H: 1H of CH$_2$ at position 5β); 1.14 (mt, 1H: 1H of CH$_2$ at position 3β); 1.44 (mt, 1H: 1H of CH$_2$ at 3γ); 1.32 (d, J=7 Hz, 3H: CH$_3$ at position 1γ); from 1.55 to 1.75 (mt, 3H: CH$_2$ at position 2β and the other H of CH$_2$ at position 3γ); 2.07 (mt, 1H: the other H of CH$_2$ at position 3β); 2.28 (s, 3H: ArCH$_3$); 3.10 (dd, J=12 and 4 Hz, 1H: 1H of CH$_2$ at position 4β); 3.17 (d, J=17 Hz, 1H: the other H of CH$_2$ at position 5β); 3.24 (s, 3H: NCH$_3$); 3.27 (t, J=12 Hz, 1H: the other H of CH$_2$ at position 4β); 3.47 and 3.58 (2 mts, 1H each: CH$_2$ at position 3δ); 3.58 and 3.73 (2 s, 3H each: ArN(CH$_3$)$_2$); 3.81 (d, J=17 Hz, 1H: 1H of CH$_2$ at position 5ε); 4.55 (mt, 1H: CH at position 3α); 4.58 and 4.79 (2 d, J=14 Hz, 1H each: O$_2$SCH$_2$Ar); 4.84 (mt, 1H: CH at position 2α); 4.92 (broad d, J=10 Hz, 1H: CH at position 1α); 5.31 (dd, J=12 and 4 Hz, 1H: CH at position 4α); 5.36 (broad d, J=5.5 Hz, 1H: CH at position 5α); 5.60 (d, J=17 Hz, 1H: the other H of CH$_2$ at position 5ε); 5.70 (d, J=8.5 Hz, 1H: CH at position 6α); 5.88 (broad q, J=7 Hz, 1H: CH at position 1β); 6.83 (d, J=9 Hz, 1H CONH at position 2); 7.08 (d, J=8 Hz, 2H: aromatic H at the ortho position with respect to CH$_3$); 7.11 (d, J=8 Hz, 2H: aromatic H at position 4δ); 7.19 (d, J=8 Hz, 2H: aromatic H at the meta position with respect to CH$_3$); from 7.20 to 7.40 (mt: the 5 aromatic H at position 6α); 7.47 (broad d, J=8.5 Hz, 1H: 1' H$_4$); 7.62 (d, J=8 Hz, 2H: aromatic H at position 4ε); 7.72 (dd, J=8.5 and 4.5 Hz, 1H: 1' H$_5$); 7.85 (mt, 1H: 1' H6); 8.41 (d, J=10 Hz, 1H: CONH at position 1); 8.55 (s, 1H: CH=N); 8.75 (d, J=8.5 Hz, 1H CONH at position 6); 11.65 (broad unresolved complex, 1H: OH).

4.8 g of 2"-(4-methylbenzylsulphonyl)-pyrimido[4,5-5γ, 5δ](4ζ-dimethylamino N oxide)-(4ζ-dedimethylamino) pristinamycin I$_E$ and 0.4 g of iron powder are introduced into a three-necked flask containing 50 cm³ of glacial acetic acid. The mixture is heated for 2 minutes at 60° C., cooled, neutralized by addition of a 10% solution of sodium bicarbonate and then extracted with 100 cm³ of dichloromethane. The organic phases are combined, dried over sodium sulphate, filtered and concentrated to dryness at 40° C. under reduced pressure (2.7 kPa) to give 4.35 g of a chestnut-coloured solid which is recrystallized from 50 cm³ of hot isopropanol. After filtration, washing of the crystals with 10 cm³ of diisopropyl ether and drying at 40° C. under reduced pressure (90 kPa), 2.06 g of 2"-(4-methylbenzylsulphonyl) pyrimido[4,5-5γ,5δ]-pristinamycin I$_E$ are obtained in the form of a beige solid melting at 188° C.

¹H NMR spectrum (400 MHz, CDCl$_3$, δ in ppm): 0.91 (t, J=7.5 Hz, 3H: CH$_3$ at position 2γ); from 1.20 to 1.40 (mt, 2H: 1H of CH$_2$ at position 3β and 1H of CH$_2$ at position 3γ); 1.31 (d, J=7 Hz, 3H: CH$_3$ at position 1γ); 1.45 (dd, J=17 and 5.5 Hz, 1H: 1H of CH$_2$ at position 5β); from 1.55 to 1.75 (mt: the 2H corresponding to 1H of CH$_2$ at position 2β and the other H of CH$_2$ at position 3γ); 1.74 (mt, 1H: the other H of CH$_2$ at position 2β); 2.08 (mt, 1H: the other H of CH$_2$ at position 3β); 2.30 (s, 3H: ArCH$_3$); 2.81 (s, 6H: ArN(CH$_3$)$_2$); 2.95 (dd, J=12 and 4.5 Hz, 1H: 1H of CH$_2$ at position 4β); 3.01 (d, J=17 Hz, 1H: the other H of CH$_2$ at position 5β); 3.19 (t, J=12 Hz, 1H: the other H of CH$_2$ at position 4β); from 3.20 to 3.35 (mt, 1H: 1H of CH$_2$ at position 3δ); 3.26 (s, 3H: NCH$_3$); 3.51 (mt, 1H: the other H of CH$_2$ at position 3δ); 3.88 (d, J=17 Hz, 1H: 1H of CH$_2$ at position 5ε); 4.50 and 4.74 (2 d, J=14 Hz, 1H each: O$_2$SCH$_2$Ar); 4.61 (dd, J=7.5 and 6 Hz, 1H: CH at position 3α); 4.80 (mt, 1H: CH at position 2α); 4.90 (broad d, J=10 Hz, 1H: CH at position 1α); 5.08 (dd, J=12 and 4.5 Hz, 1H: CH at position 4α); 5.40 (broad d, J=5.5 Hz, 1H: CH at position 5α); 5.54 (d, J=17 Hz, 1H: the other H of CH$_2$ at position 5ε); 5.66 (d, J=8.5 Hz, 1H: CH at position 6α); 5.89 (broad q, J=7 Hz, 1H: CH at position 1β); 6.29 (d, J=8 Hz, 2H: aromatic H at position 4ε); 6.53 (d, J=10 Hz, 1H: CONH at position 2); 6.84 (d, J=8 Hz, 2H: aromatic H at position 4δ); 7.12 (d, J=8 Hz, 2H: aromatic H at the ortho position with respect to CH$_3$); from 7.10 to 7.35 (mt: the 5 aromatic H at position 6α); 7.20 (d, J=8 Hz, 2H: aromatic H at the meta position with respect to CH$_3$); 7.48 (broad d, J=8.5 Hz, 1H: 1' H$_4$); 7.53 (dd, J=8.5 and 4 Hz, 1H: 1' H$_5$); 7.96 (broad d, J=4 Hz, 1H: 1' H$_6$); 8.39 (d, J=10 Hz, 1H: CONH at position 1); 8.50 (s, 1H: CH=N); 8.80 (d, J=8.5 Hz, 1H: CONH at position 6); 11.64 (s, 1H: OH).

2"-(4-Methylbenzylthio)pyrimido[4,5-5γ,5δ]-pristinamycin I$_E$ May Be Prepared in the Following Manner 4.3 g of 5δ-dimethylaminomethylene-pristinamycin I$_A$, 1 g of (4-methylbenzyl)isothiourea hydrochloride are introduced into a three-necked flask containing 35 cm³ of dimethylformamide and then 1.8 cm³ of N,N-diisopropylamine are added dropwise. The mixture is heated for 3 hours at 60° C., cooled and then diluted with 200 cm³ of distilled water. The precipitate formed is filtered to give 1 g of product which is purified by HPLC on 450 g of 10 μm C$_8$ silica [eluent: water-acetonitrile 50/50 by volume containing 0.1% trifluoroacetic acid]. The fractions are combined, the acetonitrile removed at 40° C. under reduced pressure (2.7 kPa) and the aqueous phase adjusted to pH 7–8 with water saturated with sodium bicarbonate. The mixture is extracted with 3 times 80 cm³ of dichloromethane, the organic phases are combined, dried over magnesium sulphate, filtered, concentrated to dryness and then dried at 40° C. under reduced pressure (90 Pa) to give 1.09 g of 2"-(4-methylbenzylthio)pyrimido-[4,5-5γ,5δ]pristinamycin I$_E$ in the form of a cream-coloured solid melting at 222° C.

¹H NMR spectrum (400 MHz, CDCl$_3$, δ in ppm): 0.91 (t, J=7.5 Hz, 3H: CH$_3$ at position 2γ); from 1.15 to 1.35 (mt, 3H: 1H of $CH_2$ at position 3β—1H of $CH_2$ at position 3γ and 1H of $CH_2$ at position 5β); 1.31 (d, J=7 Hz, 3H: $CH_3$ at position 1γ); from 1.55 to 1.80 (mt: the 2H corresponding to $CH_2$ at position 2β) 1.59 (mt, 1H: the other H of $CH_2$ at position 3γ); 2.05 (mt, 1H: the other H of $CH_2$ at position 3β) 2.32 (s, 3H: $ArCH_3$); 2.86 (s, 6H: $ArN(CH_3)_2$); 2.91 (dd, J=12 and 4 Hz, 1H: 1H of $CH_2$ at position 4β); 2.94 (d, J=17.5 Hz, 1H: the other H of $CH_2$ at position 5β); from 3.15 to 3.30 (mt, 1H: 1H of $CH_2$ at position 3δ); 3.21 (t, J=12 Hz, 1H: the other H of $CH_2$ at position 4β) 3.25 (s, 3H, $NCH_3$); 3.50 (mt, 1H: the other H of $CH_2$ at position 3δ); 3.76 (d, J=17 Hz, 1H: 1H of $CH_2$ at position 5ε); 4.27 and 4.39 (2 d, J=13.5 Hz, 1H each: $ArSCH_2Ar$); 4.61 (dd, J=7.5 and 5.5 Hz, 1H: CH at position 3α); 4.79 (mt, 1H: CH at position 2α); 4.88 (broad d, J=10 Hz, 1H: CH at position 1α); 5.07 (dd, J=12 and 4 Hz, 1H: CH at position 4α); 5.32 (broad d, J=5.5 Hz, 1H: CH at position 5α); 5.39 (d, J=17 Hz, 1H: the other H of $CH_2$ at position 5ε); 5.64 (d, J=8.5 Hz, 1H: CH at position 6α); 5.87 (broad q, J=7 Hz, 1H: CH at position 1β); 6.33 (d, J=8 Hz, 2H: aromatic H at position 4ε); 6.53 (d, J=10 Hz, 1H: CONH at position 2); 6.84 (d, J=8 Hz, 2H: aromatic H at position 4δ); 7.11 (d, J=8 Hz, 2H: aromatic H at the ortho position with respect to $CH_3$); from 7.15 to 7.40 (mt: the 5 aromatic H at position 6α); 7.32 (d, J=8 Hz, 2H: aromatic H at the meta position with respect to the $CH_3$); 7.44 (broad d, J=8.5 Hz, 1H: 1' $H_4$); 7.48 (dd, J=8.5 and 4 Hz, 1H: 1' $H_5$); 7.93 (broad d, J=4 Hz, 1H: 1' $H_6$); 8.19 (s, 1H: CH=N); 8.38 (d, J=10 Hz, 1H: CONH at position 1); 8.70 (d, J=8.5 Hz, 1H: CONH at position 6); 11.63 (s, 1H: OH).

EXAMPLE 26

By carrying out the procedure as in Example 25 but starting with 40 cm³ of dioxane, 2 g of 2"-(4-methylbenzylsulphonyl)pyrimido[4,5-5γ,5δ]-pristinamycin $I_E$, 1.02 cm³ of azetidine and after heating for 45 minutes at 60° C., a precipitate is obtained after cooling which is filtered, washed with 10 cm³ of diisopropyl ether and then recrystallized from 15 cm³ of methanol to give after filtration, drying at 40° C. under reduced pressure (90 Pa), 1.05 g of 2"-(1-azetidinyl)pyrimido[4,5-5γ,5δ]pristinamycin $I_E$ in the form of a white powder melting at 243° C.

¹H NMR spectrum (400 MHz, $CDCl_3$, δ in ppm): 0.92 (t, J=7.5 Hz, 3H: $CH_3$ at position 2γ); from 1.15 to 1.35 (mt, 3H: 1H of $CH_2$ at position 3β—1H of $CH_2$ at position 3γ and 1H of $CH_2$ at position 5β): 1.29 (d, J=7 Hz, 3H: $CH_3$ at position 1γ); 1.56 (mt, 1H: the other H of $CH_2$ at position 3γ); 1.65 and 1.72 (2 mts, 1H each: $CH_2$ at position 2β); 2.05 (mt, 1H: the other H of $CH_2$ at position 3β) 2.33 (mt, 2H: $CH_2$ of azetidine); 2.86 (d, J=17.5 Hz, 1H: the other H of $CH_2$ at position 5β); 2.88 (s, 6H: $ArN(CH_3)_2$); 2.92 (dd, J=12 and 4.5 Hz, 1H: 1H of $CH_2$ at position 4β); from 3.10 to 3.35 (mt, 2H: the other H of $CH_2$ at position 4β and 1H of $CH_2$ at position 3δ); 3.22 (s, 3H: $NCH_3$); 3.48 (mt, 1H: the other H of $CH_2$ at position 3δ); 3.72 Hz (d, J=17 Hz, 1H: 1H of $CH_2$ at position 5ε); 4.09 (mt, 4H: the 2 $NCH_2$ of azetidine); 4.59 (dd, J=8 and 6 Hz, 1H: CH at position 3α); 4.78 (mt, 1H: CH at position 2α); 4.88 (broad d, J=10 Hz, 1H: CH at position 1α); 5.12 (dd, J=12 and 4.5 Hz, 1H: CH at position 4α); 5.29 (d, J=17 Hz, 1H: the other H of $CH_2$ at position 5ε); 5.31 (broad d, J=6 Hz, 1H: CH at position 5α); 5.62 (d, J=8.5 Hz, 1H: CH at position 6α); 5.87 (broad q, J=7 Hz, 1H: CH at position 1β); 6.40 (d, J=8 Hz, 2H: aromatic H at position 4ε); 6.55 (d, J=9.5 Hz, 1H: CONH at position 2); 6.87 (d, J=8 Hz, 2H: aromatic H at position 4δ); from 7.15 to 7.35 (mt: the 5 aromatic H at position 6α); 7.42 (limiting AB, 2H: 1' $H_4$ and 1' $H_5$); 7.90 (mt, 1H: 1' $H_6$); 7.97 (s, 1H: CH=N); 8.40 (d, J=10 Hz, 1H: CONH at position 1); 8.63 (d, J=8.5 Hz, 1H: CONH at position 6).

EXAMPLE 27

By carrying out the procedure as in Example 22 but starting with 5 cm³ of dimethylformamide, 1.84 g of 5δ-dimethylaminomethylenepristinamycin $I_A$, 0.41 g of 4-amidinopyridinium hydrochloride, 0.235 g of sodium bicarbonate and heating for 4 hours at 65° C., a solution is obtained after cooling which is diluted with 40 cm³ of ethyl acetate and 50 cm³ of distilled water. After decantation, the aqueous phase is washed with twice 40 cm³ of ethyl acetate, the organic phases are pooled and then washed with 200 cm³ of brine, dried over magnesium sulphate, filtered and concentrated at 40° C. under reduced pressure (2.7 kPa) to give a residue which is chromatographed on 90 g of silica [eluent: dichloromethane/methanol 96/4 by volume]. 0.535 g of a product is obtained which is purified with 1.37 g of an identical product obtained by a similar preparation by HPLC on 450 g of 10 μm $C_8$ silica [eluent: water-acetonitrile 35/65 by volume containing 0.1% trifluoroacetic acid]. The fractions are combined, the acetonitrile removed at 40° C. under reduced pressure (2.7 kPa) and the aqueous phase adjusted to pH 7–8 with water saturated with sodium bicarbonate. The mixture is extracted with 3 times 100 cm³ of dichloromethane, the organic phases are combined, dried over magnesium sulphate, filtered, concentrated to dryness and then dried at 40° C. under reduced pressure 90 Pa) to give 0.73 g of a white solid which is triturated in 10 cm³ of diisopropyl ether, filtered and dried at 40° C. (90 Pa). 0.67 g of 2"-(4-pyridyl)pyrimido[4,5-5γ,5δ]-pristinamycin $I_E$ is thus obtained in the form of a white solid melting at 277° C.

¹H NMR spectrum (400 MHz, $CDCl_3$, δ in ppm): 0.92 (t, J=7.5 Hz, 3H: $CH_3$ at position 2γ); from 1.20 to 1.40 (mt, 2H: 1H of $CH_2$ at position 3β and 1H of $CH_2$ at position 3γ); 1.31 (d, J=7 Hz, 3H: $CH_3$ at position 1γ); 1.41 (dd, J=17 and 6 Hz, 1H: 1H of $CH_2$ at position 5β); 1.60 (mt, 1H: the other H of $CH_2$ at position 3γ); from 1.60 to 1.85 (mt: the 2H corresponding to $CH_2$ at position 2β); 2.07 (mt, 1H: the other H of $CH_2$ at position 3β); 2.63 (s, 6H: $ArN(CH_3)_2$); 2.92 (dd, J=12 and 4 Hz, 1H: 1H of $CH_2$ at position 4β); 3.10 (d, J=17 Hz, 1H: the other H of $CH_2$ at position 5β); from 3.20 to 3.35 (mt, 2H: 1H of $CH_2$ at position 3δ and the other H of $CH_2$ at position 4β); 3.27 (s, 3H: $NCH_3$); 3.51 (mt, 1H: the other H of $CH_2$ at position 3δ); 3.88 (d, J=17 Hz, 1H: 1H of $CH_2$ at position 5ε); 4.61 (dd, J=7.5 and 6 Hz, 1H: CH at position 3α); 4.80 (mt, 1H: CH at position 2α); 4.88 (broad d, J=10 Hz, 1H: CH at position 1α); 5.06 (dd, J=12 and 4 Hz, 1H: CH at position 4α); 5.41 (broad d, J=6 Hz, 1H: CH at position 5α); 5.52 (d, J=17 Hz: the other H of $CH_2$ at position 5ε); 5.64 (d, J=8.5 Hz, 1H: CH at position 6α); 5.88 (broad q, J=7 Hz, 1H: CH at position 1β); 6.38 (d, J=8 Hz, 2H: aromatic H at position 4ε); 6.54 (d, J=10 Hz, 1H: CONH at position 2); 6.86 (d, J=8 Hz, 2H: aromatic H at position 4δ); from 7.20 to 7.40 (mt: the 5 aromatic H at position 6α); 7.49 (broad d, J=8.5 Hz, 1H: 1'$H_4$); 7.57 (dd, J=8.5 and 4 Hz, 1H: 1' $H_5$); 8.04 (broad d, J=4 Hz, 1H: 1' $H_6$); 8.27 (d, J=5 Hz, 2H: aromatic H at position β of pyridine); 8.38 (d, J=10 Hz, 1H: CONH at position 1); 8.48 (s, 1H: CH=N; 8.72 (d, J=8.5 Hz, 1H: CONH at position 6); 8.75 (d, J=5 Hz, 2H: aromatic H at position α of pyridine); 11.66 (s, 1H: OH).

EXAMPLE 28

6 g of 5δ-dimethylaminomethylenepristinamycin $I_A$, 1.33 g of 2-amidinopyridinium hydrochloride are introduced into a three-necked flask containing 35 cm³ of dimethylformamide and then 3.4 cm³ of N,N-diiso-propylamine are added dropwise. The mixture is heated for 4 hours at 65° C., cooled and then diluted with 500 cm³ of distilled water saturated with sodium chloride. The precipitate formed is filtered and then taken up in 300 cm³ of dichloromethane. The solution obtained is dried over sodium sulphate, filtered and concentrated to dryness under reduced pressure at 40° C. (2.7 kPa) to give 4.36 g of a product which is purified by chromatography on 220 g of silica [eluent: dichloromethane/methanol 95/5 by volume]. After concentrating the fractions to dryness under reduced pressure at 40° C. (2.7 kPa), 3.15 g of a solid are obtained, which solid is recrystallized from 20 cm³ of isopropanol. The crystals are filtered, washed with 20 cm³ of diisopropyl ether and then dried at 40° C. (90 Pa) to give 1.08 g of 2"-(2-pyridyl)pyrimido[4,5-5γ,5δ]pristinamycin $I_E$ in the form of a white powder melting at 214° C.

¹H NMR spectrum (400 MHz, CDCl₃, δ in ppm): 0.92 (t, J=7.5 Hz, 3H: $CH_3$ at position 2γ); from 1.15 to 1.35 (mt, 2H: 1H of $CH_2$ at position 3β and 1H of $CH_2$ at position 3γ); 1.31 (d, J=7 Hz, 3H: $CH_3$ at position 1γ); 1.51 (dd, J=17 and 6 Hz, 1H: 1H of $CH_2$ at position 5β); from 1.55 to 1.80 (mt: the 2H corresponding to $CH_2$ at position 2β); 1.59 (mt, 1H: the other H of $CH_2$ at position 3γ); 2.06 (mt, 1H: the other H of $CH_2$ at position 3β); 2.64 (s, 6H: $ArN(CH_3)_2$); 2.93 (dd, J=12 and 4.5 Hz, 1H: 1H of $CH_2$ at position 4β); 3.13 (d, J=17 Hz, 1H: the other H of $CH_2$ at position 5β); from 3.15 to 3.30 (mt, 1H: 1H of $CH_2$ at position 3δ); 3.22 (t, J=12 Hz, 1H: the other H of $CH_2$ at position 4β); 3.26 (s, 3H: $NCH_3$); 3.51 (mt, 1H: the other H of $CH_2$ at position 3δ); 3.89 (d, J=17 Hz, 1H: 1H of $CH_2$ at position 5ε); 4.60 (dd, J=8 and 6 Hz, 1H: CH at position 3α); 4.80 (mt, 1H: CH at position 2α); 4.90 (broad d, J=10 Hz, 1H: CH at position 1α); 5.12 (dd, J=12 and 4.5 Hz, 1H: CH at position 4α); 5.42 (broad d, J=6 Hz, 1H: CH at position 5α); 5.52 (d, J=17 Hz, 1H: the other H of $CH_2$ at position 5ε); 5.65 (d, J=8.5 Hz, 1H: CH at position 6α); 5.87 (broad q, J=7 Hz, 1H: CH at position 1β); 6.28 (d, J=8 Hz, 2H: aromatic H at position 4ε); 6.56 (d, J=10 Hz, 1H: CONH at position 2); 6.85 (d, J=8 Hz, 2H: aromatic H at position 4δ); from 7.15 to 7.40 (mt: the 5 aromatic H at position 6α); 7.35 (mt, 1H: H at position 5 of pyridine); 7.46 (broad d, J=8.5 Hz, 1H: 1' H₄); 7.51 (dd, J=8.5 and 4 Hz, 1H: 1' H₅); 7.82 (split t, J=8 and 1.5 Hz, 1H: H at position 4 of pyridine); 7.99 (broad d, J=4 Hz, 1H: 1' H₆); 8.41 (d, J=10 Hz, 1H: CONH at position 1); 8.47 (d, J=8 Hz, H at position 3 of pyridine); 8.56 (s, 1H: CH═N); 8.72 (d, J=8.5 Hz, 1H: CONH at position 6); 8.82 (broad d, J=5 Hz, 1H: H at position 6 of pyridine); 11.65 (S, 1H: OH).

EXAMPLE 29

By carrying out the procedure as in Example 22 but starting with 4 cm³ of dimethylformamide, 0.92 g of 5δ-dimethylaminomethylenepristinamycin $I_A$, 0.22 g of benzamidine hydrochloride and 0.12 g of sodium bicarbonate and after 4 hours at 60° C., 1 g of a residue which is chromatographed on 170 g of silica [eluent: dichloromethane/methanol 96/4 by volume] is obtained after cooling, addition of 50 cm³ of distilled water and 20 cm³ of ethyl acetate to the reaction mixture, washing of the aqueous phase with twice 20 cm³ of ethyl acetate, decantation of the organic phase which is dried over magnesium sulphate, filtered and concentrated to dryness at 40° C. under reduced pressure (2.7 kPa). After concentration to dryness at 40° C. under reduced pressure (2.7 kPa) of the fractions, the product is triturated in 10 cm³ of diisopropyl ether, filtered and dried at 40° C. under reduced pressure (90 Pa) to give 0.49 g of 2"-phenylpyrimido[4,5-5γ,5δ]pristinamycin $I_E$ in the form of a white powder melting at 201° C.

¹H NMR spectrum (400 MHz, CDCl₃, δ in ppm): 0.92 (t, J=7.5 Hz, 3H: $CH_3$ at position 2γ); from 1.15 to 1.35 (mt, 2H: 1H of $CH_2$ at position 3β and 1H of $CH_2$ at position 3γ); 1.31 (d, J=7 Hz, 3H: $CH_3$ at position 1γ); 1.40 (dd, J=17 and 6 Hz, 1H: 1H of $CH_2$ at position 5β); 1.59 (mt: 1H: the other H of $CH_2$ at position 3γ); 1.65 (mt: 1H corresponding to 1H of $CH_2$ at position 2β); 1.74 (mt, 1H: the other H of $CH_2$ at position 2β); 2.06 (mt, 1H: the other H of $CH_2$ at position 3β); 2.64 (s, 6H: $ArN(CH_3)_2$); 2.93 (dd, J=12 and 4 Hz, 1H: 1H of $CH_2$ at position 4β); 3.09 (d, J=17 Hz, 1H: the other H of $CH_2$ at position 5β); from 3.15 to 3.30 (mt, 2H: 1H of $CH_2$ at position 3δ and the other H of $CH_2$ at position 4β); 3.27 (s, 3H: $NCH_3$); 3.50 (mt, 1H: the other H of $CH_2$ at position 3δ); 3.87 (d, J=17 Hz, 1H: 1H of $CH_2$ at position 5ε); 4.61 (dd, J=8 and 6 Hz, 1H: CH at position 3α); 4.81 (mt, 1H, CH at position 2α); 4.90 (dd, J=10 and 1.5 Hz, 1H: CH at position 1α); 5.10 (dd, J=12 and 4 Hz, 1H: CH at position 4α); 5.41 (broad d, J=6 Hz, 1H: CH at position 5α); 5.49 (d, J=17 Hz, 1H: the other H of $CH_2$ at position 5ε); 5.65 (d, J=8.5 Hz, 1H: CH at position 6α); 5.90 (split q, J=7 and 1.5 Hz, 1H: CH at position 1β); 6.30 (d, J=8 Hz, 2H: aromatic H at position 4ε); 6.56 (d, J=10 Hz, 1H: CONH at position 2); 6.87 (d, J=8 Hz, 2H: aromatic H at position 4δ); from 7.20 to 7.40 (mt: the 5 aromatic H at position 6α); from 7.40 to 7.50 (mt, 3H: aromatic H at the para and meta positions of the phenyl); 7.48 (dd, J=8.5 and 1.5 Hz, 1H: 1' H₄); 7.56 (dd, J=8.5 and 4 Hz, 1H: 1' H₅); 8.03 (dd, J=4 and 1.5 Hz, 1H: 1' H6); from 8.35 to 8.45 (mt, 3H: aromatic H at the ortho position of the phenyl and CONH at position 1); 8.44 (s, 1H: CH═N); 8.70 (d, J=8.5 Hz, 1H: CONH at position 6); 11.66 (s, 1H: OH).

EXAMPLE 30

By carrying out the procedure as in Example 22 but starting with 10 cm³ of dimethylformamide, 2 g of 5δ-dimethylaminomethylenepristinamycin $I_A$, 0.59 g of 3-aminobenzamidine hydrochloride and 0.47 g of sodium bicarbonate and after 4 hours at 60° C., a residue which is chromatographed on 200 g of silica [eluent: dichloromethane/methanol 96/4 by volume] to give 1.06 g of a solid is obtained after cooling, addition of 50 cm³ of distilled water and 40 cm³ of ethyl acetate to the reaction mixture, washing of the aqueous phase with twice 40 cm³ of ethyl acetate, decantation of the organic phase which is dried over magnesium sulphate, filtered and concentrated to dryness at 40° C. under reduced pressure (2.7 kPa). The solid is purified by HPLC on 450 g of 10 μm $C_8$ silica [eluent: water-acetonitrile 65/35 by volume containing 0.1% trifluoroacetic acid], the fractions are combined, the acetonitrile removed at 40° C. under reduced pressure (2.7 kPa) and the aqueous phase adjusted to pH 7–8 with water saturated with sodium bicarbonate. The precipitate formed is filtered, washed with diisopropyl ether, dried at 40° C. under reduced pressure (90 Pa) to give 0.31 g of 2"-(3-aminophenyl) pyrimido[4,5-5γ,5δ]pristinamycin $I_E$ in the form of a pale-yellow solid melting at 212° C.

¹H NMR spectrum (400 MHz, CDCl₃, δ in ppm): 0.93 (t, J=7.5 Hz, 3H: $CH_3$ at position 2γ); from 1.20 to 1.40 (mt, 2H: 1H of $CH_2$ at position 3β and 1H of $CH_2$ at position 3γ); 1.31 (d, J=7 Hz, 3H: $CH_3$ at position 1γ); 1.43 (dd, J=17 and 6 Hz, 1H: 1H of $CH_2$ at position 5β) from 1.50 to 1.75 (mt: the 2H corresponding to the other H of $CH_2$ at position 3γ and to 1H of $CH_2$ at position 2β) 1.76 (mt, 1H: the other H of $CH_2$ at position 2β) 2.08 (mt, 1H: the other H of $CH_2$ at position 3β); 2.69 (s, 6H: $ArN(CH_3)_2$); 2.94 (dd, J=12.5 and 4.5 Hz, 1H: 1H of $CH_2$ at position 4β); 3.10 (d, J=17 Hz, 1H: the other H of $CH_2$ at position 5β); from 3.15 to 3.35 (mt, 2H: 1H of CH$_2$ at position 3δ and the other H of CH$_2$ at position 4β) 3.28 (s, 3H: NCH$_3$); 3.51 (mt, 1H: the other H of CH$_2$ at position 3δ); 3.76 (broad s, 2H: ArNH$_2$); 3.88 (d, J=17 Hz, 1H: 1H of CH$_2$ at position 5ε); 4.63 (dd, J=8 and 6 Hz, 1H: CH at position 3α); 4.82 (mt, 1H: CH at position 2α); 4.90 (broad d, J=10 Hz, 1H: CH at position 1α); 5.11 (dd, J=12.5 and 4.5 Hz, 1H: CH at position 4α); 5.41 (broad d, J=6 Hz, 1H: CH at position 5α); 5.49 (d, J=17 Hz, 1H: the other H of CH$_2$ at position 5ε); 5.66 (d, J=8.5 Hz, 1H: CH at position 6α); 5.90 (broad q, J=7 Hz, 1H: CH at position 1β); 6.31 (d, J=8 Hz, 2H: aromatic H at position 4ε); 6.55 (d, J=10 Hz, 1H: CONH at position 2); 6.80 (dd, J=8 and 1.5 Hz, 1H: aromatic H at position 4 of 3-aminophenyl); 6.85 (d, J=8 Hz, 2H: aromatic H at position 4δ); from 7.20 to 7.40 (mt: the 6H corresponding to the 5 aromatic H at position 6α and to the aromatic H at position 5 of 3-aminophenyl); 7.49 (broad d, J=8.5 Hz, 1H: 1' H$_4$); 7.55 (dd, J=8.5 and 4 Hz, 1H: 1' H$_5$); 7.75 (broad s, 1H: aromatic H at position 2 of 3-aminophenyl); 7.82 (broad d, 1H: aromatic H at position 6 of 3-aminophenyl); 8.03 (dd, J=4 and 1.5 Hz, 1H: 1' H$_6$); 8.40 (d, J=10 Hz, 1H: CONH at position 1); 8.42 (s, 1H: CH=N); 8.70 (d, J=8.5 Hz, 1H: CONH at position 6); 11.66 (s, 1H: OH).

EXAMPLE 31

By carrying out the procedure as in Example 22 but starting with 45 cm$^3$ of dimethylformamide, 5 g of 5δ-dimethylaminomethylenepristinamycin I$_B$, 0.64 g of S-methylisothiouronium sulphate and 0.77 g of sodium bicarbonate and after 18 hours at 60° C., 3.16 g of a residue which is chromatographed on 250 g of silica [eluent: dichloromethane/methanol 95/5 by volume] to give 1.2 g of a solid are obtained after cooling, addition of 200 cm$^3$ of distilled water and 150 cm$^3$ of ethyl acetate to the reaction mixture, washing of the aqueous phase with twice 150 cm$^3$ of ethyl acetate, decantation of the organic phase which is washed with 250 cm$^3$ of distilled water, dried over magnesium sulphate, filtered and concentrated to dryness at 40° C. under reduced pressure (2.7 kPa). The solid is purified by HPLC on 450 g of 10 μm C$_8$ silica [eluent: water-acetonitrile 65/35 by volume containing 0.1% trifluoroacetic acid], the fractions are combined, the acetonitrile removed at 40° C. under reduced pressure (2.7 kpa), the aqueous phase adjusted to pH 7–8 with water saturated with sodium bicarbonate and extracted with twice 100 cm$^3$ of dichloromethane. The organic phase is decanted off, dried over magnesium sulphate, filtered and then concentrated to dryness and then dried at 40° C. under reduced pressure (90 Pa) to give 0.45 g of 2"-methylthiopyrimido[4,5-5γ,5δ](4ζ-methylamino)(4ζ-dedimethylamino)pristinamycin I$_E$ in the form of a pale-yellow solid melting at 282° C.

$^1$H NMR spectrum (400 MHz, CDCl$_3$, δ in ppm): 0.91 (t, J=7.5 Hz, 3H: CH$_3$ at position 2γ); from 1.20 to 1.40 (mt, 3H: 1H of CH$_2$ at position 3β—1H of CH$_2$ at position 3γ and 1H of CH$_2$ at position 5β) 1.32 (d, J=7 Hz, 3H: CH$_3$ at position 1γ); 1.58 (mt, 1H: the other H of CH$_2$ at position 3γ); from 1.60 to 1.85 (mt: the 2H corresponding to CH$_2$ at position 2β); Hz 2.06 (mt, 1H: the other H of CH$_2$ at position 3β) 2.64 (s, 3H: ArSCH$_3$); 2.77 (s, 3H: ArNCH$_3$); 2.89 (dd, J=12 and 4.5 Hz, 1H: 1H of CH$_2$ at position 4β); 2.97 (d, J=17.5 Hz, 1H: the other H of CH$_2$ at position 5β); 3.20 (t, J=12 Hz, 1H: the other H of CH$_2$ at position 4β); from 3.20 to 3.35 (mt, 1H: 1H of CH$_2$ at position 3δ); 3.25 (s, 3H: NCH$_3$); 3.50 (mt, 1H: the other H of CH$_2$ at position 3δ); from 3.65 to 3.85 (broad unresolved complex, 1H: ArNH); 3.75 (d, J=17 Hz, 1H: 1H of CH$_2$ at position 5ε); 4.61 (dd, J=8 and 5.5 Hz, 1H: CH at position 3α); 4.80 (mt, 1H: CH at position 2α); 4.88 (broad d, J=10 Hz, 1H: CH at position 1α); 5.03 (dd, J=12 and 4.5 Hz, 1H: CH at position 4α); 5.32 (broad d, J=6 Hz, 1H: CH at position 5α); 5.39 (d, J=17 Hz, 1H: the other H of CH$_2$ at position 5ε); 5.65 (d, J=8.5 Hz, 1H: CH at position 6α); 5.88 (broad q, J=7 Hz, 1H: CH at position 1β); 6.18 (d, J=8 Hz, 2H: aromatic H at position 4ε); 6.51 (d, J=10 Hz, 1H: CONH at position 2); 6.78 (d, J=8 Hz, 2H: aromatic H at position 4δ); from 7.20 to 7.40 (mt: the 5 aromatic H at position 6α); 7.46 (broad d, J=8.5 Hz, 1H: 1' H$_4$); 7.50 (dd, J=8.5 and 4 Hz, 1H: 1' H$_5$); 7.94 (broad d, J=4 Hz, 1H: 1' H$_6$); 8.17 (s, 1H: CH=N); 8.38 (d, J=10 Hz, 1H: CONH at position 1); 8.67 (d, J=8.5 Hz, 1H: CONH at position 6); 11.62 (s, 1H: OH).

EXAMPLE 32

97 mg of 2"-(1-pyrrolidinylpyrimido[4,5-5γ,5δ] pristinamycin I$_E$, 5.4 mg of ethylene glycol, 65 mg of acetic acid and 20 mg of tetra-n-butylammonium periodate are introduced into a round-bottomed flask containing 0.4 cm$^3$ of dichloromethane. The mixture is stirred for 4 hours at room temperature and then the reaction mixture is taken up in 8 cm$^3$ of water and 4 cm$^3$ of dichloromethane. The organic phase is decanted off, washed with 4 times 8 cm$^3$ of distilled water, decanted off, dried and then concentrated to dryness at 40° C. under reduced pressure (2.7 kPa) to give 70 mg of a solid which is purified by flash chromatography with 210 mg of an identical product obtained from a similar preparation on 15 g of silica [eluent: dichloromethane/methanol 97/3 by volume] to give after concentration to dryness of the fractions, trituration in 4 cm$^3$ of diethyl ether, filtration and drying at 20° C. under reduced pressure (90 Pa), 98 mg of 2"-(1-pyrrolidinyl)pyrimido[4,5-5γ,5δ](4ζ-methylamino)(4ζ-dedimethylamino)pristinamycin I$_E$ in the form of a cream-coloured powder melting at 222° C.

$^1$H NMR spectrum (400 MHz, CDCl$_3$, δ in ppm): 0.92 (t, J=7.5 Hz, 3H: CH$_3$ at position 2γ); from 1.20 to 1.40 (mt, 2H: 1H of CH$_2$ at position 3β and 1H of CH$_2$ at position 3γ); 1.31 (d, J=7 Hz, 3H: CH$_3$ at position 1γ); 1.48 (dd, J=17 and 6 Hz, 1H: 1H of CH$_2$ at position 5β); from 1.50 to 1.85 (mt: the 3H corresponding to the other H of CH$_2$ at position 3γ and to CH$_2$ at position 2β) 1.95 (mt, 4H: the 2 CH$_2$ of pyrrolidine); 2.04 (mt, 1H: the other H of CH$_2$ at position 3β); Hz 2.62 (s, 3H: ArNCH$_3$); 2.91 (dd, J=12.5 and 4.5 Hz, 1H: 1H of CH$_2$ at position 4β); 2.92 (d, J=17.5 Hz, 1H: the other H of CH$_2$ at position 5β) from 3.15 to 3.35 (mt, 2H: the other H of CH$_2$ at position 4β and 1H of CH$_2$ at position 3δ); 3.22 (s, 3H: NCH$_3$); from 3.45 to 3.65 (mt, 5H: the other H of CH$_2$ at position 3δ and the 2 NCH$_2$ of pyrrolidine); 3.73 (d, J=17 Hz, 1H: 1H of CH$_2$ at position 5ε); 4.60 (dd, J=6.5 and 5.5 Hz, 1H: CH at position 3α); 4.78 (mt, 1H: CH at position 2α); 4.88 (broad d, J=10 Hz, 1H: CH at position 1α); 5.14 (dd, J=12 and 4.5 Hz, 1H: CH at position 4α); 5.29 (d, J=17 Hz, 1H: the other H of CH$_2$ at position 5ε); 5.31 (unresolved complex, 1H: CH at position 5α); 5.64 (d, J=8.5 Hz, 1H: CH at position 6α); 5.87 (broad q, J=7 Hz, 1H: CH at position 1β); 6.28 (d, J=8 Hz, 2H: aromatic H at position 4ε); 6.56 (d, J=9.5 Hz, 1H: CONH at position 2); 6.82 (d, J=8 Hz, 2H: aromatic H at position 4δ); from 7.20 to 7.40 (mt: the 5 aromatic H at position 6α); 7.42 (limiting AB, 2H: 1' H$_4$ and 1' H$_5$); 7.90 (mt, 1H: 1' H$_6$); 7.98 (s, 1H: CH=N); 8.42 (d, J=10 Hz, 1H: CONH at position 1); 8.62 (d, J=8.5 Hz, 1H: CONH at position 6); 11.65 (s, 1H: OH).

EXAMPLE 33

30 g of pristinamycin I$_A$, 2.42 g of 3-aminoacrolein and then 25.8 g of ammonium acetate are introduced into a three-necked flask containing 400 cm³ of methanol. The mixture is refluxed for 3 days and then diluted with 1 liter of distilled water. The precipitate obtained is filtered, dried and then chromatographed on 1 kg of silica (eluent: dichloromethane/methanol 98/2 by volume). The solid obtained is purified by HPLC on 10 μm C$_8$ silica (eluent: water-acetonitrile 70/30 containing 0.1% trifluoroacetic acid. The fractions are combined, the acetonitrile removed at 40° C. under reduced pressure (2.7 kPa) and the aqueous phase adjusted to pH 8 with 3 cm³ of water saturated with sodium bicarbonate. The precipitate obtained is filtered, rinsed with 10 cm³ of distilled water and then 10 cm³ of diethyl ether to give after drying at 40° C. under reduced pressure (90 Pa), 0.45 g of pyrido[2,3-5γ,5δ]pristinamycin I$_E$ in the form of a white solid melting at around 170–180° C. (dec.).

¹H NMR spectrum (400 MHz, CDCl$_3$, δ in ppm): 0.92 (t, J=7.5 Hz, 3H: CH$_3$ at position 2γ); from 1.20 to 1.40 (mt, 2H: 1H of CH$_2$ at position 3β and 1H of CH$_2$ at position 3γ); 1.34 (d, J=7 Hz, 3H: CH$_3$ at position 1γ); from 1.55 to 1.85 (mt, 4H: the other H of CH$_2$ at position 3γ—CH$_2$ at position 2β and 1H of CH$_2$ at position 5β); 2.04 (mt, 1H: the other H of CH$_2$ at position 3β); 2.91 (s, 6H: ArN(CH$_3$)$_2$); 2.95 (dd, J=12 and 5 Hz, 1H: 1H of CH$_2$ at position 4β); 3.17 (t, J=12 Hz, 1H: the other H of CH$_2$ at position 4β); 3.24 (s, 3H: NCH$_3$); 3.30 (mt, 1H: 1H of CH$_2$ at position 3δ); 3.43 (broad d, J=17 Hz, 1H: the other H of CH$_2$ at position 5β); 3.52 (mt, 1H: the other H of CH$_2$ at position 3δ); 3.91 (d, J=17 Hz, 1H: 1H of CH$_2$ at position 5ε); 4.58 (dd, J=7 and 5.5 Hz, 1H: CH at position 3α); 4.81 (mt, 1H: CH at position 2α); 4.87 (dd, J=10 and 1.5 Hz, 1H: CH at position 1α); 5.13 (dd, J=12 and 5 Hz, 1H: CH at position 4α); 5.43 (mt, 1H: CH at position 5α); 5.46 (d, J=17 Hz, 1H: the other H of CH$_2$ at position 5ε); 5.65 (d, J=8.5 Hz, 1H: CH at position 6α); 5.87 (dq, J=7 and 1.5 Hz, 1H: CH at position 1β) 6.40 (d, J=8 Hz, 2H aromatic H at position 4ε); 6.58 (d, J=9.5 Hz, 1H: CONH at position 2); 6.85 (d, J=8 Hz, 2H: aromatic H at position 4δ); from 7.20 to 7.40 (mt: the 5 aromatic H at position 6α); from 7.30 to 7.45 (mt, 1H: aromatic H at position β of N); 7.43 (d, J=8 Hz, 1H: 1' H$_4$); 7.56 (dd, J=8 and 4 Hz, 1H: 1' H$_5$); 7.61 (mt, 1H: aromatic H at position γ of N); 8.13 (mt, 1H: 1' H$_6$); 8.38 (d, J=4 Hz, 1H: aromatic H at position α of N); 8.42 (d, J=10 Hz, 1H: CONH at position 1); 8.69 (d, J=8.5 Hz, 1H: CONH at position 6); 11.59 (s, 1H: OH).

3-Aminoacrolein may be prepared according to R. P. Thummel & D. K. Kohli, J. Org. Chem., 42, 2742–2747 (1977).

EXAMPLE 34

By carrying out the procedure as in Example 6 but starting with 11.4 g of 5δ-methylenepristinamycin I$_A$ in 200 cm³ of acetone, 3.8 g of 1-(2-oxopentyl)-pyridinium bromide, 10 g of ammonium acetate and heating for 3 hours under reflux, a solid is obtained which is chromatographed on 100 g of silica (eluent: acetonitrile) and then by HPLC on 450 g of 10 μm C$_8$ silica (eluent: water-acetonitrile 70/30 by volume, containing 0.1% trifluoroacetic acid). The fractions are combined, the acetonitrile removed at 40° C. under reduced pressure (2.7 kPa) and the pH of the aqueous phase adjusted to 8 by addition of water saturated with sodium bicarbonate. The precipitate is filtered, washed with 20 cm³ of distilled water and dried at 40° C. under reduced pressure (90 kPa) to give 0.8 g of 2"-propylpyrido[2,3-5γ,5δ]pristinamycin I$_E$ in the form of a white solid melting at 172° C.

¹H NMR spectrum (400 MHz, CDCl$_3$): 0.93 (t, J=7.5 Hz, 3H: CH$_3$ at position 2γ); 0.98 (t, J=7.5 Hz, 3H: CH$_3$ of propyl); from 1.20 to 1.35 (mt, 2H: 1H of CH$_2$ at position 3β and 1H of CH$_2$ at position 3γ); 1.30 (d, J=7 Hz, 3H: CH$_3$ at position 1γ); 1.58 (mt, 1H: the other H of CH$_2$ at position 3γ); from 1.50 to 1.90 (mt: the 3H corresponding to CH$_2$ at position 2β and to 1H of CH$_2$ at position 5β); 1.70 (mt, 2H: central CH$_2$ of propyl); 2.03 (mt, 1H: the other H of CH$_2$ at position 3β) 2.68 (t, J=8 Hz, 2H: ArCH$_2$ of propyl); 2.84 (s, 6H: ArN(CH$_3$)$_2$); 2.97 (dd, J=13 and 5.5 Hz, 1H: 1H of CH$_2$ at position 4β) from 3.15 to 3.35 (mt, 3H: the other H of CH$_2$ at position 5β—the other H of CH$_2$ at position 4β and 1H of CH$_2$ at position 3δ); 3.21 (s, 3H: NCH$_3$); 3.49 (mt, 1H: the other H of CH$_2$ at position 3δ); 3.92 (d, J=17 Hz, 1H: 1H of CH$_2$ at position 5ε); 4.60 (dd, J=8 and 5.5 Hz, 1H: CH at position 3α); 4.79 (mt, 1H: CH at position 2α); 4.87 (dd, J=10 and 1 Hz, 1H: CH at position 1α); 5.28 (dd, J=10 and 5.5 Hz, 1H: CH at position 4α); from 5.35 to 5.50 (mt, 2H: CH at position 5α and the other H of CH$_2$ at position 5ε); 5.63 (d, J=8 Hz, 1H: CH at position 6α); 5.88 (split q, J=7 and 1 Hz, 1H: CH at position 1β) 6.36 (d, J=8 Hz, 2H: aromatic H at position 4ε); 6.58 (d, J=9.5 Hz, 1H: CONH at position 2); 6.84 (d, J=8 Hz, 2H: aromatic H at position 4δ); 6.94 (d, J=8 Hz, 1H: aromatic H at position β with respect to N); from 7.20 to 7.45 (mt: the 8H corresponding to the 5 aromatic H at position 6α—to the aromatic H at position y with respect to N—to 1' H$_5$ and to 1' H$_4$); 7.86 (dd, J=4 and 1 Hz, 1H: 1' H$_6$); 8.43 (d, J=10 Hz, 1H: CONH at position 1); 8.66 (d, J=8 Hz, 1H: CONH at position 6); 11.64 (s, 1H: OH).

1-(2-Oxopentyl)pyridinium bromide may be prepared by analogy with 1-(2-oxopentyl)pyridinium iodide as described by R. P. SONI, J. P. SAXENA, J. Indian Chem. Soc., 58, 885–887 (1981).

3.8 g of 1-bromo-2-pentanone and 9.2 cm³ of pyridine are introduced into a three-necked flask containing 25 cm³ of ethanol and then the mixture is heated for 3 hours under reflux. After concentrating to dryness at 40° C. under reduced pressure (2.7 kPa), the residue is taken up in 200 cm³ of diisopropyl ether. After filtration, washing with 50 cm³ of diethyl ether, the precipitate is dried to give 3.8 g of a pale-yellow solid of 80% purity melting at 72° C. and which is used as it is.

1-bromo-2-pentanone may be prepared according to H. J. HA, Synth. Commun., 24, 2557, (1994).

EXAMPLE 35

By carrying out the procedure as in Example 6 but starting with 30 g of 5δ-methylenepristinamycin I$_A$ in 200 cm³ of acetone, 10 g of 1-(3-methyl-2-oxobutyl)-pyridinium bromide, 26.3 g of ammonium acetate and heating for 3 hours under reflux, 34 g of a solid are obtained, which solid is purified by 2 successive chromatographies on 1 kg of silica (eluent: methylene chloride-acetonitrile-water: 96/2/2 by volume) and then 700 g of silica (eluent: methylene chloride and then methylene chloride-methanol-acetonitrile gradient: 99/0.5/0.5 to 98/1/1 by volume). After 2 recrystallizations from the methanol, 4.3 g of product are obtained of which 2 g are purified by HPLC on 450 g of 10 μm C$_8$ silica (eluent: water-acetonitrile 70/30 by volume, containing 0.1% trifluoroacetic acid). The fractions are combined, the acetonitrile removed at 40° C. under reduced pressure (2.7 kPa) and the pH of the aqueous phase adjusted to 8 by addition of water saturated with sodium bicarbonate. The precipitate is filtered, washed with 20 cm³ of water and then with 20 cm³ of diisopropyl ether. After recrystallization from 15 cm³ of methanol, filtration, washing with 10 cm³ of methanol and 10 cm³ of diisopropyl ether and then drying at 40° C. under reduced pressure (90 Pa), 0.75 g of 2"-isopropylpyrido[2,3-5γ,5δ]pristinamycin $I_E$ is obtained in the form of white needles melting at 263° C.

$^1$H NMR spectrum (400 MHz, CDCl$_3$): 0.92 (t, J=7.5 Hz, 3H: CH$_3$ at position 2γ); from 1.20 to 1.35 (mt, 11H: 1H of CH$_2$ at position 3β—1H of CH$_2$ at position 3γ—CH$_3$ at position 1γ and the 2 CH$_3$ of isopropyl); 1.58 (mt, 1H: the other H of CH$_2$ at position 3γ); 1.66 and 1.75 (2 mts, 1H each: CH$_2$ at position 2β); 1.89 (mt: 1H corresponding to 1H of CH$_2$ at position 5β); 2.03 (mt, 1H: the other H of CH$_2$ at position 3β); 2.85 (s, 6H: ArN(CH$_3$)$_2$); from 2.95 to 3.05 (mt, 1H: ArCH of isopropyl); 2.99 (dd, J=14 and 6.5 Hz, 1H: 1H of CH$_2$ at position 4β); from 3.15 to 3.30 (mt, 3H: the other H of CH$_2$ at position 5β—the other H of CH$_2$ at position 4β and 1H of CH$_2$ at position 3δ); 3.20 (s, 3H: NCH$_3$); 3.49 (mt, 1H: the other H of CH$_2$ at position 3δ); 3.93 (d, J=17 Hz, 1H: 1H of CH$_2$ at position 5ε); 4.60 (dd, J=7.5 and 6 Hz, 1H: CH at position 3α); 4.79 (mt, 1H: CH at position 2α); 4.88 (broad d, J=10 Hz, 1H: CH at position 1α); 5.32 (dd, J=9 and 6.5 Hz, 1H: CH at position 4α); from 5.40 to 5.50 (mt, 2H: CH at position 5α and the other H of CH$_2$ at position 5ε); 5.64 (d, J=8 Hz, 1H: CH at position 6α); 5.88 (broad q, J=7 Hz, 1H: CH at position 1β); 6.39 (d, J=8 Hz, 2H: aromatic H at position 4ε); 6.60 (d, J=9.5 Hz, 1H: CONH at position 2); 6.85 (d, J=8 Hz, 2H: aromatic H at position 4δ); 6.99 (d, J=8 Hz, 1H: aromatic H at position β with respect to N); from 7.20 to 7.40 (mt: the 8H corresponding to the 5 aromatic H at position 6α—to the aromatic H at position γ with respect to N—to 1' H$_5$ and to 1' H$_4$); 7.85 (broad d, J=4 Hz, 1H: 1' H$_6$); 8.44 (d, J=10 Hz, 1H: CONH at position 1); 8.69 (d, J=8 Hz, 1H: CONH at position 6); 11.66 (s, 1H: OH).

1-(3-Methyl-2-oxobutyl)pyridinium bromide may be prepared as described by J. P. SAXENA, J. Indian Chem. Soc., 68, 99–100 (1991).

EXAMPLE 36

By carrying out the process as in Example 5 but starting with 1.5 liters of acetonitrile, 100 g of 5δ-methylenepristinamycin $I_A$, 27.1 g of 1-(3-chloro-2-oxopropyl)pyridinium chloride, 88 g of ammonium acetate and 5 hours reflux, a solid is obtained which is purified by two successive chromatographies on 1.5 kg and 100 g of silica (eluent: methylene chloride-methanol 97/3 by volume). The fractions containing the expected product are concentrated to give a solid which is purified by HPLC on 450 g of 10 μm C$_8$ silica (eluent: water-acetonitrile 70/30 by volume, containing 0.1% trifluoroacetic acid). The fractions are combined, the acetonitrile removed at 40° C. under reduced pressure (2.7 kPa) and the pH of the aqueous phase adjusted to 8 by addition of water saturated with sodium bicarbonate. The aqueous phase is extracted with twice 50 cm$^3$ of methylene chloride. The organic phases are pooled, dried over sodium sulphate, filtered, concentrated under reduced pressure (45° C., 2.7 kPa) and the solid obtained is taken up in 20 cm$^3$ of diethyl ether. After filtration and then drying at 40° C. under reduced pressure (90 Pa), 0.5 g of 2"-acetoxymethylpyrido[2,3-5γ,5δ]pristinamycin $I_E$ is obtained in the form of a cream-coloured solid melting at 206° C.

Hz $^1$H NMR spectrum (400 MHz, CDCl$_3$): 0.91 (t, J=7.5 Hz, 3H: CH$_3$ at position 2γ); 1.25 (mt, 2H: 1H of CH$_2$ at position 3β and 1H of CH$_2$ at position 3γ); 1.30 (d, J=7 Hz, 3H: CH$_3$ at position 1γ); 1.58 (mt, 1H: the other H of CH$_2$ at position 3γ); from 1.60 to 1.85 (mts: the 3H corresponding to the CH$_2$ at position 2β and to 1H of CH$_2$ at position 5β) 2.03 (mt, 1H: the other H of CH$_2$ at position 3β); 2.14 (s, 3H: OCOCH$_3$); Hz 2.84 (s, 6H: ArN(CH$_3$)$_2$); 2.96 (dd, J=13 and 5.5 Hz, 1H: 1H of CH$_2$ at position 4β); 3.14 (d, J=16.5 Hz, 1H: the other H of CH$_2$ at position 5β) from 3.15 to 3.30 (mt, 2H: the other H of CH$_2$ at position 4β and 1H of CH$_2$ at position 3δ); 3.22 (s, 3H: NCH$_3$); 3.49 (mt, 1H: the other H of CH$_2$ at position 3δ); 3.93 (d, J=17 Hz, 1H: 1H of CH$_2$ at position 5ε); 4.60 (dd, J=8 and 5.5 Hz, 1H: CH at position 3α); 4.79 (mt, 1H: CH at position 2α); 4.88 (dd, J=10 and 1 Hz, 1H: CH at position 1α); 5.07 and 5.18 (2d, J=13 Hz, 1H each: ArCH$_2$OCO); from 5.15 to 5.25 (mt, 1H: CH at position 4α); 5.40 (broad d, J=5.5 Hz, 1H: CH at position 5α); 5.45 (d, J=17 Hz, 1H: the other H of CH$_2$ at position 5ε); 5.60 (d, J=8 Hz, 1H: CH at position 6α); 5.88 (split q, J Hz=7 and 1 Hz, 1H: CH at position 1β); 6.34 (d, J=8 Hz, 2H: aromatic H at position 4ε); 6.56 (d, J=9.5 Hz, 1H: CONH at position 2); 6.85 (d, J=8 Hz, 2H: aromatic H at position 4δ); 7.15 (d, J=8 Hz, 1H: aromatic H at position β with respect to N); from 7.20 to 7.35 (mt: the 5H corresponding to aromatic H at position 6α); 7.36 (d, J=8 Hz, 1H: aromatic H at position γ with respect to N); 7.40 (mt, 2H 1' H$_5$ and 1' H$_4$); 7.89 (mt, 1H: 1'H$_6$); 8.40 (d, J=10 Hz, 1H: CONH at position 1); 8.68 (d, J=8 Hz, 1H: CONH at position 6); 11.65 (s, 1H: OH).

EXAMPLE 37

When carrying out the procedure as in Example 20 but starting with 40 cm$^3$ of acetonitrile, 2 g of 2"-chloromethylpyrido[2,3–γ,5δ]pristinamycin $I_E$, 1.5 cm$^3$ of cyclopropylamine and 0.34 g of potassium iodide, after refluxing for 24 hours 2.2 g of a foam are obtained, which foam is purified by two successive chromatographies on 60 g of silica (eluent: methylene chloride-methanol 95/5 by volume). The fractions are combined, dried over sodium sulphate, filtered and concentrated at 40° C. under reduced pressure (2.7 kPa); the foam obtained is disintegrated in 30 cm$^3$ of diethyl ether. After filtration and drying at 40° C. under reduced pressure (90 Pa), 0.55 g of 2"-cyclopropylaminomethylpyrido[2,3-5γ,5δ]pristinamycin $I_E$ is obtained in the form of a yellow solid melting at 184° C.

$^1$H NMR spectrum (400 MHz, CDCl$_3$): from 0.35 to 0.50 (mt, 4H: CH$_2$CH$_2$ of cyclopropane); 0.92 (t, J=7.5 Hz, 3H: CH$_3$ at position 2γ); 1.26 (mt, 2H: 1H of CH$_2$ at position 3β and 1H of CH$_2$ at position 3δ); 1.30 (d, J=7 Hz, 3H: CH$_3$ at position 1γ); 1.58 (mt, 1H: the other H of CH$_2$ at position 3γ); from 1.60 to 1.85 (mt: the 2H corresponding to the CH$_2$ at position 2β); 1.78 (dd, J=16 and 6.5 Hz, 1H: 1H of CH$_2$ at position 5β); 2.03 (mt, 1H: the other H of CH$_2$ at position 3β); 2.16 (mt, 1H: CH of cyclopropane); 2.86 (s, 6H: ArN(CH$_3$)$_2$); 2.97 (dd, J=13.5 and 6 Hz, 1H: 1H of CH$_2$ at position 4β); from 3.15 to 3.30 (mt, 2H: the other H of CH$_2$ at position 4β—the other H of CH$_2$ at position 5β and 1H of CH$_2$ at position 3δ); 3.22 (s, 3H: NCH$_3$); 3.49 (mt, 1H: the other H of CH$_2$ at position 3δ); 3.88 (s, 2H: ArCH$_2$N); 3.94 (d, J=17 Hz, 1H: 1H of CH$_2$ at position 5ε); 4.60 (dd, J=8 and 5.5 Hz, 1H: CH at position 3α); 4.79 (mt, 1H: CH at position 2α); 4.88 (dd, J=10 and 1 Hz, 1H: CH at position 1α); 5.26 (dd, J=10 and 6 Hz, 1H: CH at position 4α); from 5.40 to 5.50 (mt, 2H: CH at position 5α and the other H of CH$_2$ at position 5ε); 5.62 (d, J=8 Hz, 1H: CH at position 6α); 5.88 (split q, J=7 and 1 Hz, 1H: CH at position 1β); 6.36 (d, J=8 Hz, 2H: aromatic H at position 4ε); 6.57 (d, J=9.5 Hz, 1H: CONH at position 2); 6.85 (d, J =8 Hz, 2H aromatic H at position 4δ); 7.10 (d, J=8 Hz, 1H: aromatic H at position β with respect to N); from 7.20 to 7.35 (mt: the 6H corresponding to the 5 aromatic H at position 6α and to the aromatic H at position γ with respect to N); 7.39 (limiting AB, 2H: 1' H$_5$ and 1' H$_4$); 7.87 (dd, J=4 and 2 Hz, 1H: 1' H$_6$); 8.42 (d, J=10 Hz, 1H: CONH at position 1); 8.67 (d, J=8 Hz, 1H: CONH at position 6); 11.65 (unresolved complex 1H: OH).

EXAMPLE 38

By carrying out the procedure as in Example 20 but starting with 1.5 g of 2"-chloromethyl-pyrido[2,3-5γ,5δ] pristinamycin I$_E$ in 30 cm$^3$ of acetonitrile, 0.5 cm$^3$ of diethylamine, 0.26 g of potassium iodide and after refluxing for 6 hours at 45° C., 1.35 g of product are obtained, which product is purified by HPLC on 450 g of 10 μm C$_8$ silica (eluent: water-acetonitrile 60/40 by volume, containing 0.1% trifluoroacetic acid). The fractions are combined and the acetonitrile removed at 40° C. under reduced pressure (2.7 kPa). The aqueous phase is adjusted to pH 8 by addition of water saturated with sodium bicarbonate and then extracted with 300 cm$^3$ of ethyl acetate. The organic phase is decanted off, dried over sodium sulphate, filtered and then concentrated under reduced pressure (45° C., 2.7 kPa) to give a solid which is crystallized from 30 cm$^3$ of methanol. After filtration, washing with 50 cm$^3$ of diisopropyl ether and drying at 40° C. under reduced pressure (90 Pa), 0.4 g of 2"-N-diethylaminomethylpyrido[2,3-5γ,5δ]pristinamycin I$_E$ is obtained in the form of a cottony white solid melting at 264° C.

$^1$H NMR spectrum (400 MHz, CDCl$_3$): 0.92 (t, J=7.5 Hz, 3H: CH$_3$ at position 2γ); 1.04 (t, J=7 Hz, 6H: CH$_3$ of diethylamino); from 1.20 to 1.35 (mt, 2H: 1H of CH$_2$ at position 3β and 1H of CH$_2$ at position 3γ); 1.30 (d, J=7 Hz, 3H: CH$_3$ at position 1γ); 1.58 (mt, 1H: the other H of CH$_2$ at position 3γ); from 1.60 to 1.80 (mt: the 2H corresponding to CH$_2$ at position 2β); 1.85 (dd, J=16.5 and 5.5 Hz, 1H: 1H of CH$_2$ at position 5β); 2.03 (mt, 1H: the other H of CH$_2$ at position 3β); 2.55 (q, J=7 Hz, 4H: the 2 NCH$_2$ of diethylamino); 2.85 (s, 6H: ArN(CH$_3$)$_2$); 2.98 (dd, J=14 and 6 Hz, 1H: 1H of CH$_2$ at position 4β); from 3.15 to 3.30 (mt, 3H: the other H of CH$_2$ at position 4β—the other H of CH$_2$ Hz at position 5β and 1H of CH$_2$ at position 3δ); 3.21 (s, 3H: NCH$_3$); 3.50 (mt, 1H: the other H of CH$_2$ at position 3δ); 3.66 (s, 2H: ArCH$_2$N); 3.94 (d, J=17 Hz, 1H: 1H of CH$_2$ at position 5ε); 4.60 (dd, J=7.5 and 5.5 Hz, 1H: CH at position 3α); 4.79 (mt, 1H: CH at position 2α); 4.88 (broad d, J=10 Hz, 1H: CH at position 1α); 5.30 (dd, J=9 and 6 Hz, 1H: CH at position 4α); 5.42 (broad d, J=5.5 Hz, 1H: CH at position 5α); 5.43 (d, J=17 Hz, 1H: the other H of CH$_2$ at position 5ε); 5.64 (d, J=8.5 Hz, 1H: CH at position 6α); 5.88 (broad q, J=7 Hz, 1H: CH at position 1β); 6.37 (d, J=8 Hz, 2H: aromatic H at position 4ε); 6.58 (d, J=9.5 Hz, 1H: CONH at position 2); 6.85 (d, J=8 Hz, 2H: aromatic H at position 4δ); from 7.20 to 7.40 (mt: the 9H corresponding to the 5 aromatic H at position 6α—to the aromatic H at position β with respect to N—to 1' H$_4$ and to 1' H$_5$); 7.85 (broad d, J=4 Hz, 1H: 1' H$_6$); 8.43 (d, J=10 Hz, 1H: CONH at position 1); 8.68 (d, J=8.5 Hz, 1H: CONH at position 6); 11.65 (broad s, 1H: OH).

2"-Chloromethylpyrido[2,3-5γ,5δ]pristinamycin I$_E$ may be obtained as described in Example 10.

EXAMPLE 39

By carrying out the procedure as in Example 6 but starting with 5.6 g of 5δ-methylenevirginiamycin S in 100 cm$^3$ of acetonitrile, 1.15 g of 1-acetonyl-pyridinium chloride, 5.17 g of ammonium acetate and heating for 4 hours under reflux, a red oil is obtained which is chromatographed on 500 g of silica (eluent: methylene chloride-methanol 98/2 by volume) to give 2.1 g of yellow foam. The latter is purified by HPLC on 450 g of 10 μm C$_8$ silica (eluent: water-acetonitrile 65/35 by volume, containing 0.1% trifluoroacetic acid). The fractions are combined, the acetonitrile removed at 40° C. under reduced pressure (2.7 kPa), the pH of the aqueous phase adjusted to 7 by addition of water saturated with sodium bicarbonate; the precipitate obtained is filtered, washed with 20 cm$^3$ of water and then 20 cm$^3$ of diethyl ether. After filtration and drying at 40° C. under reduced pressure (90 Pa), 0.39 g of 2"-methylpyrido[2,3-5 ,5δ]-5γ-deoxyvirginiamycin S is obtained in the form of a white solid melting at 176° C.

5δ-methylenevirginiamycin S may be obtained as described.

$^1$H NMR spectrum (400 MHz, CDCl$_3$): 0.93 (t, J=7.5 Hz, 3H: CH$_3$ at position 2γ); 1.27 (mt, 2H: 1H of CH$_2$ at position 3β and 1H of CH$_2$ at position 3γ); 1.31 (d, J=7 Hz, 3H: CH$_3$ at position 1γ); from 1.50 to 1.85 (mt: the 4H corresponding to the other H of CH$_2$ at position 3γ—to the CH$_2$ at position 2β and 1H of CH$_2$ at position 5β); 2.04 (mt, 1H: the other H of CH$_2$ at position 3β); 2.50 (s, 3H: ArCH$_3$); 3.07 (dd, J=13 and 6 Hz, 1H: 1H of CH$_2$ at position 4β); from 3.15 to 3.35 (mt, 3H: the other H of CH$_2$ at position 4β—the other H of CH$_2$ at position 5β and 1H of CH$_2$ at position 3δ); 3.22 (s, 3H: NCH$_3$); 3.51 (mt, 1H: the other H of CH$_2$ at position 3δ); 3.92 (d, J=17.5 Hz, 1H: 1H of CH$_2$ at position 5ε); 4.58 (dd, J=8 and 6.5 Hz, 1H: CH at position 3α); 4.80 (mt, 1H: CH at position 2α); 4.87 (broad d, J=10 Hz, 1H: CH at position 1α); 5.34 (dd, J=10 and 6 Hz, 1H: CH at position 4α); from 5.35 to 5.45 (mt, 2H: the other H of CH$_2$ at position 5ε and CH at position 5α); 5.64 (d, J=8 Hz, 1H: CH at position 6α); 5.88 (broad q, J=7 Hz, 1H: CH at position 1β); 6.56 (d, J=9.5 Hz, 1H: CONH at position 2); from 6.95 to 7.40 (mt: the 13H corresponding to the 5 aromatic H at position 6α—to the 5 aromatic H at position 4β—to the aromatic H at position γ with respect to N—to 1' H$_4$ and to 1' H$_5$); 6.96 (d, J=8 Hz, 1H: aromatic H at position β with respect to N); 7.81 (broad d, J=4 Hz, 1H: 1' H$_6$); 8.42 (d, J=10 Hz, 1H: CONH at position 1); 8.64 (d, J=8 Hz, 1H: CONH at position 6); 11.65 (s, 1H: OH).

EXAMPLE 40

By carrying out the procedure by analogy with Example 15 but starting with 4ε-chloro-5δ-methylenepristinamycin I$_A$, 4ε-chloro-2"-(2-pyridyl)pyrido[2,3-5γ,5δ]pristinamycin I$_E$ is obtained in the form of a white solid melting at 194° C.

1H NMR spectrum (400 MHz, CDCl$_3$): 0.93 (t, J=7.5 Hz, 3H: CH$_3$ at position 2γ); from 1.20 to 1.35 (mt, 2H: 1H of CH$_2$ at position 3β and 1H of CH$_2$ at position 3γ); 1.31 (d, J=7 Hz, 3H: CH$_3$ at position 1γ); 1.58 (mt, 1H: the other H of CH$_2$ at position 3γ); from 1.60 to 1.85 (mt, the 3H corresponding to the CH$_2$ at position 2β and to 1H of CH$_2$ at position 5β); 2.04 (mt, 1H: the other H of CH$_2$ at position 3β); 2.56 (s, 6H: ArN(CH$_3$)$_2$); 2.99 (dd, J=13 and 5.5 Hz, 1H: 1H of CH$_2$ at position 4β); from 3.20 to 3.35 (mt, 2H: the other H of CH$_2$ at position 4β and 1H of CH$_2$ at position 3δ); 3.23 (s, 3H: NCH$_3$); 3.36 (d, J=16.5 Hz, 1H: the other H of CH$_2$ at position 5β); 3.51 (mt, 1H the other HzH of CH$_2$ at position 3δ); 4.01 (d, J=17 Hz, 1H: 1H of CH$_2$ at position 5ε); 4.60 (dd, J=7.5 and 6 Hz, 1H: CH at position 3α); 4.81 (mt, 1H: CH at position 2α); 4.91 (dd, J=10 and 1 Hz, 1H: CH at position 1α); 5.26 (dd, J=10 and 5.5 Hz, 1H: CH at position 4α); 5.46 (broad d, J=5.5 Hz, 1H: CH at position 5α); 5.53 (d, J=17 Hz, 1H: the other H of CH$_2$ at position 5ε); 5.63 (d, J=8.5 Hz, 1H: CH at position 6α); 5.89 (split q, J=7 and 1 Hz, 1H: CH at position 1β); 6.47 (d, J=8 Hz, 1H: aromatic H at position 4ε); 6.57 (d, J=9.5 Hz, 1H: CONH at position 2); 6.77 (dd, J=8 and 2 Hz, 1H: aromatic H at position 4δ at the para position with respect to the Cl); 7.13 (d, J=2 Hz, 1H: aromatic H at position 4δ at the ortho position with respect to the Cl); from 7.20 to 7.40 (mt: the 6H corresponding to the 5 aromatic H at position 6α and to $H_5$ of pyridine); 7.41 (broad d, J=8 Hz, 1H: 1' $H_4$); 7.50 (d, J=8 Hz, 1H: aromatic H at position γ with respect to N); 7.53 (dd, J=8 and 4.5 Hz, 1H: 1' $H_5$); 7.74 (split t, J=8 and 1.5 Hz, 1H: $H_4$ of pyridine); 7.90 (broad d, J=4.5 Hz, 1H: 1' $H_6$); 8.24 (d, J=8 Hz, 1H: aromatic H at position β with respect to N); 8.37 (d, J=8 Hz, 1H: $H_3$ of pyridine); 8.38 (d, J=10 Hz, 1H: CONH at position 1); 8.64 (d, J=8.5 Hz, 1H: CONH at position 6); 8.67 (broad d, J=4.5 Hz, 1H: $H_6$ of pyridine); 11.67 (s, 1H: OH).

EXAMPLE 41

By carrying out the procedure by analogy with Example 18 but starting with 4ε-chloro-5δ-methylenepristinamycin $I_A$, 4ε-chloro-2"-(2-pyridyl)pyrido[2,3-5γ,5δ](4ζ-methylamino)(4ζ-dedimethylamino)pristinamycin $I_E$ is obtained in the form of a white solid melting at 204° C.

$^1$H NMR spectrum (400 MHz, CDCl$_3$): 0.93 (t, J=7.5 Hz, 3H: CH$_3$ at position 2γ); 1.27 (mt, 2H: 1H of CH$_2$ at position 3β and 1H of CH$_2$ at position 3γ); 1.31 (d, J=7 Hz, 3H: CH$_3$ at position 1γ); 1.59 (mt, 1H: the other H of CH$_2$ at position 3γ); 1.67 and 1.75 (2 mts, 1H each: CH$_2$ at position 2β); 1.84 (dd, J=16.5 and 6 Hz, 1H: 1H of CH$_2$ at position 5β); 2.04 (mt, 1H: the other H of CH$_2$ at position 3β); 2.53 (s, 3H: ArNCH$_3$); 2.94 (dd, J=13.5 and 6 Hz, 1H: 1H of CH$_2$ at position 4β); from 3.15 to 3.30 (mt, 2H: the other H of CH$_2$ at position 4β and 1H of CH$_2$ at position 3δ); 3.22 (s, 3H: NCH$_3$); 3.35 (d, J=16.5 Hz, 1H: the other H of CH$_2$ at position 50β); 3.49 (mt, 1H: the other H of CH$_2$ at position 3δ); 4.00 (d, J=17 Hz, 1H: 1H of CH$_2$ at position 5ε); 4.60 (dd, J=8 and 7 Hz, 1H: CH at position 3α); 4.79 (mt, 1H: CH at position 2α); 4.89 (broad d, J=10 Hz, 1H: CH at position 1α); 5.19 (dd, J=10 and 6 Hz, 1H: CH at position 4α); from 5.45 to 5.55 (mt, 2H: CH at position 5α and the other H of CH$_2$ at position 5ε); 5.64 (d, J=8.5 Hz, 1H: CH at position 6α); 5.88 (broad q, J=7 Hz, 1H: CH at position 1β); 6.09 (d, J=8 Hz, 1H: aromatic H at position 4ε); 6.57 (d, J=9.5 Hz, 1H: CONH at position 2); 6.75 (broad d, J=8 Hz, 1H: aromatic H at position 4ε at the para position with respect to the Cl); 6.95 (broad s, 1H: aromatic H at position 4δ at the ortho position with respect to the Cl); from 7.20 to 7.40 (mt: the 6H corresponding to the 5 aromatic H at position 6α and to $H_5$ of pyridine); 7.41 (broad d, J=8 Hz, 1H: 1' $H_4$); 7.48 (d, J=8 Hz, 1H: aromatic H at position γ with respect to N); 7.51 (dd, J=8 and 4 Hz, 1H: 1' $H_5$); 7.77 (broad t, J=8 Hz, 1H: $H_4$ of pyridine); 7.97 (broad d, J=4 Hz, 1H: 1' $H_6$); 8.19 (d, J=8 Hz, 1H: aromatic H at position β with respect to N); from 8.35 to 8.45 (mt, 2H: $H_3$ of pyridine and CONH at position 1); 8.63 (d, J=8.5 Hz, 1H: CONH at position 6); 8.67 (broad d, J=4.5 Hz, 1H: $H_6$ of pyridine); 11.67 (s, 1H: OH).

EXAMPLE 42

By carrying out the procedure by analogy with Example 7 but starting with 4ε-chloro-5δ-methylenepristinamycin $I_A$, 4ε-chloro-2"-ethylpyrido[2,3-5γ,5δ]pristinamycin $I_E$ is obtained in the form of a white solid melting at 184° C.

$^1$H NMR spectrum (400 MHz, CDCl$_3$): 0.91 (t, J=7.5 Hz, 3H: CH$_3$ at position 2γ); from 1.20 to 1.40 (mt, 2H: 1H of CH$_2$ at position 3β and 1H of CH$_2$ at position 3γ); 1.27 (t, J=7.5 Hz, 3H: CH$_3$ of ethyl); 1.30 (d, J=7 Hz, 3H: CH$_3$ at position 1γ); 1.59 (mt, 1H: the other H of CH$_2$ at position 3γ); 1.67 and 1.75 (2 mts, 1H each: CH$_2$ at position 2β); 1.90 (dd, J=16 and 5.5 Hz, 1H: 1H of CH$_2$ at position 5β); 2.04 (mt, 1H: the other H of CH$_2$ at position 3β); 2.72 (s, 6H: ArN(CH$_3$)$_2$); 2.77 (mt, 2H: ArCH$_2$ of ethyl); 3.01 (dd, J=14 and 7 Hz, 1H: 1H of CH$_2$ at position 4β); from 3.15 to 3.25 (mt, 2H: the other H of CH$_2$ at position 4β); 3.19 (s, 3H NCH$_3$); from 3.25 to 3.35 (mt, 1H: 1H of CH$_2$ at position 3δ); 3.33 (d, J=16 Hz, 1H: the other H of CH$_2$ at position 5β); 3.51 (mt, 1H: the other H of CH$_2$ at position 3δ); 3.95 (d, J=17.5 Hz, 1H: 1H of CH$_2$ at position 5ε); 4.57 (broad t, J=6.5 Hz, 1H: CH at position 3α); 4.78 (mt, 1H: CH at position 2α); 4.89 (broad d, J=10 Hz, 1H: CH at position 1α); 5.34 (mt, 1H: CH at position 4α); 5.41 (d, J=17.5 Hz, 1H: the other H of CH$_2$ at position 5ε); 5.47 (broad d, J=5.5 Hz, 1H: CH at position 5α); 5.61 (d, J=8.5 Hz, 1H: CH at position 6α); 5.88 (broad q, J=7 Hz, 1H: CH at position 1β); 6.59 (mt, 2H: aromatic H at position 4ε and CONH at position 2); 6.79 (broad d, J=8 Hz, 1H: aromatic H at position 4δ at the para position with respect to the Cl); 6.98 (d, J=8 Hz, 1H: aromatic H at position β with respect to N); 7.06 (broad s, 1H: aromatic H at position 4δ at the ortho position with respect to the Cl); from 7.20 to 7.40 (mt: the 8H corresponding to the 5 aromatic H at position 6α—to the aromatic H at position γ with respect to N—to 1' $H_4$ and to 1' $H_5$); 7.82 (broad d, J=4 Hz, 1H: 1' $H_6$); 8.38 (d, J=10 Hz, 1H: CONH at position 1); 8.64 (d, J=8.5 Hz, 1H: CONH at position 6); 11.67 (c, 1H: OH).

EXAMPLE 43

By carrying out the procedure by analogy with Example 17 but starting with 4ε-chloro-5δ-methylenepristinamycin $I_A$, 4ε-chloro-2"-ethylpyrido[2,3-5γ,5δ](4ζ-methylamino)(4ζ-dedimethylamino)pristinamycin $I_E$ is obtained in the form of a white solid melting at 186° C.

$^1$H NMR spectrum (400 MHz, CDCl$_3$): 0.92 (t, J=7.5 Hz, 3H: CH$_3$ at position 2γ); from 1.20 to 1.35 (mt, 2H: 1H of CH$_2$ at position 3β and 1H of CH$_2$ at position 3γ); 1.28 (t, J=7.5 Hz, 3H: CH$_3$ of ethyl); 1.31 (d, J=7 Hz, 3H: CH$_3$ at position 1γ); 1.58 (mt, 1H: the other H of CH$_2$ at position 3γ); from 1.60 to 1.85 (mt: the 2H corresponding to the CH$_2$ at position 2β); 1.93 (dd, J=16 and 6 Hz, 1H: 1H of CH$_2$ at position 5β); 2.03 (mt, 1H: the other H of CH$_2$ at position 3β); 2.76 (mt, 2H: ArCH$_2$ of ethyl); 2.77 (s, 3H: ArNCH$_3$); 2.96 (dd, J=14 and 6.5 Hz, 1H: 1H of CH$_2$ at position 4β); from 3.10 to 3.30 (mt, 2H: the other H of CH$_2$ at position 4β and 1H of CH$_2$ at position 3δ); 3.19 (s, 3H: NCH$_3$); 3.30 (d, J=16 Hz, 1H: the other H of CH$_2$ at position 5β); 3.50 (mt, 1H: the other H of CH$_2$ at position 3δ); 3.95 (d, J=17 Hz, 1H: 1H of CH$_2$ at position 5ε); 4.21 (unresolved complex, 1H: ArNH); 4.60 (dd, J=7.5 and 5.5 Hz, 1H: CH at position 3α); 4.79 (mt, 1H: CH at position 2α); 4.88 (dd, J=10 and 1 Hz, 1H: CH at position 1α); 5.28 (dd, J=9 and 6.5 Hz, 1H: CH at position 4α); 5.42 (d, J=17 Hz, 1H: the other H of CH$_2$ at position 5ε); 5.46 (broad d, J=6 Hz, 1H: CH at position 5α); 5.63 (d, J=8 Hz, 1H: CH at position 6α); 5.89 (split q, J=7 and 1 Hz, 1H: CH at position 1β); 6.19 (d, J=8 Hz, 1H aromatic H: at position 4ε); 6.57 (d, J=9.5 Hz, 1H: CONH at position 2); 6.77 (dd, J=8 and 1.5 Hz, 1H: aromatic H at position 4δ at the para position with respect to the Cl); 6.94 (d, J=1.5 Hz, 1H: aromatic H at position 4δ at the para position with respect to the Cl); 6.98 (d, J=8 Hz, 1H: aromatic H at position β with respect to N); from 7.20 to 7.45 (mt: the 6H corresponding to the 5 aromatic H at position 6α and to the aromatic H at position γ with respect to N); 7.37 (limiting AB, 2H: 1' $H_4$ and 1' $H_5$); 7.84 (dd, J=4 and 1.5 Hz, 1H: 1' $H_6$); 8.40 (d, J=10 Hz, 1H: CONH at position 1); 8.67 (d, J=8 Hz, 1H: CONH at position 6); 11.66 (s, 1H: OH).

EXAMPLE 44

By carrying out the procedure by analogy with Example 6 but starting with 4ε-chloro-5δ-methylenepristinamycin $I_A$,4ε-chloro-2"-methylpyrido[2,3-5γ,5δ]pristinamycin $I_E$ is obtained in the form of a yellow powder melting at 210° C.

$^1$H NMR spectrum (400 MHz, CDCl$_3$): 0.93 (t, J=7.5 Hz, 3H: CH$_3$ at position 2γ); from 1.20 to 1.40 (mt, 2H: 1H of CH$_2$ at position 3β and 1H of CH$_2$ at position 3γ); 1.29 (d, J=7 Hz, 3H: CH$_3$ at position 1γ); from 1.50 to 1.80 (mt: the 3H corresponding to the other H of CH$_2$ at position 3γ and to CH$_2$ at position 2β); 1.81 (dd, J=16 and 5.5 Hz, 1H: 1H of CH$_2$ at position 5β); 2.04 (mt, 1H: the other H of CH$_2$ at position 3β); 2.48 (s, 3H: ArCH$_3$); 2.74 (s, 6H: ArN(CH$_3$)$_2$); 3.02 (dd, J=14 and 6.5 Hz, 1H: 1H of CH$_2$ at position 4β); from 3.15 to 3.30 (mt, 2H: the other H of CH$_2$ at position 4β and 1H of CH$_2$ at position 3δ); 3.20 (s, 3H: NCH$_3$); 3.28 (d, J=16 Hz, 1H: the other H of CH$_2$ at position 5β); 3.51 (mt, 1H: the other H of CH$_2$ at position 3δ); 3.96 (d, J=17 Hz, 1H: 1H of CH$_2$ at position 5ε); 4.59 (dd, J=7.5 and 7 Hz, 1H: CH at position 3α); 4.80 (mt, 1H: CH at position 2α); 4.90 (broad d, J=10 Hz, 1H: CH at position 1α); 5.31 (dd, J=9 and 6.5 Hz, 1H: CH at position 4α); 5.40 (d, J=17 Hz, 1H: the other H of CH$_2$ at position 5ε); 5.47 (broad d, J=5.5 Hz, 1H: CH at position 5α); 5.61 (d, J=8 Hz, 1H: CH at position 6α); 5.89 (broad q, J=7 Hz, 1H: CH at position 1β); 6.45 (d, J=8 Hz, 1H: aromatic H at position 4ε); 6.59 (d, J=9.5 Hz, 1H: CONH at position 2); 6.80 (broad d, J=8 Hz, 1H: aromatic H at position 4δ at the para position with respect to the Cl); 6.97 (d, J=8 Hz, 1H: aromatic H at position β with respect to N); 7.10 (broad s, 1H: aromatic H at position 4δ at the ortho position with respect to the Cl); from 7.20 to 7.35 (mt: the 6H corresponding to the 5 aromatic H at position 6α and to the aromatic H at position γ with respect to N); 7.37 (broad d, J=8 Hz, 1H 1' $H_4$); 7.42 (dd, J=8 and 4.5 Hz, 1H: 1' $H_5$); 7.84 (broad d, J=4.5 Hz, 1H: 1' $H_6$); 8.37 (d, J=10 Hz, 1H: CONH at position 1); 8.61 (d, J=8 Hz, 1H: CONH at position 6); 11.68 (s, 1H: OH).

EXAMPLE 45

4 g of 2"-hydroxymethylpyrido[2,3-5γ,5δ]pristinamycin $I_E$ and 0.48 g of selenium oxide are introduced into a three-necked flask containing 70 cm$^3$ of dioxane and the mixture is refluxed for 1 hour. The reaction mixture is filtered on Celite® and the filtrate concentrated under reduced pressure at 45° C. (2.7 kPa) to give 5.7 g of a chestnut-coloured foam which is purified by 2 successive chromatographies on 60 g of silica (eluent: methylene chloride-methanol 97/3 by volume). The fractions are combined and concentrated under reduced pressure at 45° C. (2.7 kPa). The solid obtained is stirred in 30 cm$^3$ of diethyl ether, filtered and dried at 40° C. under reduced pressure (90 Pa) to give 0.76 g of 2"-formylpyrido[2,3-5γ,5δ]pristinamycin $I_E$ in the form of a white solid melting at 202° C.

$^1$H NMR spectrum (400 MHz, CDCl$_3$): 0.92 (t, J=7.5 Hz, 3H: CH$_3$ at position 2γ); from 1.20 to 1.35 (mt, 2H: 1H of CH$_2$ at position 3β and 1H of CH$_2$ at position 3γ); 1.31 (d, J=7 Hz, 3H: CH$_3$ at position 1γ); from 1.50 to 1.75 (mt: the 3H corresponding to the other H of CH$_2$ at position 3γ—to 1H of CH$_2$ at position 2β and to 1H of CH$_2$ at position 5β); 1.74 (mt, 1H: the other H of CH$_2$ at position 2β); 2.05 (mt, 1H: the other H of CH$_2$ at position 3β); 2.79 (s, 6H: ArN(CH$_3$)$_2$); 2.95 (dd, J=13 and 5 Hz, 1H: 1H of CH$_2$ at position 4β); from 3.15 to 3.30 (mt, 3H: the other H of CH$_2$ at position 4β—the other H of CH$_2$ at position 5β and 1H of CH$_2$ at position 3δ); 3.26 (s, 3H: NCH$_3$); 3.50 (mt, 1H: the other H of CH$_2$ at position 3δ); 3.97 (d, J=18 Hz, 1H: 1H of CH$_2$ at position 5ε); 4.62 (dd, J=7.5 and 6 Hz, 1H: CH at position 3α); 4.81 (mt, 1H: CH at position 2α); 4.89 (broad d, J=10 Hz, 1H: CH at position 1α); 5.14 (dd, J=11 and 5 Hz, 1H: CH at position 4α); 5.44 (broad d, J=5.5 Hz, 1H: CH at position 5α); 5.52 (d, J=18 Hz, 1H: the other H of CH$_2$ at position 5ε); 5.62 (d, J=8.5 Hz, 1H: CH at position 6α); 5.88 (broad q, J=7 Hz, 1H: CH at position 1β); 6.29 (d, J=8 Hz, 2H: aromatic H at position 4ε); 6.56 (d, J=9.5 Hz, 1H: CONH at position 2); 6.86 (d, J=8 Hz, 2H: aromatic H at position 4δ); from 7.20 to 7.40 (mt: the 5H corresponding to the aromatic H at position 6α); 7.45 (broad d, J=8 Hz, 1H: 1' $H_4$); from 7.45 to 7.55 (mt, 2H: 1' $H_5$ and aromatic H at position γ with respect to N); 7.77 (d, J=8 Hz, 1H: aromatic H at position β with respect to N); 8.00 (broad d, J=4 Hz, 1H: 1' $H_6$); 8.40 (d, J=10 Hz, 1H: CONH at position 1); 8.69 (d, J=8.5 Hz, 1H: CONH at position 6); 9.97 (s, 1H: COH); 11.65 (s, 1H: OH).

2"-hydroxymethylpyrido[2,3-5γ,5δ]-pristinamycin $I_E$ may be obtained as described in Example 11.

EXAMPLE 46

1.7 g of 2"-formylpyrido[2,3-5γ,5δ]-pristinamycin $I_E$ and 1.4 g of ammonium acetate are introduced into a three-necked flask containing 100 cm$^3$ of dioxane and the mixture is refluxed for 1 hour. The reaction mixture is concentrated under reduced pressure and then taken up in 100 cm$^3$ of water and 100 cm$^3$ of methylene chloride. After decantation, drying of the organic phase over sodium sulphate, filtration and concentration to dryness, 1.5 g of a solid is obtained which is chromatographed on 60 g of silica (eluent: methylene chloride-methanol 97/3 by volume). The fractions are combined and then concentrated under reduced pressure at 45° C. (2.7 kPa). The solid obtained is taken up in 30 cm$^3$ of diethyl ether and then filtered and dried at 40° C. under reduced pressure (90 Pa) to give 0.32 g of 2"-carbamoylpyrido[2,3-5γ,5δ]-pristinamycin $I_E$ in the form of an orange-coloured solid melting at 226° C.

$^1$H NMR spectrum (400 MHz, CDCl$_3$): 0.92 (t, J=7.5 Hz, 3H: CH$_3$ at position 2γ); 1.26 (mt, 2H: 1H of CH$_2$ at position 3β and 1H of CH$_2$ at position 3γ); 1.30 (d, J=7 Hz, 3H: CH$_3$ at position 1γ); 1.43 (dd, J=16.5 and 5.5 Hz, 1H: 1H of CH$_2$ at position 5β); from 1.50 to 1.70 (mt: the 2H corresponding to the other H of CH$_2$ at position 3γ and to 1H of CH$_2$ at position 2β); 1.75 (mt, 1H the other H of CH$_2$ at position 2β); 2.06 (mt, 1H: the other H of CH$_2$ at position 3β); 2.79 (s, 6H: ArN (CH$_3$)$_2$); 2.93 (dd, J=12.5 and 4. 5 Hz, 1H: 1H of CH$_2$ at position 4β) 3.08 (d, J=16.5 Hz, 1H: the other H of CH$_2$ at position 5β); from 3.15 to 3.30 (mt, 2H: the other H of CH$_2$ at position 4β and 1H of CH$_2$ at position 3δ); 3.26 (s, 3H: NCH$_3$); 3.49 (mt, 1H: the other H of CH$_2$ at position 3δ); 3.94 (d, J=17.5 Hz, 1H: 1H of CH$_2$ at position 5ε); 4.62 (dd, J=8 and 6.5 Hz, 1H: CH at position 3α); 4.81 (mt, 1H: CH at position 2α); 4.89 (broad d, J=10 Hz, 1H: CH at position 1α); 5.09 (dd, J=11.5 and 4.5 Hz, 1H: CH at position 4α); 5.39 (broad d, J=5.5 Hz, 1H: CH at position 5α); 5.48 (d, J=5 Hz, 1H: 1H of CONH$_2$); 5.51 (d, J=17.5 Hz, 1H: the other H of CH$_2$ at position 5ε); 5.60 (d, J=8.5 Hz, 1H: CH at position 6α); 5.88 (broad q, J=7 Hz, 1H: CH at position 1β); 6.28 (d, J=8 Hz, 2H: aromatic H at position 4ε); 6.57 (d, J=9.5 Hz, 1H: CONH at position 2); 6.87 (d, J=8 Hz, 2H: aromatic H at position 4δ); from 7.20 to 7.40 (mt: the 5H corresponding to the aromatic H at position 6α);

7.46 (broad d, J=8 Hz, 1H: 1' $H_4$); from 7.50 to 7.60 (mt, 2H: 1' $H_5$ and aromatic H at position γ with respect to N); 7.78 (d, J=5 Hz, 1H: the other H of $CONH_2$); 7.99 (mt, 1H: 1' $H_6$); 8.00 (d, J=8 Hz, 1H: aromatic H at position β with respect to N); 8.38 (d, J=10 Hz, 1H: CONH at position 1); 8.67 (d, J=8.5 Hz, 1H: CONH at position 6); 11.67 (s, 1H: OH).

2"-formylpyrido[2,3-5γ,5δ]pristinamycin $I_E$ may be obtained as described in Example 45.

EXAMPLE 47

By carrying out the procedure as in Example 22 but starting with 40 cm³ of acetonitrile, 4.6 g of 5δ-dimethylaminomethylenepristinamycin $I_A$, 0.38 g of acetamidine and heating for 12 hours at 60° C., a solid which is chromatographed on 400 g of silica (eluent:methylene chloride-methanol 97/3 by volume) is obtained after concentrating the reaction mixture to dryness at 45° C. (2.7 kPa). The fractions are pooled, dried over sodium sulphate, filtered and concentrated at 45° C. under reduced pressure (2.7 kPa). The solid obtained is crystallized from 10 cm³ of methanol and then filtered and dried at 40° C. (90 Pa) to give 0.4 g of 2"-methylpyrimido[4,5-5γ,5δ]pristinamycin $I_E$ in the form of white crystals melting at 265° C.

$^1$H NMR spectrum (400 MHz, $CDCl_3$ with addition of $(CD_3)_2SO$ d6): 0.79 (t, J=7.5 Hz, 3H: $CH_3$ at position 2γ); from 1.05 to 1.20 (mt, 2H: 1H of $CH_2$ at position 3β and 1H of $CH_2$ at position 3γ); 1.14 (d, J=7 Hz, 3H: $CH_3$ at position 1γ); 1.24 (dd, J=17 and 5.5 Hz, 1H: 1H of $CH_2$ at position 5β); 1.46 (mt, 1H: the other H of $CH_2$ at position 3γ); 1.52 and 1.62 (2 mts, 1H each: $CH_2$ at position 2β); 1.95 (mt, 1H: the other H of $CH_2$ at position 3β); 2.51 (s, 3H: $ArCH_3$); 2.74 (s, 6H: $ArN(CH_3)_2$); from 2.75 to 2.85 (mt, 1H: 1H of $CH_2$ at position 4β); 2.83 (d, J=17 Hz, 1H: the other H of $CH_2$ at position 5β); from 3.05 to 3.20 (mt, 2H: the other H of $CH_2$ at position 4β and 1H of $CH_2$ at position 3δ); 3.13 (s, 3H: $NCH_3$); 3.37 (mt, 1H: the other H of $CH_2$ at position 3δ); 3.70 (d, J=17 Hz, 1H: 1H of $CH_2$ at position 5ε); 4.48 (dd, J=8 and 6 Hz, 1H: CH at position 3α); 4.65 (mt, 1H: CH at position 2α); 4.75 (broad d, J=10 Hz, 1H: CH at position 1α); 4.94 (dd, J=11.5 and 5 Hz, 1H: CH at position 4α); 5.24 (broad d, J=5.5 Hz, 1H: CH at position 5α); 5.30 (d, J=17 Hz, 1H: the other H of $CH_2$ at position 5ε); 5.45 (d, J=8 Hz, 1H: CH at position 6α); 5.72 (broad q, J=7 Hz, 1H: CH at position 1β); 6.20 (d, J=8 Hz, 2H: aromatic H at position 4ε); 6.54 (d, J=9.5 Hz, 1H: CONH at position 2); 6.72 (d, J=8 Hz, 2H: aromatic H at position 4δ); from 7.05 to 7.30 (mt: the 5H corresponding to the aromatic H at position 6α); 7.32 (broad d, J=8 Hz, 1H: 1' $H_4$); 7.37 (dd, J=8 and 4 Hz, 1H: 1' $H_5$); 7.81 (broad d, J=4 Hz, 1H: 1' $H_6$); 8.17 (s, 1H: CH=N); 8.22 (d, J=10 Hz, 1H: CONH at position 1); 8.56 (d, J=8 Hz, 1H: CONH at position 6); 11.52 (s, 1H: OH).

EXAMPLE 48

By carrying out the procedure as in Example 22 but starting with 40 cm³ of dimethylformamide, 1.84 g of 5δ-dimethylaminomethylenepristinamycin $I_A$, 0.41 g of 2-pyrazinecarboxamidine hydrochloride and 1 cm³ of diisopropylamine, the reaction mixture is heated for 12 hours at 65° C. 0.16 g of 2-pyrazinecarboxamidine hydrochloride is added and the heating is continued for an additional 24 hours. After treating and concentrating the reaction mixture to dryness at 45° C. (2.7 kPa), 2.1 g of solid are obtained, which solid is chromatographed on 100 g of silica (eluent: methylene chloride-methanol 97/3 by volume). The fractions are pooled, dried over sodium sulphate, filtered and concentrated at 45° C. under reduced pressure (2.7 kPa). The solid obtained is crystallized from 10 cm³ of methanol, filtered, washed with twice 5 cm³ of diisopropyl ether and then dried at 40° C. (90 Pa) to give 0.49 g of 2"-(2-pyrazinyl)pyrimido[4,5-5γ,5δ]pristinamycin $I_E$ in the form of yellow crystals melting at 254° C.

$^1$H NMR spectrum (400 MHz, $CDCl_3$): 0.93 (t, J=7.5 Hz, 3H: $CH_3$ at position 2γ); from 1.25 to 1.40 (mt, 2H: 1H of $CH_2$ at position 3β and 1H of $CH_2$ at position 3γ); 1.31 (d, J=7 Hz, 3H: $CH_3$ at position 1γ); 1.51 (dd, J=17 and 6 Hz, 1H: 1H of $CH_2$ at position 5β); from 1.55 to 1.65 (mt, 1H corresponding to the other H of $CH_2$ at position 3β); 1.67 and 1.75 (2 mts, 1H each: $CH_2$ at position 2β); 2.08 (mt, 1H: the other H of $CH_2$ at position 3β); 2.64 (s, 6H: $ArN(CH_3)_2$); 2.94 (dd, J=12 and 5 Hz, 1H: 1H of $CH_2$ at position 4β); 3.18 (d, J=17 Hz, 1H: the other H of $CH_2$ at position 5β); from 3.20 to 3.35 (mt, 1H: 1H of $CH_2$ at position 3δ and the other H of $CH_2$ at position 4β); 3.26 (s, 3H: $NCH_3$); 3.51 (mt, 1H: the other H of $CH_2$ at position 3δ); 3.90 (d, J=17.5 Hz, 1H: 1H of $CH_2$ at position 5ε); 4.61 (dd, J=8 and 6 Hz, 1H: CH at position 3α); 4.81 (mt, 1H: CH at position 2α); 4.90 (dd, J=10 and 1 Hz, 1H: CH at position 1α); 5.12 (dd, J=12 and 5 Hz, 1H: CH at position 4α); 5.45 (broad d, J=6 Hz, 1H: CH at position 5α); 5.53 (d, J=17.5 Hz, 1H: the other H of $CH_2$ at position 5ε); 5.65 (d, J=8.5 Hz, 1H: CH at position 6α); 5.89 (split q, J=7 and 1 Hz, 1H: CH at position 1β); 6.29 (d, J=8 Hz, 2H: aromatic H at position 4ε); 6.55 (d, J=10 Hz, 1H: CONH at position 2); 6.87 (d, J=8 Hz, 2H: aromatic H at position 4δ); from 7.20 to 7.40 (mt: the 5H corresponding to the aromatic H at position 6α); 7.48 (broad d, J=8.5 Hz, 1H: 1' $H_4$); 7.53 (dd, J=8.5 and 4 Hz, 1H: 1' $H_5$); 8.02 (broad d, J=4 Hz, 1H: 1' $H_6$); 8.41 (d, J=10 Hz, 1H: CONH at position 1); 8.58 (s, 1H: CH=N); 8.67 (d, J=2 Hz, 1H: H at position 5 of pyrazine); 8.74 (d, J=8.5 Hz, 1H: CONH at position 6); 8.77 (dd, J=2 and 1.5 Hz, 1H: H at position 6 of pyrazine); 9.68 (d, J=1.5 Hz, 1H: H at position 3 of pyrazine); 11.65 (s, 1H: OH).

EXAMPLE 49

By carrying out the procedure as in Example 22 but starting with 40 cm³ of dimethylformamide, 3 g of 5δ-dimethylaminomethylenepristinamycin $I_A$, 0.74 g of 1H-pyrozolecarboxamidine hydrochloride and 2 cm³ of diisopropylethylamine, the reaction mixture is heated for 4 hours at 65° C. After treating and concentrating the reaction mixture to dryness at 45° C. (2.7 kPa), 2.4 g of a solid is obtained which is chromatographed on 160 g of silica (eluent: methylene chloride-methanol 96/4 by volume). The fractions are combined, dried over sodium sulphate, filtered and concentrated at 45° C. under reduced pressure (2.7 kPa). The foam obtained is crystallized from 10 cm³ of isopropanol. After filtration, washing and drying at 40° C. (90 Pa), 0.41 g of 2"-(1-pyrazolyl)pyrimido[4,5-5γ,5δ]pristinamycin $I_E$ is obtained in the form of yellow crystals melting at 197° C.

$^1$H NMR spectrum (400 MHz, $CDCl_3$): 0.93 (t, J=7.5 Hz, 3H: $CH_3$ at position 2γ); from 1.20 to 1.35 (mt, 2H: 1H of $CH_2$ at position 3β and 1H of $CH_2$ at position 3γ); 1.31 (d, J=7 Hz, 3H: $CH_3$ at position 1γ); 1.45 (dd, J=17 and 6 Hz, 1H: 1H of $CH_2$ at position 5β); from 1.55 to 1.65 (mt, 1H corresponding to the other H of $CH_2$ at position 3γ); 1.67 and 1.75 (2 mts, 1H each: $CH_2$ at position 2β); 2.07 (mt, 1H: the other H of $CH_2$ at position 3β); 2.67 (s, 6H: $ArN(CH_3)_2$); 2.93 (dd, J=12 and 4.5 Hz, 1H: 1H of $CH_2$ at position 4β); 3.10 (d, J=17 Hz, 1H: the other H of $CH_2$ at position 5β); from 3.15 to 3.30 (mt, 1H: 1H of $CH_2$ at position 3δ and the other H of $CH_2$ at position 4β); 3.27 (s, 3H: $NCH_3$); 3.51 (mt, 1H: the other H of $CH_2$ at position 3δ); 3.84 (d, J=17

Hz, 1H: 1H: of $CH_2$ at position 5ε); 4.62 (dd, J=8 and 6 Hz, 1H: CH at position 3α); 4.81 (mt, 1H: CH at position 2α); 4.89 (broad d, J=10 Hz, 1H: CH at position 1α); 5.07 (dd, J=12 and 4.5 Hz, 1H: CH at position 4α); 5.41 (broad d, J=6 Hz, 1H: CH at position 5α); 5.48 (d, J=17 Hz, 1H: the other H of $CH_2$ at position 5ε); 5.67 (d, J=8.5 Hz, 1H: CH at position 6α); 5.89 (broad q, J=7 Hz, 1H: CH at position 1β); 6.29 (d, J=8 Hz, 2H: aromatic H at position 4ε); 6.48 (broad d, J=2 Hz, 1H: H at position 4 of pyrazole); 6.53 (d, J=10 Hz, CONH at position 2); 6.87 (d, J=8 Hz, 2H: aromatic H at position 4δ); from 7.20 to 7.40 (mt: the 5H corresponding to the aromatic H at position 6α); 7.48 (broad d, J=8.5 Hz, 1H: 1' $H_4$); 7.53 (dd, J=8.5 and 4 Hz, 1H: 1' $H_5$); 7.80 (broad s, 1H: H at position 3 of pyrozole); 8.00 (broad d, J=4 Hz, 1H: 1' $H_6$); 8.38 (d, J=10 Hz, 1H: CONH at position 1); 8.38 (s, 1H: CH=N); 8.54 (d, J=2 Hz, 1H: H at position 5 of pyrazole); 8.71 (d, J=8.5 Hz, 1H: CONH at position 6); 11.65 (s, 1H: OH).

EXAMPLE 50

By carrying out the procedure as in Example 22 but starting with 40 cm³ of dimethylformamide, 1.84 g of 5δ-dimethylaminomethylenepristinamycin $I_A$, 0.60 g of S-(2-morpholinoethyl)isothiouronium hydrochloride, 1 cm³ of diisopropylamine and heating overnight at 65° C., 1.5 g of a yellow solid which is purified by two successive chromatographies with 100 g and 200 g of silica respectively (eluent: methylene chloride-methanol 97/3 by volume) are obtained after treating and concentrating the reaction mixture to dryness at 45° C. (2.7 kPa). The fractions are pooled, dried over sodium sulphate, filtered and concentrated at 45° C. under reduced pressure (2.7 kPa). The solid obtained is taken up in 10 cm³ of diisopropyl ether. After filtration, washing and drying at 40° C. (90 Pa), 0.51 g of 2"-(2-morpholinoethylthio)pyrimido[4,5-5γ,5δ]pristinamycin $I_E$ is obtained in the form of an off-white solid melting at 187° C.

¹H NMR spectrum (400 MHz, $CDCl_3$): 0.92 (t, J=7.5 Hz, 3H: $CH_3$ at position 2γ); from 1.15 to 1.40 (mt, 3H: 1H of $CH_2$ at position 3β—1H of $CH_2$ at position 3γ and 1H of $CH_2$ at position 5β); 1.31 (d, J=7 Hz, 3H: $CH_3$ at position 1γ); from 1.50 to 1.70 (mt: the 2H corresponding to the other H of $CH_2$ at position 3γ and to 1H of $CH_2$ at position 2β); 1.75 (mt, 1H: the other H of $CH_2$ at position 2β); 2.04 (mt, 1H: the other H of $CH_2$ at position 3β); 2.53 (unresolved complex, 4H: the 2 $NCH_2$ of morpholine); 2.69 (t, J=7.5 Hz, 2H: $NCH_2$); from 2.80 to 2.95 (mt, 2H: Hzthe other H of $CH_2$ at position 5β and 1H of $CH_2$ at position 4β); 2.90 (s, 6H: $ArN(CH_3)_2$); from 3.15 to 3.35 (mt, 4H: $ArSCH_2$—the other H of $CH_2$ at position 4β and 1H of $CH_2$ at position 3δ); 3.27 (s, 3H: $NCH_3$); 3.50 (mt, 1H: the other H of $CH_2$ at position 3δ); from 3.65 to 3.80 (mt, 5H: the 2 $OCH_2$ of morpholine and 1H of $CH_2$ at position 5ε); 4.60 (dd, J=8 and 6 Hz, 1H: CH at position 3α); 4.80 (mt, 1H: CH at position 2α); 4.89 (broad d, J=10 Hz, 1H: CH at position 1α); 5.08 (dd, J=11.5 and 5 Hz, 1H: CH at position 4α); 5.33 (broad d, J=5.5 Hz, 1H: CH at position 5α); 5.40 (d, J=17 Hz, 1H: the other H of $CH_2$ at position 5ε); 5.65 (d, J=8.5 Hz, 1H: CH at position 6α); 5.88 (broad q, J=7 Hz, 1H: CH at position 1β); 6.35 (d, J=8 Hz, 2H: aromatic H at position 4ε); 6.52 (d, J=10 Hz, 1H: CONH at position 2); 6.85 (d, J=8 Hz, 2H: aromatic H at position 4δ); from 7.15 to 7.40 (mt: the 5H corresponding to the aromatic H at position 6α); 7.45 (broad d, J=8.5 Hz, 1H: 1' $H_4$); 7.49 (dd, J=8.5 and 4 Hz, 1H: 1' $H_5$); 7.92 (broad d, J=4 Hz, 1H: Hz 1 ' $H_6$); 8.16 (s, 1H: CH=N); 8.37 (d, J=10 Hz, 1H: CONH at position 1); 8.70 (d, J=8.5 Hz, 1H: CONH at position 6); 11.64 (s, 1H: OH).

S-(2-morpholinoethyl)isothiouronium dihydrochloride may be prepared according to DOHERTY Chem. Soc., 79, 5667–70, (1957) or CLINTON J. Am. Chem. Soc., 70, 950, (1948).

EXAMPLE 51

By carrying out the procedure as in Example 22 but starting with 50 cm³ of dimethylformamide, 2 g of 5δ-dimethylaminomethylenepristinamycin $I_A$, 0.67 g of S-(4-pyridylmethyl)isothiouronium hydrochloride, 1.5 cm³ of diisopropylamine and heating at 65° C. for 48 hours, a solid which is chromatographed on 40 g of silica (eluent: methylene chloride-methanol 98/2 by volume) and then HPLC on 450 g of 10 μm $C_8$ silica (eluent: water-acetonitrile 72.5/27.5 by volume, containing 0.1% trifluoroacetic acid) is obtained after treating and concentrating the reaction mixture to dryness at 45° C. (2.7 kPa). The fractions are combined, the acetonitrile removed at 40° C. under reduced pressure (2.7 kPa) and then the pH of the aqueous phase is adjusted to 7–8 by addition of water saturated with sodium bicarbonate. The precipitate obtained is filtered, dried at 40° C. under 90 Pa to give 0.22 g of 2"-(4-pyridylmethylthio)pyrimido[4,5-5γ,5δ]pristinamycin $I_E$ in the form of a white solid melting at 195° C.

¹H NMR spectrum (400 MHz, $CDCl_3$): 0.91 (t, J=7.5 Hz, 3H: $CH_3$ at position 2γ); from 1.20 to 1.40 (mt, 3H: 1H of $CH_2$ at position 3β—1H of $CH_2$ at position 3γ and 1H of $CH_2$ at position 5β); 1.31 (d, J=7 Hz, 3H: $CH_3$ at position 1γ); from 1.50 to 1.75 (mt: the 2H corresponding to 1H of $CH_2$ at position 2β and the other H of $CH_2$ at position 3γ); 1.74 (mt, 1H: the other H of $CH_2$ at position 2β); 2.05 (mt, 1H: the other H of $CH_2$ at position 3β); 2.83 (s, 6H: $ArN(CH_3)_2$); from 2.90 to 3.00 (mt, 2H: 1H of $CH_2$ at position 4β and the other H of $CH_2$ at position 5β); from 3.15 to 3.30 (mt, 2H: 1H of $CH_2$ at position 3δ and the other H of $CH_2$ at position 4β); 3.26 (s, 3H: $NCH_3$); 3.50 (mt, 1H: the other H of $CH_2$ at position 3δ); 3.76 (d, J=17 Hz, 1H: 1H of $CH_2$ at position 5ε); 4.27 and 4.39 (2 d, J=15 Hz, 1H each: $ArSCH_2Ar$); 4.61 (dd, J=7.5 and 5.5 Hz, 1H: CH at position 3α); 4.79 (mt, 1H: CH at position 2α); 4.87 (broad d, J=10 Hz, 1H: CH at position 1α); 5.07 (dd, J=12 and 4.5 Hz, 1H: CH at position 4α); 5.33 (broad d, J=5.5 Hz, 1H: CH at position 5α); 5.39 (d, J=17 Hz, 1H: the other H of $CH_2$ at position 5ε); 5.64 (d, J=8 Hz, 1H: CH at position 6α); 5.87 (broad q, J=7 Hz, 1H: CH at position 1β); 6.33 (d, J=8 Hz, 2H aromatic H at position 4ε); 6.53 (d, J=10 Hz, 1H: CONH at position 2); 6.84 (d, J=8 Hz, 2H: aromatic H at position 4δ); from 7.20 to 7.40 (mt: the 7H corresponding to aromatic H at position 6α and to H at position β of pyridine); 7.45 (broad d, J=8.5 Hz, 1H: 1' $H_4$); 7.48 (dd, J=8.5 and 4 Hz, 1H: 1' $H_5$); 7.93 (broad d, J=4 Hz, 1H: 1' $H_6$); 8.18 (s, 1H: CH=N); 8.36 (d, J=10 Hz, 1H: CONH at position 1); 8.52 (d, J=6 Hz, 2H: H at position α of pyridine); 8.72 (d, J=8 Hz, 1H: CONH at position 6); 11.63 (s, 1H: OH).

EXAMPLE 52

25 cm³ of water, 1.1 g of sodium metaperiodate and then 21 mg of ruthenium trichloride are introduced into a three-necked flask Hzcontaining 100 cm³ of acetonitrile and 5 g of 2"-methylsulphonylpyrimido[4,5-5γ,5δ]pristinamycin $I_E$ and the mixture is kept stirring for 12 hours. An additional 0.55 g of sodium periodate is again added and the mixture is kept stirring for 4 hours. 25 cm³ of water, 1.25 g of sodium thiosulphate and then 250 cm³ of methylene chloride and 150 cm³ of water are added to the reaction mixture. The organic phase is decanted off, dried over magnesium sulphate, filtered and concentrated to dryness at 40° C. under reduced pressure (2.7 kPa). The solid obtained is disintegrated in diethyl ether to give 3.57 g of a solid which is purified by 2 flash chromatographies on 250 g and 70 g of silica respectively (eluent: methylene chloride-methanol 95/5 and then 97/3 by volume). The fractions are pooled, dried over magnesium sulphate, filtered and concentrated at 45° C. under reduced pressure (2.7 kPa) to give after drying at 40° C. (90 Pa) 0.60 g of 2"-methylsulphonylpyrimido[4,5-5γ,5δ](4ζ-methylamino)-(4ζ-dedimethylamino) pristinamycin $I_E$.

$^1$H NMR spectrum (400 MHz, CDCl$_3$): 0.91 (t, J=7.5 Hz, 3H: CH$_3$ at position 2γ); from 1.20 to 1.40 (mt, 3H: 1H of CH$_2$ at position 3β—1H of CH$_2$ at position 3γ and 1H of CH$_2$ at position 5β); 1.31 (d, J=7 Hz, 3H: CH$_3$ at position 1γ); from 1.50 to 1.70 (mt: the 2H corresponding to 1H of CH$_2$ at position 2β and the other H of CH$_2$ at position 3γ); 1.74 (mt, 1H: the other H of CH$_2$ at position 2β); 2.07 (mt, 1H: the other H of CH$_2$ at position 3β); 2.82 (s, 3H: ArNCH$_3$); 2.88 (dd, J=12 and 4 Hz, 1H: 1H of CH$_2$ at position 4β); 3.10 (d, J=18 Hz, 1H: the other H of CH$_2$ at position 5β); 3.16 (t, J=12 Hz, 1H: the other H of CH$_2$ at position Hz 4β); from 3.20 to 3.30 (mt, 1H: 1H of CH$_2$ at position 3δ); 3.25 (s, 3H: NCH$_3$); 3.33 (s, 3H: SO$_2$CH$_3$); 3.50 (mt, 1H: the other H of CH$_2$ at position 3γ); 3.82 (d, J=17.5 Hz, 1H: 1H of CH$_2$ at position 5ε); 4.12 (unresolved complex, 1H: ARNH); 4.60 (dd, J=8 and 5.5 Hz, 1H: CH at position 3α); 4.80 (mt, 1H CH at position 2α); 4.90 (dd, J=10 and 1 Hz, 1H: CH at position 1α); 4.97 (dd, J=12 and 4 Hz, 1H: CH at position Hz 4α); 5.41 (broad d, J=6.5 Hz, 1H: CH at position 5α); 5.55 (d, J=17.5 Hz, 1H: the other H of CH$_2$ at position Hz 5ε); 5.65 (d, J=8.5 Hz, 1H: CH at position 6α); 5.87 (split q, J=7 and 1 Hz, 1H: 1H: CH at position 1β); 6.05 (d, J=8 Hz, 2H aromatic H at position 4ε); 6.53 (d, J=10 Hz, 1H: CONH at position 2); 6.72 (d, J=8 Hz, 2H: aromatic H at position 4δ); from 7.15 to 7.40 (mt: the 5H corresponding to the aromatic H at position 6α); 7.49 (dd, J=8.5 and 1.5 Hz, 1H: 1' H$_4$); 7.56 (dd, J=8.5 and 4 Hz, 1H: 1' H$_5$); 8.00 (dd, J=4 and 1.5 Hz, 1H: 1' H$_6$); 8.38 (d, J=10 Hz, 1H: CONH at position 1); 8.50 (s, 1H: CH=N); 8.73 (d, J=8.5 Hz, 1H: CONH at position 6); 11.63 (s, 1H: OH).

2"-methylsulphonylpyrimido[4,5-5γ,5δ]pristinamycin $I_E$ may be obtained as described in Example 24.

EXAMPLE 53

0.146 ml of 2-diethylaminoethanethiol and 47 mg of sodium hydride are added to a three-necked flask Hzcontaining 10 cm$^3$ of dimethylformamide followed, dropwise, by 1 g of potassium salt of 2"-methylsulphonylpyrimido[4,5-5γ,5δ]pristinamycin $I_E$ in 10 cm$^3$ of dimethylformamide. The mixture is kept stirring for one hour at 20° C. The reaction mixture is poured over 100 cm$^3$ of water and 10 cm$^3$ of 0.1 N hydrochloric acid are added to pH 7 and then 40 cm$^3$ of methylene chloride. The aqueous phase is decanted off and extracted with 4 times 40 cm$^3$ of methylene chloride. The organic phases are combined, dried over magnesium sulphate, filtered and then concentrated under reduced pressure. The solid obtained is disintegrated in ether to give, after filtration, 0.64 g of a solid which is purified by flash chromatography (eluent: methylene chloride-methanol 97/3 by volume). The fractions are pooled, dried over magnesium sulphate, filtered and concentrated at 45° C. under reduced pressure (2.7 kPa) to give after drying at 40° C. (90 Pa) 0.23 g of 2"-diethylaminoethylthiopyrimido[4,5-5γ,5δ]-pristinamycin $I_E$.

$^1$H NMR spectrum (400 MHz, CDCl$_3$): 0.90 (t, J=7.5 Hz, 3H: CH$_3$ at position 2γ); 1.06 (unresolved complex, 6H: the 2 CH$_3$ of diethylamine); from 1.20 to 1.35 (mt, 3H: 1H of CH$_2$ at position 3β—1H of CH$_2$ at position 3γ and 1H of CH$_2$ at position 5β); 1.30 (d, J=7 Hz, 3H: CH$_3$ at position 1γ); from 1.50 to 1.65 (mt: the 1H corresponding to the other H of CH$_2$ at position 3γ); 1.65 and 1.74 (2 mts, 1H each: CH$_2$ at position 2β); 2.05 (mt, 1H: the other H of CH$_2$ at position 3β); 2.58 (unresolved complex, 4H: the 2 NCH$_2$ of diethylamine); 2.79 (mt, 2H: NCH$_2$); from 2.85 to 3.00 (mt, 2H: 1H of CH$_2$ at position 4β and the other H of CH$_2$ at position 5β); 2.88 (s, 6H: ArN(CH$_3$)$_2$); from 3.10 to 3.30 (mt, 4H: the other H of CH$_2$ at position 4β—1H of CH$_2$ at position 3δ and ArSCH$_2$); 3.26 (s, 3H: NCH$_3$); 3.50 (mt, 1H: the other H of CH$_2$ at position 3δ); 3.76 (d, J=17.5 Hz, 1H: 1H of CH$_2$ at position 5ε); 4.60 (dd, J=7.5 and 5.5 Hz, 1H: CH at position 3α); 4.80 (mt, 1H: CH at position 2α); 4.89 (dd, J=10 and 1 Hz, 1H: CH at position 1α); 5.07 (dd, J=12 and 4.5 Hz, 1H: CH at position 4α); 5.33 (broad d, J=5.5 Hz, 1H: CH at position Hz 5α); 5.38 (d, J=17.5 Hz, 1H: the other H of CH$_2$ at position 5ε); 5.65 (d, J=8 Hz, 1H: CH at position 6α); 5.88 (split q, J=7 and 1 Hz, 1H: CH at position Hz 1α); 6.34 (d, J=8 Hz, 2H: aromatic H at position 4ε); 6.53 (d, J=10 Hz, 1H: CONH at position 2); 6.85 (d, J=8 Hz, 2H: aromatic H at position 4δ); from 7.20 to 7.40 (mt: the 5H corresponding to the aromatic H at position 6α); 7.46 (dd, J=8.5 and 1.5 Hz, 1H: 1' H$_4$); 7.49 (dd, J=8.5 and 4 Hz, 1H: 1' H$_5$); 7.92 (dd, J=4 and 1.5 Hz, 1H: 1' H$_6$); 8.15 (s, 1H: CH=N); 8.38 (d, J=10 Hz, 1H: CONH at position 1); 8.68 (d, J=8 Hz, 1H: CONH at position 6); 11.64 (unresolved complex, 1H: OH).

The potassium salt of 2"-methylsulphonylpyrimido[4,5-5γ,5δ]pristinamycin $I_E$ may be prepared in the following manner:

1.4 g of potassium bicarbonate are added to a round-bottomed flask placed under argon containing 150 cm$^3$ of acetone and 10 g of 2"-methylsulphonylpyrimido[4,5-5γ,5δ] pristinamycin $I_E$ and the mixture is kept stirring overnight. The cream-coloured precipitate is filtered, washed several times with acetone and with diethyl ether and then filtered, dried under reduced pressure to give 7.4 g of potassium salt of 2"-methylsulphonylpyrimido[4,5-5γ,5δ]pristinamycin $I_E$ which is used as it is.

The 2"-methylsulphonylpyrimido[4,5-5 ,5δ]-pristinamycin $I_E$ may be obtained as described in Example 24.

EXAMPLE 54

3.7 g of potassium salt of 2"-methylsulphonylpyrimido [4,5-5γ,5δ]pristinamycin $I_E$ and 2.2 cm$^3$ of an 8 M solution of methylamine in ethanol are added to an autoclave containing 37 cm$^3$ of dimethylformamide and the mixture is heated for 8 hours at 80° C. The reaction mixture is concentrated to dryness at 50° C. under reduced pressure (2.7 kPa) to give 4.1 g of an orange-coloured residue which is taken up in 20 cm$^3$ of water and 15 cm$^3$ of ethyl acetate. The organic phase is decanted off, washed with twice 10 cm$^3$ of water, dried over magnesium sulphate, filtered and concentrated to dryness at 35° C. under reduced pressure (2.7 kPa). 0.4 g of a beige solid is thus obtained which is purified by flash chromatography on 40 g of silica (eluent: methylene chloride-methanol 96/4 by volume). The fractions are combined, dried over magnesium sulphate, filtered and concentrated at 45° C. under reduced pressure (2.7 kPa) to give 0.16 g of a solid which is crystallized from 3.2 cm$^3$ of an acetonitrile-water mixture (50/50 by volume). After filtration and then drying at 40° C. (90 Pa), 0.13 g of 2"-methylaminopyrimido[4,5-5γ,5δ]pristinamycin $I_E$ is obtained in the form of beige crystals melting at 210–220° C.

$^1$H NMR spectrum (400 MHz, CDCl$_3$): 0.92 (t, J=7.5 Hz, 3H: CH$_3$ at position 2γ); from 1.15 to 1.35 (mt, 3H: 1H of CH$_2$ at position 3β—1H of CH$_2$ at position 3γ and 1H of CH$_2$ at position 5β); 1.30 (d, J=7 Hz, 3H: CH$_3$ at position 1γ); from 1.50 to 1.70 (mt: the 2H corresponding to the other H of CH$_2$ at position 3γ and to 1H of CH$_2$ at position 2β); 1.74 (mt, 1H: the other H of CH$_2$ at position 2β); 2.04 (mt, 1H: the other H of CH$_2$ at position 3β); from 2.80 to 3.00 (mt, 2H: 1H of CH$_2$ at position 4β and the other H of CH$_2$ at position 5β); 2.88 (s, 6H: ArN(CH$_3$)$_2$); 2.97 (d, J=5 Hz, 3H: ArNCH$_3$); from 3.15 to 3.30 (mt, 2H: the other H of CH$_2$ at position 4β and 1H of CH$_2$ at position 3δ); 3.25 (s, 3H: NCH$_3$); 3.48 (mt, 1H: the other H of CH$_2$ at position 3δ); 3.72 (d, J=17 Hz, 1H: 1H of CH$_2$ at position 5ε); 4.60 (dd, J=8 and 7 Hz, 1H: CH at position 3α); 4.80 (mt, 1H: CH at position 2α); from 4.85 to 4.95 (mt, 2H: CH at position 1α and ArNH); 5.10 (dd, J=10.5 and 4 Hz, 1H: CH at position 4α); 5.30 (mt, 1H: CH at position 5α); 5.31 (d, J=17 Hz, 1H: the other H of CH$_2$ at position 5ε); 5.64 (d, J=8 Hz, 1H: CH at position 6α); 5.88 (broad q, J=7 Hz, 1H: CH at position Hz 1β); 6.40 (d, J=8 Hz, 2H: aromatic H at position 4ε); 6.54 (d, J=10 Hz, 1H: CONH at position 2); 6.87 (d, J=8 Hz, 2H aromatic H at position 4δ); from 7.15 to 7.40 (mt: the 5H corresponding to the aromatic H at position 6α); 7.44 (limiting AB, 2H: 1' H$_4$ and 1' H$_5$); 7.91 (broad d, J=4 Hz, 1H: 1' H$_6$); 7.97 (s, 1H: CH=N); 8.38 (d, J=10 Hz, 1H: CONH at position 1); 8.64 (d, J=8 Hz, 1H: CONH at position 6); 11.65 (s, 1H: OH).

The potassium salt of 2"-methylsulphonylpyrimido[4,5-5γ,5δ]pristinamycin I$_E$ may be prepared according to Example 53.

EXAMPLE 55

By carrying out the procedure by analogy with Example 32 but starting with 20 cm$^3$ of methylene chloride, 2.3 g of 2"-(2-pyridyl)pyrimido[4,5-5γ,5δ]pristinamycin I$_E$, 0.2 g of ethylene glycol, 2.35 g of acetic acid, 0.48 g of tetra-n-butylammonium periodate and stirring for 12 hours, 3.4 g of a crude product are obtained, which product is dissolved in 70 cm$^3$ of 0.5 N sulphuric acid. The mixture is extracted with 3 times 50 cm$^3$ of ethyl acetate. After treatment and concentration, 1.58 g of yellow solid are obtained, which solid is purified by two successive chromatographies, on 100 g and 30 g of silica respectively (eluent: methylene chloride-methanol 95/5 and then methylene chloride-acetonitrile-methanol: 86/8/6 by volume). The fractions are pooled, dried over magnesium sulphate, filtered and then concentrated at 45° C. under reduced pressure (2.7 kPa). The solid obtained is taken up in 10 cm$^3$ of diisopropyl ether, filtered, washed with 10 cm$^3$ of diisopropyl ether and then dried at 40° C. under reduced pressure (90 Pa) to give 0.52 g of 2"-(2-pyridyl)pyrimido[4,5-5γ,5δ]-(4ζ-methylamino)(4ζ-dedimethylamino)pristinamycin I$_E$ in the form of a pale-yellow solid melting at 209° C.

$^1$H NMR spectrum (400 MHz, CDCl$_3$): 0.93 (t, J=7.5 Hz, 3H: CH$_3$ at position 2γ); from 1.25 to 1.40 (mt, 2H: 1H of CH$_2$ at position 3β and 1H of CH$_2$ at position 3γ); 1.32 (d, J=7 Hz, 3H: CH$_3$ at position 1γ); 1.52 (dd, J=18 and 6, 1H: 1H of CH$_2$ at position 5β); 1.62 (mt, 1H: the other H of CH$_2$ at position 3γ); from 1.60 to 1.85 (mt: the 2H corresponding to CH$_2$ at position 2β); 2.08 (mt, 1H: the other H of CH$_2$ at position 3β); 2.58 (s, 3H: ArNCH$_3$); 2.92 (dd, J=12 and 4.5 Hz, 1H: 1H of CH$_2$ at position 4β); from 3.15 to 3.30 (mt, 3H: the other H of CH$_2$ at position 5β—1H of CH$_2$ at position 3δ and the other H of CH$_2$ at position 4β); 3.27 (s, 3H: NCH$_3$); 3.51 (mt, 1H: the other H of CH$_2$ at position 3δ); 3.89 (d, J=17 Hz, 1H: 1H of CH$_2$ at position 5ε); 4.63 (dd, J=8 and 6 Hz, 1H: CH at position 3α); 4.82 (mt, 1H: CH at position 2α); 4.90 (dd, J=10 and 1 Hz, 1H: CH at position 1α); 5.10 (dd, J=11 and 4.5 Hz, 1H: CH at position 4α); 5.42 (broad d, J=6 Hz, 1H: CH at position Hz 5α); 5.53 (d, J=17 Hz, 1H: the other H of CH$_2$ at position 5ε); 5.69 (d, J=8.5 Hz, 1H: CH at position 6α); 5.89 (split q, J=7 and 1 Hz, 1H: CH at position Hz 1β); 6.16 (d, J=8 Hz, 2H: aromatic H at position 4ε); 6.56 (d, J=10 Hz, 1H: CONH at position 2); 6.79 (d, J=8 Hz, 2H: aromatic H at position 4δ); from 7.20 to 7.40 (mt: the 5H corresponding to the aromatic H at position 6α); 7.40 (broad dd, J=8 and 5 Hz, 1H: H at position 5 of pyridine); 7.48 (dd, J=8.5 and 1 Hz, 1H: 1' H$_4$); 7.53 (dd, J=8.5 and 4 Hz, 1H: 1' H$_5$); 7.85 (split t, J=8 and 2 Hz, 1H: H at position 4 of pyridine); 8.01 (dd, J=4 and 1 Hz, 1H: 1' H$_6$); 8.43 (d, J=10 Hz, 1H: CONH at position 1); 8.46 (broad d, J=8 Hz, H at position 3 of pyridine); 8.56 (s, 1H: CH=N); 8.71 (d, J=8.5 Hz, 1H: CONH at position 6); 8.84 (broad d, J=5 Hz, 1H: H at position 6 of pyridine); 11.64 (s, 1H: OH).

2"-(2-pyridyl)pyrimido[4,5-5γ,5δ]-pristinamycin I$_E$ may be obtained as described in Example 28.

EXAMPLE 56

3.9 g of 2"-azidopyrimido[4,5-5γ,5δ]-pristinamycin I$_E$ and 2.16 g of triphenylphosphine are added to a three-necked flask containing 70 cm$^3$ of tetrahydrofuran and 100 cm$^3$ of 0.1 N hydrochloric acid and the mixture is kept stirring overnight. The reaction mixture is concentrated to dryness at 40° C. under reduced pressure (2.7 kPa); the gummy residue is taken up in 50 cm$^3$ of water and 100 cm$^3$ of 0.1 N hydrochloric acid and extracted with 3 times 80 cm$^3$ of methylene chloride. After decantation, the aqueous phase is neutralized by addition of water saturated with sodium bicarbonate and extracted with 3 times 100 cm$^3$ of methylene chloride. The organic phases are pooled, dried over magnesium sulphate, filtered and concentrated at 45° C. under reduced pressure to give 3.5 g of a yellow solid which is purified by chromatography on 300 g of silica (eluent: methylene chloride-methanol: 96/4 by volume). The fractions are pooled, dried over magnesium sulphate, filtered and concentrated at 45° C. under reduced pressure (2.7 kPa) to give a yellow solid which is recrystallized from 40 cm$^3$ of isopropanol. After filtration, washing with 10 cm$^3$ of iso-propanol and drying at 40° C. under reduced pressure, 0.97 g of 2"-aminopyrimido[4,5-5γ,5δ]-pristinamycin I$_E$ is obtained in the form of a pale-yellow powder melting at 214° C.

2"-azidopyrimido[4,5-5γ,5δ]pristinamycin I$_E$ may be prepared as in Example 25 but starting with 250 cm$^3$ of dimethylformamide, 10 g of 2"-(4-methyl-benzenesulphonyl)pyrimido[4,5-5γ,5δ]pristinamycin I$_E$, 2.42 g of sodium azide and heating at 65° C. for three days. After concentrating the reaction mixture to dryness, 400 cm$^3$ of water saturated with sodium chloride are added. The orange-yellow precipitate which appeared is filtered and then taken up in 200 cm$^3$ of methylene chloride. After decantation, drying over magnesium sulphate, filtration and concentration to dryness at 40° C. under reduced pressure (2.7 kPa), a solid is obtained which is purified by chromatography on 150 g of silica (eluent: methylene chloride-methanol 96/4 by volume) to give after concentrating the fractions 3.9 g of 2"-azidopyrimido[4,5-5γ,5δ]pristinamycin I$_E$ in the form of an orange-coloured solid which is used as it is.

$^1$H NMR spectrum (400 MHz, CDCl$_3$): 0.92 (t, J=7.5 Hz, 3H: CH$_3$ at position 2γ); from 1.15 to 1.35 (mt, 3H: 1H of CH$_2$ at position 3β—1H of CH$_2$ at position 3γ and 1H of CH$_2$ at position 5β); 1.30 (d, J=7 Hz, 3H: CH$_3$ at position 1γ); 1.56 (mt, 1H: the other H of CH$_2$ at position 3γ); from 1.60 to 1.80 (mt: the 2H corresponding to CH$_2$ at position 2β); 2.04 (mt, 1H: the other H of CH$_2$ at position 3β); 2.81 (d, J=17.5 Hz, 1H: the other H of CH$_2$ at position 5β); from 2.85 to 2.95 (mt, 1H: 1H of CH$_2$ at position 4β); 2.89 (s, 6H: ArN(CH$_3$)$_2$; from 3.15 to 3.30 (mt, 2H: the other H of CH$_2$ at position 4β and 1H of CH$_2$ at position 3δ); 3.25 (s, 3H: NCH$_3$); 3.49 (mt, 1H: the other H of CH$_2$ at position 3δ); 3.71 (d, J=17 Hz, 1H: 1H of CH$_2$ at position 5ε); 4.60 (dd, J=8 and 6 Hz, 1H: CH at position 3α); 4.80 (mt, 1H: CH at position 2α); 4.86 (s, 2H: ArNH$_2$); 4.88 (broad d, J=10 Hz, 1H: CH at position 1α); 5.08 (dd, J=11.5 and 5 Hz, 1H: CH at position 4α); 5.31 (mt, 1H: CH at position 5α); 5.33 (d, J=17 Hz, 1H the other H of CH$_2$ at position 5ε); 5.64 (d, J=8.5 Hz, 1H: CH at position 6α); 5.88 (broad q, J=7 Hz, 1H: CH at position 1β); 6.40 (d, J=8 Hz, 2H: aromatic H at position 4ε); 6.54 (d, J=10 Hz, 1H: CONH at position 2); 6.86 (d, J=8 Hz, 2H: aromatic H at position 4δ); from 7.20 to 7.35 (mt: the 5H corresponding to the aromatic H at position 6α); 7.42 (dd, J=8 and 1.5 Hz, 1H 1' H$_4$); 7.45 (dd, J=8 and 4 Hz, 1H: 1' H$_5$); 7.89 (dd, J=4 and 1.5 Hz, 1H: 1' H$_6$); 7.97 (s, 1H: CH═N); 8.36 (d, J=10 Hz, 1H: CONH at position 1); Hz 8.64 (d, J=8.5 Hz, 1H: CONH at position 6); 11.65 (s, 1H: OH).

2"-(4-methylbenzenesulphonyl)pyrimido[4,5-5γ,5δ] pristinamycin I$_E$ may be obtained as described in Example 25.

EXAMPLE 57

1 g of 2"-hydroxymethylpyrido[2,3-5γ,5δ]-pristinamycin I$_E$ and 0.155 cm$^3$ of thionyl chloride are added to a three-necked flask placed under a nitrogen stream and containing 10 cm$^3$ of acetonitrile. The mixture is kept stirring for 30 minutes and 0.9 cm$^3$ of triethylamine is added. After filtering the triethylamine hydrochloride formed, a solution of the sodium salt of 2-diethylaminoethanethiol (obtained after stirring for 30 minutes from 0.324 cm$^3$ of diethylaminoethanethiol and 102 mg of sodium hydride in 20 cm$^3$ of acetonitrile) are added. After heating at 50° C. for 3 hours, the insoluble matter is removed by filtration and then washed with 20 cm$^3$ of acetonitrile. The filtrate is concentrated to dryness under reduced pressure (45° C.–2.7 kPa) and then the residue is taken up in 50 cm$^3$ of methylene chloride and 50 cm$^3$ of water. The organic phase is decanted off, washed with 25 cm$^3$ of water, dried over sodium sulphate and then filtered to give, after concentration to dryness, 1.1 g of a residue which is chromatographed on 50 g of silica (eluent: methylene chloride-methanol Hzgradient 98/2 to 90/10 by volume) to give 150 mg of product which is purified by HPLC on 450 g of 10 μm C$_8$ silica (eluent: water-acetonitrile 70/30 by volume, containing 0.1% trifluoroacetic acid). The fractions are combined and then the acetonitrile removed at 40° C. under reduced pressure (2.7 kPa). The aqueous phase is adjusted to pH 7–8 by addition of water saturated with sodium bicarbonate and then extracted with twice 25 cm$^3$ of methylene chloride. The organic phase is dried over sodium sulphate, filtered and then concentrated to dryness to give 30 mg of 2"-diethylaminoethylthiomethylpyrido[2,3-5γ,5δ] pristinamycin I$_E$ in the form of a yellow solid melting at 132° C.

$^1$H NMR spectrum (400 MHz, CDCl$_3$): 0.92 (t, J=7.5 Hz, 3H: CH$_3$ at position 2γ); 1.02 (t, J=7 Hz, 6H: CH$_3$ of diethylamino); from 1.20 to 1.35 (mt, 2H: 1H of CH$_2$ at position 3β and 1H of CH$_2$ at position 3γ); 1.29 (d, J=7 Hz, 3H: CH$_3$ at position 1γ); 1.57 (mt, 1H: the other H of CH$_2$ at position 3γ); from 1.60 to 1.80 (mt: the 2H corresponding to the CH$_2$ at position 2β); 1.88 (very broad d, J=16.5 Hz, 1H: 1H of CH$_2$ at position 5β); 2.03 (mt, 1H: the other H of CH$_2$ at position 3β); from 2.45 to 2.65 (unresolved complex, 4H: NCH$_2$ of diethylamino); from 2.60 to 2.75 (mt, 4H: SCH$_2$CH$_2$N); 2.84 (s, 6H: ArN(CH$_3$)$_2$); 2.98 (dd, J=13.5 and 6 Hz, 1H: 1H of CH$_2$ at position 4ε); from 3.10 to 3.30 (mt, 3H the other H of CH$_2$ at position 4β—the other H of CH$_2$ at position 5β and 1H of CH$_2$ at position 3δ); 3.20 (s, 3H: NCH$_3$); 3.49 (mt, 1H: the other H of CH$_2$ at position 3δ); 3.79 (s, 2H: ArCH$_2$S); 3.94 (d, J=17 Hz, 1H: 1H of CH$_2$ at position 5ε); 4.60 (dd, J=8 and 5.5 Hz, 1H: CH at position 3α); 4.79 (mt, 1H: CH at position 2α); 4.87 (dd, J=10 and 1 Hz, 1H: CH at position 1α); 5.28 (dd, J=9 and 6 Hz, 1H: CH at position 4α); 5.44 (broad d, J=5.5 Hz, 1H: CH at position 5α); 5.44 (d, J=17 Hz, 1H: the other H of CH$_2$ at position 5ε); 5.60 (d, J=8 Hz, 1H: CH at position 6α); 5.87 (split q, J=7 and 1 Hz, 1H: CH at position 1β); 6.36 (d, J=8 Hz, 2H: aromatic H at position 4ε); 6.57 (d, J=10 Hz, 1H: CONH at position 2); 6.84 (d, J=8 Hz, 2H: aromatic H at position 4δ); 7.20 (d, J=8 Hz, 1H: aromatic H at position β with respect to N); from 7.20 to 7.40 (mt: the 8H corresponding to the 5 aromatic H at position 6α—to the aromatic H at position γ with respect to N—to 1' H$_4$ and to 1' H$_5$); 7.83 (dd, J=4 and 1 Hz, 1H: 1' H$_6$); 8.40 (d, J=10 Hz, 1H: CONH at position 1); 8.67 (d, J=8 Hz, 1H: CONH at position 6); 11.65 (broad unresolved complex, 1H: OH).

2"-hydroxymethylpyrido[2,3-5γ,5δ]-pristinamycin I$_E$ may be obtained as described in Example 11.

EXAMPLE 58

4ε-Chloro-2"-tert-butylpyrido[2,3-5γ,5δ]pristinamycin I$_E$
2"-tert-Butylpyrido[2,3-5γ,5δ](4ζ-methylamino)(4ζ-dedimethylamino)pristinamycin I$_E$
4ε-Chloro-2"-tert-butylpyrido[2,3-5γ,5δ](4ζ-methylamino)(4ζ-dedimethylamino)pristinamycin I$_E$
4ε-Chloro-2"-aminopyrido[2,3-5γ,5δ]pristinamycin I$_E$
2"-Aminopyrido[2,3-5γ,5δ](4ζ-methylamino)(4ζ-dedimethylamino)pristinamycin I$_E$
4ε-Chloro-2"-aminopyrido[2,3-5γ,5δ](4ζ-methylamino)(4ζ-dedimethylamino)pristinamycin I$_E$
4ε-Chloro-3"-methoxycarbonyl-2"-methylpyrido[2,3-5γ,5δ] pristinamycin I$_E$
4ε-Chloro-2"-phenylpyrido[2,3-5γ,5δ]pristinamycin I$_E$
2"-Phenylpyrido[2,3-5γ,5δ](4ζ-methylamino)(4ζ-dedimethylamino)pristinamycin I$_E$
4ε-Chloro-2"-phenylpyrido[2,3-5γ,5δ](4ζ-methylamino)(4ζ-dedimethylamino)pristinamycin I$_E$
4ε-Chloro-2"-(4-aminophenyl)pyrido[2,3-5γ,5δ] pristinamycin I$_E$
2"-(4-aminophenyl)pyrido[2,3-5γ,5δ](4ζ-methylamino)(4ζ-dedimethylamino)pristinamycin I$_E$
4ε-Chloro-2"-(4ζ-aminophenyl)pyrido[2,3-5γ,5δ](4ζ-methylamino)(4ζ-dedimethylamino)pristinamycin I$_E$
4ε-Chloro-2"-(4-diethylaminophenyl)pyrido[2,3-5γ,5δ] pristinamycin I$_E$
2"-(4-Diethylaminophenyl)pyrido[2,3-5γ,5δ](4ζ-methylamino)(4ζ-dedimethylamino)pristinamycin I$_E$
4ε-Chloro-2"-(4-diethylaminophenyl)pyrido[2,3-5γ,5δ](4ζ-methylamino)(4ζ-dedimethylamino)pristinamycin I$_E$
4ε-Chloropyrido[2,3-5γ,5δ]pristinamycin I$_E$
Pyrido[2,3-5γ,5δ](4ζ-methylamino)(4ζ-dedimethylamino) pristinamycin I$_E$
4ε-Chloropyrido[2,3-5γ,5δ](4ζ-methylamino)(4ζ-dedimethylamino)pristinamycin I$_E$
4ε-Chloro-2"-chloromethylpyrido[2,3-5γ,5δ]-pristinamycin I$_E$
2"-Chloromethylpyrido[2,3-5γ,5δ](4ζ-methylamino)(4ζ-dedimethylamino)pristinamycin I$_E$ 4ε-Chloro-2"-chloromethylpyrido[2,3-5γ,5δ](4ζ-methylamino)(4ζ-dedimethylamino)pristinamycin I$_E$ 4ε-Chloro-3"-methoxycarbonyl-2"-methylpyrido[2,3-5γ,5δ](4ζ-methylamino)(4ζ-dedimethylamino)pristinamycin I$_E$ 4ε-Chloro-2"-(2-pyridyl)pyrido[2,3-5γ,5δ]-pristinamycin I$_E$ 4ε-Chloro-2"-morpholinomethylpyrido[2,3-5γ,5δ]-pristinamycin I$_E$ 2"-Morpholinomethylpyrido[2,3-5γ,5δ](4ζ-methylamino)(4ζ-dedimethylamino)pristinamycin I$_E$ 4ε-Chloro-2"-morpholinomethylpyrido[2,3-5γ,5δ](4ζ-methylamino)(4ζ-dedimethylamino)pristinamycin I$_E$ 4ε-Chloro-2"-(3-pyridyl)pyrido[2,3-5γ,5δ]-pristinamycin I$_E$ 2"-(3-Pyridyl)pyrido[2,3-5γ,5δ](4ζ-methylamino)(4ζ-dedimethylamino)pristinamycin I$_E$ 4ε-Chloro-2"-(3-pyridyl)pyrido[2,3-5γ,5δ](4ζ-methylamino)(4ζ-dedimethylamino)pristinamycin I$_E$ 4ε-Chloro-2"-(4-methyl-1-piperazinylmethyl)pyrido-[2,3-5γ,5δ]pristinamycin I$_E$ 2"-(4-Methyl-1-piperazinylmethyl)pyrido-[2,3-5γ,5δ](4ζ-methylamino)(4ζ-dedimethylamino)pristinamycin I$_E$ 4ε-Chloro-2"-(4-methyl-1-piperazinylmethyl)pyrido[2,3-5γ,5δ](4ζ-methylamino)(4ζ-dedimethylamino)pristinamycin I$_E$ 4ε-Chloro-2"-methylpyrido[2,3-5γ,5δ](4ζ-methylamino)(4ζ-dedimethylamino)pristinamycin I$_E$ 4ε-Chloro-2"-cyclopropylpyrido[2,3-5γ,5δ]-pristinamycin I$_E$ 2"-Cyclopropylpyrido[2,3-5γ,5δ](4ζ-methylamino)(4ζ-dedimethylamino)pristinamycin I$_E$ 4ε-Chloro-2"-cyclopropylpyrido[2,3-5γ,5δ](4ζ-methylamino)(4ζ-dedimethylamino)pristinamycin I$_E$ 4ε-Chloro-2"-hydroxymethylpyrido[2,3-5γ,5δ]-pristinamycin I$_E$ 2"-Hydroxymethylpyrido[2,3-5γ,5δ](4ζ-methylamino)(4ζ-dedimethylamino)pristinamycin I$_E$ 4ε-Chloro-2"-hydroxymethylpyrido[2,3-5γ,5δ](4ζ-methylamino)(4ζ-dedimethylamino)pristinamycin I$_E$ 4ε-Chloro-2"-propylpyrido[2,3-5γ,5δ]pristinamycin I$_E$ 2"-Propylpyrido[2,3-5γ,5δ](4ζ-methylamino)(4ζ-dedimethylamino)pristinamycin I$_E$ 4ε-Chloro-2"-propylpyrido[2,3-5γ,5δ](4ζ-methylamino)(4ζ-dedimethylamino)pristinamycin I$_E$ 4ε-Chloro-2"-isopropylpyrido[2,3-5γ,5δ]-pristinamycin I$_E$ 2"-Isopropylpyrido[2,3-5γ,5δ](4ζ-methylamino)(4ζ-dedimethylamino)pristinamycin I$_E$ 4ε-Chloro-2"-isopropylpyrido[2,3-5γ,5δ](4ζ-methylamino)(4ζ-dedimethylamino)pristinamycin I$_E$ 4ε-Chloro-2"-acetoxymethylpyrido[2,3-5γ,5δ]pristinamycin I$_E$ 2"-Acetoxymethylpyrido[2,3-5γ,5δ](4ζ-methylamino)-(4ζ-dedimethylamino)pristinamycin I$_E$ 4ε-Chloro-2"-acetoxymethylpyrido[2,3-5γ,5δ](4ζ-methylamino)(4ζ-dedimethylamino)pristinamycin I$_E$ 4ε-Chloro-2"-cyclopropylaminomethylpyrido[2,3-5γ,5δ]pristinamycin I$_E$ 2"-Cyclopropylaminomethylpyrido[2,3-5γ,5δ](4ζ-methylamino)(4ζ-dedimethylamino)pristinamycin I$_E$ 4ε-Chloro-2",3"-dimethylpyrido[2,3-5γ,5δ](4ζ-methylamino)(4ζ-dedimethylamino)pristinamycin I$_E$ 4ε-Chloro-2"-ethoxycarbonylpyrido[2,3-5γ,5δ]-pristinamycin I$_E$ 2"-Ethoxycarbonylpyrido[2,3-5γ,5δ](4ζ-methylamino)(4ζ-dedimethylamino)pristinamycin I$_E$ 4ε-Chloro-2"-ethoxycarbonylpyrido[2,3-5γ,5δ](4ζ-methylamino)(4ζ-dedimethylamino)pristinamycin I$_E$ PIA Cl: 4ε-chloro-2"-(N-diethylaminomethyl)pyrido[2,3-5γ,5δ]pristinamycin I$_E$ PIB: 2"-(N-diethylaminomethyl)pyrido[2,3-5γ,5δ](4ζ-methylamino)(4ζ-dedimethylamino)pristinamycin I$_E$ PIB Cl: 4ε-chloro-2"-(N-diethylaminomethyl)pyrido[2,3-5γ,5δ](4ζ-methylamino)(4ζ-dedimethylamino)pristinamycin I$_E$ PIA Cl: 4ε-chloro-2"-carbamoylpyrido[2,3-5γ,5δ]pristinamycin I$_E$ PIB: 2"-carbamoylpyrido[2,3-5γ,5δ](4ζ-methylamino)(4ζ-dedimethylamino)pristinamycin I$_E$ PIB Cl: 4ε-chloro-2"-carbamoylpyrido[2,3-5γ,5δ](4ζ-methylamino)(4ζ-dedimethylamino)pristinamycin I$_E$ PIA Cl: 4ε-chloro-2"-diethylaminoethylthiomethylpyrido[2,3-5γ,5δ]pristinamycin I$_E$ PIB: 2"-diethylaminoethylthiomethylpyrido[2,3-5γ,5δ](4ζ-methylamino)(4ζ-dedimethylamino)pristinamycin I$_E$ PIB Cl: 4ε-chloro-2"-diethylaminoethylthiomethylpyrido[2,3-5γ,5δ](4ζ-methylamino)(4ζ-dedimethylamino)pristinamycin I$_E$ PIA Cl: 4ε-chloro-2"-(morpholinoethylthiomethyl)-pyrido[2,3-5γ,5δ]pristinamycin I$_E$ PIB: 2"-(morpholinoethylthiomethyl)pyrido[2,3-5γ,5δ](4ζ-methylamino)(4ζ-dedimethylamino)pristinamycin I$_E$ 4ε-Chloro-2"-(morpholinoethylthiomethyl)pyrido[2,3-5γ,5δ](4ζ-methylamino)(4ζ-dedimethylamino)pristinamycin I$_E$ 4ε-Chloro-2"-(1-pyrrolidinoethylthiomethyl)pyrido[2,3-5γ,5δ]pristinamycin I$_E$ 2"-(1-Pyrrolidinoethylthiomethyl)pyrido[2,3-5γ,5δ](4ζ-methylamino)(4ζ-dedimethylamino)-pristinamycin I$_E$ 4ε-Chloro-2"-(1-pyrrolidinoethylthiomethyl)pyrido[2,3-5γ,5δ](4ζ-methylamino)(4ζ-dedimethylamino)-pristinamycin I$_E$ 4ε-Chloro-2"-(piperidinoethylthiomethyl)pyrido[2,3-5γ,5δ]pristinamycin I$_E$ 2"-(Piperidinoethylthiomethyl)pyrido[2,3-5γ,5δ](4ζ-methylamino)(4ζ-dedimethylamino)pristinamycin I$_E$ 4ε-Chloro-2"-(piperidinoethylthiomethyl)pyrido[2,3-5γ,5δ](4ζ-methylamino)(4ζ-dedimethylamino)-pristinamycin I$_E$ 4ε-Bromo-2"-tert-butylpyrido[2,3-5γ,5δ]-pristinamycin I$_E$ 4ε-Bromo-2"-tert-butylpyrido[2,3-5γ,5δ](4ζmethylamino)(4ζ-dedimethylamino)pristinamycin I$_E$ 4ε-Allyl-2"-tert-butylpyrido[2,3-5γ,5δ]-pristinamycin I$_E$ 4ε-Allyl-2"-tert-butylpyrido[2,3-5γ,5δ](4ζ-methylamino)(4ζ-dedimethylamino)pristinamycin I$_E$ 4ε-(2-Methylpropen-1-yl)-2"-tert-butylpyrido[2,3-5γ,5δ]pristinamycin I$_E$ 4ε-(2-Methylpropen-1-yl)-2"-tert-butylpyrido[2,3-5γ,5δ](4ζ-methylamino)(4ζ-dedimethylamino)pristinamycin I$_E$ 2"-tert-Butylpyrido[2,3-5γ,5δ](4ζ-diethylamino)(4ζ-dedimethylamino)pristinamycin I$_E$ 2"-tert-Butylpyrido[2,3-5γ,5δ](4ζ-N-methyl-N-allylamino)(4ζ-dedimethylamino)pristinamycin I$_E$ 2"-tert-Butylpyrido[2,3-5γ,5δ](4ζ-N-methyl-N-ethylamino)(4ζ-dedimethylamino)pristinamycin I$_E$ 2"-tert-Butylpyrido[2,3-5γ,5δ](4ζ-N-methyl-N-propylamino)(4ζ-dedimethylamino)pristinamycin I$_E$ 2"-tert-Butylpyrido[2,3-5γ,5δ](4(-N-methyl-N-(4-pyridylmethyl)amino)(4ζ-dedimethylamino)pristinamycin I$_E$ 2"-tert-Butylpyrido[2,3-5γ,5δ](4ζ-N-methyl-N-(3-pyridylmethyl)amino)(4ζ-dedimethylamino)pristinamycin I$_E$ 2"-tert-Butylpyrido[2,3-5γ,5δ](4ζ-methyl)(4ζ-dedimethylamino)pristinamycin I$_E$ 2"-tert-Butylpyrido[2,3-5γ,5δ](4ζ-tert-butyl)-(4ζ-dedimethylamino)pristinamycin I$_E$ 4ε-Bromo-2"-aminopyrido[2,3-5γ,5δ]pristinamycin I$_E$ 4ε-Bromo-2"-aminopyrido[2,3-5γ,5δ](4ζ-methylamino)(4ζ-dedimethylamino)pristinamycin $I_E$
4ε-Allyl-2"-aminopyrido[2,3-5γ,5δ]pristinamycin $I_E$
4ε-Allyl-2"-aminopyrido[2,3-5γ,5δ](4ζ-methylamino)(4ζ-dedimethylamino)pristinamycin $I_E$
4ε-(2-Methylpropen-1-yl)2"-aminopyrido[2,3-5γ,5δ]-pristinamycin $I_E$
4ε-(2-Methylpropen-1-yl)2"-aminopyrido[2,3-5γ,5δ](4ζ-methylamino)(4ζ-dedimethylamino)pristinamycin $I_E$
2"-Aminopyrido[2,3-5γ,5δ](4ζ-diethylamino)(4ζ-dedimethylamino)pristinamycin $I_E$
2"-Aminopyrido[2,3-5γ,5δ](4ζ-N-methyl-N-allylamino)(4ζ-dedimethylamino)pristinamycin $I_E$
2"-Aminopyrido[2,3-5γ,5δ](4ζ-N-methyl-N-ethylamino)(4ζ-dedimethylamino)pristinamycin $I_E$
2"-Aminopyrido[2,3-5γ,5δ](4ζ-N-methyl-N-propylamino)(4ζ-dedimethylamino)pristinamycin $I_E$
2"-Aminopyrido[2,3-5γ,5δ](4ζ-N-methyl-N-(4-pyridylmethyl)amino)(4ζ-dedimethylamino)-pristinamycin $I_E$
2"-Aminopyrido[2,3-5γ,5δ](4ζ-N-methyl-N-(3-pyridylmethyl)amino)(4ζ-dedimethylamino)-pristinamycin $I_E$
2"-Aminopyrido[2,3-5γ,5δ](4ζ-methyl)(4ζ-dedimethylamino)pristinamycin $I_E$
2"-Aminopyrido[2,3-5γ,5δ](4ζ-tert-butyl)-(4ζ-dedimethylamino)pristinamycin $I_E$
4ε-Bromo-3"-methoxycarbonyl-2"-methylpyrido[2,3-5γ,5δ]pristinamycin $I_E$
4ε-Bromo-3"-methoxycarbonyl-2"-methylpyrido[2,3-5γ,5δ](4ζ-methylamino)(4ζ-dedimethylamino)pristinamycin $I_E$
4ε-Allyl-3"-methoxycarbonyl-2"-methylpyrido[2,3-5γ,5δ]pristinamycin $I_E$
4ε-Allyl-3"-methoxycarbonyl-2"-methylpyrido[2,3-5γ,5δ](4ζ-methylamino)(4ζ-dedimethylamino)pristinamycin $I_E$
4ε-(2-Methylpropen-1-yl)-3"-methoxycarbonyl-2"-methylpyrido[2,3-5γ,5δ]pristinamycin $I_E$
4ε-(2-Methylpropen-1-yl)-3"-methoxycarbonyl-2"-methylpyrido[2,3-5γ,5δ](4ζ-methylamino)(4ζ-dedimethylamino)pristinamycin $I_E$
3"-Methoxycarbonyl-2"-methylpyrido[2,3-5γ,5δ](4ζ-diethylamino)(4ζ-dedimethylamino)pristinamycin $I_E$
3"-Methoxycarbonyl-2"-methylpyrido[2,3-5γ,5δ](4ζ-N-methyl-N-allylamino)(4ζ-dedimethylamino)pristinamycin $I_E$
3"-Methoxycarbonyl-2"-methylpyrido[2,3-5γ,5δ](4ζ-N-methyl-N-ethylamino)(4ζ-dedimethylamino)pristinamycin $I_E$
3"-Methoxycarbonyl-2"-methylpyrido[2,3-5γ,5δ](4ζ-N-methyl-N-propylamino)(4ζ-dedimethylamino)pristinamycin $I_E$
3"-Methoxycarbonyl-2"-methylpyrido[2,3-5γ,5δ](4ζ-N-methyl-N-(4-pyridylmethyl)amino)(4ζ-dedimethylamino)pristinamycin $I_E$
3"-Methoxycarbonyl-2"-methylpyrido[2,3-5γ,5δ](4ζ-N-methyl-N-(3-pyridylmethyl)amino)(4ζ-dedimethylamino)pristinamycin $I_E$
3"-Methoxycarbonyl-2"-methylpyrido[2,3-5γ,5δ](4ζ-methyl)(4ζ-dedimethylamino)pristinamycin $I_E$
3"-Methoxycarbonyl-2"-methylpyrido[2,3-5γ,5δ](4ζ-tert-butyl)(4ζ-dedimethylamino)pristinamycin $I_E$
4ε-Bromo-2"-phenylpyrido[2,3-5γ,5δ]pristinamycin $I_E$
4ε-Bromo-2"-phenylpyrido[2,3-5γ,5δ](4ζ-methylamino)(4ζ-dedimethylamino)pristinamycin $I_E$
4ε-Allyl-2"-phenylpyrido[2,3-5γ,5δ]pristinamycin $I_E$
4ε-Allyl-2"-phenylpyrido[2,3-5γ,5δ](4ζ-methylamino)(4ζ-dedimethylamino)pristinamycin $I_E$
4ε-(2-Methylpropen-1-yl)-2"-phenylpyrido[2,3-5γ,5δ]pristinamycin $I_E$
4ε-(2-Methylpropen-1-yl)-2"-phenylpyrido[2,3-5γ,5δ](4ζ-methylamino)(4ζ-dedimethylamino)pristinamycin $I_E$
2"-Phenylpyrido[2,3-5γ,5δ](4ζ-diethylamino)(4ζ-dedimethylamino)pristinamycin $I_E$
2"-Phenylpyrido[2,3-5γ,5δ](4ζ-N-methyl-N-allylamino)(4ζ-dedimethylamino)pristinamycin $I_E$
2"-Phenylpyrido[2,3-5γ,5δ](4ζ-N-methyl-N-ethylamino)(4ζ-dedimethylamino)pristinamycin $I_E$
2"-Phenylpyrido[2,3-5γ,5δ](4ζ-N-methyl-N-propylamino)(4ζ-dedimethylamino)pristinamycin $I_E$
2"-Phenylpyrido[2,3-5γ,5δ](4ζ-N-methyl-N-(4-pyridylmethyl)amino)(4ζ-dedimethylamino)pristinamycin $I_E$
2"-Phenylpyrido[2,3-5γ,5δ](4ζ-N-methyl-N-(3-pyridylmethyl)amino)(4ζ-dedimethylamino)pristinamycin $I_E$
2"-Phenylpyrido[2,3-5γ,5δ](4ζ-methyl)(4ζ-dedimethylamino)pristinamycin $I_E$
2"-Phenylpyrido[2,3-5γ,5δ](4ζ-tert-butyl)-(4ζ-dedimethylamino)pristinamycin $I_E$
4ε-Bromo-2"-(4-aminophenyl)pyrido[2,3-5γ,5δ]pristinamycin $I_E$
4ε-Bromo-2"-(4-aminophenyl)pyrido[2,3-5γ,5δ](4ζ-methylamino)(4ζ-dedimethylamino)pristinamycin $I_E$
4ε-Allyl-2"-(4-aminophenyl)pyrido[2,3-5γ,5δ]pristinamycin $I_E$
4ε-Allyl-2"-(4-aminophenyl)pyrido[2,3-5γ,5δ](4ζ-methylamino)(4ζ-dedimethylamino)pristinamycin $I_E$
4ε-(2-Methylpropen-1-yl)-2"-(4-aminophenyl)pyrido[2,3-5γ,5δ]pristinamycin $I_E$
4ε-(2-Methylpropen-1-yl)-2"-(4-aminophenyl)pyrido[2,3-5γ,5δ]4ζ-methylamino)(4ζ-dedimethylamino)pristinamycin $I_E$
2"-(4-Aminophenyl)pyrido[2,3-5γ,5δ](4ζ-diethylamino)(4ζ-dedimethylamino)pristinamycin $I_E$
2"-(4-Aminophenyl)pyrido[2,3-5γ,5δ](4ζ-N-methyl-N-allylamino)(4ζ-dedimethylamino)pristinamycin $I_E$
2"-(4-Aminophenyl)pyrido[2,3-5γ,5δ](4ζ-N-methyl-N-ethylamino)(4ζ-dedimethylamino)pristinamycin $I_E$
2"-(4-Aminophenyl)pyrido[2,3-5γ,5δ](4ζ-N-methyl-N-propylamino)(4ζ-dedimethylamino)pristinamycin $I_E$
2"-(4-Aminophenyl)pyrido[2,3-5γ,5δ](4ζ-N-methyl-N-(4-pyridylmethyl)amino)(4ζ-dedimethylamino)pristinamycin $I_E$
2"-(4-Aminophenyl)pyrido[2,3-5γ,5δ](4ζ-N-methyl-N-(3-pyridylmethyl)amino)(4ζ-dedimethylamino)pristinamycin $I_E$
2"-(4-Aminophenyl)pyrido[2,3-5γ,5δ](4ζ-methyl)(4ζ-dedimethylamino)pristinamycin $I_E$
2"-(4-Aminophenyl)pyrido[2,3-5γ,5δ](4ζ-tert-butyl)(4ζ-dedimethylamino)pristinamycin $I_E$
4ε-Bromo-2"-(4-diethylaminophenyl)pyrido[2,3-5γ,5δ]pristinamycin $I_E$
4ε-Bromo-2"-(4-diethylaminophenyl)pyrido[2,3-5γ,5δ](4ζ-methylamino)(4ζ-dedimethylamino)pristinamycin $I_E$
4ε-Allyl-2"-(4-diethylaminophenyl)pyrido[2,3-5γ,5δ]pristinamycin $I_E$
4ε-Allyl-2"-(4-diethylaminophenyl)pyrido[2,3-5γ,5δ](4ζ-methylamino)(4ζ-dedimethylamino)pristinamycin $I_E$
4ε-(2-Methylpropen-1-yl)-2"-(4-diethylaminophenyl)pyrido[2,3-5γ,5δ]pristinamycin $I_E$
4ε-(2-Methylpropen-1-yl)-2"-(4-diethylaminophenyl)pyrido[2,3-5γ,5δ](4ζ-methylamino)(4ζ-dedimethylamino)pristinamycin $I_E$
2"-(4-Diethylaminophenyl)pyrido[2,3-5γ,5δ](4ζ-diethylamino)(4ζ-dedimethylamino)pristinamycin $I_E$ 2"-(4-Diethylaminophenyl)pyrido[2,3-5γ,5δ](4ζ-N-methyl-N-allylamino)(4ζ-dedimethylamino)pristinamycin $I_E$
2"-(4-Diethylaminophenyl)pyrido[2,3-5γ,5δ](4ζ-N-methyl-N-ethylamino)(4ζ-dedimethylamino)pristinamycin $I_E$
2"-(4-Diethylaminophenyl)pyrido[2,3-5γ,5δ](4ζ-N-methyl-N-propylamino)(4ζ-dedimethylamino)pristinamycin $I_E$
2"-(4-Diethylaminophenyl)pyrido[2,3-5γ,5δ](4ζ-N-methyl-N-(4-pyridylmethyl)amino)(4ζ-dedimethylamino)pristinamycin $I_E$
2"-(4-Diethylaminophenyl)pyrido[2,3-5γ,5δ](4ζ-N-methyl-N-(3-pyridylmethyl)amino)(4ζ-dedimethylamino)pristinamycin $I_E$
2"-(4-Diethylaminophenyl)pyrido[2,3-5γ,5δ](4ζ-methyl)(4ζ-dedimethylamino)pristinamycin $I_E$
2"-(4-Diethylaminophenyl)pyrido[2,3-5γ,5δ](4ζ-tert-butyl)(4ζ-dedimethylamino)pristinamycin $I_E$
4ε-Bromopyrido[2,3-5γ,5δ]pristinamycin $I_E$
4ε-Bromopyrido[2,3-5γ,5δ](4ζ-methylamino)(4ζ-dedimethylamino)pristinamycin $I_E$
4ε-Allylpyrido[2,3-5γ,5δ]pristinamycin $I_E$
4ε-Allylpyrido[2,3-5γ,5δ](4ζ-methylamino)(4ζ-dedimethylamino)pristinamycin $I_E$
4ε-(2-Methylpropen-1-yl)pyrido[2,3-5γ,5δ]pristinamycin $I_E$
4ε-(2-Methylpropen-1-yl)pyrido[2,3-5γ,5δ](4ζ-methylamino)(4ζ-dedimethylamino)pristinamycin $I_E$
Pyrido[2,3-5γ,5δ](4ζ-diethylamino)(4ζ-dedimethylamino)pristinamycin $I_E$
Pyrido[2,3-5γ,5δ](4ζ-N-methyl-N-allylamino)(4ζ-dedimethylamino)pristinamycin $I_E$
Pyrido[2,3-5γ,5δ](4ζ-N-methyl-N-ethylamino)(4ζ-dedimethylamino)pristinamycin $I_E$
Pyrido[2,3-5γ,5δ](4ζ-N-methyl-N-propylamino)(4ζ-dedimethylamino)pristinamycin $I_E$
Pyrido[2,3-5γ,5δ](4ζ-N-methyl-N-(4-pyridylmethyl)amino)(4ζ-dedimethylamino)pristinamycin $I_E$
Pyrido[2,3-5γ,5δ](4ζ-N-methyl-N-(3-pyridylmethyl)amino)(4ζ-dedimethylamino)pristinamycin $I_E$
Pyrido[2,3-5γ,5δ](4ζ-methyl)(4ζ-dedimethylamino)pristinamycin $I_E$
Pyrido[2,3-5γ,5δ](4ζ-tert-butyl)(4ζ-dedimethylamino)pristinamycin $I_E$
4ε-Bromo-2"-chloromethylpyrido[2,3-5γ,5δ]pristinamycin $I_E$
4ε-Bromo-2"-chloromethylpyrido[2,3-5γ,5δ](4εmethylamino)(4ζ-dedimethylamino)pristinamycin $I_E$
4ε-Allyl-2"-chloromethylpyrido[2,3-5γ,5δ]pristinamycin $I_E$
4ε-Allyl-2"-chloromethylpyrido[2,3-5γ,5δ](4ζ-methylamino)(4ζ-dedimethylamino)pristinamycin $I_E$
4ε-(2-Methylpropen-1-yl)-2"-chloromethylpyrido[2,3-5γ,5δ]pristinamycin $I_E$
4ε-(2-Methylpropen-1-yl)-2"-chloromethylpyrido[2,3-5γ,5δ](4ζ-methylamino)(4ζ-dedimethylamino)pristinamycin $I_E$
2"-Chloromethylpyrido[2,3-5γ,5δ](4ζ-diethylamino)(4ζ-dedimethylamino)pristinamycin $I_E$
2"-Chloromethylpyrido[2,3-5γ,5δ](4ζ-N-methyl-N-allylamino)(4ζ-dedimethylamino)pristinamycin $I_E$
2"-Chloromethylpyrido[2,3-5γ,5δ](4ζ-N-methyl-N-ethylamino)(4ζ-dedimethylamino)pristinamycin $I_E$
2"-Chloromethylpyrido[2,3-5γ,5δ](4ζ-N-methyl-N-propylamino)(4ζ-dedimethylamino)pristinamycin $I_E$
2"-Chloromethylpyrido[2,3-5γ,5δ](4ζ-N-methyl-N-(4-pyridylmethyl)amino)(4ζ-dedimethylamino)pristinamycin $I_E$
2"-Chloromethylpyrido[2,3-5γ,5δ](4ζ-N-methyl-N-(3-pyridylmethyl)amino)(4ζ-dedimethylamino)pristinamycin $I_E$
2"-Chloromethylpyrido[2,3-5γ,5δ](4ζ-methyl)(4ζ-dedimethylamino)pristinamycin $I_E$
2"-Chloromethylpyrido[2,3-5γ,5δ](4ζ-tert-butyl)(4ζ-dedimethylamino)pristinamycin $I_E$
4ε-Bromo-2"-(2-pyridyl)pyrido[2,3-5γ,5δ]pristinamycin $I_E$
4-Bromo-2"-(2-pyridyl)pyrido[2,3-5γ,5δ](4ζ-methylamino)(4ζ-dedimethylamino)pristinamycin $I_E$
4ε-Allyl-2"-(2-pyridyl)pyrido[2,3-5γ,5δ]-pristinamycin $I_E$
4ε-Allyl-2"-(2-pyridyl)pyrido[2,3-5γ,5δ](4ζ-methylamino)(4ζ-dedimethylamino)pristinamycin $I_E$
4ε-(2-Methylpropen-1-yl)-2"-(2-pyridyl)pyrido[2,3-5γ,5δ]pristinamycin $I_E$
4ε-(2-Methylpropen-1-yl)-2"-(2-pyridyl)pyrido[2,3-5γ,5δ](4ζ-methylamino)(4ζ-dedimethylamino)pristinamycin $I_E$
2"-(2-Pyridyl)pyrido[2,3-5γ,5δ](4ζ-diethylamino)(4ζ-dedimethylamino)pristinamycin $I_E$
2"-(2-Pyridyl)pyrido[2,3-5γ,5δ](4ζ-N-methyl-N-allylamino)(4ζ-dedimethylamino)pristinamycin $I_E$
2"-(2-Pyridyl)pyrido[2,3-5γ,5δ](4ζ-N-methyl-N-ethylamino)(4ζ-dedimethylamino)pristinamycin $I_E$
2"-(2-Pyridyl)pyrido[2,3-5γ,5δ](4ζ-N-methyl-N-propylamino)(4ζ-dedimethylamino)pristinamycin $I_E$
2"-(2-Pyridyl)pyrido[2,3-5γ,5δ](4ζ-N-methyl-N-(4-pyridylmethyl)amino)(4ζ-dedimethylamino)pristinamycin $I_E$
2"-(2-Pyridyl)pyrido[2,3-5γ,5δ](4ζ-N-methyl-N-(3-pyridylmethyl)amino)(4ζ-dedimethylamino)pristinamycin $I_E$
2"-(2-Pyridyl)pyrido[2,3-5γ,5δ](4ζ-methyl)(4ζ-dedimethylamino)pristinamycin $I_E$
2"-(2-Pyridyl)pyrido[2,3-5γ,5δ](4ζ-tert-butyl)(4ζ-dedimethylamino)pristinamycin $I_E$
4ε-Bromo-2"-morpholinomethylpyrido[2,3-5γ,5δ]pristinamycin $I_E$
4ε-Bromo-2"-morpholinomethylpyrido[2,3-5γ,5δ](4ζmethylamino)(4ζ-dedimethylamino)pristinamycin $I_E$
4ε-Allyl-2"-morpholinomethylpyrido[2,3-5γ,5δ]pristinamycin $I_E$
4ε-Allyl-2"-morpholinomethylpyrido[2,3-5γ,5δ](4ζ-methylamino)(4ζ-dedimethylamino)pristinamycin $I_E$
4ε-(2-Methylpropen-1-yl)-2"-morpholinomethylpyrido[2,3-5γ,5δ]pristinamycin $I_E$
4ε-(2-Methylpropen-1-yl)-2"-morpholinomethylpyrido[2,3-5γ,5δ](4'-methylamino)(4ζ-dedimethylamino)pristinamycin $I_E$
2"-Morpholinomethylpyrido[2,3-5γ,5δ](4ζ-diethylamino)(4ζ-dedimethylamino)pristinamycin $I_E$
2"-Morpholinomethylpyrido[2,3-5γ,5δ](4ζ-N-methyl-N-allylamino)(4ζ-dedimethylamino)pristinamycin $I_E$
2"-Morpholinomethylpyrido[2,3-5γ,5δ](4ζ-N-methyl-N-ethylamino)(4ζ-dedimethylamino)pristinamycin $I_E$
2"-Morpholinomethylpyrido[2,3-5γ,5δ](4ζ-N-methyl-N-propylamino)(4ζ-dedimethylamino)pristinamycin $I_E$
2"-Morpholinomethylpyrido[2,3-5γ,5δ](4ζ-N-methyl-N-(4ζ-pyridylmethyl)amino)(4ζ-dedimethylamino)pristinamycin $I_E$
2"-Morpholinomethylpyrido[2,3-5γ,5δ](4ζ-N-methyl-N-(3-pyridylmethyl)amino)(4ζ-dedimethylamino)pristinamycin $I_E$
2"-Morpholinomethylpyrido[2,3-5γ,5δ](4ζ-methyl)(4ζ-dedimethylamino)pristinamycin $I_E$
2"-Morpholinomethylpyrido[2,3-5γ,5δ]4ζ-tert-butyl)(4ζ-dedimethylamino)pristinamycin $I_E$
4ε-Bromo-2"-(3-pyridyl)pyrido[2,3-5γ,5δ]pristinamycin $I_E$
4ε-Bromo-2"-(3-pyridyl)pyrido[2,3-5γ,5δ](4ζ-methylamino)(4ζ-dedimethylamino)pristinamycin $I_E$
4ε-Allyl-2"-(3-pyridyl)pyrido[2,3-5γ,5δ]pristinamycin $I_E$ 4ϵ-Allyl-2"-(3-pyridyl)pyrido[2,3-5γ,5δ](4ζ-methylamino)(4ζ-dedimethylamino)pristinamycin $I_E$ 4ϵ-(2-Methylpropen-1-yl)-2"-(3-pyridyl)pyrido[2,3-5γ,5δ]pristinamycin $I_E$ 4ϵ-(2-Methylpropen-1-yl)-2"-(3-pyridyl)pyrido[2,3-5γ,5δ](4ζ-methylamino)(4ζ-dedimethylamino)pristinamycin $I_E$ 2"-(3-Pyridyl)pyrido[2,3-5γ,5δ](4ζ-diethylamino)(4ζ-dedimethylamino)pristinamycin $I_E$ 2"-(3-Pyridyl)pyrido[2,3-5γ,5δ](4ζ-N-methyl-N-allylamino)(4ζ-dedimethylamino)pristinamycin $I_E$ 2"-(3-Pyridyl)pyrido[2,3-5γ,5δ](4ζ-N-methyl-N-ethylamino)(4ζ-dedimethylamino)pristinamycin $I_E$ 2"-(3-Pyridyl)pyrido[2,3-5γ,5δ](4ζ-N-methyl-N-propylamino)(4ζ-dedimethylamino)pristinamycin $I_E$ 2"-(3-Pyridyl)pyrido[2,3-5γ,5δ](4ζ-N-methyl-N-(4-pyridylmethyl)amino)(4ζ-dedimethylamino)pristinamycin $I_E$ 2"-(3-Pyridyl)pyrido[2,3-5γ,5δ](4ζ-N-methyl-N-(3-pyridylmethyl)amino)(4ζ-dedimethylamino)pristinamycin $I_E$ 2"-(3-Pyridyl)pyrido[2,3-5γ,5δ](4-methyl)(4ζ-dedimethylamino)pristinamycin $I_E$ 2"-(3-Pyridyl)pyrido[2,3-5γ,5δ](4-tert-butyl)(4ζ-dedimethylamino)pristinamycin $I_E$ 4ϵ-Bromo-2"-(4-methyl-1-piperazinylmethyl)pyrido[2,3-5γ,5δ]pristinamycin $I_E$ 4ϵ-Bromo-2"-(4-methyl-1-piperazinylmethyl)pyrido[2,3-5γ,5δ](4ζ-methylamino)(4ζ-dedimethylamino)pristinamycin $I_E$ 4ϵ-Allyl-2"-(4-methyl-1-piperazinylmethyl)pyrido[2,3-5γ,5δ]pristinamycin $I_E$ 4ϵ-Allyl-2"-(4-methyl-1-piperazinylmethyl)pyrido[2,3-5γ,5δ](4ζ-methylamino)(4ζ-dedimethylamino)pristinamycin $I_E$ 4ϵ-(2-Methylpropen-1-yl)-2"-(4-methyl-1-piperazinylmethyl)pyrido[2,3-5γ,5δ]pristinamycin $I_E$ 4ϵ-(2-Methylpropen-1-yl)-2"-(4-methyl-1-piperazinylmethyl)pyrido[2,3-5γ,5δ](4ζ-methylamino)(4ζ-dedimethylamino)pristinamycin $I_E$ 2"-(4-Methyl-1-piperazinylmethyl)pyrido[2,3-5γ,5δ](4ζ-diethylamino)(4ζ-dedimethylamino)pristinamycin $I_E$ 2"-(4-Methyl-1-piperazinylmethyl)pyrido[2,3-5γ,5δ](4ζ-N-methyl-N-allylamino)(4ζ-dedimethylamino)pristinamycin $I_E$ 2"-(4-Methyl-1-piperazinylmethyl)pyrido[2,3-5γ,5δ](4ζ-N-methyl-N-ethylamino)(4ζ-dedimethylamino)pristinamycin $I_E$ 2"-(4-Methyl-1-piperazinylmethyl)pyrido[2,3-5γ,5δ](4ζ-N-methyl-N-propylamino)(4ζ-dedimethylamino)pristinamycin $I_E$ 2"-(4-Methyl-1-piperazinylmethyl)pyrido[2,3-5γ,5δ](4ζ-N-methyl-N-(4-pyridylmethyl)amino)(4ζ-dedimethylamino)pristinamycin $I_E$ 2"-(4-Methyl-1-piperazinylmethyl)pyrido[2,3-5γ,5δ](4ζ-N-methyl-N-(3-pyridylmethyl)amino)(4ζ-dedimethylamino)pristinamycin $I_E$ 2"-(4-Methyl-1-piperazinylmethyl)pyrido[2,3-5γ,5δ](4ζ-methyl)(4ζ-dedimethylamino)pristinamycin $I_E$ 2"-(4-Methyl-1-piperazinylmethyl)pyrido[2,3-5γ,5δ](4ζ-tert-butyl)(4ζ-dedimethylamino)pristinamycin $I_E$ 4ϵ-Bromo-2"-ethylpyrido[2,3-5γ,5δ]pristinamycin $I_E$ 4ϵ-Bromo-2"-ethylpyrido[2,3-5γ,5δ](4ζ-methylamino)(4ζ-dedimethylamino)pristinamycin $I_E$ 4ϵ-Allyl-2"-ethylpyrido[2,3-5γ,5δ]pristinamycin $I_E$ 4ϵ-Allyl-2"-ethylpyrido[2,3-5γ,5δ](4ζ-methylamino)(4ζ-dedimethylamino)pristinamycin $I_E$ 4ϵ-(2-Methylpropen-1-yl)-2"-ethylpyrido[2,3-5γ,5δ]pristinamycin $I_E$ 4ϵ-(2-Methylpropen-1-yl)-2"-ethylpyrido[2,3-5γ,5δ](4ζ-methylamino)(4ζ-dedimethylamino)pristinamycin $I_E$ 2"-Ethylpyrido[2,3-5γ,5δ](4ζ-diethylamino)(4ζ-dedimethylamino)pristinamycin $I_E$ 2"-Ethylpyrido[2,3-5γ,5δ](4ζ-N-methyl-N-allylamino)(4ζ-dedimethylamino)pristinamycin $I_E$ 2"-Ethylpyrido[2,3-5γ,5δ](4ζ-N-methyl-N-ethylamino)(4ζ-dedimethylamino)pristinamycin $I_E$ 2"-Ethylpyrido[2,3-5γ,5δ](4ζ-N-methyl-N-propylamino)(4ζ-dedimethylamino)pristinamycin $I_E$ 2"-Ethylpyrido[2,3-5γ,5δ](4ζ-N-methyl-N-(4-pyridylmethyl)amino)(4ζ-dedimethylamino)pristinamycin $I_E$ 2"-Ethylpyrido[2,3-5γ,5δ](4ζ-N-methyl-N-(3-pyridylmethyl)amino)(4ζ-dedimethylamino)pristinamycin $I_E$ 2"-Ethylpyrido[2,3-5γ,5δ](4ζ-methyl)-(4ζ-dedimethylamino)pristinamycin $I_E$ 2"-Ethylpyrido[2,3-5γ,5δ](4ζ-tert-butyl)-(4ζ-dedimethylamino)pristinamycin $I_E$ 4ϵ-Bromo-2"-cyclopropylpyrido[2,3-5γ,5δ]pristinamycin $I_E$ 4ϵ-Bromo-2"-cyclopropylpyrido[2,3-5γ,5δ](4ζ-methylamino)(4ζ-dedimethylamino)pristinamycin $I_E$ 4ϵ-Allyl-2"-cyclopropylpyrido[2,3-5γ,5δ]pristinamycin $I_E$ 4ϵ-Allyl-2"-cyclopropylpyrido[2,3-5γ,5δ](4ζ-methylamino)(4ζ-dedimethylamino)pristinamycin $I_E$ 4ϵ-(2-Methylpropen-1-yl)-2"-cyclopropylpyrido[2,3-5γ,5δ]pristinamycin $I_E$ 4ϵ-(2-Methylpropen-1-yl)-2"-cyclopropylpyrido[2,3-5γ,5δ](4ζ-methylamino)(4ζ-dedimethylamino)pristinamycin $I_E$ 2"-Cyclopropylpyrido[2,3-5γ,5δ](4ζ-diethylamino)(4ζ-dedimethylamino)pristinamycin $I_E$ 2"-Cyclopropylpyrido[2,3-5γ,5δ](4ζ-N-methyl-N-allylamino)(4ζ-dedimethylamino)pristinamycin $I_E$ 2"-Cyclopropylpyrido[2,3-5γ,5δ](4ζ-N-methyl-N-ethylamino)(4ζ-dedimethylamino)pristinamycin $I_E$ 2"-Cyclopropylpyrido[2,3-5γ,5δ](4ζ-N-methyl-N-propylamino)(4ζ-dedimethylamino)pristinamycin $I_E$ 2"-Cyclopropylpyrido[2,3-5γ,5δ](4ζ-N-methyl-N-(4-pyridylmethyl)amino)(4ζ-dedimethylamino)pristinamycin $I_E$ 2"-Cyclopropylpyrido[2,3-5γ,5δ](4ζ-N-methyl-N-(3-pyridylmethyl)amino)(4ζ-dedimethylamino)pristinamycin $I_E$ 2"-Cyclopropylpyrido[2,3-5γ,5δ](4ζ-methyl)-(4ζ-dedimethylamino)pristinamycin $I_E$ 2"-Cyclopropylpyrido[2,3-5γ,5δ](4ζ-tert-butyl)(4ζ-dedimethylamino)pristinamycin $I_E$ 4ϵ-Bromo-2"-hydroxymethylpyrido[2,3-5γ,5δ]pristinamycin $I_E$ 4ϵ-Bromo-2"-hydroxymethylpyrido[2,3-5γ,5δ](4ϵmethylamino)(4ζ-dedimethylamino)pristinamycin $I_E$ 4ϵ-Allyl-2"-hydroxymethylpyrido[2,3-5γ,5δ]pristinamycin $I_E$ 4-Allyl-2"-hydroxymethylpyrido[2,3-5γ,5δ](4ϵ-methylamino)(4ζ-dedimethylamino)pristinamycin $I_E$ 4ϵ-(2-Methylpropen-1-yl)-2"-hydroxymethylpyrido[2,3-5γ,5δ]pristinamycin $I_E$ 4ϵ-(2-Methylpropen-1-yl)-2"-hydroxymethylpyrido[2,3-5γ,5δ](4ζ-methylamino)(4ζ-dedimethylamino)pristinamycin $I_E$ 2"-Hydroxymethylpyrido[2,3-5γ,5δ](4ζ-diethylamino)(4ζ-dedimethylamino)pristinamycin $I_E$ 2"-Hydroxymethylpyrido[2,3-5γ,5δ](4ζ-N-methyl-N-allylamino)(4ζ-dedimethylamino)pristinamycin $I_E$ 2"-Hydroxymethylpyrido[2,3-5γ,5δ](4ζ-N-methyl-N-ethylamino)(4ζ-dedimethylamino)pristinamycin $I_E$ 2"-Hydroxymethylpyrido[2,3-5γ,5δ](4ζ-N-methyl-N-propylamino)(4ζ-dedimethylamino)pristinamycin $I_E$ 2"-Hydroxymethylpyrido[2,3-5γ,5δ](4ζ-N-methyl-N-(4-pyridylmethyl)amino)(4ζ-dedimethylamino)pristinamycin $I_E$ 2"-Hydroxymethylpyrido[2,3-5γ,5δ](4ζ-N-methyl-N-(3-pyridylmethyl)amino)(4ζ-dedimethylamino)pristinamycin $I_E$ 2"-Hydroxymethylpyrido[2,3-5γ,5δ](4ζ-methyl)(4ζ-dedimethylamino)pristinamycin $I_E$ 2"-Hydroxymethylpyrido[2,3-5γ,5δ](4ζ-tert-butyl)(4ζ-dedimethylamino)pristinamycin $I_E$ 4ε-Bromo-2"-propylpyrido[2,3-5γ,5δ]pristinamycin $I_E$ 4ε-Bromo-2"-propylpyrido[2,3-5γ,5δ](4ζ-methylamino)(4ζ-dedimethylamino)pristinamycin $I_E$ 4ε-Allyl-2"-propylpyrido[2,3-5γ,5δ]pristinamycin $I_E$ 4ε-Allyl-2"-propylpyrido[2,3-5γ,5δ](4ζ-methylamino)(4ζ-dedimethylamino)pristinamycin $I_E$ 4ε-(2-Methylpropen-1-yl)-2"-propylpyrido[2,3-5γ,5δ]pristinamycin $I_E$ 4ε-(2-Methylpropen-1-yl)-2"-propylpyrido[2,3-5γ,5δ](4εmethylamino)(4ζ-dedimethylamino)pristinamycin $I_E$ 2"-Propylpyrido[2,3-5γ,5δ](4ζ-diethylamino)-(4ζ-dedimethylamino)pristinamycin $I_E$ 2"-Propylpyrido[2,3-5γ,5δ](4ζ-N-methyl-N-allylamino)(4ζ-dedimethylamino)pristinamycin $I_E$ 2"-Propylpyrido[2,3-5γ,5δ](4ζ-N-methyl-N-ethylamino)(4ζ-dedimethylamino)pristinamycin $I_E$ 2"-Propylpyrido[2,3-5γ,5δ](4ζ-N-methyl-N-propylamino)(4ζ-dedimethylamino)pristinamycin $I_E$ 2"-Propylpyrido[2,3-5γ,5δ](4ζ-N-methyl-N-(4-pyridylmethyl)amino)(4ζ-dedimethylamino)pristinamycin $I_E$ 2"-Propylpyrido[2,3-5γ,5δ](4ζ-N-methyl-N-(3-pyridylmethyl)amino)(4ζ-dedimethylamino)pristinamycin $I_E$ 2"-Propylpyrido[2,3-5γ,5δ](4ζ-methyl)(4ζ-dedimethylamino)pristinamycin $I_E$ 2"-Propylpyrido[2,3-5γ,5δ](4ζ-tert-butyl)(4ζ-dedimethylamino)pristinamycin $I_E$ 4ε-Bromo-2"-isopropylpyrido[2,3-5γ,5δ]pristinamycin $I_E$ 4ε-Bromo-2"-isopropylpyrido[2,3-5γ,5δ](4ζ-methylamino)(4ζ-dedimethylamino)pristinamycin $I_E$ 4ε-Allyl-2"-isopropylpyrido[2,3-5γ,5δ]pristinamycin $I_E$ 4ε-Allyl-2"-isopropylpyrido[2,3-5γ,5δ](4ζ-methylamino)(4ζ-dedimethylamino)pristinamycin $I_E$ 4ε-(2-Methylpropen-1-yl)-2"-isopropylpyrido[2,3-5γ,5δ]pristinamycin $I_E$ 4ε-(2-Methylpropen-1-yl)-2"-isopropylpyrido[2,3-5γ,5δ](4ζ-methylamino)(4ζ-dedimethylamino)pristinamycin $I_E$ 2"-Isopropylpyrido[2,3-5γ,5δ](4ζ-diethylamino)-(4ζ-dedimethylamino)pristinamycin $I_E$ 2"-Isopropylpyrido[2,3-5γ,5δ](4ζ-N-methyl-N-allylamino)(4ζ-dedimethylamino)pristinamycin $I_E$ 2"-Isopropylpyrido[2,3-5γ,5δ](4ζ-N-methyl-N-ethylamino)(4ζ-dedimethylamino)pristinamycin $I_E$ 2"-Isopropylpyrido[2,3-5γ,5δ](4ζ-N-methyl-N-propylamino)(4ζ-dedimethylamino)pristinamycin $I_E$ 2"-Isopropylpyrido[2,3-5γ,5δ](4ζ-N-methyl-N-(4-pyridylmethyl)amino)(4ζ-dedimethylamino)pristinamycin $I_E$ 2"-Isopropylpyrido[2,3-5γ,5δ](4ζ-N-methyl-N-(3-pyridylmethyl)amino)(4ζ-dedimethylamino)pristinamycin $I_E$ 2"-Isopropylpyrido[2,3-5γ,5δ](4ζ-methyl)-(4ζ-dedimethylamino)pristinamycin $I_E$ 2"-Isopropylpyrido[2,3-5γ,5δ](4ζ-tert-butyl)(4ζ-dedimethylamino)pristinamycin $I_E$ 4ε-Bromo-2"-acetoxymethylmethylpyrido[2,3-5γ,5δ]pristinamycin $I_E$ 4ε-Bromo-2"-acetoxymethylmethylpyrido[2,3-5γ,5δ](4ζ-methylamino)(4ζ-dedimethylamino)pristinamycin $I_E$ 4ε-Allyl-2"-acetoxymethylmethylpyrido[2,3-5γ,5δ]pristinamycin $I_E$ 4ε-Allyl-2"-acetoxymethylmethylpyrido[2,3-5γ,5δ](4ζ-methylamino)(4ζ-dedimethylamino)pristinamycin $I_E$ 4ε-(2-Methylpropen-1-yl)-2"-acetoxymethylpyrido[2,3-5γ,5δ]pristinamycin $I_E$ 4ε-(2-Methylpropen-1-yl)-2"-acetoxymethylpyrido[2,3-5γ,5δ](4ζ-methylamino)(4ζ-dedimethylamino)pristinamycin $I_E$ 2"-Acetoxymethylpyrido[2,3-5γ,5δ](4ζ-diethyl-amino)(4ζ-dedimethylamino)pristinamycin $I_E$ 2"-Acetoxymethylpyrido[2,3-5γ,5δ](4ζ-N-methyl-N-allylamino)(4ζ-dedimethylamino)pristinamycin $I_E$ 2"-Acetoxymethylpyrido[2,3-5γ,5δ](4ζ-N-methyl-N-ethylamino)(4ζ-dedimethylamino)pristinamycin $I_E$ 2"-Acetoxymethylpyrido[2,3-5γ,5δ](4ζ-N-methyl-N-propylamino)(4ζ-dedimethylamino)pristinamycin $I_E$ 2"-Acetoxymethylpyrido[2,3-5γ,5δ](4ζ-N-methyl-N-(4-pyridylmethyl)amino)(4ζ-dedimethylamino)pristinamycin $I_E$ 2"-Acetoxymethylpyrido[2,3-5γ,5δ](4ζ-N-methyl-N-(3-pyridylmethyl)amino)(4ζ-dedimethylamino)pristinamycin $I_E$ 2"-Acetoxymethylpyrido[2,3-5γ,5δ](4ζ-methyl)(4ζ-dedimethylamino)pristinamycin $I_E$ 2"-Acetoxymethylpyrido[2,3-5γ,5δ]4ζ-tert-butyl)(4ζ-dedimethylamino)pristinamycin $I_E$ 4ε-Bromo-2"-cyclopropylaminomethylpyrido[2,3-5γ,5δ]pristinamycin $I_E$ 4ε-Bromo-2"-cyclopropylaminomethylpyrido[2,3-5γ,5δ](4ζ-methylamino)(4ζ-dedimethylamino)pristinamycin $I_E$ 4ε-Allyl-2"-cyclopropylaminomethylpyrido[2,3-5γ,5δ]pristinamycin $I_E$ 4ε-Allyl-2"-cyclopropylaminomethylpyrido[2,3-5γ,5δ](4ζ-methylamino)(4ζ-dedimethylamino)pristinamycin $I_E$ 4ε-(2-Methylpropen-1-yl)-2"-cyclopropylaminomethylpyrido[2,3-5γ,5δ]pristinamycin $I_E$ 4ε-(2-Methylpropen-1-yl)-2"-cyclopropylaminomethylpyrido[2,3-5γ,5δ](4ζ-methylamino)(4ζ-dedimethylamino)pristinamycin $I_E$ 2"-Cyclopropylaminomethylpyrido[2,3-5γ,5δ](4ζ-diethylamino)(4ζ-dedimethylamino)pristinamycin $I_E$ 2"-Cyclopropylaminomethylpyrido[2,3-5γ,5δ](4ζ-N-methyl-N-allylamino)(4ζ-dedimethylamino)pristinamycin $I_E$ 2"-Cyclopropylaminomethylpyrido[2,3-5γ,5δ](4ζ-N-methyl-N-ethylamino)(4ζ-dedimethylamino)pristinamycin $I_E$ 2"-Cyclopropylaminomethylpyrido[2,3-5γ,5δ](4ζ-N-methyl-N-propylamino)(4ζ-dedimethylamino)pristinamycin $I_E$ 2"-Cyclopropylaminomethylpyrido[2,3-5γ,5δ](4ζ-N-methyl-N-(4-pyridylmethyl)amino)(4ζ-dedimethylamino)pristinamycin $I_E$ 2"-Cyclopropylaminomethylpyrido[2,3-5γ,5δ](4ζ-N-methyl-N-(3-pyridylmethyl)amino)(4ζ-dedimethylamino)pristinamycin $I_E$ 2"-Cyclopropylaminomethylpyrido[2,3-5γ,5δ](4ζ-methyl)(4ζ-dedimethylamino)pristinamycin $I_E$ 2"-Cyclopropylaminomethylpyrido[2,3-5γ,5δ](4ζ-tert-butyl)(4ζ-dedimethylamino)pristinamycin $I_E$ 4ε-Bromo-2",3"-dimethylpyrido[2,3-5γ,5δ]pristinamycin $I_E$ 4ε-Bromo-2",3"-dimethylpyrido[2,3-5γ,5δ](4ζmethylamino)(4ζ-dedimethylamino)pristinamycin I$_E$
4ε-Allyl-2",3"-dimethylpyrido[2,3-5γ,5δ]pristinamycin I$_E$
4ε-Allyl-2",3"-dimethylpyrido[2,3-5γ,5δ](4ζ-methylamino)(4ζ-dedimethylamino)pristinamycin I$_E$
4ε-(2-Methylpropen-1-yl)-2",3"-dimethylpyrido[2,3-5γ,5δ]pristinamycin I$_E$
4ε-(2-Methylpropen-1-yl)-2",3"-dimethylpyrido[2,3-5γ,5δ](4ζ-methylamino)(4ζ-dedimethylamino)pristinamycin I$_E$
2",3"-Dimethylpyrido[2,3-5γ,5δ](4ζ-diethylamino)(4ζ-dedimethylamino)pristinamycin I$_E$
2",3"-Dimethylpyrido[2,3-5γ,5δ](4ζ-N-methyl-N-allylamino)(4ζ-dedimethylamino)pristinamycin I$_E$
2",3"-Dimethylpyrido[2,3-5γ,5δ](4ζ-N-methyl-N-ethylamino)(4ζ-dedimethylamino)pristinamycin I$_E$
2",3"-Dimethylpyrido[2,3-5γ,5δ](4ζ-N-methyl-N-propylamino)(4ζ-dedimethylamino)pristinamycin I$_E$
2",3"-Dimethylpyrido[2,3-5γ,5δ](4ζ-N-methyl-N-(4-pyridylmethyl)amino)(4ζ-dedimethylamino)pristinamycin I$_E$
2",3"-Dimethylpyrido[2,3-5γ,5δ](4ζ-N-methyl-N-(3-pyridylmethyl)amino)(4ζ-dedimethylamino)pristinamycin I$_E$
2",3"-Dimethylpyrido[2,3-5γ,5δ](4ζ-methyl)(4ζ-dedimethylamino)pristinamycin I$_E$
2",3"-Dimethylpyrido[2,3-5γ,5δ](4ζ-tert-butyl)(4ζ-dedimethylamino)pristinamycin I$_E$
4ε-Bromo-2"-ethoxycarbonylpyrido[2,3-5γ,5δ]pristinamycin I$_E$
4ε-Bromo-2"-ethoxycarbonylpyrido[2,3-5γ,5δ](4ζ-methylamino)(4ζ-dedimethylamino)pristinamycin I$_E$
4ε-Allyl-2"-ethoxycarbonylpyrido[2,3-5γ,5δ](4ζ-methylamino)(4ζ-dedimethylamino)pristinamycin I$_E$
4ε-Allyl-2"-ethoxycarbonylpyrido[2,3-5γ,5δ](4ζ-methylamino)(4ζ-dedimethylamino)pristinamycin I$_E$
4ε-(2-Methylpropen-1-yl)-2"-ethoxycarbonylpyrido[2,3-5γ,5δ]pristinamycin I$_E$
4ε-(2-Methylpropen-1-yl)-2"-ethoxycarbonylpyrido[2,3-5γ,5δ](4ζ-methylamino)(4ζ-dedimethylamino)pristinamycin I$_E$
2"-Ethoxycarbonylpyrido[2,3-5γ,5δ](4ζ-diethyl-amino)(4ζ-dedimethylamino)pristinamycin I$_E$
2"-Ethoxycarbonylpyrido[2,3-5γ,5δ](4ζ-N-methyl-N-allylamino)(4ζ-dedimethylamino)pristinamycin I$_E$
2"-Ethoxycarbonylpyrido[2,3-5γ,5δ](4ζ-N-methyl-N-ethylamino)(4ζ-dedimethylamino)pristinamycin I$_E$
2"-Ethoxycarbonylpyrido[2,3-5γ,5δ](4ζ-N-methyl-N-propylamino)(4ζ-dedimethylamino)pristinamycin I$_E$
2"-Ethoxycarbonylpyrido[2,3-5γ,5δ](4ζ-N-methyl-N-(4-pyridylmethyl)amino)(4ζ-dedimethylamino)pristinamycin I$_E$
2"-Ethoxycarbonylpyrido[2,3-5γ,5δ](4ζ-N-methyl-N-(3-pyridylmethyl)amino)(4ζ-dedimethylamino)pristinamycin I$_E$
2"-Ethoxycarbonylpyrido[2,3-5γ,5δ](4ζ-methyl)(4ζ-dedimethylamino)pristinamycin I$_E$
2"-Ethoxycarbonylpyrido[2,3-5γ,5δ](4ζ-tert-butyl)(4ζ-dedimethylamino)pristinamycin I$_E$
4ε-Bromo-2"-(N-diethylaminomethyl)pyrido[2,3-5γ,5δ]pristinamycin I$_E$
4ε-Bromo-2"-(N-diethylaminomethyl)pyrido[2,3-5γ,5δ](4ζ-methylamino)(4ζ-dedimethylamino)pristinamycin I$_E$
4ε-Allyl-2"-(N-diethylaminomethyl)pyrido[2,3-5γ,5δ]pristinamycin I$_E$
4ε-Allyl-2"-(N-diethylaminomethyl)pyrido[2,3-5γ,5δ](4ζ-methylamino)(4ζ-dedimethylamino)pristinamycin I$_E$
4ε-(2-Methylpropen-1-yl)-2"-(N-diethylamino-methyl)pyrido[2,3-5γ,5δ]pristinamycin I$_E$
4ε-(2-Methylpropen-1-yl)-2"-(N-diethylaminomethyl)pyrido[2,3-5γ,5δ](4ζ-methylamino)(4ζ-dedimethylamino)pristinamycin I$_E$
2"-(N-Diethylaminomethyl)pyrido[2,3-5γ,5δ](4ζ-diethylamino)(4ζ-dedimethylamino)pristinamycin I$_E$
2"-(N-Diethylaminomethyl)pyrido[2,3-5γ,5δ](4ζ-N-methyl-N-allylamino)(4ζ-dedimethylamino)pristinamycin I$_E$
2"-(N-Diethylaminomethyl)pyrido[2,3-5γ,5δ](4ζ-N-methyl-N-ethylamino)(4ζ-dedimethylamino)pristinamycin I$_E$
2"-(N-Diethylaminomethyl)pyrido[2,3-5γ,5δ](4ζ-N-methyl-N-propylamino)(4ζ-dedimethylamino)pristinamycin I$_E$
2"-(N-Diethylaminomethyl)pyrido[2,3-5γ,5δ](4ζ-N-methyl-N-(4-pyridylmethyl)amino)-(4ζ-dedimethylamino)pristinamycin I$_E$
2"-(N-Diethylaminomethyl)pyrido[2,3-5γ,5δ](4ζ-N-methyl-N-(3-pyridylmethyl)amino)(4ζ-dedimethylamino)pristinamycin I$_E$
2"-(N-Diethylaminomethyl)pyrido[2,3-5γ,5δ](4ζ-methyl)(4ζ-dedimethylamino)pristinamycin I$_E$
2"-(N-Diethylaminomethyl)pyrido[2,3-5γ,5δ](4ζ-tert-butyl)(4ζ-dedimethylamino)pristinamycin I$_E$
4ε-Bromo-2"-carbamoylpyrido[2,3-5γ,5δ]pristinamycin I$_E$
4ε-Bromo-2"-carbamoylpyrido[2,3-5γ,5δ](4ζ-methylamino)(4ζ-dedimethylamino)pristinamycin I$_E$
4ε-Allyl-2"-carbamoylpyrido[2,3-5γ,5δ]pristinamycin I$_E$
4ε-Allyl-2"-carbamoylpyrido[2,3-5γ,5δ](4ζ-methylamino)(4ζ-dedimethylamino)pristinamycin I$_E$
4ε-(2-methylpropen-1-yl)2"-carbamoylpyrido[2,3-5γ,5δ]pristinamycin I$_E$
4ε-(2-methylpropen-1-yl)-2"-carbamoylpyrido[2,3-5γ,5δ](4ζmethylamino)(4ζ-dedimethylamino)pristinamycin I$_E$
2"-Carbamoylpyrido[2,3-5γ,5δ](4ζ-diethylamino)(4ζ-dedimethylamino)pristinamycin I$_E$
2"-Carbamoylpyrido[2,3-5γ,5δ](4ζ-N-methyl-N-allylamino)(4ζ-dedimethylamino)pristinamycin I$_E$
2"-Carbamoylpyrido[2,3-5γ,5δ](4ζ-N-methyl-N-ethylamino)(4ζ-dedimethylamino)pristinamycin I$_E$
2"-Carbamoylpyrido[2,3-5γ,5δ](4ζ-N-methyl-N-propylamino)(4ζ-dedimethylamino)pristinamycin I$_E$
2"-Carbamoylpyrido[2,3-5γ,5δ](4ζ-N-methyl-N-(4-pyridylmethyl)amino)(4ζ-dedimethylamino)pristinamycin I$_E$
2"-Carbamoylpyrido[2,3-5γ,5δ](4ζ-N-methyl-N-(3-pyridylmethyl)amino)(4ζ-dedimethylamino)pristinamycin I$_E$
2"-Carbamoylpyrido[2,3-5γ,5δ](4ζ-methyl)(4ζ-dedimethylamino)pristinamycin I$_E$
2"-Carbamoylpyrido[2,3-5γ,5δ](4ζ-tert-butyl)(4ζ-dedimethylamino)pristinamycin I$_E$
2"-Methoxypyrimido[4,5-5γ,5δ](4ζ-methylamino)(4ζ-dedimethylamino)pristinamycin I$_E$
2"-Methoxypyrimido[4,5-5γ,5δ]-4ε-chloropristinamycin I$_E$
2"-Methoxypyrimido[4,5-5γ,5δ](4ζ-methylamino)(4ζ-dedimethylamino)-4ε-chloropristinamycin I$_E$
2"-(4-Pyridyl)pyrimido[4,5-5γ,5δ](4ζ-methylamino)(4ζ-dedimethylamino)pristinamycin I$_E$
2"-(4-Pyridyl)pyrimido[4,5-5γ,5δ]-4ε-chloropristinamycin I$_E$
2"-(4-Pyridyl)pyrimido[4,5-5γ,5δ](4ζ-methylamino)(4ζ-dedimethylamino)-4ε-chloropristinamycin I$_E$
2"-Methylthiopyrimido[4,5-5γ,5δ]-4ε-chloropristinamycin I$_E$
2"-(3-Aminophenyl)pyrimido[4,5-5γ,5δ](4ζ-methylamino)(4ζ-dedimethylamino)pristinamycin I$_E$ 2"-(3-Aminophenyl)pyrimido[4,5-5γ,5δ]-4ε-chloropristinamycin I_E
2"-(3-Aminophenyl)pyrimido[4,5-5γ,5δ](4ζ-methylamino)(4ζ-dedimethylamino)-4ε-chloropristinamycin I_E
2"-Methylthiopyrimido[4,5-5γ,5δ](4ζ-methylamino)(4ζ-dedimethylamino)pristinamycin I_E
2"-(1-Pyrrolidinyl)pyrimido[4,5-5γ,5δ]-4ε-chloropristinamycin I_E
2"-(1-Azetidinyl)pyrimido[4,5-5γ,5δ](4ζ-methylamino)(4ζ-dedimethylamino)pristinamycin I_E
2"-(1-Azetidinyl)pyrimido[4,5-5γ,5δ]-4ε-chloropristinamycin I_E
2"-(1-Azetidinyl)pyrimido[4,5-5γ,5δ](4ζ-methylamino)(4ζ-dedimethylamino)-4ε-chloropristinamycin I_E
2"-(3-Pyridyl)pyrimido[4,5-5γ,5δ]pristinamycin I_E
2"-(3-Pyridyl)pyrimido[4,5-5γ,5δ](4ζ-methylamino)(4ζ-dedimethylamino)pristinamycin I_E
2"-(3-Pyridyl)pyrimido[4,5-5γ,5δ]-4ε-chloropristinamycin I_E
2"-(3-Pyridyl)pyrimido[4,5-5γ,5δ](4ζ-methylamino)(4ζ-dedimethylamino)-4ε-chloropristinamycin I_E
2"-(2-Pyridyl)pyrimido[4,5-5γ,5δ]-4ε-chloropristinamycin I_E
2"-(1-Pyrrolidinyl)pyrimido[4,5-5γ,5δ](4ζ-methylamino)(4ζ-dedimethylamino)-4ε-chloropristinamycin I_E
2"-Methylpyrimido[4,5-5γ,5δ](4ζ-methylamino)(4ζ-dedimethylamino)pristinamycin I_E
2"-Methylpyrimido[4,5-5γ,5δ]-4ε-chloropristinamycin I_E
2"-Methylpyrimido[4,5-5γ,5δ](4ζ-methylamino)(4ζ-dedimethylamino)-4ε-chloropristinamycin I_E
2"-(2-Pyridyl)pyrimido[4,5-5γ,5δ](4ζ-methylamino)(4ζ-dedimethylamino)-4ε-chloropristinamycin I_E
2"-(2-Pyrazinyl)pyrimido[4,5-5γ,5δ](4ζ-methylamino)(4ζ-dedimethylamino)pristinamycin I_E
2"-(2-Pyrazinyl)pyrimido[4,5-5γ,5δ]-4ε-chloropristinamycin I_E
2"-(2-Pyrazinyl)pyrimido[4,5-5γ,5δ](4ζ-methylamino)(4ζ-dedimethylamino)-4ε-chloropristinamycin I_E
2"-(2-Morpholinoethylthio)pyrimido[4,5-5γ,5δ](4ζ-methylamino)(4ζ-dedimethylamino)pristinamycin I_E
2"-(2-Morpholinoethylthio)pyrimido[4,5-5γ,5δ]-4ε-chloropristinamycin I_E
2"-(2-Morpholinoethylthio)pyrimido[4,5-5γ,5δ](4ζ-methylamino)(4ζ-dedimethylamino)-4ε-chloropristinamycin I_E
2"-Aminopyrimido[4,5-5γ,5δ](4ζ-methylamino)(4ζ-dedimethylamino)pristinamycin I_E
2"-Aminopyrimido[4,5-5γ,5δ]-4ε-chloropristinamycin I_E
2"-Aminopyrimido[4,5-5γ,5δ](4ζ-methylamino)(4ζ-dedimethylamino)-4ε-chloropristinamycin I_E
2"-(1-Pyrazol)pyrimido[4,5-5γ,5δ](4ζ-methylamino)(4ζ-dedimethylamino)pristinamycin I_E
2"-(1-Pyrazol)pyrimido[4,5-5γ,5δ]-4ε-chloropristinamycin I_E
2"-(1-Pyrazol)pyrimido[4,5-5γ,5δ](4ζ-methylamino)(4ζ-dedimethylamino)-4ε-chloropristinamycin I_E
2"-(Diethylaminoethylthio)pyrimido[4,5-5γ,5δ](4ζ-methylamino)(4ζ-dedimethylamino)pristinamycin I_E
2"-(Diethylaminoethylthio)pyrimido[4,5-5γ,5δ]-4ε-chloropristinamycin I_E
2"-(Diethylaminoethylthio)pyrimido[4,5-5γ,5δ](4ζ-methylamino)(4ζ-dedimethylamino)-4ε-chloropristinamycin I_E
2"-Methylaminopyrimido[4,5-5γ,5δ](4ζ-methylamino)(4ζ-dedimethylamino)pristinamycin I_E
2"-Methylaminopyrimido[4,5-5γ,5δ]-4ε-chloropristinamycin I_E
2"-Methylaminopyrimido[4,5-5γ,5δ](4ζ-methylamino)(4ζ-dedimethylamino)-4ε-chloropristinamycin I_E
2"-Methylsulphonylpyrimido[4,5-5γ,5δ](4ζ-methylamino)(4ζ-dedimethylamino)pristinamycin I_E
2"-Methylsulphonylpyrimido[4,5-5γ,5δ]-4ε-chloropristinamycin I_E
2"-Methylsulphonylpyrimido[4,5-5γ,5δ](4ζ-methylamino)(4ζ-dedimethylamino)-4ε-chloropristinamycin I_E
2"-(4-Aminophenyl)pyrimido[4,5-5γ,5δ]pristinamycin I_E
2"-(4-Aminophenyl)pyrimido[4,5-5γ,5δ](4ζ-methylamino)(4ζ-dedimethylamino)pristinamycin I_E
2"-(4-Aminophenyl)pyrimido[4,5-5γ,5δ]-4ε-chloropristinamycin I_E
2"-(4-Aminophenyl)pyrimido[4,5-5γ,5δ](4ζ-methylamino)(4ζ-dedimethylamino)-4ε-chloropristinamycin I_E
2"-Trifluoromethylpyrimido[4,5-5γ,5δ]pristinamycin I_E
2"-Trifluoromethylpyrimido[4,5-5γ,5δ](4ζ-methylamino)(4ζ-dedimethylamino)pristinamycin I_E
2"-Trifluoromethylpyrimido[4,5-5γ,5δ]-4ε-chloropristinamycin I_E
2"-Trifluoromethylpyrimido[4,5-5γ,5δ](4ζ-methylamino)(4ζ-dedimethylamino)-4ε-chloropristinamycin I_E
2"-Cyclopropylpyrimido[4,5-5γ,5δ]pristinamycin I_E
2"-Cyclopropylpyrimido[4,5-5γ,5δ](4ζ-methylamino)(4ζ-dedimethylamino)pristinamycin I_E
2"-Cyclopropylpyrimido[4,5-5γ,5δ]-4ε-chloropristinamycin I_E
2"-Cyclopropylpyrimido[4,5-5γ,5δ](4ζ-methylamino)(4ζ-dedimethylamino)-4ε-chloropristinamycin I_E
2"-Morpholinomethylpyrimido[4,5-5γ,5δ]pristinamycin I_E
2"-Morpholinomethylpyrimido[4,5-5γ,5δ](4ζ-methylamino)(4ζ-dedimethylamino)pristinamycin I_E
2"-Morpholinomethylpyrimido[4,5-5γ,5δ]-4ε-chloropristinamycin I_E
2"-Morpholinomethylpyrimido[4,5-5γ,5δ](4ζ-methylamino)(4ζ-dedimethylamino)-4ε-chloropristinamycin I_E
2"-Ethylpyrimido[4,5-5γ,5δ]pristinamycin I_E
2"-Ethylpyrimido[4,5-5γ,5δ](4ζ-methylamino)(4ζ-dedimethylamino)pristinamycin I_E
2"-Ethylpyrimido[4,5-5γ,5δ]-4ε-chloropristinamycin I_E
2"-Ethylpyrimido[4,5-5γ,5(δ](4ζ-methylamino)(4ζ-dedimethylamino)-4ε-chloropristinamycin I_E
2"-Propylpyrimido[4,5-5γ,5δ]pristinamycin I_E
2"-Propylpyrimido[4,5-5γ,5δ](4ζ-methylamino)(4ζ-dedimethylamino)pristinamycin I_E
2"-Propylpyrimido[4,5-5γ,5δ]-4ε-chloropristinamycin I_E
2"-Propylpyrimido[4,5-5γ,5δ](4ζ-methylamino)(4ζ-dedimethylamino)-4ε-chloropristinamycin I_E
2"-Isopropylpyrimido[4,5-5γ,5δ]pristinamycin I_E
2"-Isopropylpyrimido[4,5-5γ,5δ](4ζ-methylamino)(4ζ-dedimethylamino)pristinamycin I_E
2"-Isopropylpyrimido[4,5-5γ,5δ]-4ε-chloropristinamycin I_E
2"-Isopropylpyrimido[4,5-5γ,5δ](4ζ-methylamino)(4ζ-dedimethylamino)-4ε-chloropristinamycin I_E
2"-Cyclopropylaminomethylpyrimido[4,5-5γ,5δ]pristinamycin I_E
2"-Cyclopropylaminomethylpyrimido[4,5-5γ,5δ](4ζ-methylamino)(4ζ-dedimethylamino)pristinamycin I_E
2"-Cyclopropylaminomethylpyrimido[4,5-5γ,5δ]-4ε-chloropristinamycin I_E
2"-Cyclopropylaminomethylpyrimido[4,5-5γ,5δ](4ζ-methylamino)(4ζ-dedimethylamino)-4ε-chloropristinamycin I_E
4ε-Bromo-2"-methoxypyrimido[4,5-5γ,5δ]pristinamycin I_E
4ε-Bromo-2"-methoxypyrimido[4,5-5γ,5δ](4-methylamino)(4-dedimethylamino)pristinamycin I_E 4ε-Allyl-2"-methoxypyrimido[4,5-5γ,5δ]pristinamycin I_E
4ε-Allyl-2"-methoxypyrimido[4,5-5γ,5δ](4ζ-methylamino)(4ζ-dedimethylamino)pristinamycin I_E
4ε-(2-methylpropen-1-yl)-2"-methoxypyrimido[4,5-5γ,5δ]pristinamycin I_E
4ε-(2-methylpropen-1-yl)-2"-methoxypyrimido[4,5-5γ,5δ](4ζ-methylamino)(4ζ-dedimethylamino)pristinamycin I_E
2"-Methoxypyrimido[4,5-5γ,5δ](4ζ-diethylamino)(4ζ-dedimethylamino)pristinamycin I_E
2"-Methoxypyrimido[4,5-5γ,5δ](4ζ-N-methyl-N-allylamino)(4ζ-dedimethylamino)pristinamycin I_E
2"-Methoxypyrimido[4,5-5γ,5δ](4ζ-N-methyl-N-ethylamino)(4ζ-dedimethylamino)pristinamycin I_E
2"-Methoxypyrimido[4,5-5γ,5δ](4ζ-N-methyl-N-propylamino)(4ζ-dedimethylamino)pristinamycin I_E
2"-Methoxypyrimido[4,5-5γ,5δ](4ζ-N-methyl-N-(4-pyridylmethyl)amino)(4ζ-dedimethylamino)pristinamycin I_E
2"-Methoxypyrimido[4,5-5γ,5δ](4ζ-N-methyl-N-(3-pyridylmethyl)amino)(4ζ-dedimethylamino)pristinamycin I_E
2"-Methoxypyrimido[4,5-5γ,5δ](4ζ-methyl)(4ζ-dedimethylamino)pristinamycin I_E
2"-Methoxypyrimido[4,5-5γ,5δ](4ζ-tert-butyl)(4ζ-dedimethylamino)pristinamycin I_E
4ε-Bromo-2"-(4-pyridyl)pyrimido[4,5-5γ,5δ]pristinamycin I_E
4ε-Bromo-2"-(4-pyridyl)pyrimido[4,5-5γ,5δ](4ζ-methylamino)(4ζ-dedimethylamino)pristinamycin I_E
4ε-Allyl-2"-(4-pyridyl)pyrimido[4,5-5γ,5δ]pristinamycin I_E
4ε-Allyl-2"-(4-pyridyl)pyrimido[4,5-5γ,5δ](4ζ-methylamino)(4ζ-dedimethylamino)pristinamycin I_E
4ε-(2-Methylpropen-1-yl)-2"-(4-pyridyl)pyrimido[4,5-5γ,5δ]pristinamycin I_E
4ε-(2-Methylpropen-1-yl)-2"-(4-pyridyl)pyrimido[4,5-5γ,5δ](4ζ-methylamino)(4ζ-dedimethylamino)pristinamycin I_E
2"-(4-Pyridyl)pyrimido[4,5-5γ,5δ](4ζ-diethylamino)(4ζ-dedimethylamino)pristinamycin I_E
2"-(4-Pyridyl)pyrimido[4,5-5γ,5δ](4ζ-N-methyl-N-allylamino)(4ζ-dedimethylamino)pristinamycin I_E
2"-(4-Pyridyl)pyrimido[4,5-5γ,5δ](4ζ-N-methyl-N-ethylamino)(4ζ-dedimethylamino)pristinamycin I_E
2"-(4-Pyridyl)pyrimido[4,5-5γ,5δ](4ζ-N-methyl-N-propylamino)(4ζ-dedimethylamino)pristinamycin I_E
2"-(4-Pyridyl)pyrimido[4,5-5γ,5δ](4ζ-N-methyl-N-(4-pyridylmethyl)amino)(4ζ-dedimethylamino)pristinamycin I_E
2"-(4-Pyridyl)pyrimido[4,5-5γ,5δ](4ζ-N-methyl-N-(3-pyridylmethyl)amino)(4ζ-dedimethylamino)pristinamycin I_E
2"-(4-Pyridyl)pyrimido[4,5-5γ,5δ](4ζ-methyl)(4ζ-dedimethylamino)pristinamycin I_E
2"-(4-Pyridyl)pyrimido[4,5-5γ,5δ](4ζ-tert-butyl)(4ζ-dedimethylamino)pristinamycin I_E
4ε-Bromo-2"-methylthiopyrimido[4,5-5γ,5δ]pristinamycin I_E
4ε-Bromo-2"-methylthiopyrimido[4,5-5γ,5δ](4ζ-methylamino)(4ζ-dedimethylamino)pristinamycin I_E
4ε-Allyl-2"-methylthiopyrimido[4,5-5γ,5δ]pristinamycin I_E
4ε-Allyl-2"-methylthiopyrimido[4,5-5γ,5δ](4ζ-methylamino)(4ζ-dedimethylamino)pristinamycin I_E
4ε-(2-Methylpropen-1-yl)-2"-methylthiopyrimido[4,5-5γ,5δ]pristinamycin I_E
4ε-(2-Methylpropen-1-yl)-2"-methylthiopyrimido[4,5-5γ,5δ](4ζ-methylamino)(4ζ-dedimethylamino)pristinamycin I_E
2"-Methylthiopyrimido[4,5-5γ,5δ](4ζ-diethylamino)(4ζ-dedimethylamino)pristinamycin I_E
2"-Methylthiopyrimido[4,5-5γ,5δ](4ζ-N-methyl-N-allylamino)(4ζ-dedimethylamino)pristinamycin I_E
2"-Methylthiopyrimido[4,5-5γ,5δ](4ζ-N-methyl-N-ethylamino)(4ζ-dedimethylamino)pristinamycin I_E
2"-Methylthiopyrimido[4,5-5γ,5δ](4ζ-N-methyl-N-propylamino)(4ζ-dedimethylamino)pristinamycin I_E
2"-Methylthiopyrimido[4,5-5γ,5δ](4ζ-N-methyl-N-(4-pyridylmethyl)amino)(4ζ-dedimethylamino)pristinamycin I_E
2"-Methylthiopyrimido[4,5-5γ,5δ](4ζ-N-methyl-N-(3-pyridylmethyl)amino)(4ζ-dedimethylamino)pristinamycin I_E
2"-Methylthiopyrimido[4,5-5γ,5δ](4ζ-methyl)(4ζ-dedimethylamino)pristinamycin I_E
2"-Methylthiopyrimido[4,5-5γ,5δ](4ζ-tert-butyl)(4ζ-dedimethylamino)pristinamycin I_E
4ε-Bromo-2"-(3-aminophenyl)pyrimido[4,5-5γ,5δ]pristinamycin I_E
4ε-Bromo-2"-(3-aminophenyl)pyrimido[4,5-5γ,5δ](4ζ-methylamino)(4ζ-dedimethylamino)pristinamycin I_E
4ε-Allyl-2"-(3-aminophenyl)pyrimido[4,5-5γ,5δ]pristinamycin I_E
4ε-Allyl-2"-(3-aminophenyl)pyrimido[4,5-5γ,5δ](4ζ-methylamino)(4ζ-dedimethylamino)pristinamycin I_E
4ε-(2-Methylpropen-1-yl)-2"-(3-aminophenyl)pyrimido[4,5-5γ,5δ]pristinamycin I_E
4ε-(2-Methylpropen-1-yl)-2"-(3-aminophenyl)pyrimido[4,5-5γ,5δ](4ζ-methylamino)(4ζ-dedimethylamino)pristinamycin I_E
2"-(3-Aminophenyl)pyrimido[4,5-5γ,5δ](4ζ-diethylamino)(4ζ-dedimethylamino)pristinamycin I_E
2"-(3-Aminophenyl)pyrimido[4,5-5γ,5δ](4ζ-N-methyl-N-allylamino)(4ζ-dedimethylamino)pristinamycin I_E
2"-(3-Aminophenyl)pyrimido[4,5-5γ,5δ](4ζ-N-methyl-N-ethylamino)(4ζ-dedimethylamino)pristinamycin I_E
2"-(3-Aminophenyl)pyrimido[4,5-5γ,5δ](4ζ-N-methyl-N-propylamino)(4ζ-dedimethylamino)pristinamycin I_E
2"-(3-Aminophenyl)pyrimido[4,5-5γ,5δ](4ζ-N-methyl-N-(4-pyridylmethyl)amino)(4ζ-dedimethylamino)pristinamycin I_E
2"-(3-Aminophenyl)pyrimido[4,5-5γ,5δ](4ζ-N-methyl-N-(3-pyridylmethyl)amino)(4ζ-dedimethylamino)pristinamycin I_E
2"-(3-Aminophenyl)pyrimido[4,5-5γ,5δ](4ζ-methyl)(4ζ-dedimethylamino)pristinamycin I_E
2"-(3-Aminophenyl)pyrimido[4,5-5γ,5δ](4ζ-tert-butyl)(4ζ-dedimethylamino)pristinamycin I_E
4ε-Bromo-2"-(1-pyrrolidinyl)pyrimido[4,5-5γ,5δ](4ζ-methylamino)(4ζ-dedimethylamino)pristinamycin I_E
4ε-Allyl-2"-(1-pyrrolidinyl)pyrimido[4,5-5γ,5δ]pristinamycin I_E
4ε-Allyl-2"-(1-pyrrolidinyl)pyrimido[4,5-5γ,5δ](4ζ-methylamino)(4ζ-dedimethylamino)pristinamycin I_E
4ε-(2-Methylpropen-1-yl)-2"-(1-pyrrolidinyl)pyrimido[4,5-5γ,5δ]pristinamycin I_E
4ε-(2-Methylpropen-1-yl)-2"-(1-pyrrolidinyl)pyrimido[4,5-5γ,5δ](4ζ-methylamino)(4ζ-dedimethylamino)pristinamycin I_E
2"-(1-Pyrrolidinyl)pyrimido[4,5-5γ,5δ](4ζ-diethylamino)(4ζ-dedimethylamino)pristinamycin I_E
2"-(1-Pyrrolidinyl)pyrimido[4,5-5γ,5δ](4ζ-N-methyl-N-allylamino)(4ζ-dedimethylamino)pristinamycin I_E
2"-(1-Pyrrolidinyl)pyrimido[4,5-5γ,5δ](4ζ-N-methyl-N-ethylamino)(4ζ-dedimethylamino)pristinamycin I_E
2"-(1-Pyrrolidinyl)pyrimido[4,5-5γ,5δ](4ζ-N-methyl-N-propylamino)(4ζ-dedimethylamino)pristinamycin I_E 2"-(1-Pyrrolidinyl)pyrimido[4,5-5γ,5δ](4ζ-N-methyl-N-(4-pyridylmethyl)amino)(4ζ-dedimethylamino)pristinamycin $I_E$ 2"-(1-Pyrrolidinyl)pyrimido[4,5-5γ,5δ](4ζ-N-methyl-N-(3-pyridylmethyl)amino)(4ζ-dedimethylamino)pristinamycin $I_E$ 2"-(1-Pyrrolidinyl)pyrimido[4,5-5γ,5δ](4ζ-methyl)(4ζ-dedimethylamino)pristinamycin $I_E$ 2"-(1-Pyrrolidinyl)pyrimido[4,5-5γ,5δ](4ζ-tert-butyl)(4ζ-dedimethylamino)pristinamycin $I_E$ 4ε-Bromo-2"-(1-azetidinyl)pyrimido[4,5-5γ,5δ]pristinamycin $I_E$ 4ε-Bromo-2"-(1-azetidinyl)pyrimido[4,5-5γ,5δ](4ζ-methylamino)(4ζ-dedimethylamino)pristinamycin $I_E$ 4ε-Allyl-2"-(1-azetidinyl)pyrimido[4,5-5γ,5δ]pristinamycin $I_E$ 4ε-Allyl-2"-(1-azetidinyl)pyrimido[4,5-5γ,5δ](4ζ-methylamino)(4ζ-dedimethylamino)pristinamycin $I_E$ 4ε-(2-Methylpropen-1-yl)-2"-(1-azetidinyl)pyrimido[4,5-5γ,5δ]pristinamycin $I_E$ 4ε-(2-Methylpropen-1-yl)-2"-(1-azetidinyl)pyrimido[4,5-5γ,5δ](4ζ-methylamino)(4ζ-dedimethylamino)pristinamycin $I_E$ 2"-(1-Azetidinyl)pyrimido[4,5-5γ,5δ](4ζ-diethylamino)(4ζ-dedimethylamino)pristinamycin $I_E$ 2"-(1-Azetidinyl)pyrimido[4,5-5γ,5δ](4ζ-N-methyl-N-allylamino)(4ζ-dedimethylamino)pristinamycin $I_E$ 2"-(1-Azetidinyl)pyrimido[4,5-5γ,5δ](4ζ-N-methyl-N-ethylamino)(4ζ-dedimethylamino)pristinamycin $I_E$ 2"-(1-Azetidinyl)pyrimido[4,5-5γ,5δ](4ζ-N-methyl-N-propylamino)(4ζ-dedimethylamino)pristinamycin $I_E$ 2"-(1-Azetidinyl)pyrimido[4,5-5γ,5δ](4ζ-N-methyl-N-(4-pyridylmethyl)amino)(4ζ-dedimethylamino)pristinamycin $I_E$ 2"-(1-Azetidinyl)pyrimido[4,5-5γ,5δ](4ζ-N-methyl-N-(3-pyridylmethyl)amino)(4ζ-dedimethylamino)pristinamycin $I_E$ 2"-(1-Azetidinyl)pyrimido[4,5-5γ,5δ](4ζ-methyl)(4ζ-dedimethylamino)pristinamycin $I_E$ 2"-(1-Azetidinyl)pyrimido[4,5-5γ,5δ](4ζ-tert-butyl)(4ζ-dedimethylamino)pristinamycin $I_E$ 4ε-Bromo-2"-(3-pyridyl)pyrimido[4,5-5γ,5δ]pristinamycin $I_E$ 4ε-Bromo-2"-(3-pyridyl)pyrimido[4,5-5γ,5δ](4ζ-methylamino)(4ζ-dedimethylamino)pristinamycin $I_E$ 4ε-Allyl-2"-(3-pyridyl)pyrimido[4,5-5γ,5δ]pristinamycin $I_E$ 4ε-Allyl-2"-(3-pyridyl)pyrimido[4,5-5γ,5δ](4ζ-methylamino)(4ζ-dedimethylamino)pristinamycin $I_E$ 4ε-(2-Methylpropen-1-yl)-2"-(3-pyridyl)pyrimido[4,5-5γ,5δ]pristinamycin $I_E$ 4ε-(2-Methylpropen-1-yl)-2"-(3-pyridyl)pyrimido[4,5-5γ,5δ](4ζ-methylamino)(4ζ-dedimethylamino)pristinamycin $I_E$ 2"-(3-Pyridyl)pyrimido[4,5-5γ,5δ](4ζ-diethylamino)(4ζ-dedimethylamino)pristinamycin $I_E$ 2"-(3-Pyridyl)pyrimido[4,5-5γ,5δ](4ζ-N-methyl-N-allylamino)(4ζ-dedimethylamino)pristinamycin $I_E$ 2"-(3-Pyridyl)pyrimido[4,5-5γ,5δ](4ζ-N-methyl-N-ethylamino)(4ζ-dedimethylamino)pristinamycin $I_E$ 2"-(3-Pyridyl)pyrimido[4,5-5γ,5δ](4ζ-N-methyl-N-propylamino)(4ζ-dedimethylamino)pristinamycin $I_E$ 2"-(3-Pyridyl)pyrimido[4,5-5γ,5δ](4ζ-N-methyl-N-(4-pyridylmethyl)amino)(4ζ-dedimethylamino)pristinamycin $I_E$ 2"-(3-Pyridyl)pyrimido[4,5-5γ,5δ](4ζ-N-methyl-N-(3-pyridylmethyl)amino)(4ζ-dedimethylamino)pristinamycin $I_E$ 2"-(3-Pyridyl)pyrimido[4,5-5γ,5δ](4ζ-methyl)(4ζ-dedimethylamino)pristinamycin $I_E$ 2"-(3-Pyridyl)pyrimido[4,5-5γ,5δ](4ζ-tert-butyl)(4ζ-dedimethylamino)pristinamycin $I_E$ 4ε-Bromo-2"-(2-pyridyl)pyrimido[4,5-5γ,5δ]pristinamycin $I_E$ 4ε-Bromo-2"-(2-pyridyl)pyrimido[4,5-5γ,5δ](4ζ-methylamino)(4ζ-dedimethylamino)pristinamycin $I_E$ 4ε-Allyl-2"-(2-pyridyl)pyrimido[4,5-5γ,5δ]pristinamycin $I_E$ 4ε-Allyl-2"-(2-pyridyl)pyrimido[4,5-5γ,5δ](4ζ-methylamino)(4ζ-dedimethylamino)pristinamycin $I_E$ 4ε-(2-Methylpropen-1-yl)-2"-(2-pyridyl)pyrimido[4,5-5γ,5δ]pristinamycin $I_E$ 4ε-(2-Methylpropen-1-yl)-2"-(2-pyridyl)pyrimido[4,5-5γ,5δ](4ζ-methylamino)(4ζ-dedimethylamino)pristinamycin $I_E$ 2"-(2-Pyridyl)pyrimido[4,5-5γ,5δ](4ζ-diethylamino)(4ζ-dedimethylamino)pristinamycin $I_E$ 2"-(2-Pyridyl)pyrimido[4,5-5γ,5δ](4ζ-N-methyl-N-allylamino)(4ζ-dedimethylamino)pristinamycin $I_E$ 2"-(2-Pyridyl)pyrimido[4,5-5γ,5δ](4ζ-N-methyl-N-ethylamino)(4ζ-dedimethylamino)pristinamycin $I_E$ 2"-(2-Pyridyl)pyrimido[4,5-5γ,5δ](4ζ-N-methyl-N-propylamino)(4ζ-dedimethylamino)pristinamycin $I_E$ 2"-(2-Pyridyl)pyrimido[4,5-5γ,5δ](4ζ-N-methyl-N-(4-pyridylmethyl)amino)(4ζ-dedimethylamino)pristinamycin $I_E$ 2"-(2-Pyridyl)pyrimido[4,5-5γ,5δ](4ζ-N-methyl-N-(3-pyridylmethyl)amino)(4ζ-dedimethylamino)pristinamycin $I_E$ 2"-(2-Pyridyl)pyrimido[4,5-5γ,5δ](4ζ-methyl)(4ζ-dedimethylamino)pristinamycin $I_E$ 2"-(2-Pyridyl)pyrimido[4,5-5γ,5δ](4ζ-tert-butyl)(4ζ-dedimethylamino)pristinamycin $I_E$ 4ε-Bromo-2"-methylpyrimido[4,5-5γ,5δ]pristinamycin $I_E$ 4ε-Bromo-2"-methylpyrimido[4,5-5γ,5δ](4ζ-methylamino)(4ζ-dedimethylamino)pristinamycin $I_E$ 4ε-Allyl-2"-methylpyrimido[4,5-5γ,5δ]pristinamycin $I_E$ 4ε-Allyl-2"-methylpyrimido[4,5-5γ,5δ](4ζ-methylamino)(4ζ-dedimethylamino)pristinamycin $I_E$ 4ε-(2-Methylpropen-1-yl)-2"-methylpyrimido[4,5-5γ,5δ]pristinamycin $I_E$ 4ε-(2-Methylpropen-1-yl)-2"-methylpyrimido[4,5-5γ,5δ](4ζ-methylamino)(4ζ-dedimethylamino)pristinamycin $I_E$ 2"-Methylpyrimido[4,5-5γ,5δ](4ζ-diethylamino)(4ζ-dedimethylamino)pristinamycin $I_E$ 2"-Methylpyrimido[4,5-5γ,5δ](4ζ-N-methyl-N-allylamino)(4ζ-dedimethylamino)pristinamycin $I_E$ 2"-Methylpyrimido[4,5-5γ,5δ](4ζ-N-methyl-N-ethylamino)(4ζ-dedimethylamino)pristinamycin $I_E$ 2"-Methylpyrimido[4,5-5γ,5δ](4ζ-N-methyl-N-propylamino)(4ζ-dedimethylamino)pristinamycin $I_E$ 2"-Methylpyrimido[4,5-5γ,5δ](4ζ-N-methyl-N-(4-pyridylmethyl)amino)(4ζ-dedimethylamino)pristinamycin $I_E$ 2"-Methylpyrimido[4,5-5γ,5δ](4ζ-N-methyl-N-(3-pyridylmethyl)amino)(4ζ-dedimethylamino)pristinamycin $I_E$ 2"-Methylpyrimido[4,5-5γ,5δ](4ζ-methyl)(4ζ-dedimethylamino)pristinamycin $I_E$ 2"-Methylpyrimido[4,5-5γ,5δ](4ζ-tert-butyl)(4ζ-dedimethylamino)pristinamycin $I_E$ 4ε-Bromo-2"-(2-pyrazinyl)pyrimido[4,5-5γ,5δ]pristinamycin $I_E$ 4ε-Bromo-2"-(2-pyrazinyl)pyrimido[4,5-5γ,5δ](4ζ-methylamino)(4ζ-dedimethylamino)pristinamycin $I_E$ 4ε-Allyl-2"-(2-pyrazinyl)pyrimido[4,5-5γ,5δ]pristinamycin $I_E$ 4ε-Allyl-2"-(2-pyrazinyl)pyrimido[4,5-5γ,5δ](4ζ-methylamino)(4ζ-dedimethylamino)pristinamycin I$_E$ 4ε-(2-methylpropen-1-yl)-2"-(2-pyrazinyl)pyrimido[4,5-5γ,5δ]pristinamycin I$_E$ 4ε-(2-methylpropen-1-yl)-2"-(2-pyrazinyl)pyrimido[4,5-5γ,5δ](4ζ-methylamino)(4ζ-dedimethylamino)pristinamycin I$_E$ 2"-(2-Pyrazinyl)pyrimido[4,5-5γ,5δ](4ζ-diethylamino)(4ζ-dedimethylamino)pristinamycin I$_E$ 2"-(2-Pyrazinyl)pyrimido[4,5-5γ,5δ](4ζ-N-methyl-N-allylamino)(4ζ-dedimethylamino)pristinamycin I$_E$ 2"-(2-Pyrazinyl)pyrimido[4,5-5γ,5δ](4ζ-N-methyl-N-ethylamino)(4ζ-dedimethylamino)pristinamycin I$_E$ 2"-(2-Pyrazinyl)pyrimido[4,5-5γ,5δ](4ζ-N-methyl-N-propylamino)(4ζ-dedimethylamino)pristinamycin I$_E$ 2"-(2-Pyrazinyl)pyrimido[4,5-5γ,5δ](4ζ-N-methyl-N-(4-pyridylmethyl)amino)(4ζ-dedimethylamino)pristinamycin I$_E$ 2"-(2-Pyrazinyl)pyrimido[4,5-5γ,5δ](4ζ-N-methyl-N-(3-pyridylmethyl)amino)(4ζ-dedimethylamino)pristinamycin I$_E$ 2"-(2-Pyrazinyl)pyrimido[4,5-5γ,5δ](4ζ-methyl)(4ζ-dedimethylamino)pristinamycin I$_E$ 2"-(2-Pyrazinyl)pyrimido[4,5-5γ,5δ](4ζ-tert-butyl)(4ζ-dedimethylamino)pristinamycin I$_E$ 4ε-Bromo-2"-(2-morpholinoethylthio)pyrimido[4,5-5γ,5δ]pristinamycin I$_E$ 4ε-Bromo-2"-(2-morpholinoethylthio)pyrimido[4,5-5γ,5δ](4ζ-methylamino)(4ζ-dedimethylamino)pristinamycin I$_E$ 4ε-Allyl-2"-(2-morpholinoethylthio)pyrimido[4,5-5γ,5δ]pristinamycin I$_E$ 4ε-Allyl-2"-(2-morpholinoethylthio)pyrimido[4,5-5γ,5δ](4ζ-methylamino)(4ζ-dedimethylamino)pristinamycin I$_E$ 4ε-(2-methylpropen-1-yl)-2"-(2-morpholinoethylthio)pyrimido[4,5-5γ,5δ]pristinamycin I$_E$ 4ε-(2-methylpropen-1-yl)-2"-(2-morpholinoethylthio)pyrimido[4,5-5γ,5δ](4ζ-methylamino)(4ζ-dedimethylamino)pristinamycin I$_E$ 2"-(2-Morpholinoethylthio)pyrimido[4,5-5γ,5δ](4ζ-diethylamino)(4ζ-dedimethylamino)pristinamycin I$_E$ 2"-(2-Morpholinoethylthio)pyrimido[4,5-5γ,5δ](4ζ-N-methyl-N-allylamino)(4ζ-dedimethylamino)pristinamycin I$_E$ 2"-(2-Morpholinoethylthio)pyrimido[4,5-5γ,5δ](4ζ-N-methyl-N-ethylamino)(4ζ-dedimethylamino)pristinamycin I$_E$ 2"-(2-Morpholinoethylthio)pyrimido[4,5-5γ,5δ](4ζ-N-methyl-N-propylamino)(4ζ-dedimethylamino)pristinamycin I$_E$ 2"-(2-Morpholinoethylthio)pyrimido[4,5-5γ,5δ](4ζ-N-methyl-N-(4-pyridylmethyl)amino)(4ζ-dedimethylamino) pristinamycin I$_E$ 2"-(2-Morpholinoethylthio)pyrimido[4,5-5γ,5δ](4ζ-N-methyl-N-(3-pyridylmethyl)amino)(4ζ-dedimethylamino)pristinamycin I$_E$ 2"-(2-Morpholinoethylthio)pyrimido[4,5-5γ,5δ](4ζ-methyl)(4-dedimethylamino)pristinamycin I$_E$ 2"-(2-Morpholinoethylthio)pyrimido[4,5-5γ,5δ](4ζ-tert-butyl)(4ζ-dedimethylamino)pristinamycin I$_E$ 4ε-Bromo-2"-aminopyrimido[4,5-5γ,5δ]pristinamycin I$_E$ 4ε-Bromo-2"-aminopyrimido[4,5-5γ,5δ](4ζ-methylamino)(4ζ-dedimethylamino)pristinamycin I$_E$ 4ε-Allyl-2"-aminopyrimido[4,5-5γ,5δ]pristinamycin I$_E$ 4ε-Allyl-2"-aminopyrimido[4,5-5γ,5δ](4ζ-methylamino)(4ζ-dedimethylamino)pristinamycin I$_E$ 4ε-(2-Methylpropen-1-yl)-2"-aminopyrimido[4,5-5γ,5δ]pristinamycin I$_E$ 4ε-(2-Methylpropen-1-yl)-2"-aminopyrimido[4,5-5γ,5δ](4ζ-methylamino)(4ζ-dedimethylamino)pristinamycin I$_E$ 2"-Aminopyrimido[4,5-5γ,5δ](4ζ-diethylamino)(4ζ-dedimethylamino)pristinamycin I$_E$ 2"-Aminopyrimido[4,5-5γ,5δ](4ζ-N-methyl-N-allylamino)(4ζ-dedimethylamino)pristinamycin I$_E$ 2"-Aminopyrimido[4,5-5γ,5δ](4ζ-N-methyl-N-ethylamino)(4ζ-dedimethylamino)pristinamycin I$_E$ 2"-Aminopyrimido[4,5-5γ,5δ](4ζ-N-methyl-N-propylamino)(4ζ-dedimethylamino)pristinamycin I$_E$ 2"-Aminopyrimido[4,5-5γ,5δ](4ζ-N-methyl-N-(4-pyridylmethyl)amino)(4ζ-dedimethylamino)pristinamycin I$_E$ 2"-Aminopyrimido[4,5-5γ,5δ](4ζ-N-methyl-N-(3-pyridylmethyl)amino)(4ζ-dedimethylamino)pristinamycin I$_E$ 2"-Aminopyrimido[4,5-5γ,5δ](4ζ-methyl)(4ζ-dedimethylamino)pristinamycin I$_E$ 2"-Aminopyrimido[4,5-5γ,5δ](4ζ-tert-butyl)-(4ζ-dedimethylamino)pristinamycin I$_E$ 4ε-Bromo-2"-(1-pyrazolyl)pyrimido[4,5-5γ,5δ]pristinamycin I$_E$ 4ε-Bromo-2"-(1-pyrazolyl)pyrimido[4,5-5γ,5δ](4ζ-methylamino)(4ζ-dedimethylamino)pristinamycin I$_E$ 4ε-Allyl-2"-(1-pyrazolyl)pyrimido[4,5-5γ,5δ]pristinamycin I$_E$ 4ε-Allyl-2"-(1-pyrazolyl)pyrimido[4,5-5γ,5δ](4ζ-methylamino)(4ζ-dedimethylamino)pristinamycin I$_E$ 4ε-(2-Methylpropen-1-yl)-2"-(1-pyrazolyl)pyrimido[4,5-5γ,5δ]pristinamycin I$_E$ 4ε-(2-Methylpropen-1-yl)-2"-(1-pyrazolyl)pyrimido[4,5-5γ,5δ](4ζ-methylamino)(4ζ-dedimethylamino)pristinamycin I$_E$ 2"-(1-Pyrazolyl)pyrimido[4,5-5γ,5δ](4ζ-diethylamino)(4ζ-dedimethylamino)pristinamycin I$_E$ 2"-(1-Pyrazolyl)pyrimido[4,5-5γ,5δ](4ζ-N-methyl-N-allylamino)(4ζ-dedimethylamino)pristinamycin I$_E$ 2"-(1-Pyrazolyl)pyrimido[4,5-5γ,5δ](4ζ-N-methyl-N-ethylamino)(4ζ-dedimethylamino)pristinamycin I$_E$ 2"-(1-Pyrazolyl)pyrimido[4,5-5γ,5δ](4ζ-N-methyl-N-propylamino)(4ζ-dedimethylamino)pristinamycin I$_E$ 2"-(1-Pyrazolyl)pyrimido[4,5-5γ,5δ](4ζ-N-methyl-N-(4-pyridylmethyl)amino)(4ζ-dedimethylamino)pristinamycin I$_E$ 2"-(1-Pyrazolyl)pyrimido[4,5-5γ,5δ](4ζ-N-methyl-N-(3-pyridylmethyl)amino)(4ζ-dedimethylamino)pristinamycin I$_E$ 2"-(1-Pyrazolyl)pyrimido[4,5-5γ,5δ](4ζ-methyl)(4ζ-dedimethylamino)pristinamycin I$_E$ 2"-(1-Pyrazolyl)pyrimido[4,5-5γ,5δ](4ζ-tert-butyl)(4ζ-dedimethylamino)pristinamycin I$_E$ 4ε-Bromo-2"-(diethylaminoethylthio)pyrimido[4,5-5γ,5δ]pristinamycin I$_E$ 4ε-Bromo-2"-(diethylaminoethylthio)pyrimido[4,5-5γ,5δ](4ζ-methylamino)(4ζ-dedimethylamino)pristinamycin I$_E$ 4ε-Allyl-2"-(diethylaminoethylthio)pyrimido[4,5-5γ,5δ]pristinamycin I$_E$ 4ε-Allyl-2"-(diethylaminoethylthio)pyrimido[4,5-5γ,5δ](4ζ-methylamino)(4ζ-dedimethylamino)pristinamycin I$_E$ 4ε-(2-Methylpropen-1-yl)-2"-(diethylaminoethylthio)pyrimido[4,5-5γ,5δ]pristinamycin I$_E$ 4ε-(2-Methylpropen-1-yl)-2"-(diethylaminoethylthio)pyrimido[4,5-5γ,5δ](4ζ-methylamino)(4ζ-dedimethylamino)pristinamycin I$_E$ 2"-(1-Pyrazolyl)pyrimido[4,5-5γ,5δ](4ζ-diethylamino)(4ζ-dedimethylamino)pristinamycin I$_E$ 2"-(Diethylaminoethylthio)pyrimido[4,5-5γ,5δ](4ζ-N-methyl-N-allylamino)(4ζ-dedimethylamino)pristinamycin I$_E$ 2"-(Diethylaminoethylthio)pyrimido[4,5-5γ,5δ](4ζ-N-methyl-N-ethylamino)(4ζ-dedimethylamino)pristinamycin $I_E$ 2"-(Diethylaminoethylthio)pyrimido[4,5-5γ,5δ](4ζ-N-methyl-N-propylamino)(4ζ-dedimethylamino)pristinamycin $I_E$ 2"-(Diethylaminoethylthio)pyrimido[4,5-5γ,5δ](4ζ-N-methyl-N-(4-pyridylmethyl)amino)(4ζ-dedimethylamino)pristinamycin $I_E$ 2"-(Diethylaminoethylthio)pyrimido[4,5-5γ,5δ](4ζ-N-methyl-N-(3-pyridylmethyl)amino)(4ζ-dedimethylamino)pristinamycin $I_E$ 2"-(Diethylaminoethylthio)pyrimido[4,5-5γ,5δ](4ζ-methyl)(4ζ-dedimethylamino)pristinamycin $I_E$ 2"-(Diethylaminoethylthio)pyrimido[4,5-5γ,5δ](4ζ-tert-butyl)(4ζ-dedimethylamino)pristinamycin $I_E$ 4ε-Bromo-2"-methylaminopyrimido[4,5-5γ,5δ]pristinamycin $I_E$ 4ε-Bromo-2"-methylaminopyrimido[4,5-5γ,5δ](4ζ-methylamino)(4ζ-dedimethylamino)pristinamycin $I_E$ 4ε-Allyl-2"-methylaminopyrimido[4,5-5γ,5δ]pristinamycin $I_E$ 4ε-Allyl-2"-methylaminopyrimido[4,5-5γ,5δ](4ζ-methylamino)(4ζ-dedimethylamino)pristinamycin $I_E$ 4ε-(2-Methylpropen-1-yl)-2"-methylaminopyrimido[4,5-5γ,5δ]pristinamycin $I_E$ 4ε-(2-Methylpropen-1-yl)-2"-methylaminopyrimido[4,5-5γ,5δ](4ζ-methylamino)(4ζ-dedimethylamino)pristinamycin $I_E$ 2"-Methylaminopyrimido[4,5-5γ,5δ](4ζ-diethylamino)(4ζ-dedimethylamino)pristinamycin $I_E$ 2"-Methylaminopyrimido[4,5-5γ,5δ](4ζ-N-methyl-N-allylamino)(4ζ-dedimethylamino)pristinamycin $I_E$ 2"-Methylaminopyrimido[4,5-5γ,5δ](4ζ-N-methyl-N-ethylamino)(4ζ-dedimethylamino)pristinamycin $I_E$ 2"-Methylaminopyrimido[4,5-5γ,5δ](4ζ-N-methyl-N-propylamino)(4ζ-dedimethylamino)pristinamycin $I_E$ 2"-Methylaminopyrimido[4,5-5γ,5δ](4ζ-N-methyl-N-(4-pyridylmethyl)amino)(4ζ-dedimethylamino)pristinamycin $I_E$ 2"-Methylaminopyrimido[4,5-5γ,5δ](4ζ-N-methyl-N-(3-pyridylmethyl)amino)(4ζ-dedimethylamino)pristinamycin $I_E$ 2"-Methylaminopyrimido[4,5-5γ,5δ](4ζ-methyl)(4ζ-dedimethylamino)pristinamycin $I_E$ 2"-Methylaminopyrimido[4,5-5γ,5δ](4ζ-tert-butyl)(4ζ-dedimethylamino)pristinamycin $I_E$ 4ε-Bromo-2"-methylsulphonylpyrimido[4,5-5γ,5δ]pristinamycin $I_E$ 4ε-Bromo-2"-methylsulphonylpyrimido[4,5-5γ,5δ](4ζ-methylamino)(4ζ-dedimethylamino)pristinamycin $I_E$ 4ε-Allyl-2"-methylsulphonylpyrimido[4,5-5γ,5δ]pristinamycin $I_E$ 4ε-Allyl-2"-methylsulphonylpyrimido[4,5-5γ,5δ](4ζ-methylamino)(4ζ-dedimethylamino)pristinamycin $I_E$ 4ε-(2-methylpropen-1-yl)-2"-methylsulphonylpyrimido[4,5-5γ,5δ]pristinamycin $I_E$ 4ε-(2-methylpropen-1-yl)-2"-methylsulphonylpyrimido[4,5-5γ,5δ](4ζ-methylamino)(4ζ-dedimethylamino)pristinamycin $I_E$ 2"-methylsulphonylpyrimido[4,5-5γ,5δ](4ζ-diethylamino)(4ζ-dedimethylamino)pristinamycin $I_E$ 2"-methylsulphonylpyrimido[4,5-5γ,5δ](4ζ-N-methyl-N-allylamino)(4ζ-dedimethylamino)pristinamycin $I_E$ 2"-methylsulphonylpyrimido[4,5-5γ,5δ](4ζ-N-methyl-N-ethylamino)(4ζ-dedimethylamino)pristinamycin $I_E$ 2"-methylsulphonylpyrimido[4,5-5γ,5δ](4ζ-N-methyl-N-propylamino)(4ζ-dedimethylamino)pristinamycin $I_E$ 2"-methylsulphonylpyrimido[4,5-5γ,5δ](4ζ-N-methyl-N-(4-pyridylmethyl)amino)(4ζ-dedimethylamino)pristinamycin $I_E$ 2"-methylsulphonylpyrimido[4,5-5γ,5δ](4ζ-N-methyl-N-(3-pyridylmethyl)amino)(4ζ-dedimethylamino)pristinamycin $I_E$ 2"-methylsulphonylpyrimido[4,5-5γ,5δ](4ζ-methyl)(4ζ-dedimethylamino)pristinamycin $I_E$ 2"-methylsulphonylpyrimido[4,5-5γ,5δ](4ζ-tert-butyl)(4ζ-dedimethylamino)pristinamycin $I_E$ 4ε-Bromo-2"-(4-aminophenyl)pyrimido[4,5-5γ,5δ]pristinamycin $I_E$ 4ε-Bromo-2"-(4-aminophenyl)pyrimido[4,5-5γ,5δ](4ζ-methylamino)(4ζ-dedimethylamino)pristinamycin $I_E$ 4ε-Allyl-2"-(4-aminophenyl)pyrimido[4,5-5γ,5δ]pristinamycin $I_E$ 4ε-Allyl-2"-(4-aminophenyl)pyrimido[4,5-5γ,5δ](4ζ-methylamino)(4ζ-dedimethylamino)pristinamycin $I_E$ 4ε-(2-Methylpropen-1-yl)-2"-(4-aminophenyl)pyrimido[4,5-5γ,5δ]pristinamycin $I_E$ 4ε-(2-Methylpropen-1-yl)-2"-(4-aminophenyl)pyrimido[4,5-5γ,5δ](4ζ-methylamino)(4ζ-dedimethylamino)pristinamycin $I_E$ 2"-(4-Aminophenyl)pyrimido[4,5-5γ,5δ](4ζ-diethylamino)(4ζ-dedimethylamino)pristinamycin $I_E$ 2"-(4-Aminophenyl)pyrimido[4,5-5γ,5δ](4ζ-N-methyl-N-allylamino)(4ζ-dedimethylamino)pristinamycin $I_E$ 2"-(4-Aminophenyl)pyrimido[4,5-5γ,5δ](4ζ-N-methyl-N-ethylamino)(4ζ-dedimethylamino)pristinamycin $I_E$ 2"-(4-Aminophenyl)pyrimido[4,5-5γ,5δ](4ζ-N-methyl-N-propylamino)(4ζ-dedimethylamino)pristinamycin $I_E$ 2"-(4-Aminophenyl)pyrimido[4,5-5γ,5δ](4ζ-N-methyl-N-(4-pyridylmethyl)amino)(4ζ-dedimethylamino)pristinamycin $I_E$ 2"-(4-Aminophenyl)pyrimido[4,5-5γ,5δ](4ζ-N-methyl-N-(3-pyridylmethyl)amino)(4ζ-dedimethylamino)pristinamycin $I_E$ 2"-(4-Aminophenyl)pyrimido[4,5-5γ,5δ](4ζ-methyl)(4ζ-dedimethylamino)pristinamycin $I_E$ 2"-(4-Aminophenyl)pyrimido[4,5-5γ,5δ](4ζ-tert-butyl)(4ζ-dedimethylamino)pristinamycin $I_E$ 4ε-Bromo-2"-trifluoromethylpyrimido[4,5-5γ,5δ]pristinamycin $I_E$ 4ε-Bromo-2"-trifluoromethylpyrimido[4,5-5γ,5δ](4ζ-methylamino)(4ζ-dedimethylamino)pristinamycin $I_E$ 4ε-Allyl-2"-trifluoromethylpyrimido[4,5-5γ,5δ]pristinamycin $I_E$ 4ε-Allyl-2"-trifluoromethylpyrimido[4,5-5γ,5δ](4ζ-methylamino)(4ζ-dedimethylamino)pristinamycin $I_E$ 4ε-(2-Methylpropen-1-yl)-2"-trifluoromethylpyrimido[4,5-5γ,5δ]pristinamycin $I_E$ 4ε-(2-Methylpropen-1-yl)-2"-trifluoromethylpyrimido[4,5-5γ,5δ](4ζ-methylamino)(4ζ-dedimethylamino)pristinamycin $I_E$ 2"-Trifluoromethylpyrimido[4,5-5γ,5δ](4ζ-diethylamino)(4ζ-dedimethylamino)pristinamycin $I_E$ 2"-Trifluoromethylpyrimido[4,5-5γ,5δ](4ζ-N-methyl-N-allylamino)(4ζ-dedimethylamino)pristinamycin $I_E$ 2"-Trifluoromethylpyrimido[4,5-5γ,5δ](4ζ-N-methyl-N-ethylamino)(4ζ-dedimethylamino)pristinamycin $I_E$ 2"-Trifluoromethylpyrimido[4,5-5γ,5δ](4ζ-N-methyl-N-propylamino)(4ζ-dedimethylamino)pristinamycin $I_E$ 2"-Trifluoromethylpyrimido[4,5-5γ,5δ](4ζ-N-methyl-N-(4-pyridylmethyl)amino)(4ζ-dedimethylamino)pristinamycin $I_E$ 2"-Trifluoromethylpyrimido[4,5-5γ,5δ](4ζ-N-methyl-N-(3-pyridylmethyl)amino)(4ζ-dedimethylamino)pristinamycin $I_E$ 2"-Trifluoromethylpyrimido[4,5-5γ,5δ](4ζ-methyl)(4ζ-dedimethylamino)pristinamycin I$_E$
2"-Trifluoromethylpyrimido[4,5-5γ,5δ](4ζ-tert-butyl)(4ζN-dedimethylamino)pristinamycin I$_E$
4ε-Bromo-2"-cyclopropylpyrimido[4,5-5γ,5δ]pristinamycin I$_E$
4ε-Bromo-2"-cyclopropylpyrimido[4,5-5γ,5δ](4ζ-methylamino)(4ζ-dedimethylamino)pristinamycin I$_E$
4ε-Allyl-2"-cyclopropylpyrimido[4,5-5γ,5δ]pristinamycin I$_E$
4ε-Allyl-2"-cyclopropylpyrimido[4,5-5γ,5δ](4ζ-methylamino)(4ζ-dedimethylamino)pristinamycin I$_E$
4ε-(2-Methylpropen-1-yl)-2"-cyclopropylpyrimido[4,5-5γ,5δ]pristinamycin I$_E$
4ε-(2-Methylpropen-1-yl)-2"-cyclopropylpyrimido[4,5-5γ,5δ](4ζ-methylamino)(4ζ-dedimethylamino)pristinamycin I$_E$
2"-cyclopropylpyrimido[4,5-5γ,5δ](4ζ-diethylamino)(4ζ-dedimethylamino)pristinamycin I$_E$
2"-cyclopropylpyrimido[4,5-5γ,5δ](4ζ-N-methyl-N-allylamino)(4ζ-dedimethylamino)pristinamycin I$_E$
2"-cyclopropylpyrimido[4,5-5γ,5δ](4ζ-N-methyl-N-ethylamino)(4ζ-dedimethylamino)pristinamycin I$_E$
2"-cyclopropylpyrimido[4,5-5γ,5δ](4ζ-N-methyl-N-propylamino)(4ζ-dedimethylamino)pristinamycin I$_E$
2"-cyclopropylpyrimido[4,5-5γ,5δ](4ζ-N-methyl-N-(4-pyridylmethyl)amino)(4ζ-dedimethylamino)pristinamycin I$_E$
2"-cyclopropylpyrimido[4,5-5γ,5δ](4ζ-N-methyl-N-(3-pyridylmethyl)amino)(4ζ-dedimethylamino)pristinamycin I$_E$
2"-cyclopropylpyrimido[4,5-5γ,5δ](4ζ-methyl)(4ζ-dedimethylamino)pristinamycin I$_E$
2"-cyclopropylpyrimido[4,5-5γ,5δ](4ζ-tert-butyl)(4ζ-dedimethylamino)pristinamycin I$_E$
4ε-Bromo-2"-morpholinomethylpyrimido[4,5-5γ,5δ]pristinamycin I$_E$
4ε-Bromo-2"-morpholinomethylpyrimido[4,5-5γ,5δ](4ζ-methylamino)(4ζ-dedimethylamino)pristinamycin I$_E$
4ε-Allyl-2"-morpholinomethylpyrimido[4,5-5γ,5δ]pristinamycin I$_E$
4ε-Allyl-2"-morpholinomethylpyrimido[4,5-5γ,5δ](4ζ-methylamino)(4ζ-dedimethylamino)pristinamycin I$_E$
4ε-(2-Methylpropen-1-yl)-2"-morpholinomethylpyrimido[4,5-5γ,5δ]pristinamycin I$_E$
4ε-(2-Methylpropen-1-yl)-2"-morpholinomethylpyrimido[4,5-5γ,5δ](4ζ-methylamino)(4ζ-dedimethylamino)pristinamycin I$_E$
2"-Morpholinomethylpyrimido[4,5-5γ,5δ](4ζ-diethylamino)(4ζ-dedimethylamino)pristinamycin I$_E$
2"-Morpholinomethylpyrimido[4,5-5γ,5δ](4ζ-N-methyl-N-allylamino)(4ζ-dedimethylamino)pristinamycin I$_E$
2"-Morpholinomethylpyrimido[4,5-5γ,5δ](4ζ-N-methyl-N-ethylamino)(4ζ-dedimethylamino)pristinamycin I$_E$
2"-Morpholinomethylpyrimido[4,5-5γ,5δ](4ζ-N-methyl-N-propylamino)(4ζ-dedimethylamino)pristinamycin I$_E$
2"-Morpholinomethylpyrimido[4,5-5γ,5δ](4ζ-N-methyl-N-(4-pyridylmethyl)amino)(4ζ-dedimethylamino)pristinamycin I$_E$
2"-Morpholinomethylpyrimido[4,5-5γ,5δ](4ζ-N-methyl-N-(3-pyridylmethyl)amino)(4ζ-dedimethylamino)pristinamycin I$_E$
2"-Morpholinomethylpyrimido[4,5-5γ,5δ](4ζ-methyl)(4ζ-dedimethylamino)pristinamycin I$_E$
2"-Morpholinomethylpyrimido[4,5-5γ,5δ](4ζ-tert-butyl)(4ζ-dedimethylamino)pristinamycin I$_E$
4ε-Bromo-2"-ethylpyrimido[4,5-5γ,5δ]pristinamycin I$_E$
4ε-Bromo-2"-ethylpyrimido[4,5-5γ,5δ](4ζ-methylamino)(4ζ-dedimethylamino)pristinamycin I$_E$
4ε-Allyl-2"-ethylpyrimido[4,5-5γ,5δ]pristinamycin I$_E$
4ε-Allyl-2"-ethylpyrimido[4,5-5γ,5δ](4ζ-methylamino)(4ζ-dedimethylamino)pristinamycin I$_E$
4ε-(2-Methylpropen-1-yl)-2"-ethylpyrimido[4,5-5γ,5δ]pristinamycin I$_E$
4ε-(2-Methylpropen-1-yl)-2"-ethylpyrimido[4,5-5γ,5δ](4ζ-methylamino)(4ζ-dedimethylamino)pristinamycin I$_E$
2"-Ethylpyrimido[4,5-5γ,5δ](4ζ-diethylamino)(4ζ-dedimethylamino)pristinamycin I$_E$
2"-Ethylpyrimido[4,5-5γ,5δ](4ζ-N-methyl-N-allylamino)(4ζ-dedimethylamino)pristinamycin I$_E$
2"-Ethylpyrimido[4,5-5γ,5δ](4ζ-N-methyl-N-ethylamino)(4ζ-dedimethylamino)pristinamycin I$_E$
2"-Ethylpyrimido[4,5-5γ,5δ](4ζ-N-methyl-N-propylamino)(4ζ-dedimethylamino)pristinamycin I$_E$
2"-Ethylpyrimido[4,5-5γ,5δ](4ζ-N-methyl-N-(4-pyridylmethyl)amino)(4ζ-dedimethylamino)pristinamycin I$_E$
2"-Ethylpyrimido[4,5-5γ,5δ]4ζ-N-methyl-N-(3-pyridylmethyl)amino)(4ζ-dedimethylamino)pristinamycin I$_E$
2"-Ethylpyrimido[4,5-5γ,5δ](4ζ-methyl)(4ζ-dedimethylamino)pristinamycin I$_E$
2"-Ethylpyrimido[4,5-5γ,5δ](4ζ-tert-butyl)(4ζ-dedimethylamino)pristinamycin I$_E$
4ε-Bromo-2"-propylpyrimido[4,5-5γ,5δ]pristinamycin I$_E$
4ε-Bromo-2"-propylpyrimido[4,5-5γ,5δ](4ζ-methylamino)(4ζ-dedimethylamino)pristinamycin I$_E$
4ε-Allyl-2"-propylpyrimido[4,5-5γ,5δ]pristinamycin I$_E$
4ε-Allyl-2"-propylpyrimido[4,5-5γ,5δ](4ζ-methylamino)(4ζ-dedimethylamino)pristinamycin I$_E$
4ε-(2-Methylpropen-1-yl)-2"-propylpyrimido[4,5-5γ,5δ]pristinamycin I$_E$
4ε-(2-Methylpropen-1-yl)-2"-propylpyrimido[4,5-5γ,5δ](4ζ-methylamino)(4ζ-dedimethylamino)pristinamycin I$_E$
2"-Propylpyrimido[4,5-5γ,5δ](4ζ-diethylamino)(4ζ-dedimethylamino)pristinamycin I$_E$
2"-Propylpyrimido[4,5-5γ,5δ](4ζ-N-methyl-N-allylamino)(4ζ-dedimethylamino)pristinamycin I$_E$
2"-Propylpyrimido[4,5-5γ,5δ](4ζ-N-methyl-N-ethylamino)(4ζ-dedimethylamino)pristinamycin I$_E$
2"-Propylpyrimido[4,5-5γ,5δ](4ζ-N-methyl-N-propylamino)(4ζ-dedimethylamino)pristinamycin I$_E$
2"-Propylpyrimido[4,5-5γ,5δ](4ζ-N-methyl-N-(4-pyridylmethyl)amino)(4ζ-dedimethylamino)pristinamycin I$_E$
2"-Propylpyrimido[4,5-5γ,5δ](4ζ-N-methyl-N-(3-pyridylmethyl)amino)(4ζ-dedimethylamino)pristinamycin I$_E$
2"-Propylpyrimido[4,5-5γ,5δ](4ζ-methyl)(4ζ-dedimethylamino)pristinamycin I$_E$
2"-Propylpyrimido[4,5-5γ,5δ](4ζ-tert-butyl)(4ζ-dedimethylamino)pristinamycin I$_E$
4ε-Bromo-2"-isopropylpyrimido[4,5-5γ,5δ]pristinamycin I$_E$
4ε-Bromo-2"-isopropylpyrimido[4,5-5γ,5δ](4ζ-methylamino)(4ζ-dedimethylamino)pristinamycin I$_E$
4ε-Allyl-2"-isopropylpyrimido[4,5-5γ,5δ]pristinamycin I$_E$
4ε-Allyl-2"-isopropylpyrimido[4,5-5γ,5δ](4ζ-methylamino)(4ζ-dedimethylamino)pristinamycin I$_E$
4ε-(2-Methylpropen-1-yl)-2"-isopropylpyrimido[4,5-5γ,5δ]pristinamycin I$_E$
4ε-(2-Methylpropen-1-yl)-2"-isopropylpyrimido[4,5-5γ,5δ](4ζ-methylamino)(4ζ-dedimethylamino)pristinamycin I$_E$
2"-Isopropylpyrimido[4,5-5γ,5δ](4ζ-diethylamino)(4ζ-dedimethylamino)pristinamycin I$_E$ 2"-Isopropylpyrimido[4,5-5γ,5δ](4ζ-N-methyl-N-allylamino)(4ζ-dedimethylamino) pristinamycin I$_E$
2"-Isopropylpyrimido[4,5-5γ,5δ](4ζ-N-methyl-N-ethylamino)(4ζ-dedimethylamino) pristinamycin I$_E$
2"-Isopropylpyrimido[4,5-5γ,5δ](4ζ-N-methyl-N-propylamino)(4ζ-dedimethylamino)pristinamycin I$_E$
2"-Isopropylpyrimido[4,5-5γ,5δ](4ζ-N-methyl-N-(4-pyridylmethyl)amino)(4ζ-dedimethylamino) pristinamycin I$_E$
2"-Isopropylpyrimido[4,5-5γ,5δ](4ζ-N-methyl-N-(3-pyridylmethyl)amino)(4ζ-dedimethylamino) pristinamycin I$_E$
2"-Isopropylpyrimido[4,5-5γ,5δ](4ζ-methyl)(4ζ-dedimethylamino)pristinamycin I$_E$
2"-Isopropylpyrimido[4,5-5γ,5δ](4ζ-tert-butyl)(4ζ-dedimethylamino)pristinamycin I$_E$
4ε-Bromo-2"-cyclopropylaminomethylpyrimido[4,5-5γ,5δ] pristinamycin I$_E$
4ε-Bromo-2"-cyclopropylaminomethylpyrimido[4,5-5γ,5δ](4ζ-methylamino)(4ζ-dedimethylamino)pristinamycin I$_E$
4ε-Allyl-2"-cyclopropylaminomethylpyrimido[4,5-5γ,5δ] pristinamycin I$_E$
4ε-Allyl-2"-cyclopropylaminomethylpyrimido[4,5-5γ,5δ](4ζ-methylamino)(4ζ-dedimethylamino)pristinamycin I$_E$
4ε-(2-Methylpropen-1-yl)-2"-cyclopropylaminomethylpyrimido[4,5-5γ,5δ] pristinamycin I$_E$
4ε-(2-Methylpropen-1-yl)-2"-cyclopropylaminomethylpyrimido[4,5-5γ,5δ](4ζ-methylamino)(4ζ-dedimethylamino)pristinamycin I$_E$
2"-Cyclopropylaminomethylpyrimido[4,5-5γ,5δ](4ζ-diethylamino)(4ζ-dedimethylamino)pristinamycin I$_E$
2"-Cyclopropylaminomethylpyrimido[4,5-5γ,5δ](4ζ-N-methyl-N-allylamino)(4ζ-dedimethylamino) pristinamycin I$_E$
2"-Cyclopropylaminomethylpyrimido[4,5-5γ,5δ](4ζ-N-methyl-N-ethylamino)(4ζ-dedimethylamino) pristinamycin I$_E$
2"-Cyclopropylaminomethylpyrimido[4,5-5γ,5δ](4ζ-N-methyl-N-propylamino)(4ζ-dedimethylamino) pristinamycin I$_E$
2"-Cyclopropylaminomethylpyrimido[4,5-5γ,5δ](4ζ-N-methyl-N-(4-pyridylmethyl)amino)(4ζ-dedimethylamino) pristinamycin I$_E$
2"-Cyclopropylaminomethylpyrimido[4,5-5γ,5δ](4ζ-N-methyl-N-(3-pyridylmethyl)amino)(4ζ-dedimethylamino) pristinamycin I$_E$
2"-Cyclopropylaminomethylpyrimido[4,5-5γ,5δ](4ζ-methyl)(4ζ-dedimethylamino)pristinamycin I$_E$
2"-Cyclopropylaminomethylpyrimido[4,5-5γ,5δ](4ζ-tert-butyl)(4ζ-dedimethylamino)pristinamycin I$_E$

PREPARATION OF THE INTERMEDIATES

EXAMPLE A

Method a 170 mg of pristinamycin I$_B$ dissolved in 0.5 cm$^3$ of dry dimethylformamide are placed in a three-necked flask maintained under a nitrogen atmosphere, and then 0.026 cm$^3$ of 3,3-dimethylallyl bromide dissolved in 0.2 cm$^3$ of dry dimethylformamide is added. After stirring for 3 hours at room temperature, the reaction mixture is diluted with 10 cm$^3$ of distilled water and then washed with twice 20 cm$^3$ of ethyl acetate. The organic phase is decanted off, washed with water, dried over magnesium sulphate, filtered and then concentrated under reduced pressure (2.7 kPa) to give a solid which is taken up in ethyl ether and then dried. The solid is purified by flash chromatography (eluent: dichloromethane-methanol 97/3) to give 57 mg of 4-N-(2-methyl-2-buten-4-yl)pristinamycin I$_B$ in the form of a pale-yellow solid melting at 170° C.

$^1$H NMR spectrum (400 MHz, CDCl$_3$, δ in ppm): 1.70 (s, 6H: CH$_3$); 2.85 (s, 3H: ArNCH$_3$); 2.87 (mt, 1H: 1H of CH$_2$ at position 4β); 3.23 (s, 3H: NCH$_3$); 3.30 (t, J=12 Hz, 1H: the other H of CH$_2$ at position 4β); 3.82 and 3.91 (2 dd, J=16.5 and 5 Hz, 1H each: ArNCH$_2$); 5.08 (mt, 1H: CH=); 5.18 (dd, J=12 and 4 Hz, 1H: 4α); 6.62 (d, J=8.5 Hz, 2H: aromatic H at position 4ε); 7.03 (d, J=8.5 Hz, 2H: aromatic H at position 45δ).

Method b 660 mg of pristinamycin I$_B$ dissolved in 3.3 cm$^3$ of dry chloroform (over amylene) are placed in a three-necked flask maintained under a nitrogen atmosphere, and then 65 mg of NaHCO$_3$ powder are added. After stirring for one hour, 0.09 cm$^3$ of 3,3-dimethylallyl bromide dissolved in 0.9 cm$^3$ of dry chloroform (over amylene) is added. After stirring for 18 hours at room temperature, the reaction mixture is diluted with 20 cm$^3$ of chloroform and then washed with 3 times 5 cm$^3$ of distilled water. The organic phase is decanted off, dried over magnesium sulphate, filtered and then concentrated under reduced pressure (2.7 kPa) to give a solid which is taken up in 20 cm$^3$ of ether and then dried. This solid is purified by flash chromatography (eluent: dichloromethane-methanol 97/3) to give 360 mg of 4-N-(2-methyl-2-buten-4-yl)pristinamycin I$_B$ in the form of a pale-yellow solid melting at 170° C.

EXAMPLE B 1.7 g of pristinamycin I$_B$ in 5.1 cm$^3$ of dry dimethylformamide are placed in a three-necked flask maintained under a nitrogen atmosphere, and then 310 mg of crotyl bromide are added. The mixture is stirred for 22 hours at room temperature. The reaction mixture is diluted with 50 cm$^3$ of distilled water, with stirring, and then extracted with twice 20 cm$^3$ of ethyl acetate. The aqueous phase is decanted off and the organic phase is washed with twice 10 cm$^3$ of distilled water, decanted off, dried over magnesium sulphate, filtered and then concentrated under reduced pressure (2.7 kPa) to give 1.1 g of a yellow oil which is purified by flash chromatography (eluent: dichloromethane-methanol 97/3) to give 0.62 g of 4-N-(2-butenyl)pristinamycin I$_B$ in the form of a white solid melting at 180° C.

$^1$H NMR spectrum (400 MHz, CDCl$_3$, δ in ppm): 1.70 (d, J=6 Hz, 3H: CH$_3$); from 2.85 to 2.90 (mt, 1H: 1H of CH$_2$ at position 4β); 2.90 (s, 3H: ArNCH$_3$); 3.28 (s, 3H: NCH$_3$); 3.32 (t, J=12 Hz, 1H: the other H of CH$_2$ at position 4β); 3.81 and 3.91 (2 broad d, J=18 Hz, 1H each: ArNCH$_2$); 5.22 (dd, J=12 and 4 Hz, 1H: 4α); 5.43 and 5.57 (d mt and dq respectively, J=14 Hz and J=14 and 6 Hz, 1H each: CH=CH); 6.62 (d, J=8 Hz, 2H: aromatic H at position 4ε); 7.05 (d, J=8 Hz, 2H: aromatic H at position 4δ).

EXAMPLE C

By carrying out the procedure as in Example A but starting with 2.5 g of pristinamycin I$_B$, 400 mg of bromoacetic acid in 8 cm$^3$ of dry dimethylformamide, 2.1 g of a white solid are obtained after stirring for 48 hours at room temperature, which solid is purified by flash chromatography (successive eluents: dichloromethane-methanol 95/5 then 90/10 then 80/20) to give 1.1 g of an oil which is taken up in dichloromethane, acidified to pH 4 with acetic acid and then washed with distilled water.

The organic phase is decanted off, dried over magnesium sulphate, filtered and then concentrated under reduced pressure (2.7 kPa), and then taken up in diethyl ether to give 750 mg of 4-N-(carboxymethyl)pristinamycin $I_B$ in the form of a white solid melting at 230° C.

$^1$H NMR spectrum (400 MHz, CDCl$_3$, δ in ppm): 2.85 (dd, J=12 and 4 Hz, 1H: 1H of CH$_2$ at position 4β); 3.03 (s, 3H: ArNCH$_3$); from 3.10 to 3.40 (mt, 1H: the other H of CH$_2$ at position 4β); 3.25 (s, 3H: NCH$_3$); 4.04 (limiting AB, J=18 Hz, 2H: ArNCH$_2$); 5.25 (dd, J=12 and 4 Hz, 1H: 4α); 6.62 (d, J=8 Hz, 2H: aromatic H at position 4ε); 7.07 (d, J=8 Hz, 2H: aromatic H at position 4δ).

EXAMPLE D

By carrying out the procedure as in Example A but starting with 1 g of pristinamycin $I_B$, 0.1 ml of allyl bromide in 3 cm$^3$ of dry dimethylformamide, 620 mg of a white solid are obtained after stirring for 72 hours at room temperature, which solid is purified by flash chromatography (eluent: dichloromethane-methanol 97/3) to give 290 mg of 4-N-allylpristinamycin $I_B$ in the form of a white-yellow solid melting at 208° C.

$^1$H NMR spectrum (400 MHz, CDCl$_3$, δ in ppm): 2.88 (dd, J=12 and 4 Hz, 1H: 1H of CH$_2$ at position 4β); 2.90 (s, 3H: ArNCH$_3$); 3.21 (s, 3H: NCH$_3$); 3.29 (t, J=12 Hz, 1H: the other H of CH$_2$ at position 4β); 3.85 and 3.95 (2 broad d, J=18 Hz, 1H each: ArNCH$_2$); 5.10 and 5.17 (2 d respectively, J=17 Hz and J=11.5 Hz, 1H each: =CH$_2$); 5.20 (dd, J=12 and 4 Hz, 1H: 4α); 5.78 (mt, 1H: CH=); 6.60 (d, J=8 Hz, 2H: aromatic H at position 4ε); 7.02 (d, J=8 Hz, 2H: aromatic H at position 4δ).

EXAMPLE E

By carrying out the procedure as in Example A but starting with 1 g of pristinamycin $I_B$ in 3 cm$^3$ of dry dimethylformamide and 230 mg of cinnamyl bromide, 0.8 g of a white solid is obtained after 72 hours at room temperature, which solid is purified by flash chromatography (eluent: dichloromethane-methanol 97/3) to give 0.31 g of 4-N-cinnamylpristinamycin $I_B$ in the form of a white solid melting at 204° C.

$^1$H NMR spectrum (600 MHz, CDCl$_3$, δ in ppm): 2.90 (dd, J=12.5 and 4 Hz, 1H: 1H of CH$_2$ at position 4β); 2.97 (s, 3H: ArNCH$_3$); 3.24 (s, 3H: NCH$_3$); 3.33 (t, J=12.5 Hz, 1H: the other H of CH$_2$ at position 4β); 4.70 (limiting AB, J=18 and 5.5 Hz, 2H: ArNCH$_2$); 5.20 (dd, J=12.5 and 4 Hz, 1H: 4α); 6.23 and 6.52 (broad d and dt respectively, J=16.5 and 5.5 Hz and J=16.5 Hz, 1H each: CH=CH); 6.68 (d, J=8 Hz, 2H aromatic H at position 4ε); 7.07 (d, J=8 Hz, 2H: aromatic H at position 4δ); from 7.25 to 7.40 (mt, 5H: aromatic H of phenyl).

EXAMPLE F

By carrying out the procedure as in Example A but starting with 1 g of pristinamycin $I_B$ in 3 cm$^3$ of dry dimethylformamide and 240 mg of benzyl bromide, 0.85 g of a white solid is obtained after 72 hours at room temperature, which solid is purified by flash chromatography (eluent: dichloromethane-methanol 97/3) to give 0.64 g of 4-N-benzylpristinamycin $I_B$ in the form of a white solid melting at a temperature greater than 260° C.

$^1$H NMR spectrum (400 MHz, CDCl$_3$, δ in ppm): 2.86 (dd, J=12.5 and 4 Hz, 1H: 1H of CH$_2$ at position 4β); 3.10 (s, 3H: ArNCH$_3$); 3.26 (s, 3H: NCH$_3$); 3.32 (t, J=12.5 Hz, 1H: the other H of CH$_2$ at position 4β); 4.52 and 4.69 (2 d, J=18 Hz, 1H each: ArNCH$_2$); 5.16 (dd, J=12.5 and 4 Hz, 1H: 4α); 6.59 (d, J=8 Hz, 2H: aromatic H at position 4ε); 7.01 (d, J=8 Hz, 2H: aromatic H at position 4δ); 7.18 (mt, 2H: H at the ortho position of the benzyl); 7.28 (mt, 2H: H at the meta position of the benzyl); 7.40 (t, J=7.5 Hz, 1H: H at the para position of the benzyl).

EXAMPLE G

By carrying out the procedure as in Example A but starting with 1 g of pristinamycin $I_B$ in 3 cm$^3$ of dry dimethylformamide and 200 mg of ethyl iodide, 0.65 g of a pale-yellow solid is obtained after 5 hours at 60° C. and then 72 hours at room temperature and after adding an additional 20 mg of ethyl iodide and heating at 60° C. for 4 hours, which solid is purified by flash chromatography (eluent: dichloromethane-methanol 97/3) to give 0.37 g of 4-N-ethylpristinamycin $I_B$ in the form of a white solid melting at a temperature greater than 260° C.

$^1$H NMR spectrum (400 MHz, CDCl$_3$, δ in ppm): 1.10 (t, J=7 Hz, 3H: CH$_3$ of ethyl); 2.87 (s, 3H: ArNCH$_3$); 2.90 (dd, J=12.5 and 4 Hz, 1H: 1H of CH$_2$ at position 4β); 3.25 (s, 3H: NCH$_3$); 3.32 (t, J=12.5 Hz, 1H: the other H of CH$_2$ at position 4β); 3.39 (mt, 2H: ArNCH$_2$); 5.21 (dd, J=12.5 and 4 Hz, 1H: 4α); 6.60 (d, J=8 Hz, 2H: aromatic H at position 4ε); 7.04 (d, J=8 Hz, 2H: aromatic H at position 4δ).

EXAMPLE H 1 g of pristinamycin $I_B$ in 3 cm$^3$ of dry dimethylformamide is placed in a three-necked flask maintained under a nitrogen atmosphere, and then 175 mg of a mixture of about 20% 4-bromo-1-butene, 15% of bromomethylcyclopropane and 65% of bromocyclabutane and 195 mg of sodium iodide are added. The mixture is stirred for 72 hours at room temperature and then heated for 7 hours at 60° C. 175 mg of this mixture are again added and then the stirring is continued for 48 hours. The reaction mixture is diluted with 50 cm$^3$ of distilled water, with stirring, and then extracted with twice 20 cm$^3$ of ethyl acetate. The aqueous phase is decanted off and then the organic phase is washed with twice 10 cm$^3$ of distilled water, decanted off, dried over magnesium sulphate, filtered and then concentrated under reduced pressure (2.7 kPa) to give 800 mg of a white powder which is purified by flash chromatography (eluent: dichloromethane-methanol 98/2) and then by high-performance liquid chromatography (HPLC) to give 220 mg of 4-N-(but-2-enyl)pristinamycin $I_B$ in the form of a white solid melting at 190° C.

$^1$H NMR spectrum (300 MHz, CDCl$_3$, δ in ppm): 2.29 (mt, 2H: CH$_2$); 2.88 (dd, J=12 and 4 Hz, 1H: 1H of CH$_2$ at position 4β); 2.90 (s, 3H: ArNCH$_3$); 3.25 (s, 3H: NCH$_3$); 3.31 (t, J=12 Hz, 1H: the other H of CH$_2$ at position 4β); 3.38 (mt, 2H: ArNCH$_2$); 5.05 and 5.10 (2 dd, respectively J=10.5 and 2 Hz and J=16.5 and 2 Hz, 1H each: =CH$_2$); 5.20 (dd, J=12 and 4 Hz, 1H: 4α); 5.78 (mt, 1H: CH=); 6.62 (d, J=8 Hz, 2H: aromatic H at position 4ε); 7.04 (d, J=8 Hz, 2H: aromatic H at position 4δ).

EXAMPLE I 1 g of pristinamycin $I_B$ in 3 cm$^3$ of dry dimethylformamide is placed in a three-necked flask maintained under a nitrogen atmosphere, and then 175 mg of a mixture of about 20% 4-bromo-1-butene, 15% of bromomethylcyclopropane and 65% of bromocyclobutane and 195 mg of sodium iodide are added. The mixture is stirred for 72 hours at room temperature and then heated for 7 hours at 60° C. 175 mg of this mixture are again added and then the stirring is continued for 48 hours. The reaction mixture is diluted with 50 cm$^3$ of distilled water, with stirring, and then extracted with twice 20 cm$^3$ of ethyl acetate. The aqueous phase is decanted off and then the organic phase is washed with twice 10 cm³ of distilled water, decanted off, dried over magnesium sulphate, filtered and then concentrated under reduced pressure (2.7 kPa) to give 800 mg of a white powder which is purified by flash chromatography (eluent: dichloromethane-methanol 98/2) and then by HPLC chromatography to give 222 mg of 4-N-cyclopropylmethylpristinamycin $I_B$ in the form of a white solid melting at 190° C.

$^1$H NMR spectrum (300 MHz, CDCl₃, δ in ppm): 0.20 and 0.53 (2 mts, 2H each: CH₂ of cyclopropane); 0.92 (mt, 1H: CH of cyclopropane); 2.90 (dd, J=12.5 and 4 Hz, 1H: 1H of CH₂ at position 4β); 2.93 (s, 3H: ArNCH₃); 3.13 and 3.25 (dd and mt respectively, J=15 and 7 Hz, 1H each: ArNCH₂); 3.25 (s, 3H: NCH₃); 3.32 (t, J=12.5 Hz, 1H: the other H of CH₂ at position 4β); 5.20 (dd, J=12.5 and 4 Hz, 1H: 4α); 6.67 (d, J=8 Hz, 2H: aromatic H at position 4ε); 7.04 (d, J=8 Hz, 2H: aromatic H at position 4δ).

EXAMPLE J 2 g of pristinamycin $I_B$ in 10 cm³ of dry dimethylformamide are placed in a three-necked flask maintained under a nitrogen atmosphere, and then 460 mg of 4-chloromethylpyridine hydrochloride and 350 mg of sodium iodide are added. The mixture is stirred for 5 hours at 60° C. The reaction mixture is poured over 150 cm³ of distilled water and then extracted with 3 times 100 cm³ of ethyl acetate. The aqueous phase is decanted off and then the organic phase dried over magnesium sulphate, filtered and then concentrated under reduced pressure (2.7 kPa) to give 2.6 g of a yellow oil which is purified by 2 flash chromatographies (eluent: dichloromethane-methanol 97/3) to give 130 mg of 4-N-(4-pyridylmethyl)pristinamycin $I_B$ in the form of a white solid melting at 260° C.

$^1$H NMR spectrum (300 MHz, CDCl₃, δ in ppm): 2.90 (dd, J=12.5 and 4 Hz, 1H: 1H of CH₂ at position 4β); 3.07 (s, 3H: ArNCH₃); 3.27 (s, 3H: NCH₃); 3.32 (t, J=12.5 Hz, 1H: the other H of CH₂ at position 4β); 4.50 and 4.63 (2 d, J=17 Hz Hz, 1H each: ArNCH₂); 5.16 (dd, J=12.5 and 4 Hz, 1H: 4α); 6.59 (d, J=8 Hz, 2H: aromatic H at position 4ε); 7.01 (d, J=8 Hz, 2H: aromatic H at position 4δ); 7.13 (d, J=5.5 Hz; 2H: H at position β of pyridine); 8.60 (d, J=5.5 Hz; 2H: H at position α of pyridine).

EXAMPLE K

By carrying out the procedure as in Example A but starting with 1 g of pristinamycin $I_B$ in 3 cm³ of dry dimethylformamide and 237 mg of iodobutane, 0.94 g of a pale-yellow solid is obtained after 48 hours at 60° C. and then 72 hours at room temperature, which solid is purified by flash chromatography (eluent: dichloromethane-methanol 98/2) to give 0.23 g of Hz 4-N-butylpristinamycin $I_B$ in the form of a white solid melting at 170° C.

$^1$H NMR spectrum (300 MHz, CDCl₃, δ in ppm): 0.95 (t, J=7.5 Hz, 3H: CH₃ of butyl); 1.35 and 1.55 (2 mts, 2H each: CH₂CH₂ of butyl); 2.90 (s, 3H: ArNCH3); 2.90 (dd, J=12.5 and 4 Hz, 1H: 1H of CH₂ at position 4β); from 3.20 to 3.40 (mt, 3H: the other H of CH₂ at position 4β and ArNCH₂); 3.28 (s, 3H: NCH₃); 5.21 (dd, J=12.5 and 4 Hz, 1H: 4α); 6.60 (d, J=8 Hz, 2H: aromatic H at position 4ε); 7.05 (d, J=8 Hz, 2H: aromatic H at position 4δ).

EXAMPLE L

By carrying out the procedure as in Example A but starting with 3 g of pristinamycin $I_B$ in 15 cm³ of dry dimethylformamide and 720 mg of iodopropane, 2.07 g of a pale-yellow oil are obtained after 22 hours at 50° C., which oil is purified by 2 flash chromatographies (eluent: dichloromethane-methanol 98/2 and dichloromethane-methanol 99/1) to give 0.49 g of 4-N-propylpristinamycin $I_B$ in the form of a white solid melting at 220° C. (dec.).

$^1$H NMR spectrum (300 MHz, CDCl₃, δ in ppm): 0.95 (t, J=7.5 Hz, 3H: CH₃ of propyl); 1.58 (mt, 2H: CH₂ of propyl); 2.88 (mt, 1H: 1H of CH₂ at position 4β); 2.90 (s, 3H: ArNCH₃); from 3.15 to 3.40 (mt, 3H: the other H of CH₂ at position 4β and ArNCH₂); 3.25 (s, 3H: NCH₃); 5.20 (dd, J=12.5 and 4 Hz, 1H: 4α); 6.60 (d, J=8 Hz, 2H: aromatic H at position 4ε); 7.03 (d, J=8 Hz, 2H: aromatic H at position 4δ).

EXAMPLE M

By carrying out the procedure as in Example A but starting with 2 g of pristinamycin $I_B$ in 5 cm³ of dry dimethylformamide and 480 mg of 2-iodopropane, 2.07 g of a pale-yellow oil are obtained after 6 hours at 60° C. and then 17 hours at room temperature, which oil is purified by flash chromatography (eluent: dichloromethane-methanol 97/3) to give 0.19 g of 4-N-isopropylpristinamycin $I_B$ in the form of a white solid melting at 220° C. (dec.).

$^1$H NMR spectrum (300 MHz, CDCl₃, δ in ppm): 1.14 and 1.17 (2 d, J=6.5 Hz, 6H: CH₃ of isopropyl); 2.68 (s, 3H: ArNCH₃); 2.88 (dd, J=12 and 4 Hz, 1H: 1H of CH₂ at position 4β); 3.23 (s, 3H: NCH₃); 3.30 (t, J=12 Hz, 1H: the other H of CH₂ at position 4β); 3.90 (mt, 1H: ArNCH); 5.20 (dd, J=12 and 4 Hz, 1H: 4α); 6.68 (d, J=8 Hz, 2H: aromatic H at position 4ε); 7.03 (d, J=8 Hz, 2H: aromatic H at position 4δ).

EXAMPLE N

By carrying out the procedure as in Example A but starting with 3 g of pristinamycin $I_B$ in 15 cm³ of dry dimethylformamide and 780 mg of 3-methyl-2-propane iodide, 3.86 g of a solid are obtained after 70 hours at room temperature and then addition of an additional 160 mg of 3-methyl-2-propane iodide and heating at 50° C. for 24 hours, which solid is purified by flash chromatography (eluent: dichloromethane-methanol 98/2) to give 690 mg of 4-N-isobutylpristinamycin $I_B$ in the form of a white solid melting at 190° C. (dec.).

$^1$H NMR spectrum (300 MHz, CDCl₃, δ in ppm): 0.93 (d, J=7 Hz, 6H: CH₃ of isobutyl); 2.05 (mt, 1H: CH of isobutyl); 2.92 (dd, J=12.5 and 4 Hz, 1H: 1H of CH₂ at position 4β); 2.98 (s, 3H: ArNCH₃); 3.10 and 3.18 (2 dd, J=15 and 7.5 Hz, 1H each: ArNCH₂); 3.30 (s, 3H: NCH₃); 3.35 (t, J=12.5 Hz, 1H: the other H of CH₂ at position 4β); 5.20 (dd, J=12.5 and 4 Hz, 1H: 4δ); 6.60 (d, J=8 Hz, 2H: aromatic H at position 4ε); 7.03 (d, J=8 Hz, 2H: aromatic H at position 4δ).

EXAMPLE O 3 g of pristinamycin $I_B$ in 15 cm³ of dry dimethylformamide are placed in a three-necked flask maintained under a nitrogen atmosphere, and then 690 mg of 3-chloromethylpyridine hydrochloride and 350 mg of sodium iodide are added. The mixture is stirred for 24 hours at 60° C. and then for 48 hours at room temperature. The reaction mixture is poured over 50 cm³ of distilled water supplemented with sodium bicarbonate and then extracted with 3 times 50 cm³ of ethyl acetate. The aqueous phase is decanted off and then the organic phase dried over magnesium sulphate, filtered and then concentrated under reduced pressure (2.7 kPa) to give 2.96 g of a yellow solid which is purified by flash chromatography (eluent: dichloromethane-methanol 98/2) to give 409 mg of 4-N-(3-pyridylmethyl) pristinamycin $I_B$ in the form of a white solid melting at 186° C.

$^1$H NMR spectrum (400 MHz, CDCl$_3$, δ in ppm): 2.87 (dd, J=12.5 and 4 Hz, 1H: 1H of CH$_2$ at position 4β); 3.05 (s, 3H: ArNCH$_3$); 3.23 (s, 3H: NCH$_3$); 3.29 (t, J=12.5 Hz, 1H: the other H of CH$_2$ at position 4β); 4.50 and 4.65 (2 d, J=18 Hz, 1H each: ArNCH$_2$); 5.15 (dd, J=12.5 and 4 Hz, 1H: 4α); 6.62 (d, J=8 Hz, 2H: aromatic H at position 4ε); 7.05 (d, J=8 Hz, 2H: aromatic H at position 4δ); 7.35 (mt, 1H: H at position 5 of pyridine); 7.42 (broad d, J=8 Hz, 1H: H at position 4 of pyridine); 8.45 (broad d, J=5 Hz, 1H: H at position 6 of pyridine); 8.58 (broad s, 1H: H at position 2 of pyridine).

EXAMPLE P 3 g of pristinamycin $I_B$ in 15 cm$^3$ of dry dimethylformamide are placed in a three-necked flask maintained under a nitrogen atmosphere, and then 690 mg of 2-chloromethylpyridine hydrochloride and 70 mg of sodium iodide are added. The mixture is stirred for 2 hours at 60° C. and then an additional 0.48 g of sodium iodide is added and the stirring is maintained for 23 hours at 60° C. The reaction mixture is poured over 150 cm$^3$ of distilled water supplemented with sodium bicarbonate and then extracted with 3 times 100 cm$^3$ of ethyl acetate. The aqueous phase is decanted off and then the organic phases are pooled and then washed with an aqueous solution of sodium sulphite. The organic phase is decanted off, dried over magnesium sulphate, filtered and then concentrated under reduced pressure (2.7 kPa) to give 3.34 g of a yellow solid which is purified by flash chromatography (eluent: dichloromethane-methanol 98/2) to give 1.16 g of 4-N-(2-pyridylmethyl) pristinamycin $I_B$ in the form of a white solid melting at 190° C.

$^1$H NMR spectrum (400 MHz, CDCl$_3$, δ in ppm): 2.85 (dd, J=12.5 and 4 Hz, 1H: 1H of CH$_2$ at position 4β); 3.15 (s, 3H: ArNCH$_3$); 3.24 (s, 3H: NCH$_3$); 3.29 (t, J=12.5 Hz, 1H: the other H of CH$_2$ at position 4β); 4.55 and 4.83 (2 d, J=18 Hz, 1H each: ArNCH$_2$); 5.10 (dd, J=12.5 and 4 Hz, 1H: 4α); 6.57 (d, J=8 Hz, 2H: aromatic H at position 4ε); 6.99 (mt, 1H: H at position 3 of pyridine); 7.00 (d, J=8 Hz, 2H: aromatic H at position 4δ); 7.08 (dd, J=7.5 and 5 Hz; 1H: H at position 5 of pyridine); 7.80 (dt, J=7.5 and 1 Hz, 1H: H at position 4 of pyridine); 8.57 (broad d, J=5 Hz; 1H: H at position 6 of pyridine).

EXAMPLE Q 5 g of pristinamycin $I_B$ in 7 cm$^3$ of dry dimethylformamide are placed in a three-necked flask maintained under a nitrogen atmosphere, and then 0.66 g of 1-chloro-3-hydroxypropane, 50 mg of sodium iodide and 580 mg of potassium bicarbonate are added. The mixture is stirred for 22 hours at 70° C. The reaction mixture is cooled, poured over 30 cm$^3$ of distilled water and then extracted with 3 times 40 cm$^3$ of ethyl acetate. The aqueous phase is decanted off and then the organic phase dried over magnesium sulphate, filtered and then concentrated under reduced pressure (2.7 kPa) to give 5.41 g of a solid which is purified by flash chromatography (eluent: dichloromethane-methanol 98/2) to give 0.28 g of 4-N-(3-hydroxy-3-propyl) pristinamycin $I_B$ in the form of a white solid melting at 186° C.

$^1$H NMR spectrum (400 MHz, CDCl$_3$, δ in ppm): 1.75 (mt, 2H: central CH$_2$ of propyl); 2.88 (mt, 1H: 1H of CH$_2$ at position 4β); 2.90 (s, 3H: ArNCH$_3$); 3.24 (s, 3H: NCH$_3$); 3.30 (t, J=12.5 Hz, 1H: the other H of CH$_2$ at position 4β); 3.43 and 3.62 (2 mts, 2H each: ArNCH$_2$ and CH$_2$O); 5.20 (dd, J=12.5 and 4 Hz, 1H: 4:α); 6.68 (unresolved complex, 2H: aromatic H at position 4ε); 7.03 (d, J=8 Hz, 2H: aromatic H at position 4δ).

EXAMPLE R

By carrying out the procedure as in Example Q but starting with 4 g of pristinamycin $I_B$, 1.7 cm$^3$ of 3-(dioxo-1,2-ethylene)bromopropane in 12 cm$^3$ of dry dimethylformamide, 3.8 g of a yellow solid are obtained after heating for 24 hours at 60° C., which solid is purified by flash chromatography (eluent: dichloromethane-methanol 97/3) to give 0.81 g of 4-N-[2-(1,3-dioxolan-2-yl) ethyl]pristinamycin $I_B$ in the form of a white solid melting at a temperature greater than 260° C.

$^1$H NMR spectrum (400 MHz, CDCl$_3$, δ in ppm): 1.91 (mt, 2H: central CH$_2$); 2.87 (s, 3H: ArNCH$_3$); 2.88 (dd, J=12 and 4 Hz, 1H: 1H of CH$_2$ at position 4β); 3.25 (s, 3H: NCH$_3$); 3.29 (t, J=12 Hz, 1H: the other H of CH$_2$ at position 4β); 3.35 to 3.55 (mt, 2H: ArNCH$_2$); 3.87 and 3.97 (2 mts, 2H each: OCH$_2$CH$_2$O); 4.92 (t, J=4 Hz, 1H: OCHO); 5.21 (dd, J=12 and 4 Hz, 1H: 4α); 6.64 (d, J=8 Hz, 2H: aromatic H at position 4ε); 7.04 (d, J=8 Hz, 2H: aromatic H at position 4δ).

EXAMPLE S

By carrying out the procedure as in Example A but starting with 0.53 g of 4ε-chloropristinamycin $I_B$, 0.082 cm$^3$ of allyl bromide in 3 cm$^3$ of dry dimethylformamide, a solid is obtained after 7 hours at 50° C. and then addition of an additional 0.5 cm$^3$ of allyl bromide and heating for 2 hours 30 minutes, which solid is purified by flash chromatography (eluent: dichloromethane-methanol 98/2) to give 77 mg of 4-N-allyl-4ε-chloropristinamycin $I_B$ in the form of a very light yellow solid melting at 175° C. (dec.).

$^1$H NMR spectrum (300 MHz, CDCl$_3$, δ in ppm): 2.71 (s, 3H: ArNCH$_3$); 2.93 (dd, J=12 and 4 Hz, 1H: 1H of CH$_2$ at position 4β); 3.21 (s, 3H: NCH$_3$); 3.33 (t, J=12 Hz, 1H: the other H of CH$_2$ at position 4β); 3.58 (d, J=6 Hz, 2H: ArNCH$_2$); 5.20 and 5.27 (2 dd, respectively J=11 and 1 Hz and J=16 and 1 Hz, 1H each: =CH$_2$); 5.30 (dd, J=12 and 4 Hz, 1H: 4α); from 5.75 to 5.95 (mt, 1H: CH=); 6.95 (d, J=8 Hz, 1H: aromatic H at position 4ε); 7.03 (dd, J=8 and 1.5 Hz, 1H: aromatic H at position 4δ); 7.18 (d, J=1.5 Hz, 1H: aromatic H at position 4δ and at the ortho position with respect to the Cl).

4ε-Chloropristinamycin $I_B$ may be prepared as described in Patent Application EP 772630.

EXAMPLE T 0.3 g of 4-N-ethoxycarbonylmethylpristinamycin $I_B$ in 3.5 cm$^3$ of dichloromethane is placed in a round-bottomed flask and then 51 mg of N-chlorosuccinimide are added. The mixture is stirred for 5 days at room temperature. The reaction mixture is concentrated to dryness under reduced pressure (2.7 kPa) at 30° C. The solid obtained is stirred 3 times in 5 cm$^3$ of distilled water, filtered, washed with 3 times 3 cm$^3$ of ether to give a yellow solid which is recrystallized from 4 cm$^3$ of ethanol. After filtration of the crystals and drying under reduced pressure (135 Pa) at 50° C., 0.15 g of 4ε-chloro-(4-N-ethoxy-carbonylmethyl) pristinamycin $I_B$ is obtained in the form of light beige crystals melting at 176° C.

¹H NMR spectrum (300 MHz, CDCl₃, δ in ppm): 1.34 (t, J=7 Hz, 3H: CH₃ of ethyl); 2.95 (dd, J=12 and 4 Hz, 1H: 1H of CH₂ at position 4β); 3.05 (s, 3H: ArNCH₃); 3.32 (s, 3H: NCH₃4); 3.38 (t, J=12 Hz, 1H: the other H of CH₂ at position 4β); 3.85 and 4.19 (2 d, J=17.5 Hz, 1H each: ArNCH₂); 4.22 (q, J=7 Hz, 2H: CH₂ of ethyl); 5.29 (dd, J=12 and 4 Hz, 1H 4α); 7.10 (d, J=8.5 Hz, 1H: aromatic H at position 4ε); 7.25 (mt, 2H: aromatic H at position 4δ).

4-N-Ethoxycarbonylmethylpristinamycin I$_B$ may be prepared as described below in Example AD.

EXAMPLE U

By carrying out the procedure as in Example T but starting with 0.3 g of 4-N-ethylpristinamycin I$_B$ and 0.545 g of N-chlorosuccinimide in 3.5 cm³ of dichloromethane, 0.33 g of a solid is obtained after stirring for one week at room temperature, which solid is recrystallized from 6 cm³ of ethanol. After filtration of the crystals and drying under reduced pressure (135 Pa) at 50° C., 0.15 g of 4ε-chloro-4-N-ethylpristinamycin I$_B$ is obtained in the form of light beige crystals melting at >260° C.

¹H NMR spectrum (400 MHz, CDCl₃, δ in ppm): 1.16 (t, J=7 Hz, 3H: CH₃ of ethyl); 2.70 (s, 3H: ArNCH₃); 2.92 (dd, J=12 and 4 Hz, 1H: 1H of CH₂ at position 4β); 3.00 (q, J=7 Hz, 2H: NCH₂ of ethyl); 3.22 (s, 3H: NCH₃); 3.33 (t, J=12 Hz, 1H: the other H of CH₂ at position 4β); 5.22 (dd, J=12 and 4 Hz, 1H: 4α); 6.95 (d, J=8 Hz, 1H: aromatic H at position 4ε); 7.03 (dd, J=8 and 1.5 Hz, 1H: aromatic H at position 4δ); 7.23 (d, J=1.5 Hz, 1H: aromatic H at position 4δ and at the ortho position with respect to the Cl).

EXAMPLE V

By carrying out the procedure as in Example T but starting with 200 mg of 4-N-isobutylpristinamycin I$_B$, 44 mg of N-chlorosuccinimide and 3 cm³ of dichloromethane, 99 mg of a white solid are obtained after stirring for 36 hours at room temperature and then for 40 minutes under reflux, which solid is stirred in 10 cm³ of water, filtered and then rinsed to give 690 mg of 4-N-isobutylpristinamycin I$_B$ in the form of a white solid melting at 190° C. (dec.).

¹H NMR spectrum (400 MHz, CDCl₃, δ in ppm): 0.88 (d, J=7 Hz, 6H: CH₃ of isobutyl); 1.80 (mt, 1H: CH of isobutyl); 2.69 (s, 3H: ArNCH₃); 2.75 (limiting AB, 2H: ArNCH₂); 2.95 (dd, J=12 and 4 Hz, 1H: 1H of CH₂ at position 4β); 3.25 (s, 3H: NCH₃); 3.34 (t, J=12 Hz, 1H: the other H of CH₂ at position 4β); 5.27 (dd, J=12 and 4 Hz, 1H: 4α); 6.99 (d, J=8 Hz, 1H: aromatic H at position 4ε); 7.06 (broad d, J=8 Hz, 1H: aromatic H at position 4δ); from 7.25 to 7.40 (mt, 1H: aromatic H at position 4δ and at the ortho position with respect to the Cl).

EXAMPLE W

By carrying out the procedure as in Example T but starting with 224 mg of 4-N-(4-pyridylmethyl)pristinamycin I$_B$, 32 mg of N-chlorosuccinimide and 3 cm³ of acetonitrile, a beige solid is obtained after stirring for 2 hours at 65° C., which solid is stirred in 10 cm³ of water, filtered and then rinsed and then purified by flash chromatography (eluent: dichloromethane-methanol 98/2) to give 190 mg of 4ε-chloro-4-N-pyridylmethyl)pristinamycin I$_B$ in the form of a white pale-yellow solid melting at 232° C. (dec.).

¹H NMR spectrum (300 MHz, CDCl₃, δ in ppm): 2.67 (s, 3H: ArNCH₃); 2.97 (dd, J=12.5 and 4 Hz, 1H: 1H of CH₂ at position 4β); 3.24 (s, 3H: NCH₃); 3.32 (t, J=12.5 Hz, 1H: the other H of CH₂ at position 4β); 4.10 (s, 2H: ArNCH₂); 5.29 (dd, J=12.5 and 4 Hz, 1H: 4α); 6.99 (d, J=8 Hz, 1H: aromatic H at position 4ε); 7.06 (broad d, J=8 and 1.5 Hz, 1H: aromatic H at position 4δ); from 7.15 to 7.40 (mt, 1H: aromatic H at position 4δ and at the ortho position with respect to the Cl); 7.37 (d, J=6 Hz; 2H: H at position β of pyridine); 8.57 (d, J=6 Hz; 2H: H at position α of pyridine).

EXAMPLE X

By carrying out the procedure as in Example T but starting with 260 mg of 4-N-(3-pyridylmethyl)pristinamycin I$_B$, 37 mg of N-chlorosuccinimide and 3 cm³ of acetonitrile, 270 mg of a white solid are obtained after stirring for 20 hours at 65° C., which solid is stirred in 10 cm³ of water, filtered and then rinsed to give 120 mg of 4ε-chloro-4-N-(3-pyridylmethyl)pristinamycin I$_B$ in the form of a white solid melting at 258° C. (dec.).

¹H NMR spectrum (300 MHz, CDCl₃, δ in ppm): 2.65 (s, 3H: ArNCH₃); 2.98 (dd, J–12 and 4 Hz, 1H: 1H of CH₂ at position 4β); 3.23 (s, 3H: NCH₃); 3.33 (t, J=12 Hz, 1H: the other H of CH₂ at position 4β); 4.13 (s, 2H: ArNCH₂); 5.19 (dd, J=12 and 4 Hz, 1H: 4α); 7.00 (d, J=8 Hz, 1H: aromatic H at position 4ε); 7.08 (dd, J=8 and 1.5 Hz, 1H: aromatic H at position 4δ); from 7.15 to 7.40 (mt, 2H: aromatic H at position 4δ and at the ortho position with respect to the Cl and H at position 5 of pyridine); 7.80 (mt, 1H: H at position 4 of pyridine); 8.55 (broad d, J=6 Hz; 1H: H at position 6 of pyridine); 8.65 (broad s, 1H: H at position 2 of pyridine).

EXAMPLE Y 2 g of pristinamycin I$_B$ in 6 cm³ of dry dimethylformamide are placed in a three-necked flask maintained under a nitrogen atmosphere, and then 1.46 g of 4-pyridylmethyl bromoacetate hydrobromide and 0.33 cm³ of triethylamine are added. The mixture is stirred for 18 hours at 60° C. The reaction mixture is cooled, poured over 100 cm³ of distilled water and then extracted with 4 times 30 cm³ of ethyl acetate. The aqueous phase is decanted off and then the organic phase washed again with 3 times 10 cm³ of distilled water, decanted off and then dried over magnesium sulphate, filtered and then concentrated under reduced pressure (2.7 kPa) to give 1.2 g of a pale-yellow solid which is purified by flash chromatography (eluent: dichloromethane-methanol 97/3) to give 0.53 g of a solid which is repurified by HPLC to give 197 mg of (4-N-pyridylmethoxycarbonylmethyl) pristinamycin I$_B$ in the form of a white powder melting at 252° C.

4-Pyridylmethyl bromoacetate hydrobromide may be prepared in the following manner 1.09 g of 4-hydroxymethylpyridine dissolved in 20 cm³ of chloroform (dry over amylene) are placed in a three-necked flask maintained under a nitrogen atmosphere and then 0.88 cm³ of bromoacetyl bromide dissolved in 2 cm³ of chloroform is added over 1 hour at room temperature. After stirring for 24 hours, an additional 10% bromoacetyl bromide is added and then the stirring is continued for 24 hours. The reaction mixture is filtered, taken up in chloroform and then in ether. The resulting solid is dried under reduced pressure to give 2.1 g of a solid which is used as it is in the next step.

¹H NMR spectrum (400 MHz, CDCl₃, δ in ppm): 2.92 (dd, J=12 and 4 Hz, 1H: 1H of CH₂ at position 4β); 3.08 (s, 3H: ArNCH₃); 3.27 (s, 3H: NCH₃); 3.33 (t, J=12 Hz, 1H: the other H of CH₂ at position 4β); 4.17 (s, 2H: ArNCH₂); 5.19 (s, 2H: COOCH₂); 5.25 (dd, J=12 and 4 Hz, 1H: 4α); 6.67 (d, J=8.5 Hz, 2H: aromatic H at position 4ε); 7.07 (d, J=8.5 Hz, 2H: aromatic H at position 4δ); 7.22 (d, J=5.5 Hz, 2H: H β of pyridine); 8.59 (d, J=5.5 Hz, 2H: H α of pyridine).

EXAMPLE Z

By carrying out the procedure as in Example Y but starting with 1.5 g of pristinamycin $I_B$ and 640 mg of N-methyl-N-(1-methylpiperid-4-yl)bromoacetamide hydrobromide in 4.5 cm³ of dry dimethylformamide and after stirring for 72 hours at room temperature, a solution is obtained after evaporation of a portion of the dimethylformamide at 50° C. under a partial pressure, which solution is taken up in 15 cm³ of distilled water. The reaction mixture is washed with twice 15 cm³ of ethyl acetate. The aqueous phase is decanted off, adjusted to pH 5–6, washed again with ethyl acetate and then alkalinized to pH 8 with 0.1 N sodium hydroxide. The aqueous phase is supplemented with sodium chloride and then extracted with 15 cm³ of methylene chloride. The organic phase is washed with 2 cm³ of water, decanted off, dried over magnesium sulphate, filtered and then concentrated under reduced pressure (2.7 kPa) to give 1.1 g of a pale-yellow solid which is dissolved in 30 cm³ of a methylene chloride/methanol concentrated ammonia mixture (70/20/1 by volume) and then supplemented with 5.5 g of silica. After stirring for 45 minutes, the mixture is filtered, rinsed with twice the same volume of mixture of solvents and then concentrated to dryness. The product obtained is concreted from 15 cm³ of ether and then filtered to give 680 mg of [N-(1-methylpiperid-4-yl)-N-methylaminocarbonylmethyl]pristinamycin $I_B$ in the form of a white solid melting at 210° C.

$^1$H NMR spectrum (400 MHz, CDCl$_3$, δ in ppm): from 1.60 to 2.10 and from 2.75 to 3.00 (2 mts, respectively 6H and 2H: CH$_2$CH$_2$N of piperidine); 2.30 (s, 3H: NCH$_3$ of piperidine); 2.85 (s, 3H: CONCH$_3$); from 2.80 to 3.00 (mt, 1H: 1H of CH$_2$ at position 4β); 3.00 (s, 3H: ArNCH$_3$); 3.22 (s, 3H: NCH$_3$); 3.28 (t, J=12 Hz, 1H: the other H of CH$_2$ at position 4β); 4.04 (s, 2H: ArNCH$_2$); 4.45 (mt, 1H: CONCH); 5.25 (dd, J=12 and 4 Hz, 1H: 4β); 6.60 (d, J=8.5 Hz, 2H: aromatic H at position 4ε); 7.00 (d, J=8.5 Hz, 2H: aromatic H at position 4δ).

N-Methyl-N-(1-methylpiperid-4-yl)bromo-acetamide hydrobromide may be obtained in the following manner:

1.45 g of 1-methyl-4-methylaminopiperidine in 30 cm³ of dry dimethylformamide are placed in a three-necked flask maintained under nitrogen at 5° C. and then 0.95 g of bromoacetyl bromide dissolved in 10 cm³ of chloroform is added over 1 hour. After 18 hours at room temperature, the reaction mixture is concentrated, the residue taken up in 30 cm³ of ether and then stirred for 3 hours. The resulting solid is filtered, washed with ether and then dried under reduced pressure (2.7 kPa) to give 3.2 g of N-methyl-N-(1-methylpiperid-4-yl)-bromoacetamide hydrobromide in the form of a pale-yellow solid which is used as it is.

EXAMPLE AA

By carrying out the procedure as in Example Y but starting with 2.4 g of pristinamycin $I_B$ and 0.91 g of (1-ethoxycarbonylpiperid-4-yl)bromoacetamide in 7.5 cm³ of dry dimethylformamide and after stirring for 96 hours at room temperature, a solution is obtained which is diluted with 80 cm³ of distilled water. The mixture is adjusted to pH 8 with sodium bicarbonate, supplemented with sodium chloride and then extracted with twice 20 cm³ of ethyl acetate. The aqueous phase is decanted off and then re-extracted with twice 20 cm³ of ethyl acetate. The organic phases are pooled, dried over magnesium sulphate, filtered and then concentrated under reduced pressure (2.7 kPa) to give a pale-yellow solid which is taken up in ether to give after filtration and drying 2.6 g of a pale-yellow powder which is purified by flash chromatography (eluent: dichloromethane-methanol 97/3) to give 1.1 g of [N-(1-ethoxycarbonylpiperid-4-yl)aminocarbonyl-methyl]pristinamycin $I_B$ in the form of a white solid melting at 195° C.

$^1$H NMR spectrum (400 MHz, CDCl$_3$, δ in ppm): 1.23 (t, J=7 Hz, CH$_3$ of ethyl); from 1.20 to 1.50 and from 1.70 to 1.95 (2 mts, 2H each: CH$_2$ of piperidine); 2.85 and from 3.90 to 4.15 (mt and unresolved complex respectively, 2H and 3H respectively: NCH$_2$ and NCH of piperidine); 2.95 (dd, J=12.5 and 4 Hz, 1H: 1H of CH$_2$ at position 4β); 2.97 (s, 3H: ArNCH$_3$); 3.25 (s, 3H: NCH$_3$); 3.34 (t, J=12.5 Hz, 1H: the other H of CH$_2$ at position 4β); 3.79 and 3.90 (2 d, J=18 Hz, 1H each: ArNCH$_2$); 4.20 (q, J=7 Hz, 2H: COOCH$_2$ of ethyl); 5.19 (dd, J=12.5 and 4 Hz, 1H: 4α); 6.55 (mt, 1H: CONH); 6.63 (d, J=8 Hz, 2H: aromatic H at position 4ε); 7.15 (d, J=8 Hz, 2H: aromatic H at position 4δ).

(1-Ethoxycarbonylpiperid-4-yl)bromoacetamide may be prepared in the following manner:

860 mg of 1-ethoxycarbonyl-4-aminopiperidine and then 15 cm³ of dry chloroform (over amylene) and 0.84 cm³ of triethylamine are placed in a three-necked flask maintained over nitrogen. The mixture is cooled to 5° C. and then 0.48 cm³ of bromoacetyl bromide dissolved in 2 cm² of dry chloroform is added over 45 minutes and the stirring is continued for 5 hours at room temperature. The chloroform is evaporated off under reduced pressure and the mixture taken up in 20 cm³ of ethyl acetate and 120 cm³ of distilled water. The organic phase is decanted off, washed with twice 5 cm³ of water and then dried over magnesium sulphate, filtered, concentrated under reduced pressure (2.7 kPa) to give a pale-yellow solid which is taken up in ether to give after filtration and drying 970 mg of (1-ethoxycarbonylpiperid-4-yl)bromoacetamide in the form of a white powder which is used as it is.

EXAMPLE AB

By carrying out the procedure as in Example Y but starting with 3 g of pristinamycin $I_B$ and 1.53 g of N-(1-benzylpiperid-4-yl)bromoacetamide hydrobromide in 9 cm³ of dry dimethylformamide and after stirring for 72 hours at room temperature, a solution is obtained which is diluted with 120 cm³ of distilled water. The mixture is adjusted to pH 8 and then extracted with 3 times 30 cm³ of ethyl acetate. The organic phase is decanted off, washed with 30 cm³ of water and then dried over magnesium sulphate, filtered and then concentrated under reduced pressure (2.7 kPa) to give a pale-yellow solid which is taken up in ether to give after filtration and drying 3.3 g of a white powder which is purified by flash chromatography (eluent: dichloromethane-methanol 97/3) to give 0.95 g of [(1-benzylpiperid-4-yl)aminocarbonylmethyl]pristinamycin $I_B$ in the form of a white solid melting at 195° C.

$^1$H NMR spectrum (300 MHz, CDCl$_3$, δ in ppm): from 1.35 to 1.65 and from 1.95 to 2.20 (2 mts, 2H each: CH$_2$ of piperidine); from 2.70 to 2.85 and from 3.25 to 3.40 (2 mts, 2H: NCH$_2$ of piperidine); 2.95 (dd, J=12 and 4 Hz, 1H: 1H of CH$_2$ at position 4β); 2.97 (s, 3H: ArNCH$_3$); 3.26 (s, 3H: NCH$_3$); 3.35 (t, J=12 Hz, 1H: the other H of CH$_2$ at position 4β); 3.47 (s, 2H: NCH$_2$Ar); 3.80 and 3.90 (2 d, J=18 Hz, 1H each: ArNCH$_2$); from 3.75 to 3.95 (mt, 1H: NCH of piperidine); 5.25 (dd, J=12 and 4 Hz, 1H: 4α); 6.50 (d, J=7.5 Hz, 1H: CONH); 6.65 (d, J=8.5 Hz, aromatic H at position 4ε); 7.15 (d, J=8.5 Hz, 2H: aromatic H at position 4δ); from 7.15 to 7.40 (mt, 5H: aromatic H of benzyl).

N-(1-Benzylpiperid-4-yl)bromoacetamide hydrobromide may be obtained in the following manner 950 mg of 4 amino 1 benzylpiperidine and then 15 cm³ of dry chloroform (over amylene) are placed in a three-necked flask maintained under nitrogen. The mixture is cooled to 5° C. and then 0.47 cm³ of bromoacetyl bromide dissolved in 5 cm³ of dry chloroform is added over 45 minutes and the stirring is continued for 30 minutes at 5° C. The chloroform is evaporated under reduced pressure and the mixture is taken up in 15 cm³ of ether to give after filtration and drying 2 g of N-(1-benzylpiperid-4-yl)bromoacetamide hydrobromide in the form of a white powder which is used as it is.

EXAMPLE AC 605 mg of [(1-benzylpiperid-4-yl)amino-carbonylmethyl] pristinamycin $I_B$ in 12 cm³ of methanol and 6 cm³ of dichloromethane, 120 mg of 10% palladium on carbon and then 0.22 cm³ of 2.5 N hydrochloric ether are placed in a three-necked flask maintained under nitrogen. The mixture is placed under a hydrogen atmosphere at 18° C. and then heated to 33° C. After 3 days the mixture is purged with nitrogen, filtered on Clarcel®, concentrated under reduced pressure and then taken up in 15 cm³ of water. The solution is adjusted to pH 8 with 1 N sodium hydroxide, supplemented with sodium chloride and then extracted with dichloromethane. The organic phase is decanted off, washed with water saturated with sodium chloride, dried over magnesium sulphate, filtered and then concentrated under reduced pressure (2.7 kPa) to give a solid which is stirred for 18 hours in 11.2 cm³ of 0.1 N hydrochloric acid. The medium is adjusted to pH 8 by addition of 11.2 cm³ of 0.1 N sodium hydroxide and then supplemented with 3.6 g of sodium chloride. After stirring for 2 hours, the precipitate is filtered, rinsed with a minimum of ice-cold water and then taken up in ether. The solid is taken up in dichloromethane, dried over magnesium sulphate, filtered and then dried at 35° C. under reduced pressure (90 Pa) to give 270 mg of [(4-piperidinyl)aminocarbonylmethyl]pristinamycin $I_B$ in the form of a cream-coloured solid melting at 230° C.

$^1$H NMR spectrum (400 MHz, CDCl₃, δ in ppm): from 1.45 to 1.65 and from 1.80 to 2.00 (2 mts, 2H each: CH₂ of piperidine); from 2.65 to 2.85 and from 3.05 to 3.25 (2 mts, 2H each: NCH₂ of piperidine); 2.95 (dd, J=12 and 4 Hz, 1H: 1H of CH₂ at position 4β); 2.98 (s, 3H: ArNCH₃); 3.27 (s, 3H: NCH₃); 3.32 (t, J=12 Hz, 1H: the other H of CH₂ at position 4β); 3.80 and 3.88 (2 d, J=18 Hz, 1H each: ArNCH₂); 3.95 (mt, 1H: CONCH of piperidine); 5.22 (dd, J=12 and 4 Hz, 1H: 4α); 6.63 (d, J=8.5 Hz, 2H: aromatic H at position 4ε); 6.68 (d, J=8 Hz, 1H: CONH); 7.10 (d, J=8.5 Hz, 2H: aromatic H at position 4δ).

EXAMPLE AD 15 g of pristinamycin $I_A$ in 30 cm³ of dry dimethylformamide are placed in a three-necked flask maintained under a nitrogen atmosphere and then 2.2 cm³ of ethyl bromoacetate are added. The mixture is stirred for 22 hours at 80° C. After cooling, the reaction mixture is diluted with 300 cm³ of distilled water and then stirred. The precipitate formed is filtered, rinsed with 3 times 50 cm³ of distilled water and then with ether. The resulting solid is solubilized in ethyl acetate, filtered and then washed in a separating funnel with 3 times 50 cm³ of distilled water. The organic phase is decanted off, dried over magnesium sulphate, filtered and then concentrated under reduced pressure (2.7 kPa) to give 7.2 g of a brown oil which is purified by flash chromatography (eluent: dichloromethane-methanol 98/2) to give 3.2 g of 4-N-(ethoxycarbonylmethyl]pristinamycin $I_B$ in the form of a white solid melting at 244° C.

$^1$H NMR spectrum (400 MHz, CDCl₃, δ in ppm): 1.28 (t, J=7 Hz, 3H: CH₃ of ethyl); 2.90 (dd, J=12.5 and 4 Hz, 1H: 1H of CH₂ at position 4β); 3.05 (s, 3H: ArNCH₃); 3.26 (s, 3H: NCH₃); 3.34 (t, J=12.5 Hz, 1H: the other H of CH₂ at position 4β); 4.02 and 4.08 (2 d, J=18 Hz, 1H each: ArNCH₂); 4.20 (q, J=7 Hz, 2H: CH₂ of ethyl); 5.22 (dd, J=12.5 and 4 Hz, 1H: 4α); 6.62 (d, J=8.5 Hz, 2H: aromatic H at position 4ε); 7.07 (d, J=8.5 Hz, 2H: aromatic H at position 4δ).

EXAMPLE AE

By carrying out the procedure as in Example AD but starting with 1.5 g of pristinamycin $I_A$ in 3 cm³ of dry dimethylformamide and 240 mg of bromoacetonitrile, 0.8 g of a white solid is obtained after 6 hours at 80° C. which is purified by flash chromatography (eluent: dichloromethane-methanol 97/3) to give 0.48 g of 4-N-cyanomethylpristinamycin $I_B$ in the form of a white solid melting at 258° C.

$^1$H NMR spectrum (300 MHz, CDCl₃, δ in ppm): 2.95 (dd, J=12 and 4 Hz, 1H: 1H of CH₂ at position 4β); 2.97 (s, 3H: ArNCH₃); 3.20 (s, 3H: NCH₃); 3.32 (t, J=12 Hz, 1H: the other H of CH₂ at position 4β); 4.10 (limiting AB, J=18 Hz, 2H: ArNCH₂); 5.23 (dd, J=12 and 4 Hz, 1H: 4α); 6.75 (d, J=8 Hz, 2H: aromatic H at position 4ε); 7.09 (d, J=8 Hz, 2H: aromatic H at position 4δ).

EXAMPLE AF

5δ-Methylenepristinamycin $I_B$ may be obtained in the following manner.

10 cm³ of methanol and 1 cm³ of morpholine are placed in a three-necked flask maintained under a nitrogen atmosphere and then 0.6 cm³ of methanesulphonic acid is slowly added while the temperature is maintained below 20° C. 0.17 g of polyoxymethylene and then 1 g of pristinamycin $I_B$ are then added with stirring. The milky suspension obtained is heated for 4 hours at 40° C. and then stirred for 12 hours at room temperature. The mixture is concentrated to dryness, taken up in 20 cm³ of ethyl acetate and 20 cm³ of distilled water, filtered on Clarcel® and then decanted off. The aqueous phase is extracted with twice 10 cm³ of ethyl acetate and then the organic phases are pooled, washed with 30 cm³ of an aqueous solution of sodium chloride, decanted off, dried over sodium sulphate and then concentrated under reduced pressure (2.7 kPa) to a volume of 50 cm³. The organic phase of 50 cm³ thus concentrated is added, in a three-necked flask, with stirring, to 35 cm³ of distilled water, 1.3 cm³ of acetic acid and 0.16 g of sodium acetate trihydrate. The mixture is heated for 3 hours at 40–45° C. and then after cooling, a saturated sodium bicarbonate solution is added to a pH of 5–6. The aqueous phase is decanted off, extracted with 20 cm³ of ethyl acetate and then the organic phases are combined and washed with 30 cm³ of bicarbonated distilled water. The aqueous phase is decanted off and then extracted with 20 cm³ of ethyl acetate. All the organic phases are pooled, washed with a saturated aqueous sodium chloride solution, dried over sodium sulphate, filtered and concentrated to dryness under reduced pressure to give 1.03 g of a solid which is purified by two successive flash chromatographies (eluent: methylene chloride-methanol 96/4) to give 0.21 g of a product which is concreted from 5 cm³ of diethyl ether. After filtration and drying at 50° C. under reduced pressure (90 Pa), 169 mg of 5δ-methylenepristinamycin $I_B$ are obtained in the form of an off-white solid melting at 210° C. (not very sharp).

$^1$H NMR spectrum (300 MHz, CDCl₃, δ in ppm): 0.66 (dd, J=16.5 and 6 Hz, 1H: 1H of CH₂ at position 5β); 0.91

(t, J=7.5 Hz, 3H: CH₃ at position 2γ); from 1.15 to 1.35 (mt, 2H: 1H of CH₂ at position 3β and 1H of CH₂ at position 3γ); 1.33 (d, J=7 Hz, 3H: CH₃ at position 1γ); from 1.50 to 1.85 (mt: 3H corresponding to the other H of CH₂ at position 3γ and to the CH₂ at position 2β); 2.03 (mt, 1H: the other H of CH₂ at position 3β); 2.50 (d, J=16.5 Hz, 1H: the other H of CH₂ at position 5β); 2.81 (s, 3H: ArNCH₃); 2.88 (dd, J=12 and 4.5 Hz, 1H: 1H of CH₂ at position 4β); from 3.20 to 3.35 (mt, 2H: 1H of CH₂ at position 3δ and the other H of CH₂ at position 4β); 3.26 (s, 3H: NCH₃); 3.52 (mt, 1H: the other H of CH₂ at position 3δ); 3.59 (broad d, J=16.5 Hz, 1H: 1H of CH₂ at position 5ε); from 3.65 to 3.90 (broad unresolved complex, 1H: ArNH); 4.60 (dd, J=9 and 6 Hz, 1H: CH at position 3α); 4.82 (mt, 1H: CH at position 2α); 4.88 (dd, J=10 and 1 Hz, 1H: CH at position 1α); 5.05 (dd, J=12 and 4.5 Hz, 1H: CH at position 4α); 5.28 (broad d, J=16.5 Hz, 1H: the other H of CH₂ at position 5ε); 5.28 (d, J=6 Hz, 1H: CH at position 5α); 5.35 and 6.17 (2 broad s, 1H each: =CH₂); 5.84 (d, J=9 Hz, 1H: CH at position 6α); 5.90 (dq, J=7 and 1 Hz, CH at position 1β); 6.46 (d, J=8 Hz, 2H: aromatic H at position 4ε); 6.50 (d, J=10 Hz, CONH at position 2); 6.91 (d, J=8 Hz, 2H: aromatic H at position 4δ); from 7.15 to 7.35 (mt: the 5 aromatic H at position 6); 7.47 (limiting AB, 2H: 1'H₄ and 1'H₅); 7.82 (dd, J=4 and 2 Hz, 1H: 1'H₆); 8.38 (d, J=10 Hz, 1H: CONH at position 1); 8.73 (d, J=9 Hz, 1H: CONH at position 6); 11.60 (s, 1H: OH).

The products of the above examples may be treated by analogy with the methods described in Examples 1 to 33 in order to prepare the streptogramin derivatives of general formula (I).

The present invention also relates to the pharmaceutical compositions containing at least one streptogramin derivative according to the invention, in the pure state, combined with at least one group A streptogramin derivative, where appropriate in salt form, and/or in the form of a combination with one or more compatible and pharmaceutically acceptable diluents or adjuvants.

The compositions according to the invention may be used by the oral, parenteral, topical or rectal route or in the form of aerosols.

As solid compositions for oral administration, tablets, pills, gelatin capsules, powders or granules may be used. In these compositions, the active product according to the invention, generally in the form of a combination, is mixed with one or more inert diluents or adjuvants, such as sucrose, lactose or starch. These compositions may comprise substances other than diluents, for example a lubricant such as magnesium stearate or a coating intended for a controlled release.

As liquid compositions for oral administration, there may be used solutions which are pharmaceutically acceptable, suspensions, emulsions, syrups and elixirs containing inert diluents such as water or paraffin oil. These compositions may also comprise substances other than diluents, for example wetting, sweetening or flavouring products.

Compositions for parenteral administration may be emulsions or sterile solutions. As solvent or vehicle, there may be used propylene glycol, a polyethylene glycol, vegetable oils, in particular olive oil, or injectable organic esters, for example ethyl oleate. These compositions may also contain adjuvants, in particular wetting, isotonizing, emulsifying, dispersing and stabilizing agents.

Sterilization may be carried out in several ways, for example with the aid of a bacteriological filter, by irradiation or by heating. They may also be prepared in the form of sterile solid compositions which may be dissolved at the time of use in sterile water or any other injectable sterile medium.

Compositions for topical administration may be, for example, creams, ointments, lotions or aerosols.

Compositions for rectal administration are suppositories or rectal capsules which contain, in addition to the active ingredient, excipients such as cocoa butter, semisynthetic glycerides or polyethylene glycols.

The compositions may also be aerosols. For use in the form of liquid aerosols, the compositions may be stable sterile solutions or solid compositions which are dissolved at the time of use in apyrogenic sterile water, in saline or any other pharmaceutically acceptable vehicle. For use in the form of dry aerosols intended to be directly inhaled, the active ingredient is finely divided and combined with a water-soluble solid diluent or vehicle with a particle size distribution of 30 to 80 µm, for example dextran, mannitol or lactose.

In human therapy, the new streptogramin derivatives according to the invention are particularly useful in the treatment of infections of bacterial origin. The doses depend on the desired effect and the duration of treatment. The doctor will determine the dosage which he judges to be the most appropriate depending on the treatment, depending on the age, weight and degree of infection and other factors specific to the subject to be treated. Generally, the doses are between 1 and 3 g of active product in 2 or 3 doses per day orally for an adult.

The following example illustrates a composition according to the invention.

EXAMPLE

Tablets containing a dose of 250 mg of active ingredient and having the following composition are prepared according to the usual technique:

2"-methylpyrido[2,3 5γ,5δ]pristinamycin I$_E$ . . . 75 mg pristinamycin II$_B$ . . . 175 mg excipient: starch, hydrated silica, dextrin, gelatin, magnesium stearate: qs . . . 500 mg

What is claimed is:

1. A compound of formula (IX)

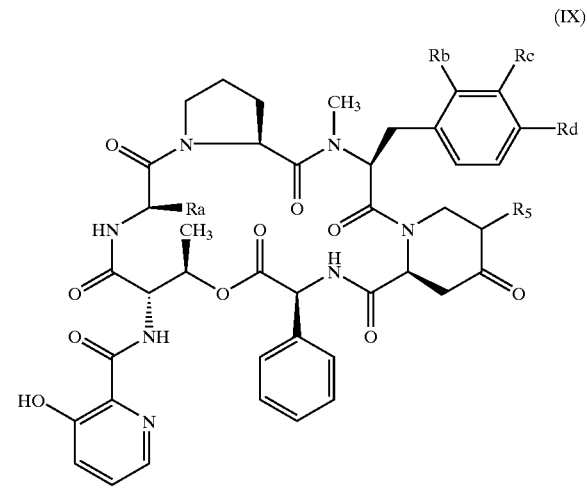

wherein (A)—Ra is a methyl group,
—R$_5$ is chosen from disubstituted methylenyl groups of formula:

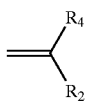

wherein:
(a) $R_2$ is chosen from a hydrogen atom and $C_1$–$C_3$ alkyl groups and
 $R_4$ is a hydrogen atom, or
(b) $R_2$ is a hydrogen atom and
 $R_4$ is chosen from a hydrogen atom and dialkylamino groups,
—Rb, Rc, and Rd axe defined as follows:
(1)—Rb and Rc are each a hydrogen atom, and
 —Rd is chosen from a hydrogen atom, a methylamino group, and a dimethylamino group, or
(2)—Rb is a hydrogen atom,
 —Rc is chosen from a hydrogen atom, a chlorine atom, a bromine atom, and $C_3$–$C_5$ alkenyl groups, and
 —Rd is chosen from —N(CH$_3$)R''' groups, wherein —R''' is chosen from
  (a) alkyl groups, $C_2$–$C_4$ hydroyalkyl groups, and $C_2$–$C_8$ alkenyl groups, wherein said $C_2$–$C_8$ alkenyl groups are optionally substituted with a group chosen from
   (i) an unsubstituied phenyl group, $C_3$–$C_6$ cycloalkyl groups, a methyl group, a benzyl group,
   (ii) a beuzyl group substituted with at least one substituent chosen from halogen atoms, a hydroxyl group, alkyl groups, alkyloxy groups, alkylthio groups, alkylsulphinyl groups, alkylsulphonyl groups, an amino group, aikylamino groups, and dialkylamino groups,
   (iii) heterocyclylmethygroups and heterocyclylethyl groups, wherein said heterocyclyl portions of said heterocyclylmethyl groups and said heterocyclylethyl groups are chosen from saturated and unsaturated 5- to 6-membered heterocyclyl groups comprising from 1 to 2 heteroatoms chosen from a sulphur atom, an oxygen atom, and a nitrogen atom, and wherein said heterocyclyl groups are optionally substituted with a group chosen from alkyl groups, $C_2$–$C_8$ alkenyl groups, $C_3$–$C_6$ cycloalkyl groups, saturated and unsaturated 4- to 6-membered heterocyclyl groups, an unsubstituted phenyl group, a substituted phenyl group as defined above in (a)(ii),
  (b) a cyanomethyl group, and
  (c) —CH$_2$CORe groups, wherein Re is chosen from
   (i) —OR'e groups, wherein R'e is chosen from a hydrogen atom, $C_1$–$C_6$ alkyl groups, $C_2$–$C_6$ alkenyl groups, a beuzyl group, and hererocyclylmethyl groups, wherein said heterocyclyl portion is chosen from 5- to 6-membared heterocyclyl groups comprising from 1 to 2 hereroatoms chosen from a sulphur atom, an oxygen atom, and a nitrogen atom,
   (ii) alkylamino groups, alkylmethylamino groups, heterocyclylamino grouops and heterocyclylmethyl amino groups, wherein said heterocyclyl portion of said heterocyclylamino groups and said heterocyelylmethylamino groups is chosen from 5- to 6-membered saturated hetarocyclyl groups comprising from 1 to 2 heteroatoms chosen from a sulphur atom, an oxygen atom, and a nitrogen atom, and wherein said heterocyclyl groups are optionally substituted with a group chosen from alkyl groups, a benzyl group, and alkyloxycarbonyl groups, or
(3)—Rb is a hydrogen atom,
 —Rd is chosen from an —NHCH$_3$ group and an —N(CH$_3$)$_2$ group, and Rc is chosen from a chlorine atom, and a bromine atom, or when Rd is an —N(CH$_3$)$_2$ group, Rc is chosen from $C_3$–$C_5$ alkenyl groups, or
(4)—Rb and Rd are each a hydrogen atom, and
 —Rc is chosen from halogen atoms, alkylamino groups, dialkylamino groups, alkyloxy groups, a trifluoromethoxy group, thioalkyl groups, $C_1$–$C_6$ alkyl groups, and trihalomethyl groups, or
(5)—Rb and Rc are each a hydrogen atom, and
 —Rd is chosen from halogen atoms, an ethylamino group, a diethylamino group, a methylethylamino group, alkyloxy groups, a trifluoromethoxy group, alkylthio groups, alkylsulphinyl groups, alkylsulphonyl groups, $C_1$–$C_6$ alkyl groups, a phenyl group, and trihalomethyl groups, or
(6)—Rb is a hydrogen atom,
 —Rc is chosen from halogen atoms, alkylamino groups, dialkylamino groups, alkyloxy groups, a trifluoromethoxy group, thioalkyl groups, and $C_1$–$C_3$ alkyl groups, and
 —Rd is chosen from halogen atoms, an amino group, alkylamino groups, dialkylamino groups, alkyloxy groups, a trifluoromethoxy group, thioalkyl groups, $C_1$–$C_4$ alkyl groups, and trihalomethyl groups, or
(7)—Re is a hydrogen atom, and
 —Rb and Rd are each a methyl group, or
(B)—Ra is an ethyl group,
 —Rb, Rc and Rd are defined as above in (2) to (7), and
 —R$_5$ is chosen from disubstituted methylenyl groups of fonnula:

wherein $R_2$ and $R_4$ are defined as above, or
(C)—R$_5$ is a hydrogen atom,
 —Ra is a methyl group or an ethyl gronp, and
 —Rb, Rc, and Rd are defined as above in (2), provided that R''' is not a methyl or an ethyl group when Rb and Rc are hydrogen atoms.

* * * * *